(12) United States Patent
Baeschlin et al.

(10) Patent No.: US 7,888,351 B2
(45) Date of Patent: Feb. 15, 2011

(54) ORGANIC COMPOUNDS

(75) Inventors: Daniel Kaspar Baeschlin, Arlesheim (CH); Garry Fenton, Harlow (GB); Kenji Namoto, Basel (CH); Nils Ostermann, Binzen (DE); Richard Sedrani, Basel (CH); Finton Sirockin, St. Louis (FR)

(73) Assignee: Novartis AG, Basel (CH)

( * ) Notice: Subject to any disclaimer, the term of this patent is extended or adjusted under 35 U.S.C. 154(b) by 73 days.

(21) Appl. No.: 12/296,792

(22) PCT Filed: Apr. 10, 2007

(86) PCT No.: PCT/EP2007/003185

§ 371 (c)(1),
(2), (4) Date: Oct. 10, 2008

(87) PCT Pub. No.: WO2007/115821

PCT Pub. Date: Oct. 18, 2007

(65) Prior Publication Data

US 2009/0281069 A1 Nov. 12, 2009

(30) Foreign Application Priority Data

Apr. 11, 2006 (GB) ................... 0607309.2
Oct. 17, 2006 (EP) ................... 06122445

(51) Int. Cl.
| | | |
|---|---|---|
| C07D 279/12 | (2006.01) | |
| C07D 237/08 | (2006.01) | |
| C07D 233/96 | (2006.01) | |
| C07D 241/12 | (2006.01) | |
| C07D 295/104 | (2006.01) | |
| C07D 211/18 | (2006.01) | |
| C07D 211/22 | (2006.01) | |
| C07D 211/24 | (2006.01) | |
| C07D 221/22 | (2006.01) | |
| C07D 213/70 | (2006.01) | |
| C07D 221/04 | (2006.01) | |

(52) U.S. Cl. ................ 514/227.8; 514/252.02; 514/252.04; 514/255.05; 514/228.2; 514/233.5; 514/235.8; 514/236.8; 514/305; 514/321; 514/326; 514/339; 544/58.6; 544/126; 544/333; 544/406; 544/238; 546/133; 546/137; 546/183; 546/245; 546/242

(58) Field of Classification Search ............. None
See application file for complete search history.

(56) References Cited

U.S. PATENT DOCUMENTS

| | | | |
|---|---|---|---|
| 4,292,323 | A | 9/1981 | Tahbaz |
| 5,449,686 | A | 9/1995 | Christensen, IV et al. |
| 6,518,289 | B1 | 2/2003 | Bryans et al. |
| 6,632,836 | B1 | 10/2003 | Baker et al. |
| 2003/0162754 | A1 | 8/2003 | Ligon |
| 2003/0199567 | A1 | 10/2003 | Taylor |
| 2007/0265261 | A1* | 11/2007 | Edwards et al. ......... 514/235.5 |

FOREIGN PATENT DOCUMENTS

| | | |
|---|---|---|
| BE | 616646 A | 8/1962 |
| EP | 0837061 A | 4/1998 |
| EP | 1679069 A | 7/2006 |
| JP | 50-010309 B | 1/1993 |
| WO | WO-01/087866 A | 11/2001 |
| WO | WO-02/043763 A | 6/2002 |
| WO | WO-02/46138 A | 6/2002 |
| WO | WO-02/085839 A | 10/2002 |
| WO | WO-03/000180 A2 | 1/2003 |
| WO | WO-03/000181 A1 | 1/2003 |
| WO | WO-03/000676 A1 | 1/2003 |
| WO | WO-03/004498 A1 | 1/2003 |
| WO | WO-03/043985 A1 | 5/2003 |
| WO | WO-03/063797 A2 | 8/2003 |
| WO | WO-03/082817 A1 | 10/2003 |
| WO | WO-2004/007468 A1 | 1/2004 |
| WO | WO-2004/032836 A2 | 4/2004 |
| WO | WO-2005/105096 A2 | 11/2005 |
| WO | WO-2005/108384 A | 11/2005 |
| WO | 2005/121089 A | 12/2005 |
| WO | WO-2007/081857 A | 7/2007 |

OTHER PUBLICATIONS

Bundgaard, H. ed. (1985). *Design of Prodrugs*. Elsevier.
Elliott, J. M. et al. (Jul. 8, 2002). "4,4-disubstituted cyclohexylamine NK1 receptor antagonists I," *Bioorganic And Medicinal Chemistry Letters* 12(13):1755-1758.
Greene, T. W. and Wuts, P. G. M. (1991). *Protective Groups in Organic Synthesis*, 2nd edition, Wiley-Interscience.
Higuchi, T. and Stella, V. (Sep. 10, 1974). "Pro-drugs as Novel Delivery Systems," *A.C.S. Symposium Series*, vol. 14. Edward B. Roche, ed.
International Search Report and Written Opinion mailed May 23, 2008, for PCT Application No. PCT/EP2007/011304 filed Dec. 20, 2007, 15 pages.

(Continued)

Primary Examiner—Rebecca L Anderson
Assistant Examiner—Michael Barker
(74) *Attorney, Agent, or Firm*—Morrison & Foerster LLP

(57) ABSTRACT

The present invention relates to compounds of the formula;

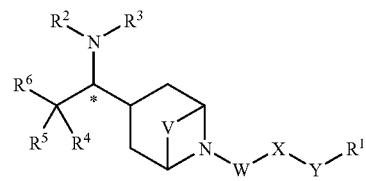

and their use in therapy.

14 Claims, No Drawings

OTHER PUBLICATIONS

International Search Report mailed May 19, 2008, for PCT Application No. PCT/EP2007/003185 filed Apr. 10, 2007, 2 pages.

Judkins, B. et al. (1996). "A Versatile Synthesis of Amides from Nitriles via Amidoximes," *Synthetic Communications* 26(23), 4351-4367.

Korom, S. et al. (May 27, 1997). "Inhibition of CD26/dipeptidyl peptidase IV activity in vivo prolongs cardiac allograft survival in rat recipients," *Transplantation* 63(10):1495-1500.

McOmie, J W F, Ed. (1973) *Protective Groups in Organic Chemistry*. Plenum Press.

Nordhoff et al. (Mar. 15, 2006). "The reversed binding of beta-phenethylamine inhibitors of DPP-IV: X-ray structures and properties of novel fragment and elaborated inhibitors," *Bioorganic &Medicinal Chemistry Letters* 16(6):1744-1748.

Prescott, Ed., (1976). *Methods in Cell Biology*, vol. XIV, Academic Press, New York, N.Y., p. 33.

Ravin, L. J. (1985). "Preformulation," Chapter 76 in *Remington's Pharmaceutical Sciences*, 17th ed., Mack Publishing Company, Easton, Pa., US, pp. 1409-1423.

Roche, E. B., Ed. (1987). *Bioreversible Carriers in Drug Design* American Pharmaceutical Association and Pergamon Press.

Rummey et al. (Mar. 1, 2006). "In silico fragment-based discovery of DPP-IV S1 pocket binders," *Bioorganic &Medicinal Chemistry Letters* 16(5):1405-1409.

Silverman, R B., Ed. (2004). *The Organic Chemistry of Drug Design and Drug Action*, 2nd edition, Elsevier.

Stahl et al, Eds, (2002). *Handbook of Pharmaceutical Salts: Properties, Selection, and Use*. Verlag Helvetica Chimica Acta and Wiley-VCH.

* cited by examiner

ORGANIC COMPOUNDS

This application is the National Stage of Application No. PCT/EP2007/003185, filed on Apr. 10, 2007, which claims benefit under 35 U.S.C. §119(a)-(d) or (f) or 365(b) of GB Application No. 0517740J, filed Apr. 11, 2006, and EP Application No. 06122445.7, filed Oct. 17, 2006, the contents of which are incorporated herein by reference in their entirety.

FIELD OF THE INVENTION

The present invention relates to compounds and their use in therapy.

BACKGROUND TO THE INVENTION

Dipeptidylpeptidase-IV (DPP-IV) is a serine protease which cleaves N-terminal dipeptides from a peptide chain containing, in general, a proline residue in the penultimate position. DPP-IV is widely expressed in mammalian tissue as a type II integral membrane protein. The protease is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic transmembrane domain.

DPP-IV has many physiologically relevant substrates including chemokines (e.g. eotaxin and macrophage-derived chemokine), neuropeptides (e.g. neuropeptide Y and substance P), vasoactive peptides, and incretins (e.g. GLP-1 and GIP). GLP-1 (glucagon-like peptide-1) is a hormone produced in the L cells of the distal small intestine in response to ingested nutrients. GLP-1 receptor binding on various tissues stimulates insulin gene expression, biosynthesis and glucose-dependent insulin secretion, inhibits glucagon secretion, promotes satiety, slows gastric emptying and promotes growth of pancreatic beta cells.

Although the biological role of DPP-IV in mammalian systems has not been completely established, it is believed to play an important role in neuropeptide metabolism, T-cell activation, attachment of cancer cells to the endothelium and the entry of HIV into lymphoid cells. It has also been discovered that DPP-IV is responsible for inactivating glucagon-like peptide-1 (GLP-1). Since GLP-1 is a major stimulator of pancreatic insulin secretion and has direct beneficial effects on glucose disposal, DPP-IV inhibition appears to represent an attractive approach for treating, for example, non-insulin-dependent diabetes mellitus (NIDDM).

DPP-IV has also been shown to play a part in the immune response. Expressed by T-CD4+ lymphocytes, where it is synonymous with the antigen CD26, DPP-IV plays an important part in the mechanism of transplant rejection (Transplantation 1997, 63 (10), 1495-500). By allowing more selective suppression of the immune response, inhibition of DPP-IV accordingly represents an extremely promising approach in the prevention of transplant rejection in transplant patients.

Inhibitors of DPP-IV are described inter alia in WO-A-03/000180, WO-A-000181, WO-A-004498, WO-A-03/082817, WO-A-04/032836, WO-A-04/007468, EP1679069 and WO-A-05/121089.

SUMMARY OF THE INVENTION

A first aspect of the invention is a compound of the Formula (I):

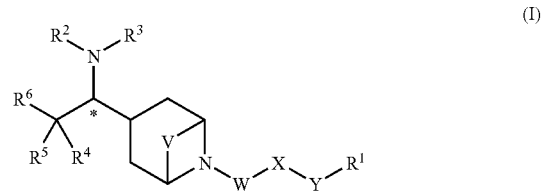

wherein
the asterisk * designates a chiral centre of (R) or (S) configuration;
V is absent or is ethylene;
W is —C(O) or —S(O)$_l$—;
X is a linker having 1 to 12 (e.g. 1 to 6) in-chain atoms and comprising one or more linkages selected from —O—, —C(O)—, —S(O)$_l$, —N($R^9$)— and hydrocarbylene optionally substituted with 1, 2, 3, 4 or 5 $R^{11}$;
Y is a linker selected from —O—, —N($R^9$)—, —C(O)—, —C(O)O—, —C(O)N($R^9$)—, —S(O)$_l$ and —S(O)$_l$N($R^9$);
$R^1$ is selected from hydrogen; —N($R^9$)($R^{10}$); hydrocarbyl optionally substituted with 1, 2, 3, 4 or 5 $R^{11}$; hydrocarbyloxy optionally substituted with 1, 2, 3, 4 or 5 $R^{11}$; and —($CH_2$)$_k$-heterocyclyl optionally substituted with 1, 2, 3, 4 or 5 $R^{11}$;
or, when Y is —N($R^9$)—, $R^1$ and $R^9$ taken together with the nitrogen atom to which they are attached may form a heterocycle, wherein said heterocycle is bound to X via said nitrogen atom and is optionally substituted with 1, 2, 3, 4 or 5 $R^{11}$;
$R^2$ and $R^3$ are each independently selected from $R^8$, —$OR^8$, —C(O)$R^8$, —C(O)$OR^8$ and —S(O)$_l R^9$;
$R^4$ and $R^5$ are each independently selected from hydrogen, hydroxy, halogen and $C_{1-6}$ alkyl optionally substituted with 1, 2, 3, 4 or 5 $R^{11}$;
$R^6$ is aryl or heteroaryl, either of which is optionally substituted with 1, 2, 3, 4 or 5 $R^{11}$;
$R^8$ is selected from hydrogen; hydrocarbyl optionally substituted with 1, 2, 3, 4 or 5 $R^{11}$; and —($CH_2$)$_k$-heterocyclyl optionally substituted with 1, 2, 3, 4 or 5 $R^{11}$;
$R^9$ and $R^{10}$ are each independently selected from $R^8$, —$OR^8$, —C(O)$R^8$, —C(O)$OR^8$ and —S(O)$_l R^8$; or $R^9$ and $R^{10}$ taken together with a nitrogen atom to which they are attached form heterocyclyl optionally substituted with 1, 2, 3, 4 or 5 $R^{11}$;
each $R^{11}$ is independently selected from $R^{12}$; hydrocarbyl optionally substituted with 1, 2, 3, 4 or 5 $R^{12}$; and —($CH_2$)$_k$-heterocyclyl optionally substituted with 1, 2, 3, 4 or 5 $R^{12}$;
$R^{12}$ is independently selected from halogen, trifluoromethyl, cyano, nitro, oxo, =$NR^{13}$, —$OR^{13}$, —C(O)$R^{13}$, —C(O)N($R^{13}$)$R^{14}$, —C(O)$OR^{13}$, —OC(O)$R^{13}$, —S(O)$_l R^{13}$, —S(O)$_l$N($R^{13}$)$R^{14}$, —N($R^{13}$)$R^{14}$, —N($R^{13}$)N($R^{13}$)$R^{14}$, —N($R^{13}$)C(O)$R^{14}$ and —N($R^{13}$)S(O)$_l R^{13}$;
$R^{13}$ and $R^{14}$ are each independently hydrogen or selected from hydrocarbyl and —($CH_2$)$_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; or
$R^{13}$ and $R^{14}$ are each independently hydrogen or selected from hydrocarbyl and —($CH_2$)$_k$-heterocyclyl, either of which is optionally substituted with 1, 2, 3, 4 or 5 substituents independently selected from oxo, halogen, cyano, amino, hydroxy, $C_{1-6}$ alkyl and $C_{1-6}$ alkoxy;

k is 0, 1, 2, 3, 4, 5 or 6; and l is 0, 1, or 2;

or a pharmaceutically acceptable salt or prodrug thereof.

In some embodiments, when X is $C_{1-6}$ alkylene, —O—$C_{1-6}$ alkylene- or —N($R^9$)—$C_{1-6}$ alkylene- and Y is —O—, —S— or —N($R^9$), said $C_{1-6}$ alkylene linkage of X is substituted with 1, 2, 3, 4 or 5 $R^{11}$, wherein at least one of said $R^{11}$ is other than halogen or $C_{1-6}$ alkyl.

A second aspect of the invention is a compound of the invention for therapeutic use.

Another aspect of the invention is a pharmaceutical formulation comprising a compound of the invention and, optionally, a pharmaceutically acceptable diluent or carrier.

A further aspect of the invention is a product comprising a compound of the invention and a therapeutic agent; as a combined preparation for simultaneous, separate or sequential use in therapy.

Another aspect of the invention is the use of a compound of the invention for the manufacture of a medicament for the treatment or prevention of a disease or condition selected from non-insulin-dependent diabetes mellitus, arthritis, obesity, allograft transplantation, calcitonin-osteoporosis, heart failure, impaired glucose metabolism or impaired glucose tolerance, neurodegenerative diseases, cardiovascular or renal diseases, and neurodegenerative or cognitive disorders.

Another aspect of the invention is the use of a compound of the invention for the manufacture of a medicament for producing a sedative or anxiolytic effect, attenuating post-surgical catabolic changes or hormonal responses to stress, reducing mortality and morbidity after myocardial infarction, modulating hyperlipidemia or associated conditions, or lowering VLDL, LDL or Lp(a) levels.

Another aspect of the invention is a method of treating or preventing a disease or condition in a patient, which comprises administering a therapeutically effective amount of a compound of the invention.

The compounds of the invention can exist in different forms, such as free acids, free bases, esters and other prodrugs, salts and tautomers, for example, and the disclosure includes all variant forms of the compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

DESCRIPTION OF VARIOUS EMBODIMENTS

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g cyclopropylmethyl); cycloalkyl (e.g. cyclopropyl, cyclobutyl, cyclopentyl or cyclohexyl); aryl (e.g. phenyl, naphthyl or fluorenyl) and the like. When hydrocarbyl is a cycloalkyl it can be attached to the chemical moiety in the form of a spiro substitution.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. When the heterocyclyl is a heterocycloalkyl it can be attached to the chemical moiety in the form of a spiro substitution.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, 1,3-Dioxo-1,3-dihydro-isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, 3,4-dihydro-2H-isoquinolin-1-one, 3,4-dihydro-2H-isoquinolinyl, and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl, tetrahydropyranyl, tetrahydrofuranyl, 1,3-dihydro-isoindolyl 1,3-Dioxo-1,3-dihydro-isoindolyl, 3,4-dihydro-2H-isoquinolinyl, 3,4-dihydro-2H-isoquinolinyl-1-one and the like.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic.

This term includes reference to groups such as pyridazinyl, pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I. In a particular, halogen may be F or Cl, of which F is more common.

Spiro

The term "spiro" as used herein includes 3- to 6-cycloalkyl or 5- to 6-heterocycloalkyl groups which can optionally be substituted by 1, 2, 3 or 4, $R^{13}$. Non limitative examples of spiro groups are;

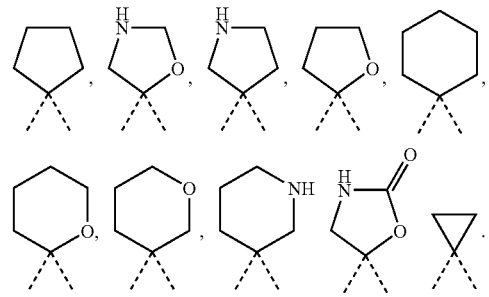

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Pharmaceutically Acceptable

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

Independently

Where two or more moieties are described as being "each independently" selected from a list of atoms or groups, this means that the moieties may be the same or different. The identity of each moiety is therefore independent of the identities of the one or more other moieties.

Compounds

The invention provides compounds of the Formula (I):

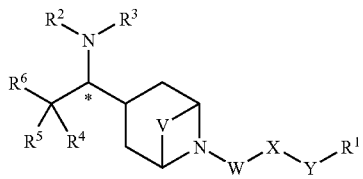

(I)

wherein
the asterisk * designates a chiral centre of (R) or (S) configuration; and
V, W, X, Y, R$^1$, R$^2$, R$^3$, R$^4$, R$^5$ and R$^6$ are as defined herein;
or a pharmaceutically acceptable salt or prodrug thereof.

As indicated above, the stereochemical configuration of the chiral centre indicated by * (i.e. the carbon atom to which the group —N(R$^2$)(R$^3$) is attached) may be (R) or (S). Of particular mention are compounds of the invention in which the stereochemical configuration at said carbon atom is (R), i.e. compounds of the following Formula:

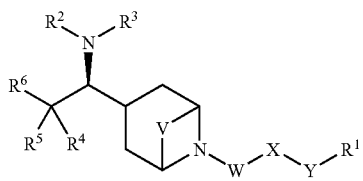

(I,(R))

or a pharmaceutically acceptable salt or prodrug thereof.

A compound of the invention may be in the form of a racemate or in a substantially pure form (e.g. a form having a purity of greater than 80% purity, in particular greater than 90%, 95% or 99%) of a single enantiomer or diastereomer. Thus, one embodiment of the invention is a substantially pure form of a compound of Formula (I, (R)).

Embodiments of the invention are described below. It will be appreciated that the features specified in each embodiment may be combined with other specified features, to provide further embodiments.

V

V is absent or is ethylene. The invention therefore includes compounds of the following Formulae:

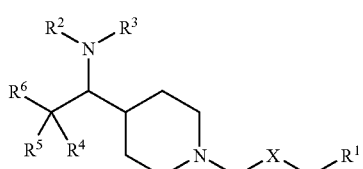

(II)

-continued

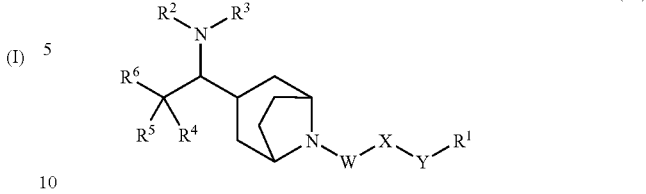

(III)

or, in each case, a pharmaceutically acceptable salt or prodrug thereof.

Where V is ethylene (i.e. compounds of Formula (III)), the relative orientation of the ethylene bridge and the hydrogen atom located p- to the nitrogen atom of the piperidine ring is often exo, as illustrated below:

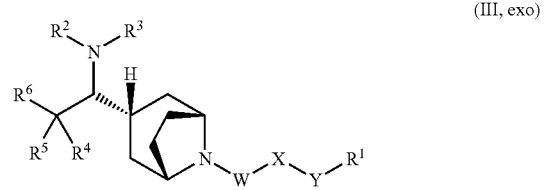

(III, exo)

The term "exo" in this context means that the ethylene bridge and the hydrogen atom shown in the Formula above are on the same side of the piperidine ring.

The present invention also concerns the herein described compounds and claims wherein the bridged piperidine ring is in the configuration exo as described in the above paragraph.

—W—X—Y—

In Formula (I), W is —C(O)— or —S(O)$_f$—; X is a linker having 1 to 12 (e.g. 1 to 6) in-chain atoms and comprising one or more linkages selected from —O—, —C(O)—, —S(O)$_f$—, —N(R$^9$)— and hydrocarbylene optionally substituted with 1, 2, 3, 4 or 5 R$^{11}$; and Y is a linker selected from —O—, —N(R$^9$), —C(O), —C(O)O—, —C(O)N(R$^9$), —S(O)$_f$— and —S(O)$_f$N(R$^9$).

W is usually —C(O)— or —S(O)$_2$—.

Where X comprises one or more hydrocarbylene linkages, the or each linkage may be aliphatic and/or carbocyclic (e.g. cycloalkylene). Of particular mention are aliphatic, e.g. alkylenic, hydrocarbylene linkages. Aliphatic linkages are usually C$_{1-6}$ aliphatic linkages, examples including C$_{1-6}$ alkylene linkages. Carbocyclylene is usually C$_{3-7}$ carbocyclylene, including cycloalkylene (e.g. C$_{3-6}$ cycloalkylene, especially cyclopropylene). In the case of carbocyclylene-containing linkages, at least one (usually 1, 2, 3 or 4, especially 1 or 2 but in other cases 3 or 4) of the in-ring atoms forms or is included in the linkage. A hydrocarbylene linkage is often aliphatic, in particular C$_{1-6}$ alkylene. In one class of compounds, X comprises a hydrocarbylene linkage which is directly bonded to W. In another class of compounds, X comprises an arylene (e.g. phenylene) linkage which is optionally substituted with 1, 2, 3, 4 or 5 R$^{11}$. In certain compounds, said arylene linkage is directly bonded in W. Of particular mention are compounds comprising a phenylene linkage optionally substituted with 1, 2, 3, 4 or 5 R$^{11}$, wherein said phenylene linkage is directly bonded to W.

X may comprise at least one linkage selected from —N(R$^9$), and aliphatic or cyclic hydrocarbylene (e.g. C$_{1-6}$ alkylene or cycloalkylene), either of which is optionally substituted with 1, 2, 3, 4 or 5 R$^{11}$. In particular, X may comprise at least one linker selected from —N(R⁹)— and C₁₋₆ alkylene (e.g. C₁, C₂ or C₃ alkylene) optionally substituted with 1, 2, 3, 4 or 5 R¹¹. When X comprises —N(R⁹)—, R⁹ is usually hydrogen or selected from C₁₋₆ alkyl (e.g. C₁, C₂, C₃ or C₄ alkyl), —(CH₂)$_k$-carbocyclyl and —(CH₂)$_k$-heterocyclyl, any of which is optionally substituted with 1, 2, 3, 4 or 5 R¹¹.

Of mention are compounds in which X is a linker having 1 to 12 (e.g. 1 to 6) in-chain atoms and comprising one or more linkages selected from —O—, —C(O)—, —S(O)$_r$—, —N(R⁹)— and C₁₋₆ aliphatic (e.g. C₁₋₆ alkylene) optionally substituted with 1, 2, 3, 4 or 5 R¹¹;

In one embodiment, X is selected from one of the following linkers:

—X¹—;
—X¹—X²—;
—X¹—X²—X³—,
—X¹—X²—X³—X⁴;
—X¹—X²—X³—X⁴—X⁵—;
—X¹—X²—X³—X⁴—X⁵—X⁶—;
—X¹—X²—X³—X⁴—X⁵—X⁶—X⁷—; and
—X¹—X²—X³—X⁴—X⁵—X⁶—X⁷—X⁸—;

wherein X¹, X², X³, X⁴, X⁵, X⁶, X⁷ and X⁸ are each independently selected from —O—, —C(O)—, —S(O)$_r$, —N(R⁹)— and hydrocarbylene (e.g. C₁₋₆ alkylene) optionally substituted with 1, 2, 3, 4 or 5 R¹¹. More usually, X is —X¹— or —X¹—X²—.

Of mention are compounds in which X¹ is hydrocarbylene (e.g. C₁₋₆ alkylene, C₂₋₆ alkenylene or carbocyclylene) optionally substituted with 1, 2, 3, 4 or 5 R¹¹. For example, X¹ may be C₁₋₆ alkylene optionally substituted with 1, 2, 3, 4 or 5 R¹¹. In particular, X¹ may be methylene or ethylene, either of which is optionally substituted with 1, 2, 3 or 4 substituents independently selected from halogen (e.g. fluorine or chlorine), amino and hydroxy. Alternatively, X¹ may be arylene, e.g. phenylene, optionally substituted with 1, 2, 3, 4 or 5 R¹¹.

Also of mention is a class of compounds in which X² is —N(R⁹)—, wherein R⁹ is usually hydrogen or selected from C₁₋₆ alkyl (e.g. C₁, C₂, C₃ or C₄ alkyl), —(CH₂)$_k$-carbocyclyl and —(CH₂)$_k$-heterocyclyl, any of which is optionally substituted with 1, 2, 3, 4 or 5 R¹¹. In particular, —N(R⁹)— may be —NH— or —N(CH₃)—. In compounds where X¹ is arylene (e.g. phenylene), X² is often C₁₋₆ alkylene (e.g. C₁ or C₂ alkylene) optionally substituted with 1, 2, 3, 4 or 5 R¹¹.

Also included are compounds in which X¹ is C₁₋₆ alkylene substituted, e.g. at the 1- or 2-position relative to W (which is typically carbonyl or sulphonyl), by at least one R¹¹. In this case, the at least one R¹¹ is often selected from halogen, trifluoromethyl, cyano, nitro, oxo, =NR¹³, —OR¹³, —C(O)R¹³, —C(O)N(R¹³)R¹⁴, —C(O)OR¹³, —OC(O)R¹³, —S(O)$_j$R¹³, —S(O)$_j$N(R¹³)R¹⁴, —N(R¹³)R¹⁴, —N(R¹³)N(R¹³)R¹⁴, —N(R¹³)C(O)R¹⁴, —N(R¹³)S(O)$_j$R¹³, hydrocarbyl (which is other than C₁₋₆ alkyl, and is often —(CH₂)$_k$-carbocyclyl) optionally substituted with 1, 2, 3, 4 or 5 R¹²; and —(CH₂)$_k$-heterocyclyl optionally substituted with 1, 2, 3, 4 or 5 R¹². In this case, R¹³ and R¹⁴ are often each independently selected from hydrogen, C₁₋₄ alkyl, —(CH₂)$_k$-carbocyclyl (e.g. phenyl, cyclopropyl or benzyl) and, —(CH₂)$_k$-heterocyclyl. Exemplary R¹¹ moieties include carbamate, phenyl, benzyl, —NH—C(O)—(C₁₋₆ alkyl), oxo, sulphonamido, urea, thiourea and acyl groups.

Also included are compounds in which X¹ is an arylene preferably selected from;

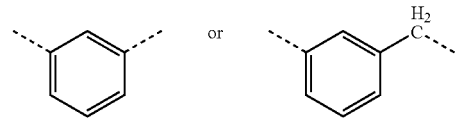

In certain compounds, Y is —C(O), —C(O)O—, —C(O)N(R⁹)—, —S(O), —S(O)₂— or —S(O)$_t$N(R⁹)—. In particular, Y is often —C(O)—, —C(O)O—, —S(O)— or —S(O)₂—.

In some embodiments, when X is C₁₋₆ alkylene, —O—C₁₋₆ alkylene- or —N(R⁹)C₁₋₆ alkylene-, Y is —O—, —S— or —N(R⁹)— and R⁷ is hydrogen, said C₁₋₆ alkylene linkage of X is substituted with 1, 2, 3, 4 or 5 R¹¹, wherein at least one of said R¹¹ is other than halogen or C₁₋₆ alkyl. In this case, at least one R¹¹, e.g. the or each R¹¹ is often independently selected from trifluoromethyl, cyano, nitro, oxo, =NR¹³, —OR¹³, —C(O)R¹³, —C(O)N(R¹³)R¹⁴, —C(O)OR¹³, —OC(O)R¹³, —S(O)$_j$R¹³, —S(O)$_j$N(R¹³)R¹⁴, —N(R¹³)R¹⁴, —N(R¹³)N(R¹³)R¹⁴, —N(R¹³)C(O)R¹⁴, —N(R¹³)S(O)$_j$R¹³, hydrocarbyl (which is other than C₁₋₆ alkyl, and is often —(CH₂)$_k$-carbocyclyl) optionally substituted with 1, 2, 3, 4 or 5 R¹²; and —(CH₂)$_k$-heterocyclyl optionally substituted with 1, 2, 3, 4 or 5 R¹². In this case, R¹³ and R¹⁴ are often each independently selected from hydrogen, C₁₋₆ alkyl, —(CH₂)$_k$-carbocyclyl (e.g. phenyl, cyclopropyl or benzyl) and, —(CH₂)$_k$-heterocyclyl. Exemplary R¹¹ moieties include carbamate, sulphonamido, urea, thiourea and acyl groups. Carbocyclyl and heterocyclyl may for example be 5, 6 or 7-membered saturated or unsaturated rings, e.g. phenyl.

The linker —W—X—Y— often comprises 3, 4 or 5, especially 4 or 5, in-chain atoms.

Of particular mention are compounds of the following Formula:

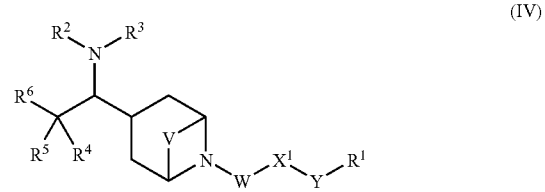

(IV)

wherein X¹ is —N(R⁹)— or hydrocarbylene (e.g. C₁₋₆ alkylene) optionally substituted with 1, 2, 3, 4 or 5 R¹¹;

or a pharmaceutically acceptable salt or prodrug thereof.

With regard to Formula (IV), Y is often —C(O), —C(O)O—, —C(O)N(R⁹)—, —S(O)—, —S(O)₂— or —S(O)$_t$N(R⁹). In particular, Y is often —C(O)—, —C(O)—, —S(O)— or —S(O)₂—.

Examples of the linker —W—X¹—Y— are described in the table below:

| No. | W | X¹ | Y |
|---|---|---|---|
| 1 | —C(O)— | —N(R⁹)— | —C(O)— |
| 2 | —C(O)— | C₁₋₆ alkylene | —C(O)— |
| 3 | —C(O)— | —N(R⁹)— | —S(O)₂— |
| 4 | —C(O)— | C₁₋₆ alkylene | —S(O)₂— |
| 5 | —S(O)₁— | —N(R⁹)— | —C(O)— |
| 6 | —S(O)₁— | C₁₋₆ alkylene | —C(O)— |
| 7 | —S(O)₁— | C₁₋₆ alkylene | —S(O)₂— |

Further examples of the linker —W—X$^1$—Y— are described in the table below:

| No. | W | X$^1$ | Y |
|---|---|---|---|
| 1 | —C(O)— | C$_{1-6}$ alkylene | —S(O)$_2$— |
| 2 | —S(O)$_1$— | C$_{1-6}$ alkylene | —C(O)— |

Further examples of the linker —W—X$^1$—Y— are described in the table below:

| No. | W | X$^1$ | Y |
|---|---|---|---|
| 1 | —C(O)— | C$_{1-6}$ alkylene | —C(O)—N(R$^9$)— |
| 2 | —C(O)— | —CH$_2$— | —C(O)—NH— |
| 3 | —C(O)— | 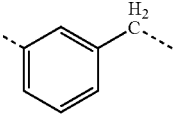 | —C(O)— |
| 4 | —C(O)— | 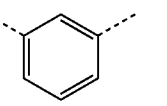 | —C(O)— |
| 5 | —C(O)— | 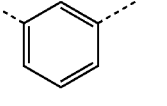 | —N(R$^9$)— |
| 6 | —C(O)— | 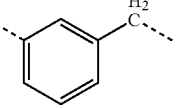 | —N(R$^9$)— |
| 7 | —C(O)— | arylene | —C(O)— |
| 8 | —C(O)— | C$_{1-6}$ alkylene | —C(O)— |
| 9 | —C(O)— | arylene | —N(R$^9$)— |
| 10 | —C(O)— | —CH$_2$— | —C(O)— |
| 11 | —C(O)— | —CH(CH$_3$)— | —C(O)— |
| 12 | —C(O)— | —C(CH$_3$)$_2$— | —C(O)— |
| 13 | —C(O)— | —CH$_2$CH$_2$— | —C(O)— |

In one embodiment in the above compounds wherein Y is —N(R$^9$)—, R$^1$ and R$^9$ taken together form a 5- or 6-membered heterocyclyl optionally substituted by 1, 2, 3, 4 or 5 R$^{11}$. The formed 5- or 6-membered heterocyclyl is for instance 1-methyl-imidazolidine-2,4-dione, imidazolidine-2,4-dione, thiazoldine-2,4-dione, pyrrolidine-2,5-dione, isoindole-1,3-dione, or pyrrolidinyl-2-oxo.

Further examples of the linker —W—X$^1$—Y— are described in the table below:

| No. | W | X$^1$ | Y |
|---|---|---|---|
| 1 | —C(O)— | —CH$_2$— | —S(O)$_2$— |
| 2 | —C(O)— | —CH(CH$_3$)— | —S(O)$_2$— |
| 3 | —C(O)— | —C(CH$_3$)$_2$— | —S(O)$_2$— |
| 4 | —C(O)— | —CH$_2$CH$_2$— | —S(O)$_2$— |
| 5 | —S(O)$_2$— | —CH$_2$— | —C(O)— |
| 6 | —S(O)$_2$— | —CH(CH$_3$)— | —C(O)— |
| 7 | —S(O)$_2$— | —C(CH$_3$)$_2$— | —C(O)— |
| 8 | —S(O)$_2$— | —CH$_2$CH$_2$— | —C(O)— |

Further examples of the linker —W—X$^1$—Y— are described in the table below:

| No. | W | X$^1$ | Y |
|---|---|---|---|
| 1 | —C(O)— | C$_{1-6}$ alkylene | —C(O)— |
| 2 | —S(O)$_1$— | C$_{1-6}$ alkylene | —S(O)$_2$— |

Further examples of the linker —W—X$^1$—Y— are described in the table below:

| No. | W | X$^1$ | Y |
|---|---|---|---|
| 1 | —C(O)— | —CH$_2$— | —C(O)— |
| 2 | —C(O)— | —CH(CH$_3$)— | —C(O)— |
| 3 | —C(O)— | —C(CH$_3$)$_2$— | —C(O)— |
| 4 | —C(O)— | —CH$_2$CH$_2$— | —C(O)— |

Also of particular mention are compounds of the above Formula wherein X$^1$ is carbocyclylene (e.g. cycloalkylene or arylene) optionally substituted with 1, 2, 3, 4 or 5 R$^{11}$; or a pharmaceutically acceptable salt or prodrug thereof.

Further examples of the linker —W—X$^1$—Y— are described in the table below:

| No. | W | X$^1$ | Y |
|---|---|---|---|
| 1 | —C(O)— | cycloalkylene | —S(O)$_2$— |
| 2 | —S(O)$_1$— | cycloalkylene | —C(O)— |
| 3 | —C(O)— | cycloalkylene | —C(O)— |
| 4 | —S(O)$_1$— | cycloalkylene | —S(O)$_2$— |

Further examples of the linker —W—X$^1$—Y— are described in the table below:

| No. | W | X$^1$ | Y |
|---|---|---|---|
| 1 | —C(O)— | cyclopropylene | —S(O)$_2$— |
| 2 | —S(O)$_1$— | cyclopropylene | —C(O)— |
| 3 | —C(O)— | cyclopropylene | —C(O)— |
| 4 | —S(O)$_1$— | cyclopropylene | —S(O)$_2$— |

Further examples of the linker —W—X$^1$—Y— are described in the table below:

| No. | W | X$^1$ | Y |
|---|---|---|---|
| 1 | —C(O)— | arylene | —S(O)$_2$— |
| 2 | —S(O)$_1$— | arylene | —C(O)— |
| 3 | —C(O)— | arylene | —C(O)— |
| 4 | —S(O)$_1$— | arylene | —S(O)$_2$— |

Further examples of the linker —W—X$^1$—Y— are described in the table below:

| No. | W | X$^1$ | Y |
|---|---|---|---|
| 1 | —C(O)— | phenylene | —S(O)$_2$— |
| 2 | —S(O)$_1$— | phenylene | —C(O)— |

| No. | W | $X^1$ | Y |
|---|---|---|---|
| 3 | —C(O)— | phenylene | —C(O)— |
| 4 | —S(O)$_1$— | phenylene | —S(O)$_2$— |

Also of mention are compounds of the following Formula:

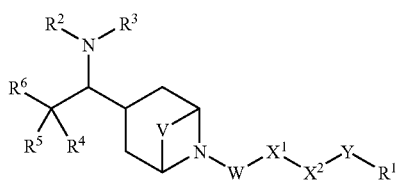

(V)

wherein one of $X^1$ and $X^2$ is —N($R^9$)—; and the other is $C_{1-6}$ alkylene optionally substituted with 1, 2, 3, 4 or 5 $R^{11}$;

or a pharmaceutically acceptable salt or prodrug thereof.

With regard to Formula (V), Y is often —C(O)—, —C(O)O—, —C(O)N($R^9$)—, —S(O)—, —S(O)$_2$— or —S(O)$_t$N($R^9$). In particular, Y is often —C(O)—, —C(O)—, —S(O)— or —S(O)$_2$—

Examples of the linker —W—$X^1$—$X^2$—Y— are described in the table below:

| No. | W | $X^1$ | $X^2$ | Y |
|---|---|---|---|---|
| 1 | —C(O)— | $C_{1-6}$ alkylene | —O— | —C(O)— |
| 2 | —C(O)— | $C_{1-6}$ alkylene | —N($R^9$)— | —C(O)— |
| 3 | —C(O)— | —O— | $C_{1-6}$ alkylene | —C(O)— |
| 4 | —C(O)— | —N($R^9$)— | $C_{1-6}$ alkylene | —C(O)— |
| 5 | —C(O)— | $C_{1-6}$ alkylene | —N($R^9$)— | —S(O)$_2$— |
| 6 | —C(O)— | —O— | $C_{1-6}$ alkylene | —S(O)$_2$— |
| 7 | —C(O)— | —N($R^9$)— | $C_{1-6}$ alkylene | —S(O)$_2$— |
| 8 | —S(O)$_1$— | $C_{1-6}$ alkylene | —O— | —C(O)— |
| 9 | —S(O)$_1$— | $C_{1-6}$ alkylene | —N($R^9$)— | —C(O)— |
| 10 | —S(O)$_1$— | —N($R^9$)— | $C_{1-6}$ alkylene | —C(O)— |
| 11 | —S(O)$_1$— | $C_{1-6}$ alkylene | —N($R^9$)— | —S(O)$_2$— |
| 12 | —S(O)$_1$— | —N($R^9$)— | $C_{1-6}$ alkylene | —S(O)$_2$— |

Examples of the linker —W—$X^1$—$X^2$—Y— are described in the table below:

| No. | W | $X^1$ | $X^2$ | Y |
|---|---|---|---|---|
| 1 | —S(O)$_t$— | $C_{1-6}$ alkylene | —N($R^9$)— | —C(O)—O— |
| 2 | —S(O)$_t$— | —CH$_2$CH$_2$— | —N($R^9$)— | —C(O)—O— |
| 3 | —C(O)— | arylene | —N($R^9$)— | —C(O)— |
| 4 | —C(O)— | *m-phenylene* | —N($R^9$)— | —C(O)— |
| 5 | —C(O)— | *phenylene-CH$_2$* | —N($R^9$)— | —C(O)— |
| 6 | —C(O)— | *m-phenylene* | $C_{1-6}$ alkylene | —N($R^9$)— |
| 7 | —C(O)— | *m-phenylene* | —CH$_2$CH$_2$— | —N($R^9$)— |

Further examples of the linker —W—$X^1$—$X^2$—Y— are described in the table below:

| No. | W | $X^1$ | $X^2$ | Y |
|---|---|---|---|---|
| 1 | —C(O)— | $C_{1-6}$ alkylene | —N($R^9$)— | —C(O)— |
| 2 | —C(O)— | $C_{1-6}$ alkylene | —N($R^9$)— | —S(O)$_2$— |
| 3 | —S(O)$_2$— | $C_{1-6}$ alkylene | —N($R^9$)— | —C(O)— |
| 4 | —S(O)$_2$— | $C_{1-6}$ alkylene | —N($R^9$)— | —S(O)$_2$— |

Further examples of the linker —W—$X^1$—$X^2$—Y— are described in the table below:

| No. | W | $X^1$ | $X^2$ | Y |
|---|---|---|---|---|
| 1 | —C(O)— | —CH$_2$— | —N($R^9$)— | —C(O)— |
| 2 | —C(O)— | —CH$_2$— | —N($R^9$)— | —S(O)$_2$— |
| 3 | —C(O)— | —CH(CH$_3$)— | —N($R^9$)— | —C(O)— |
| 4 | —C(O)— | —CH(CH$_3$)— | —N($R^9$)— | —S(O)$_2$— |
| 5 | —C(O)— | —C(CH$_3$)$_2$— | —N($R^9$)— | —C(O)— |
| 6 | —C(O)— | —C(CH$_3$)$_2$— | —N($R^9$)— | —S(O)$_2$— |
| 7 | —C(O)— | —CH$_2$CH$_2$— | —N($R^9$)— | —C(O)— |
| 8 | —C(O)— | —CH$_2$CH$_2$— | —N($R^9$)— | —S(O)$_2$— |
| 9 | —S(O)$_2$— | —CH$_2$— | —N($R^9$)— | —C(O)— |
| 10 | —S(O)$_2$— | —CH$_2$— | —N($R^9$)— | —S(O)$_2$— |
| 11 | —S(O)$_2$— | —CH(CH$_3$)— | —N($R^9$)— | —C(O)— |
| 12 | —S(O)$_2$— | —CH(CH$_3$)— | —N($R^9$)— | —S(O)$_2$— |
| 13 | —S(O)$_2$— | —C(CH$_3$)$_2$— | —N($R^9$)— | —C(O)— |
| 14 | —S(O)$_2$— | —C(CH$_3$)$_2$— | —N($R^9$)— | —S(O)$_2$— |
| 15 | —S(O)$_2$— | —CH$_2$CH$_2$— | —N($R^9$)— | —C(O)— |
| 16 | —S(O)$_2$— | —CH$_2$CH$_2$— | —N($R^9$)— | —S(O)$_2$— |

A further example of the linker —W—$X^1$—$X^2$—Y— is described in the table below:

| No. | W | $X^1$ | $X^2$ | Y |
|---|---|---|---|---|
| 1 | —C(O)— | —CH(CH$_3$)— | —NH— | —C(O)— |

In each of the various tables above, $R^9$ is usually hydrogen or selected from $C_{1-6}$ alkyl (e.g. $C_1$, $C_2$, $C_3$ or $C_4$ alkyl), —(CH$_2$)$_k$-carbocyclyl and —(CH$_2$)$_k$-heterocyclyl, any of which is optionally substituted with 1, 2, 3, 4 or 5 $R^{11}$. In particular, —N($R^9$)— may be —NH— or —N(CH$_3$)—.

Where $C_{1-6}$ alkylene (e.g. —CH$_2$—, —CH(CH$_3$)—, —C(CH$_3$)$_2$— or —CH$_2$CH$_2$—), cycloalkylene (e.g. cyclopropylene) or arylene (e.g. phenylene) are mentioned in the various tables, they may be substituted with 1, 2, 3, 4 or 5 $R^{11}$, more usually being unsubstituted or substituted by 1 or 2 substituents selected from hydroxy, amino, halogen (e.g. fluorine or chlorine), $C_{1-4}$ alkyl (e.g. $C_1$, $C_2$, $C_3$ or $C_4$ alkyl) optionally substituted with 1, 2, 3, 4 or 5 $R^{12}$, and arylene (e.g. phenylene) optionally substituted with 1, 2, 3, 4 or 5 $R^{12}$, where $R^{12}$ is, for example, —C(O)NH$_2$. Also, where $C_{1-6}$ alkylene is mentioned, it may be exchanged for $C_{3-6}$ carbocyclylene (e.g. cyclopropylene). Where cyclopropylene is mentioned, it may be regarded as having 1 or 2 in-chain atoms, typically 1 in-chain atom.

$R^1$ $R^1$ is selected from hydrogen; —N($R^9$)($R^{10}$); hydrocarbyl optionally substituted with 1, 2, 3, 4 or 5 $R^{11}$; hydrocarbyloxy optionally substituted with 1, 2, 3, 4 or 5 $R^{11}$; and —(CH$_2$)$_k$-heterocyclyl optionally substituted with 1, 2, 3, 4 or 5 $R^{11}$. Alternatively, when Y is —N($R^9$)—, $R^1$ and $R^9$ taken together with the nitrogen atom to which they are attached form a heterocycle, wherein said heterocycle is bound to X via said nitrogen atom and is optionally substituted with 1, 2, 3, 4 or 5 $R^{11}$.

In one embodiment of the invention, $R^1$ is —N($R^9$)($R^{10}$). In this case, $R^9$ and $R^{10}$ are usually each independently hydrogen or selected from $C_{1-4}$ alkyl (e.g. $C_1$, $C_2$, $C_3$ or $C_4$ alkyl), —(CH$_2$)$_k$-carbocyclyl (e.g. —(CH$_2$)$_k$-cycloalkyl or —(CH$_2$)-aryl) and (CH$_2$-heterocyclyl, any of which is optionally substituted with 1, 2, 3, 4 or 5 $R^{11}$. For example, $R^9$ and $R^{10}$ may be each independently hydrogen or $C_{1-4}$ alkyl (e.g methyl or ethyl) optionally substituted with 1, 2, 3, 4 or 5 $R^{11}$. Of mention are compounds in which at least one of $R^9$ and $R^{10}$ is $C_{1-6}$ alkyl group substituted with $C_{1-4}$ alkoxy. In particular, —N($R^9$)($R^{10}$) may be amino, methylamino, dimethylamino or (methoxymethyl)methylamino.

In another embodiment of the invention, $R^1$ is hydrocarbyl optionally substituted with 1, 2, 3, 4 or 5 $R^{11}$. In this case, $R^1$ is often selected from $C_{1-6}$ alkyl (e.g. $C_1$, $C_2$, $C_3$ or $C_4$ alkyl) or —(CH$_2$)$_k$-carbocyclyl (e.g. —(CH$_2$)$_k$-cycloalkyl or —(CH$_2$)$_k$-aryl), either of which is optionally substituted with 1, 2, 3, 4 or 5 $R^{11}$. In particular, $R^1$ may be $C_{1-6}$ alkyl (e.g. $C_1$, $C_2$, $C_3$ or $C_4$ alkyl), —(CH$_2$)$_k$-cycloalkyl (e.g. cyclopropyl, cyclobutyl or cyclopropylmethyl) or —(CH$_2$)$_k$-aryl (e.g. phenyl or benzyl), any of which is optionally substituted with 1, 2, 3, 4 or 5 $R^{11}$. Of particular mention are methyl; methoxymethyl; cyclopropyl optionally substituted with 1 or 2 $R^{11}$; and phenyl optionally substituted with 1, 2, 3, 4 or 5 $R^{11}$.

In another embodiment of the invention, $R^1$ is hydrocarbyloxy optionally substituted with 1, 2, 3, 4 or 5 $R^{11}$. In this case, $R^1$ is often selected from $C_{1-6}$ alkyl (e.g. $C_1$, $C_2$, $C_3$ or $C_4$ alkyl) or —O—(CH$_2$)$_k$-carbocyclyl (e.g. —O—(CH$_2$)$_k$-cycloalkyl or —O—(CH$_2$)$_k$-aryl), either of which is optionally substituted with 1, 2, 3, 4 or 5 $R^{11}$. In particular, $R^1$ may be $C_{1-6}$ alkyl (e.g. $C_1$, $C_2$, $C_3$ or $C_4$ alkyloxy), —O—(CH$_2$)$_k$-cycloalkyl (e.g. cyclopropyloxy, cyclobutyloxy or cyclopropylmethyloxy) or —O—(CH$_2$)$_k$-aryl (e.g. —O-phenyl or —O-benzyl), any of which is optionally substituted with 1, 2, 3, 4 or 5 $R^{11}$. Of particular mention are methyl; methoxymethyl; cyclopropyl optionally substituted with 1 or 2 $R^{11}$; and phenyl optionally substituted with 1, 2, 3, 4 or 5 $R^{11}$.

In a further embodiment, $R^1$ is —(CH$_2$)$_k$-heterocyclyl optionally substituted with 1, 2, 3, 4 or 5 $R^{11}$. Typically, k is 0, 1 or 2, more usually 0. The heterocyclyl group may be heterocycloalkyl or heteroaryl, either of which is optionally substituted with 1, 2, 3, 4 or 5 $R^{11}$. Exemplary heterocyclyl groups include oxiranyl, azirinyl, 1,2-oxathiolanyl, imidazolyl, thienyl, furyl, tetrahydrofuryl, pyranyl, imidazolyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piridinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, 3,4-dihydro-2H-isoquinolin-1-one, 3,4-dihydro-2H-isoquinolinyl, tetrehydropyranyl, 1,3-dihydroisoindolyl, 1,3-Dioxo-1,3-dihydro-isoindolyl, 3,4-dihydro-2H-isoquinolinyl, 3,4-dihydro-2H-isoquinolinyl-1-one, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, any of which is optionally substituted with 1, 2, 3, 4 or 5 $R^{11}$. Of particular mention are imidazolyl, oxazolyl, morpholinyl, 1,4-benzodioxanyl, pyrimidyl, and pyrazinyl, any of which is optionally substituted with 1, 2, 3, 4 or 5 $R^{11}$. Also of mention are 1,3-dioxo-isoindolyl, 2-oxo-pyrrolidinyl and 2,4-dioxo-thiazolidin-3-yl, any of which is optionally substituted with 1, 2 or 3 $R^{11}$.

In compounds in which Y is —C(O)—, $R^1$ is often $C_{1-6}$ alkyl (e.g. $C_1$, $C_2$, $C_3$ or $C_4$ alkyl), cycloalkyl (e.g. cyclopropyl), aryl (e.g. phenyl) or heterocyclyl (e.g. imidazolyl, oxazolyl, morpholinyl, 1,4-benzodioxanyl or pyrazinyl), any of which is optionally substituted with 1, 2, 3, 4 or 5 $R^{11}$.

In compounds in which Y is —S(O)$_2$— or —S(O)N($R^9$)—, $R^1$ is often hydrogen, $C_{1-6}$ alkyl, cycloalkyl (e.g. cyclopropyl or cyclopropylmethyl), aryl (e.g. phenyl) or heterocyclyl (e.g. imidazolyl, oxazolyl, morpholinyl, 1,4-benzodioxanyl or pyrazinyl), any of which is optionally substituted with 1, 2, 3, 4 or 5 $R^{11}$. Alternatively, $R^1$ may often be —N($R^9$)($R^{10}$), e.g. amino, $C_{1-6}$ alkylamino or di($C_{1-6}$ alkyl)amino.

Of particular mention are compounds in which $R^1$ is morpholin-4-yl or cyclopropyl, either of which is optionally substituted with 1, 2, 3, 4 or 5 $R^{11}$.

In another embodiment, Y is —N($R^9$)—, and —N($R^9$)$R^1$ taken together form a nitrogen-containing heterocycle optionally substituted with 1, 2, 3, 4 or 5 $R^{11}$. The heterocyclyl group may be heterocycloalkyl or heteroaryl, either of which is optionally substituted with 1, 2, 3, 4 or 5 $R^{11}$. Exemplary nitrogen-containing heterocyclyl groups include azirinyl, imidazolyl, pyranyl, 2H-pyrrolyl, pyrrolyl, pyrrolinyl, pyrrolidinyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrimidinyl, piperidyl, piperazinyl, pyridazinyl, morpholinyl, thiomorpholinyl, piridinyl, indolizinyl, isoindolyl, 3H-indolyl, indolyl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, 2,3-Dihydro-benzo[1,4]dioxine, Dihydro-benzodioxine, tetrahydropyranyl, tetrahydrofuranyl, 1,3-Dioxo-1,3-dihydro-isoindolyl any of which is optionally substituted with 1, 2, 3, 4 or 5 $R^{11}$. Of mention are indolyl, isoindolyl, pyrrolidinyl and thiazolidin-3-yl, any of which is optionally substituted with 1, 2, 3, 4 or 5 $R^{11}$. Of particular mention are 1,3-dioxo-isoindolyl, 2-oxo-pyrrolidinyl and 2,4-dioxo-thiazolidin-3-yl, any of which is optionally substituted with 1, 2 or 3 $R^{11}$.

Where $R^1$ is substituted with $R^{11}$, the or each $R^{11}$ is often independently selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_i$—$C_{1-6}$ alkyl, —NH($C_{1-6}$ alkyl), and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

Where $R^1$ is substituted with $R^{11}$, the or each $R^{11}$ is often independently selected from halogen (e.g. fluorine, chlorine or bromine), hydroxy, cyano, amino, oxo, —C(O)OH, —C(O)—NH$_2$, —C(O)—NH—C$_{1-6}$ alkyl, C$_{1-6}$ alkyl, C$_{1-6}$ alkoxy (e.g. C$_1$, C$_2$, C$_3$ or C$_4$ alkoxy), —O-aryl (e.g. —O-phenyl), —(CH$_2$)$_k$-phenyl, —(CH$_2$)$_k$-heterocycyl, —(CH$_2$)$_k$-cycloalkyl, —C(O)-heterocycyl, —C(O)—C$_{1-6}$ alkyl, —C(O)O—C$_{1-6}$ alkyl, —S(O)$_j$—C$_{1-6}$ alkyl, —NH(C$_{1-6}$ alkyl), —NH—C(O)—(C$_{1-6}$ alkyl), 6- or 5-membered cycloaryl, a spiro group (e.g. via a cyclopropyl) and —N(C$_{1-6}$ alkyl)$_2$, wherein any C$_{1-6}$ alkyl group present is optionally substituted with 1, 2, 3, 4 or 5 substituents independently selected from halogen, cyano, amino, hydroxy and C$_{1-6}$ alkoxy.

$R^2$ & $R^3$ $R^2$ and $R^3$ are each independently selected from $R^8$, —OR$^8$, —C(O)R$^8$, —C(O)OR$^8$ and —S(O)$_j$R$^9$.

In one embodiment of the invention, $R^2$ and $R^3$ are each independently hydrogen; hydroxy; or selected from C$_{1-6}$ alkyl, 6 alkoxy, —(CH$_2$)-cycloalkyl, —(CH$_2$)$_k$-heterocycloalkyl, —(CH$_2$)$_k$-aryl and —(CH$_2$)$_k$-heteroaryl, any of which is optionally substituted with 1, 2, 3, 4, 5 or 6 $R^{11}$.

In another embodiment, $R^2$ is hydrogen; and $R^3$ is hydrogen, hydroxy, C$_{1-4}$ alkyl, C$_{1-6}$ alkoxy, —(CH$_2$)$_k$-cycloalkyl or —(CH$_2$)$_k$-aryl, any of which alkyl, alkoxy, cycloalkyl and aryl groups is optionally substituted with 1, 2, 3, 4 or 5 $R^{11}$, wherein the or each $R^{11}$ is, for example, hydroxy, halogen (for example, chlorine or fluorine); C$_1$, C$_2$, C$_3$ or C$_4$ alkyl, for example methyl, ethyl, propyl, isopropyl, n-butyl, sec-butyl or tert-butyl, any of which is optionally substituted with 1, 2, 3 or 4 halogen (e.g. fluorine or chlorine) atoms, an example being trifluoromethyl; C$_1$, C$_2$, C$_3$ or C$_4$ alkoxy, for example methoxy, ethoxy, propoxy, isopropoxy, butoxy or tert-butoxy, any of which is optionally substituted with 1, 2, 3 or 4 halogen (e.g. fluorine or chlorine) atoms, and in particular $R^3$ is hydrogen, methyl, cyclopropylmethyl or benzyl.

In a further embodiment, $R^2$ and $R^3$ are each hydrogen.

$R^4$ & $R^5$ $R^4$ and $R^5$ are each independently selected from hydrogen, hydroxy, halogen and C$_{1-6}$ alkyl optionally substituted with 1, 2, 3, 4 or 5 $R^{11}$.

In one embodiment, $R^4$ and $R^5$ are each independently hydrogen, hydroxy, halogen (for example, chlorine or fluorine); or C$_1$, C$_2$, C$_3$ or C$_4$ alkyl, for example methyl, ethyl, propyl, isopropyl, n-butyl, sec-butyl or tert-butyl, any of which is optionally substituted with 1, 2, 3 or 4 halogen (e.g. fluorine or chlorine) atoms, an example being trifluoromethyl.

In another embodiment, $R^4$ is hydrogen, hydroxy, halogen (for example, chlorine or fluorine); or C$_1$, C$_2$, C$_3$ or C$_4$ alkyl, for example methyl, ethyl, propyl, isopropyl, n-butyl, sec-butyl or tert-butyl, any of which is optionally substituted with 1, 2, 3 or 4 halogen (e.g. fluorine or chlorine) atoms, an example being trifluoromethyl; and $R^5$ is typically hydrogen.

In a further embodiment, $R^4$ is hydrogen, hydroxy, fluorine, chlorine or C$_1$, C$_2$, C$_3$ or C$_4$ alkyl; and $R^5$ is hydrogen.

In a further embodiment, $R^4$ is hydrogen, hydroxy, fluorine, chlorine or methyl; and $R^5$ is hydrogen.

In a further embodiment, $R^4$ and $R^5$ are each hydrogen.

$R^6$ $R^6$ is aryl or heteroaryl, either of which is optionally substituted with 1, 2, 3, 4 or 5 $R^{11}$.

In one embodiment of the invention, $R^6$ is aryl, in particular phenyl or naphthyl, either of which is optionally substituted with 1, 2, 3, 4 or 5 $R^{11}$. In embodiments, $R^6$ is phenyl optionally substituted with 1, 2, 3, 4 or 5 $R^{11}$, wherein the or each $R^{11}$ is, for example, hydroxy, halogen (for example, chlorine or fluorine); C$_1$, C$_2$, C$_3$ or C$_4$ alkyl, for example methyl, ethyl, propyl, isopropyl, n-butyl, sec-butyl or tert-butyl, any of which is optionally substituted with 1, 2, 3 or 4 halogen (e.g. fluorine or chlorine) atoms, an example being trifluoromethyl; or C$_1$, C$_2$, C$_3$ or C$_4$ alkoxy, for example methoxy, ethoxy, propoxy, isopropoxy, butoxy, tert-butoxy, any of which is optionally substituted with 1, 2, 3 or 4 halogen (e.g. fluorine or chlorine) atoms. For example, $R^6$ may be phenyl optionally substituted with 1, 2, 3, 4 or 5 halogen (e.g. fluorine) atoms.

In a further embodiment, $R^6$ is a group selected from:

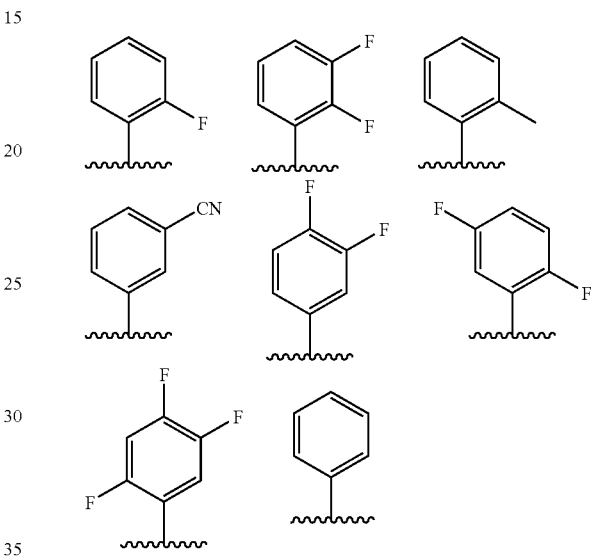

In a further embodiment, $R^6$ is 2,4,5-trifluorophenyl.

In another embodiment, $R^6$ is heteroaryl (often monocyclic), for example, thienyl or benzothiophenyl, and is optionally substituted with 1, 2, 3, 4 or 5 $R^{11}$, wherein the or each $R^{11}$ is, for example, hydroxy, halogen (for example, chlorine or fluorine); C$_1$, C$_2$, C$_3$ or C$_4$ alkyl, for example methyl, ethyl, propyl, isopropyl, n-butyl, sec-butyl or tert-butyl, any of which is optionally substituted with 1, 2, 3 or 4 halogen (e.g. fluorine or chlorine) atoms, an example being trifluoromethyl; or C$_1$, C$_2$, C$_3$ or C$_4$ alkoxy, for example methoxy, ethoxy, propoxy, isopropoxy, butoxy, tert-butoxy, any of which is optionally substituted with 1, 2, 3 or 4 halogen (e.g. fluorine or chlorine) atoms.

$R^{11}$

Each $R^{11}$ is independently selected from $R^{12}$; hydrocarbyl (e.g. C$_{1-6}$ alkyl or —(CH$_2$)$_k$-aryl) optionally substituted with 1, 2, 3, 4 or 5 $R^{12}$; and —(CH$_2$)$_k$-heterocyclyl optionally substituted with 1, 2, 3, 4 or 5 $R^{12}$; wherein $R^{12}$ is independently selected from halogen, trifluoromethyl, cyano, nitro, oxo, =NR$^{13}$, —OR$^{13}$, —C(O)R$^{13}$, —C(O)N(R$^{13}$)R$^{14}$, —C(O)OR$^{13}$, —OC(O)R$^{13}$, —S(O)$_j$R$^{13}$, —S(O)$_j$N(R$^{13}$)R$^{14}$—N(R$^{13}$)R$^4$, —N(R$^{13}$)N(R$^{13}$)R$^{14}$, —N(R$^{13}$)C(O)R$^{14}$ and —N(R$^{13}$)S(O)$_j$R$^{13}$; and $R^{13}$ and $R^{14}$ are each independently hydrogen or selected from hydrocarbyl (e.g. C$_{1-6}$ alkyl or —(CH$_2$)$_k$-aryl, or —(CH$_2$)$_k$-cycloalkyl) and —(CH$_2$)$_k$-heterocyclyl, either of which is optionally substituted with 1, 2, 3, 4 or 5 substituents independently selected from halogen, cyano, amino, hydroxy, C$_{1-6}$ alkyl and C$_{1-6}$ alkoxy, or selected from oxo, halogen, cyano, amino, hydroxy, C$_{1-6}$ alkyl and C$_{1-6}$ alkoxy.

Typically, each $R^{11}$ is independently selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_1$— alkyl, —S(O)$_f$—$C_{1-6}$alkyl-NH($C_{1-6}$ alkyl) and —N($C_{1-6}$ alkyl)$_2$, wherein any $C_{1-6}$ alkyl group present is optionally substituted with 1, 2, 3, 4 or 5 substituents independently selected from halogen, cyano, amino, hydroxy and $C_{1-6}$ alkoxy.

Typically, each $R^{11}$ is independently selected from halogen (e.g. fluorine, chlorine or bromine), hydroxy, cyano, amino, —C(O)OH, $C_{1-6}$ alkyl, $C_{1-6}$ alkoxy (e.g. $C_1$, $C_2$, $C_3$ or $C_4$ alkoxy), —C(O)—$C_{1-6}$ alkyl, —C(O)O—$C_{1-6}$ alkyl, —S(O)$_f$—$C_{1-6}$ alkyl, —(CH$_2$)$_k$-cycloalkyl, —(CH$_2$)$_k$-aryl, —(CH$_2$)$_k$-heterocyclyl, —NH—(CH$_2$)$_k$-aryl, —NH—(CH$_2$)$_k$-cycloalkyl, —NH—C(O)—(CH$_2$)$_k$-aryl, —NH—C(O)—(CH$_2$)$_k$-cycloalkyl, —N($C_{1-6}$ alkyl)-(CH$_2$)$_k$-aryl, —N($C_{1-6}$ alkyl)(CH$_2$)$_k$-cycloalkyl, —NH($C_{1-6}$ alkyl) and —N($C_{1-6}$ alkyl)$_2$, wherein any $C_{1-6}$ alkyl group or aryryl or present is optionally substituted with 1, 2, 3, 4 or 5 substituents independently selected from halogen, cyano, amino, hydroxy and $C_{1-6}$ alkoxy.

For the avoidance of doubt, where a group is substituted with more than one $R^{11}$, each $R^{11}$ is independently selected from the range of substituents specified. The same applies to compounds of the invention comprising more than one $R^{11}$ substituent; each $R^{11}$ is selected independently of any other $R^{11}$ substituent present in the compound. As previously indicated, where $R^{11}$ is halo, particularly fluoro, any number of hydrogens may in principle be replaced.

A particular embodiment of the invention is a compound of the following Formula:

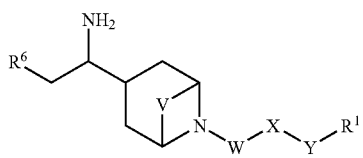

(VI)

or a pharmaceutically acceptable salt or prodrug thereof.

The invention therefore includes compounds of the following Formulae:

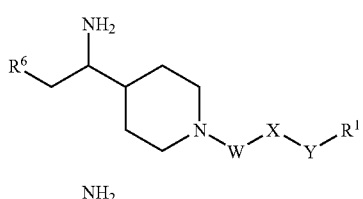

(VII)

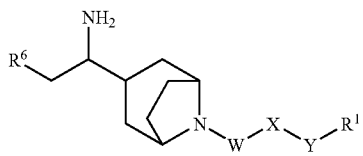

(VIII)

or, in each case, a pharmaceutically acceptable salt or prodrug thereof.

Another embodiment of the invention is a compound of the following Formula:

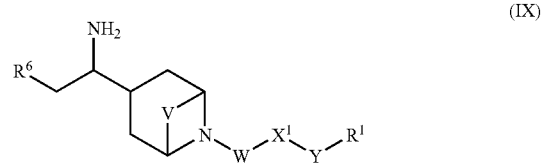

(IX)

wherein $X^1$ is selected from —O—, —C(O)—, —S(O)$_f$—, —N($R^9$)— and hydrocarbylene (e.g. $C_{1-6}$ alkylene) optionally substituted with 1, 2, 3, 4 or 5 $R^{11}$;

or a pharmaceutically acceptable salt or prodrug thereof.

The invention therefore includes compounds of the following Formulae:

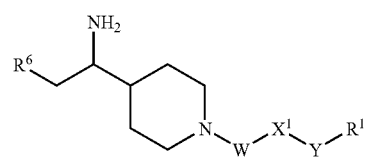

(X)

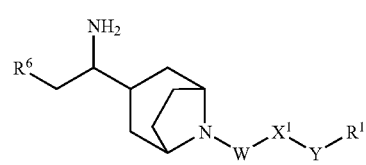

(XI)

or, in each case, a pharmaceutically acceptable salt or prodrug thereof.

A further embodiment of the invention is a compound of the following Formula:

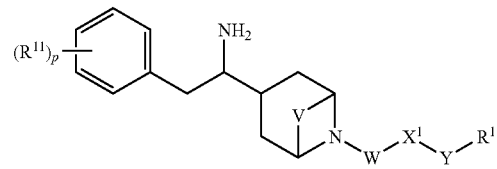

(XII)

wherein p is 0, 1, 2, 3, 4 or 5 or p is 0, 1, 2 or 3;

or a pharmaceutically acceptable salt or prodrug thereof.

The invention therefore includes compounds of the following Formulae:

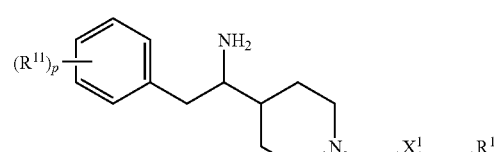

(XIII)

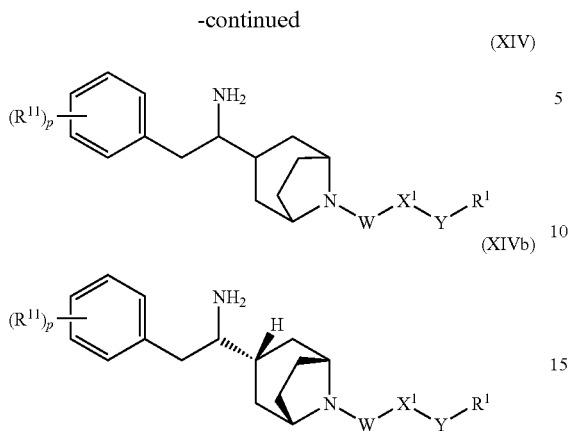

(XIV)

(XIVb)

or, in each case, a pharmaceutically acceptable salt or prodrug thereof.

With regard to Formulae (IX) to (XIV) and (XIVb), $X^1$ may be defined as in Formula (IV), i.e. $X^1$ is —N($R^9$)— or hydrocarbylene (e.g. $C_{1-6}$ alkylene) optionally substituted with 1, 2, 3, 4 or 5 $R^{11}$. Y is often —C(O), —C(O)O—, —C(O)N($R^9$)—, —S(O)—, —S(O)$_2$— or —S(O)$_i$N($R^9$). In particular, Y is often —C(O)—, —C(O)—, —S(O)— or —S(O)$_2$—.

Of particular mention are compounds of any of Formulae (IX) to (XIV) and (XIVb) in which —W—$X^1$—Y— is one of the following linkers:

| No. | W | $X^1$ | Y |
|---|---|---|---|
| 1 | —C(O)— | —N($R^9$)— | —C(O)— |
| 2 | —C(O)— | $C_{1-6}$ alkylene | —C(O)— |
| 3 | —C(O)— | —N($R^9$)— | —S(O)$_2$— |
| 4 | —C(O)— | $C_{1-6}$ alkylene | —S(O)$_2$— |
| 5 | —S(O)$_1$— | —N($R^9$)— | —C(O)— |
| 6 | —S(O)$_1$— | $C_{1-6}$ alkylene | —C(O)— |
| 7 | —S(O)$_1$— | $C_{1-6}$ alkylene | —S(O)$_2$— |

Also of mention are compounds of any of said Formulae in which —W—$X^1$—Y— is one of the following linkers:

| No. | W | $X^1$ | Y |
|---|---|---|---|
| 1 | —C(O)— | $C_{1-6}$ alkylene | —S(O)$_2$— |
| 2 | —S(O)$_1$— | $C_{1-6}$ alkylene | —C(O)— |

Also of mention are compounds of any of said Formulae in which —W—$X^1$—Y— is one of the following linkers:

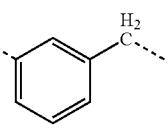

| No. | W | $X^1$ | Y |
|---|---|---|---|
| 1 | —C(O)— | $C_{1-6}$ alkylene | —C(O)—N($R^9$)— |
| 2 | —C(O)— | —CH$_2$— | —C(O)—NH— |
| 3 | —C(O)— | (m-phenylene-CH$_2$) | —C(O)— |
| 4 | —C(O)— | (m-phenylene) | —C(O)— |
| 5 | —C(O)— | (m-phenylene) | —N($R^9$)— |
| 6 | —C(O)— | (m-phenylene-CH$_2$) | —N($R^9$)— |
| 7 | —C(O)— | arylene | —C(O)— |
| 8 | —C(O)— | $C_{1-6}$ alkylene | —C(O)— |
| 9 | —C(O)— | arylene | —N($R^9$)— |
| 10 | —C(O)— | —CH$_2$— | —C(O)— |
| 11 | —C(O)— | —CH(CH$_3$)— | —C(O)— |
| 12 | —C(O)— | —C(CH$_3$)$_2$— | —C(O)— |
| 13 | —C(O)— | —CH$_2$CH$_2$— | —C(O)— |

In one embodiment in the above compounds wherein Y is —N($R^9$)—, $R^1$ and $R^9$ taken together form a 5- or 6-membered heterocyclyl optionally substituted by 1, 2, 3, 4 or 5 $R^{11}$. The formed 5- or 6-membered heterocyclyl is for instance 1-methyl-imidazolidine-2,4-dione, imidazolidine-2,4-dione, thiazoldine-2,4-dione, pyrrolidine-2,5-dione, isoindole-1,3-dione, or pyrrolidinyl-2-oxo.

Also of mention are compounds of any of said Formulae in which —W—$X^1$—Y— is one of the following linkers:

| No. | W | $X^1$ | Y |
|---|---|---|---|
| 1 | —C(O)— | —CH$_2$— | —S(O)$_2$— |
| 2 | —C(O)— | —CH(CH$_3$)— | —S(O)$_2$— |
| 3 | —C(O)— | —C(CH$_3$)$_2$— | —S(O)$_2$— |
| 4 | —C(O)— | —CH$_2$CH$_2$— | —S(O)$_2$— |
| 5 | —S(O)$_2$— | —CH$_2$— | —C(O)— |
| 6 | —S(O)$_2$— | —CH(CH$_3$)— | —C(O)— |
| 7 | —S(O)$_2$— | —C(CH$_3$)$_2$— | —C(O)— |
| 8 | —S(O)$_2$— | —CH$_2$CH$_2$— | —C(O)— |

In the case of the table directly above, $R^1$ is often a 6-membered heterocyclyl which may be unsubstituted or substituted with 1, 2, 3, 4 or 5 $R^{11}$. In the case of the table directly above, in particular the first row thereof, $R^1$ is often morpholinyl (e.g. morpholin-4-yl) which may be unsubstituted or substituted with 1, 2, 3, 4 or 5 $R^{11}$.

Also of mention are compounds of any of said Formulae in which —W—$X^1$—Y— is one of the following linkers:

| No. | W | $X^1$ | Y |
|---|---|---|---|
| 1 | —C(O)— | $C_{1-6}$ alkylene | —C(O)— |
| 2 | —S(O)$_1$— | $C_{1-6}$ alkylene | —S(O)$_2$— |

Also of mention are compounds of any of said Formulae in which —W—$X^1$—Y— is one of the following linkers:

| No. | W | X¹ | Y |
|---|---|---|---|
| 1 | —C(O)— | —CH₂— | —C(O)— |
| 2 | —C(O)— | —CH(CH₃)— | —C(O)— |
| 3 | —C(O)— | —C(CH₃)₂— | —C(O)— |
| 4 | —C(O)— | —CH₂CH₂— | —C(O)— |

Also of particular mention are compounds of the above Formula wherein X¹ is carbocyclylene (e.g. cycloalkylene or arylene) optionally substituted with 1, 2, 3, 4 or 5 R¹¹; or a pharmaceutically acceptable salt or prodrug thereof.

Also of mention are compounds of any of said Formulae in which —W—X¹—Y— is one of the following linkers:

| No. | W | X¹ | Y |
|---|---|---|---|
| 1 | —C(O)— | cycloalkylene | —S(O)₂— |
| 2 | —S(O)₁— | cycloalkylene | —C(O)— |
| 3 | —C(O)— | cycloalkylene | —C(O)— |
| 4 | —S(O)₁— | cycloalkylene | —S(O)₂— |

Also of mention are compounds of any of said Formulae in which —W—X¹—Y— is one of the following linkers:

| No. | W | X¹ | Y |
|---|---|---|---|
| 1 | —C(O)— | cyclopropylene | —S(O)₂— |
| 2 | —S(O)₁— | cyclopropylene | —C(O)— |
| 3 | —C(O)— | cyclopropylene | —C(O)— |
| 4 | —S(O)₁— | cyclopropylene | —S(O)₂— |

Also of mention are compounds of any of said Formulae in which —W—X¹—Y— is one of the following linkers:

| No. | W | X¹ | Y |
|---|---|---|---|
| 1 | —C(O)— | arylene | —S(O)₂— |
| 2 | —S(O)₁— | arylene | —C(O)— |
| 3 | —C(O)— | arylene | —C(O)— |
| 4 | —S(O)₁— | arylene | —S(O)₂— |

Also of mention are compounds of any of said Formulae in which —W—X¹—Y— is one of the following linkers:

| No. | W | X¹ | Y |
|---|---|---|---|
| 1 | —C(O)— | phenylene | —S(O)₂— |
| 2 | —S(O)₁— | phenylene | —C(O)— |
| 3 | —C(O)— | phenylene | —C(O)— |
| 4 | —S(O)₁— | phenylene | —S(O)₂— |

A further embodiment of the invention is a compound of the following Formula:

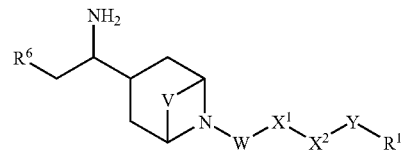

(XV)

wherein X¹ and X² are each independently selected from —O—, —C(O)—, —S(O)$_r$, —N(R⁹) and C$_{1-6}$ alkylene optionally substituted with 1, 2, 3, 4 or 5 R¹¹;

or a pharmaceutically acceptable salt or prodrug thereof.

The invention therefore includes compounds of the following Formulae:

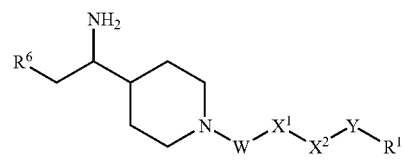

(XVI)

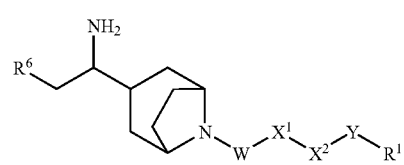

(XVII)

or, in each case, a pharmaceutically acceptable salt or prodrug thereof.

A further embodiment of the invention is a compound of the following Formula:

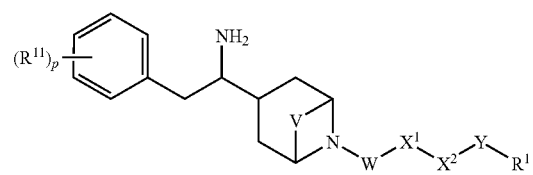

(XVIII)

wherein p is 0, 1, 2, 3, 4 or 5;

or a pharmaceutically acceptable salt or prodrug thereof.

The invention therefore includes compounds of the following Formulae:

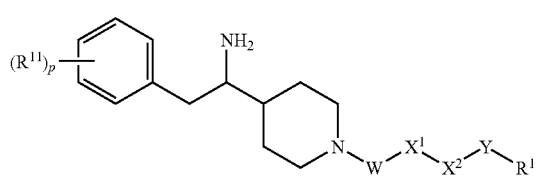

(XIX)

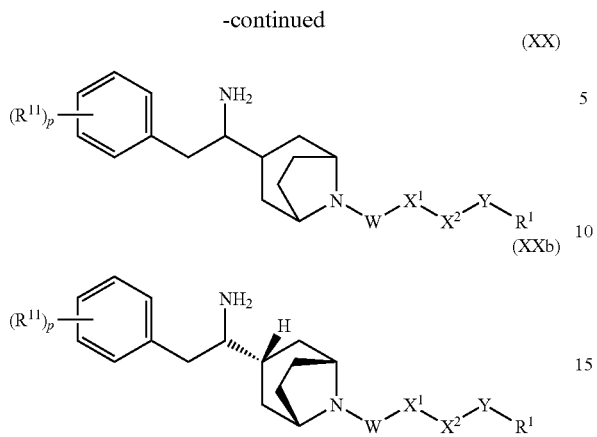

or, in each case, a pharmaceutically acceptable salt or prodrug thereof.

With regard to Formulae (XV) to (XX) or (XXb), $X^1$ and $X^2$ may be defined as in Formula (V), i.e. one of $X^1$ and $X^2$ is —N($R^9$)—; and the other is $C_{1-6}$ alkylene optionally substituted with 1, 2, 3, 4 or 5 $R^{11}$. Y is often —C(O)—, —C(O)O—, —C(O)N($R^9$), —S(O)—, —S(O)$_2$— or —S(O)$_i$N($R^9$) In particular, Y is often —C(O)—, —C(O)—, —S(O) or —S(O)$_2$—.

Of particular mention are compounds of any of Formulae (XV) to (XX) in which —W—$X^1$—$X^2$—Y— is one of the following linkers:

| No. | W | $X^1$ | $X^2$ | Y |
|---|---|---|---|---|
| 1 | —C(O)— | $C_{1-6}$ alkylene | —O— | —C(O)— |
| 2 | —C(O)— | —O— | —N($R^9$)— | —C(O)— |
| 3 | —C(O)— | $C_{1-6}$ alkylene | —N($R^9$)— | —C(O)— |
| 4 | —C(O)— | —O— | $C_{1-6}$ alkylene | —C(O)— |
| 5 | —C(O)— | —N($R^9$)— | $C_{1-6}$ alkylene | —C(O)— |
| 6 | —C(O)— | $C_{1-6}$ alkylene | —N($R^9$)— | —S(O)$_2$— |
| 7 | —C(O)— | —O— | $C_{1-6}$ alkylene | —S(O)$_2$— |
| 8 | —C(O)— | —N($R^9$)— | $C_{1-6}$ alkylene | —S(O)$_2$— |
| 9 | —S(O)$_i$— | $C_{1-6}$ alkylene | —O— | —C(O)— |
| 10 | —S(O)$_i$— | $C_{1-6}$ alkylene | —N($R^9$)— | —C(O)— |
| 11 | —S(O)$_i$— | —N($R^9$)— | $C_{1-6}$ alkylene | —C(O)— |
| 12 | —S(O)$_i$— | $C_{1-6}$ alkylene | —N($R^9$)— | —S(O)$_2$— |
| 13 | —S(O)$_i$— | —N($R^9$)— | $C_{1-6}$ alkylene | —S(O)$_2$— |

Also of mention are compounds of any of said Formulae in which —W—$X^1$—$X^2$—Y— is one of the following linkers:

| 1 | —S(O)$_i$— | $C_{1-6}$ alkylene | —N($R^9$)— | —C(O)—O— |
| 2 | —S(O)$_i$— | —CH$_2$CH$_2$— | —N($R^9$)— | —C(O)—O— |
| 3 | —C(O)— | arylene | —N($R^9$)— | —C(O)— |
| 4 | —C(O)— | (m-phenylene) | —N($R^9$)— | —C(O)— |
| 5 | —C(O)— | (m-C$_6$H$_4$-CH$_2$) | —N($R^9$)— | —C(O)— |
| 6 | —C(O)— | (m-phenylene) | $C_{1-6}$ alkylene | —N($R^9$)— |
| 7 | —C(O)— | (m-phenylene) | —CH$_2$CH$_2$— | —N($R^9$)— |

Also of mention are compounds of any of said Formulae in which —W—$X^1$—$X^2$—Y— is one of the following linkers:

| No. | W | $X^1$ | $X^2$ | Y |
|---|---|---|---|---|
| 1 | —C(O)— | $C_{1-6}$ alkylene | —N($R^9$)— | —C(O)— |
| 2 | —C(O)— | $C_{1-6}$ alkylene | —N($R^9$)— | —S(O)$_2$— |
| 3 | —S(O)$_2$— | $C_{1-6}$ alkylene | —N($R^9$)— | —C(O)— |
| 4 | —S(O)$_2$— | $C_{1-6}$ alkylene | —N($R^9$)— | —S(O)$_2$— |

Also of mention are compounds of any of said Formulae in which —W—$X^1$—$X^2$—Y— is one of the following linkers:

| No. | W | $X^1$ | $X^2$ | Y |
|---|---|---|---|---|
| 1 | —C(O)— | —CH$_2$— | —N($R^9$)— | —C(O)— |
| 2 | —C(O)— | —CH$_2$— | —N($R^9$)— | —S(O)$_2$— |
| 3 | —C(O)— | —CH(CH$_3$)— | —N($R^9$)— | —C(O)— |
| 4 | —C(O)— | —CH(CH$_3$)— | —N($R^9$)— | —S(O)$_2$— |
| 5 | —C(O)— | —C(CH$_3$)$_2$— | —N($R^9$)— | —C(O)— |
| 6 | —C(O)— | —C(CH$_3$)$_2$— | —N($R^9$)— | —S(O)$_2$— |
| 7 | —C(O)— | —CH$_2$CH$_2$— | —N($R^9$)— | —C(O)— |
| 8 | —C(O)— | —CH$_2$CH$_2$— | —N($R^9$)— | —S(O)$_2$— |
| 9 | —S(O)$_2$— | —CH$_2$— | —N($R^9$)— | —C(O)— |
| 10 | —S(O)$_2$— | —CH$_2$— | —N($R^9$)— | —S(O)$_2$— |
| 11 | —S(O)$_2$— | —CH(CH$_3$)— | —N($R^9$)— | —C(O)— |
| 12 | —S(O)$_2$— | —CH(CH$_3$)— | —N($R^9$)— | —S(O)$_2$— |
| 13 | —S(O)$_2$— | —C(CH$_3$)$_2$— | —N($R^9$)— | —C(O)— |
| 14 | —S(O)$_2$— | —C(CH$_3$)$_2$— | —N($R^9$)— | —S(O)$_2$— |
| 15 | —S(O)$_2$— | —CH$_2$CH$_2$— | —N($R^9$)— | —C(O)— |
| 16 | —S(O)$_2$— | —CH$_2$CH$_2$— | —N($R^9$)— | —S(O)$_2$— |

A further example of the linker —W—$X^1$—$X^2$—Y— is described in the table below:

| No. | W | $X^1$ | $X^2$ | Y |
|---|---|---|---|---|
| 1 | —C(O)— | —CH(CH$_3$)— | —NH— | —C(O)— |

In the case of the linker described in the table directly above, $R^1$ is especially cycloalkyl (e.g. cyclopropyl) and may be unsubstituted or substituted with 1, 2, 3, 4 or 5 $R^{11}$.

In each of the various tables above, $R^9$ is usually hydrogen or selected from Con alkyl (e.g. $C_1$, $C_2$, $C_3$ or $C_4$ alkyl), —(CH$_2$)carbocyclyl and —(CH$_2$)$_k$-heterocyclyl, any of which is optionally substituted with 1, 2, 3, 4 or 5 $R^{11}$. In particular, —N($R^9$)— may be —NH— or —N(CH$_3$)—.

Where $C_{1-6}$ alkylene (e.g. —CH$_2$—, —CH(CH$_3$)—, —C(CH$_3$)$_2$— or —CH$_2$CH$_2$—), cycloalkylene (e.g. cyclopropylene) or arylene (e.g. phenylene) are mentioned in the various tables, they may be substituted with 1, 2, 3, 4 or 5 $R^{11}$, more usually being unsubstituted or substituted by 1 or 2 substituents selected from hydroxy, amino, halogen (e.g. fluorine or chlorine), $C_{1-6}$ alkyl (e.g. $C_1$, $C_2$, $C_3$ or $C_4$ alkyl) optionally substituted with 1, 2, 3, 4 or 5 $R^{12}$, and arylene (e.g. phenylene) optionally substituted with 1, 2, 3, 4 or 5 $R^2$, where $R^{12}$ is, for example, —C(O)NH$_2$. Also, where $C_{1-6}$ alkylene is mentioned, it may be exchanged for $C_{3-6}$ carbocyclylene (e.g. cyclopropylene). Where cyclopropylene is mentioned, it may be regarded as having 1 or 2 in-chain atoms, typically 1 in-chain atom.

In one embodiment are the hereinabove described compounds wherein $X^1$ or $X^2$ is an alkylene or arylene and wherein $X^1$ or $X^2$ are is substituted by 1, 2, 3, 4 or 5 $R^{11}$, preferably 1 or 2 $R^{11}$. Preferably the $R^{11}$ substituents are independently selected from a spiro group, $C_{1-6}$ alky, —O—$C_{1-6}$ alky, —NH—C(O)—($C_{1-6}$ alky), phenyl, benzyl, hydroxy, halogen, amino, wherein the alkyl group is optionally substituted by amino, hydroxy, —C(O)N($C_{1-6}$ alky)($C_{1-4}$ alky), —C(O)—NH($C_{1-6}$ alky), —C(O)NH$_2$, ($C_{1-6}$ alky), or halogen.

In one embodiment in the above compounds wherein Y is —N($R^9$)—, $R^1$ and $R^9$ taken together form a 5- or 6-membered heterocyclyl optionally substituted by 1, 2, 3, 4 or 5 $R^{11}$. The formed 5- or 6-membered heterocyclyl is for instance 1-methyl-imidazolidine-2,4-dione, imidazolidine-2,4-dione, thiazoldine-2,4-dione, pyrrolidine-2,5-dione or pyrrolidinyl-2-oxo.

Examples of compounds of the invention include those shown below. It will of course be appreciated that, where appropriate, each compound may be in the form of the free compound, an acid or base addition salt, or a prodrug. Where a nitrogen atom forming only two bonds is shown, this generally represents NH.

B1

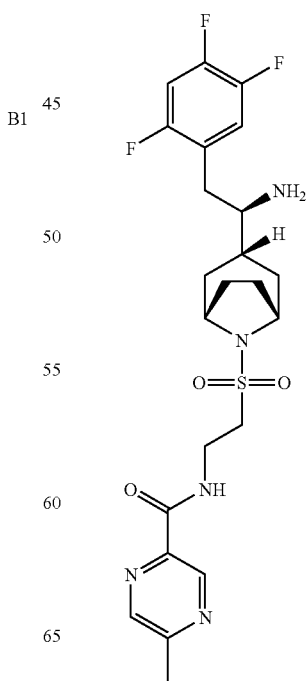

C1

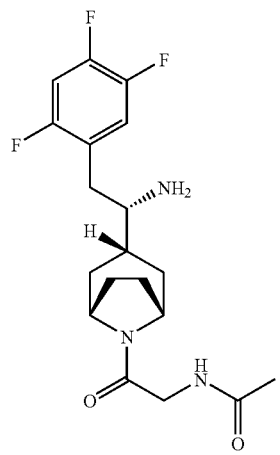

C2

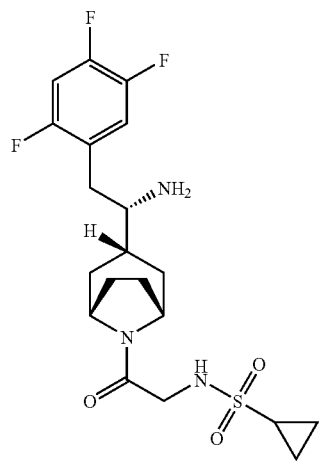

D1

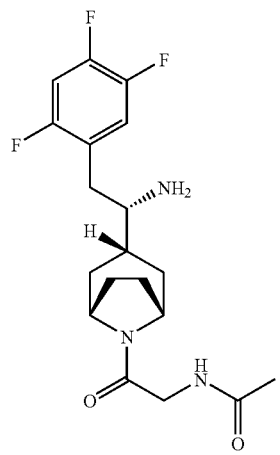

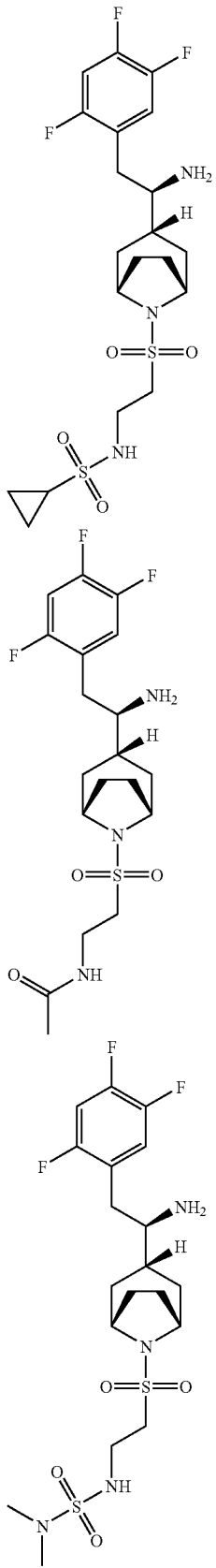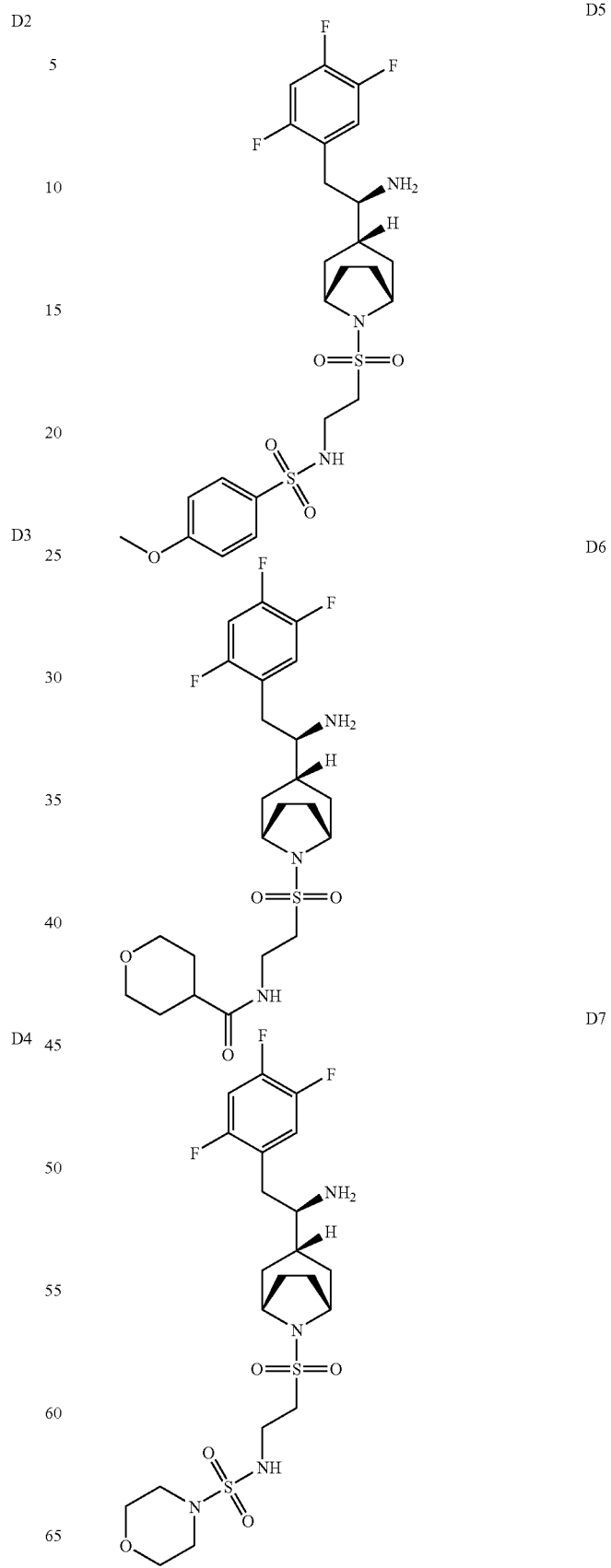

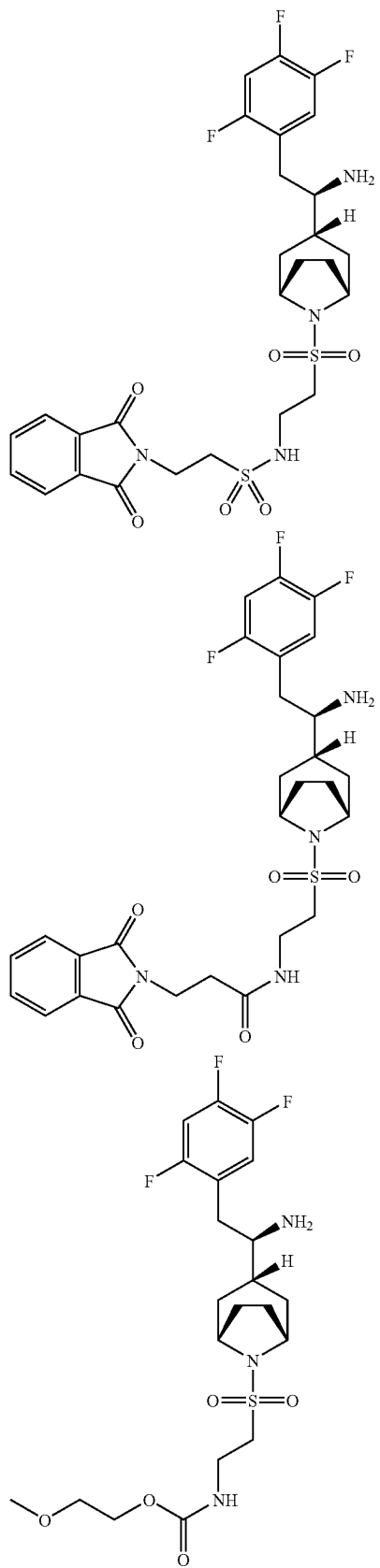
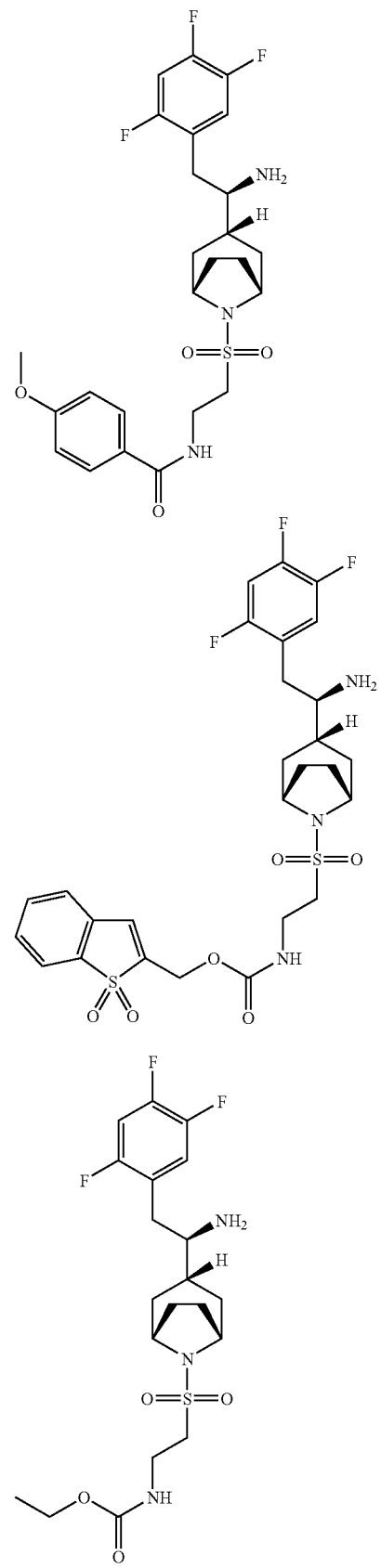

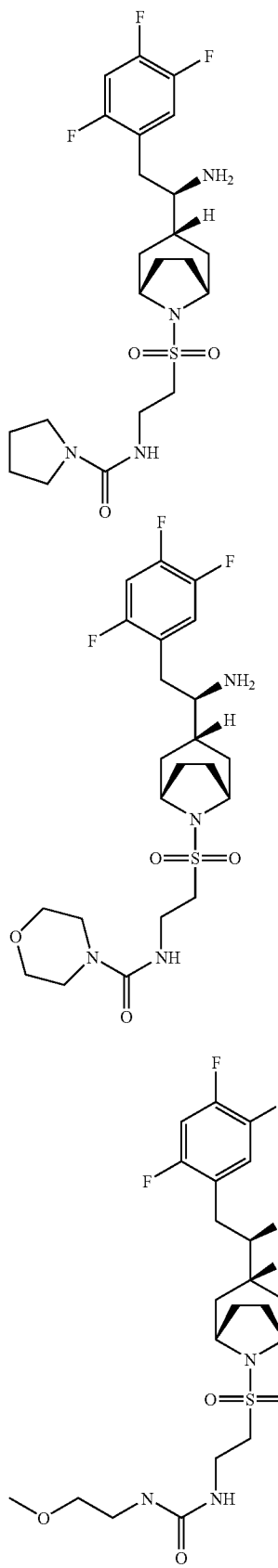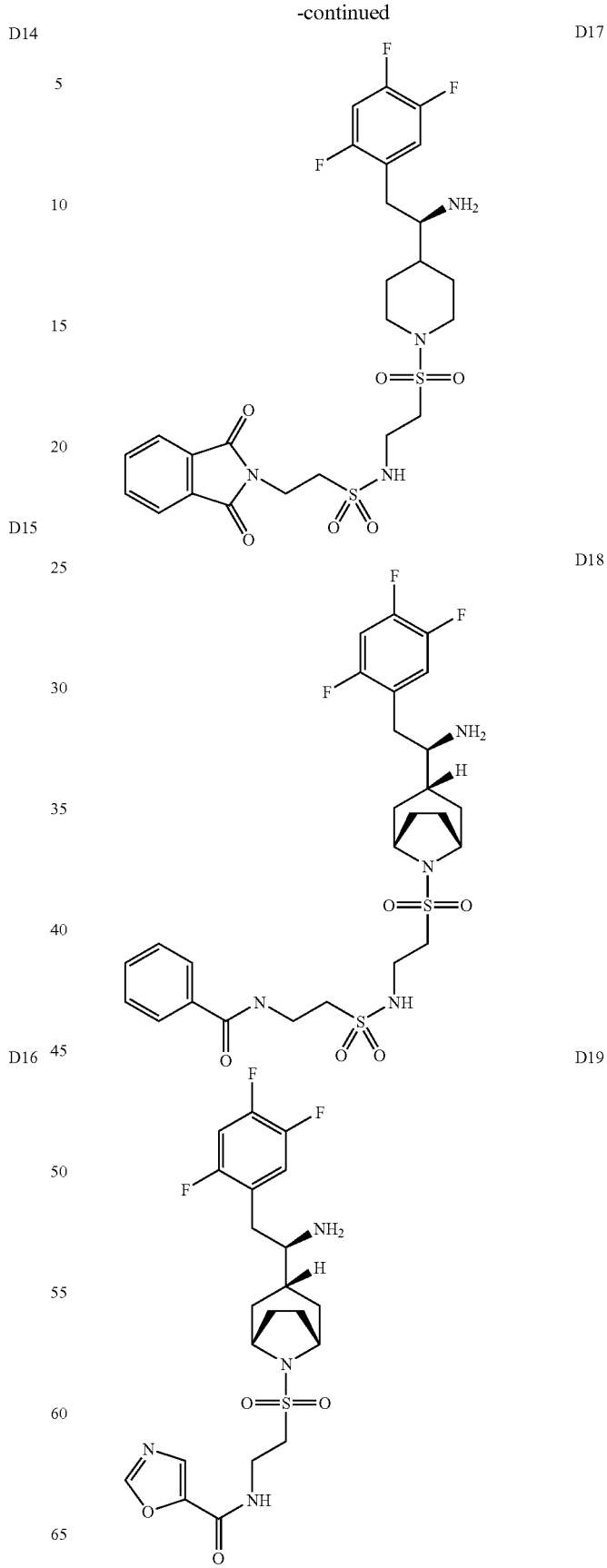

E1 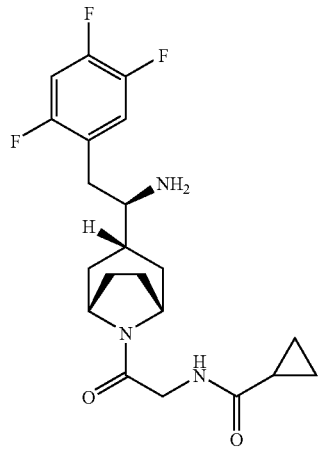
E2 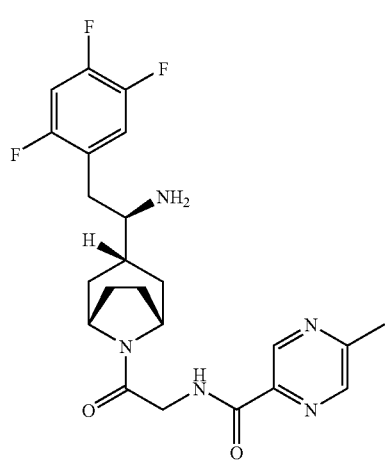
E3 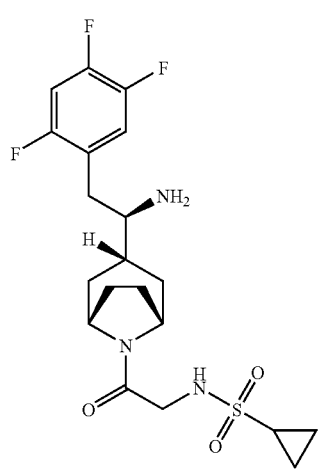
E4 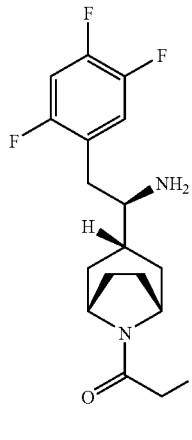
E5 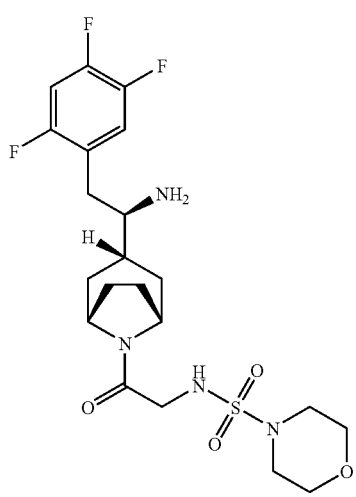
E6 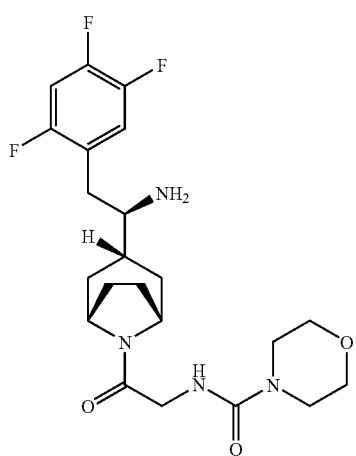

37
-continued
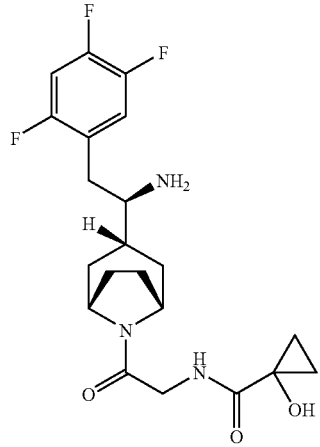
38
-continued
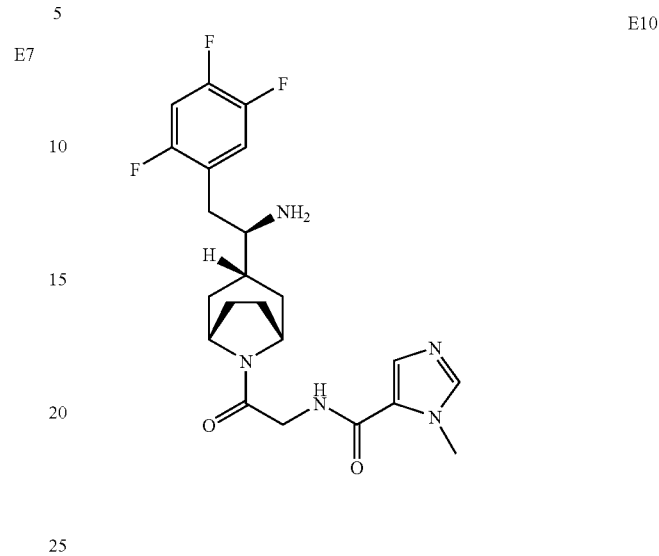
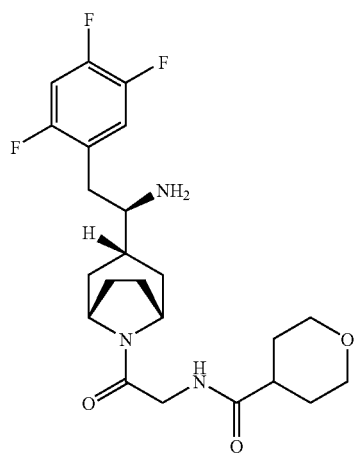
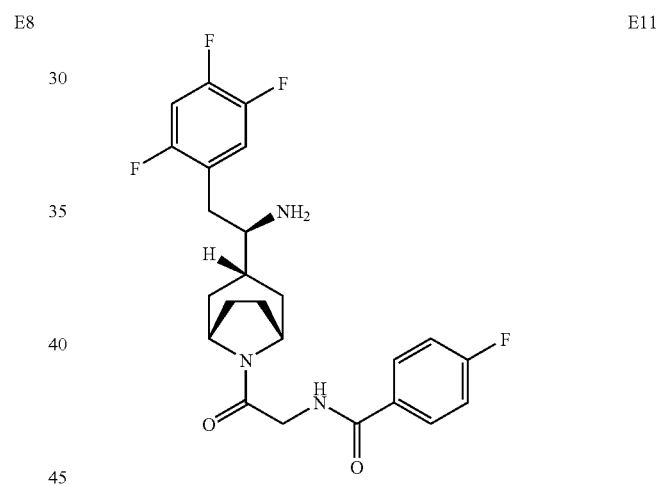
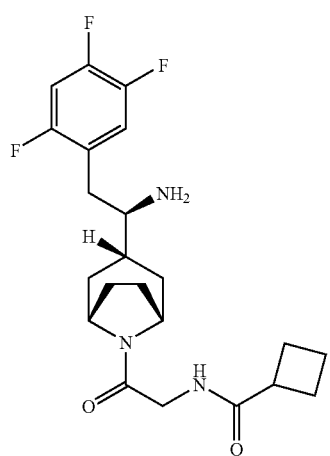
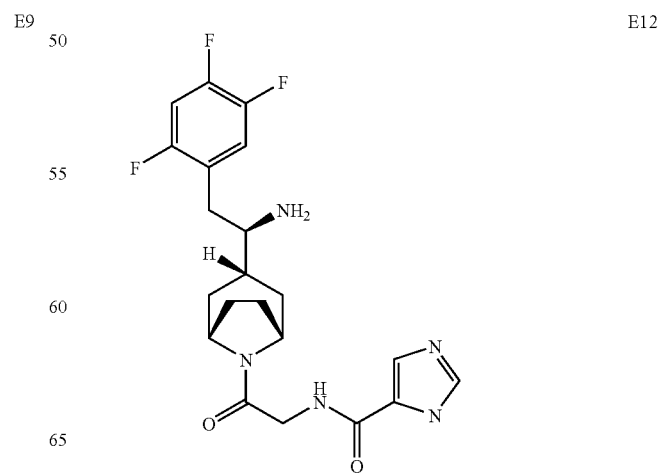

-continued
E13
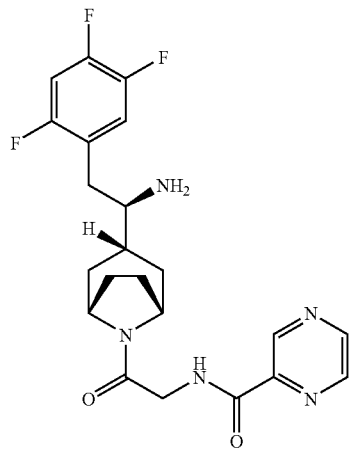
E14
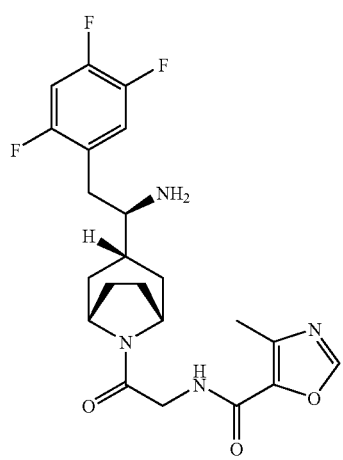
E15
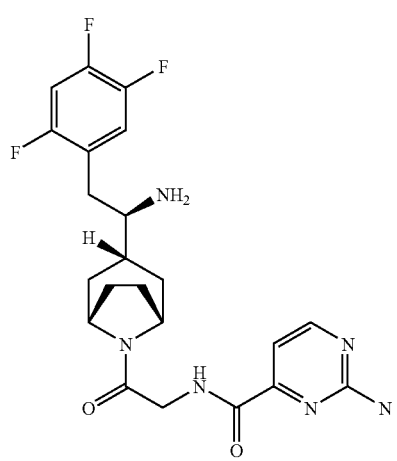
-continued
E16
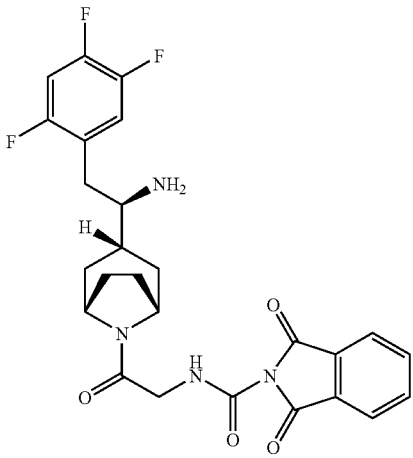
E17
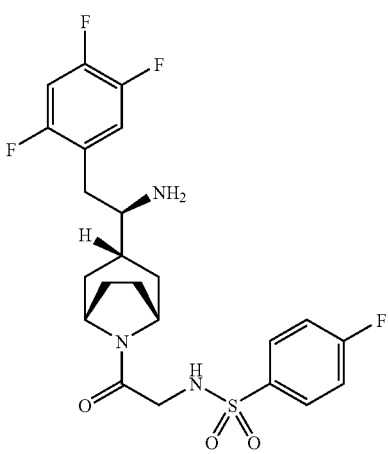
E18
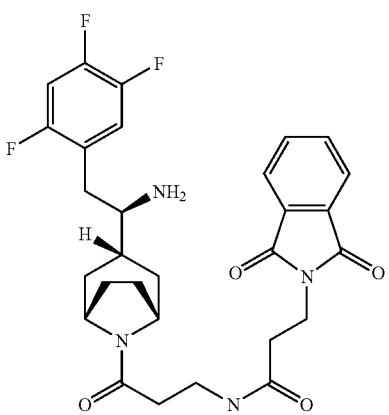

E19 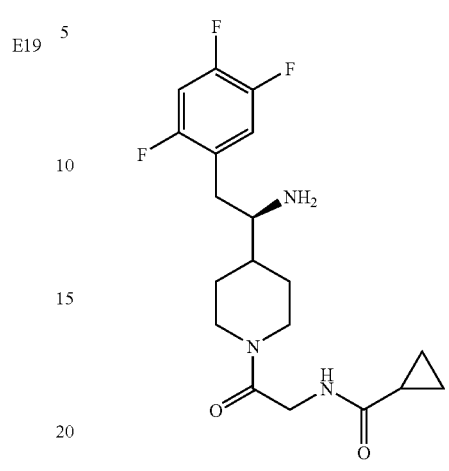
E20 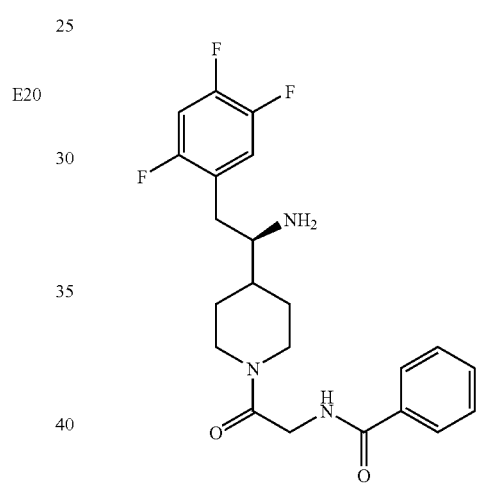
E21 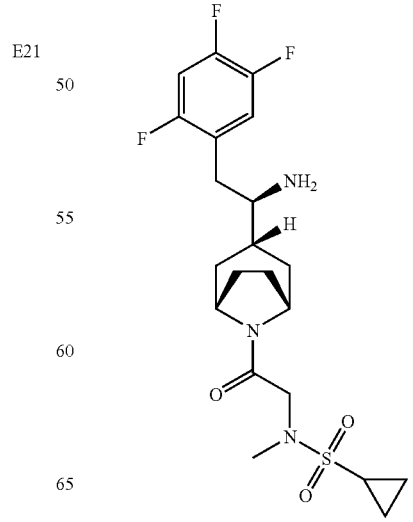
E22 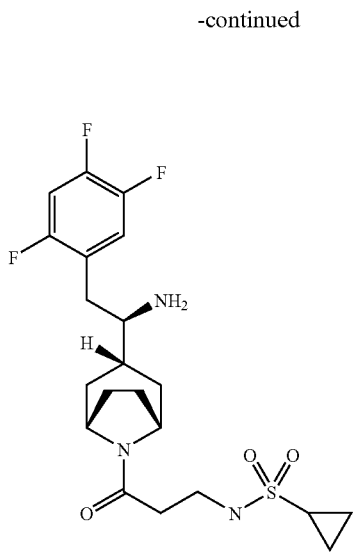
E23 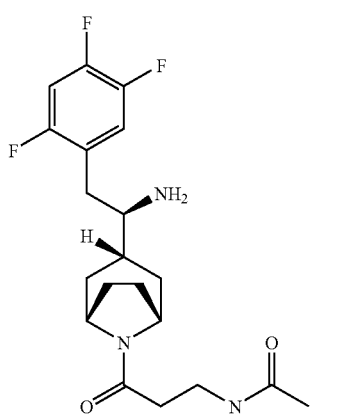
F1 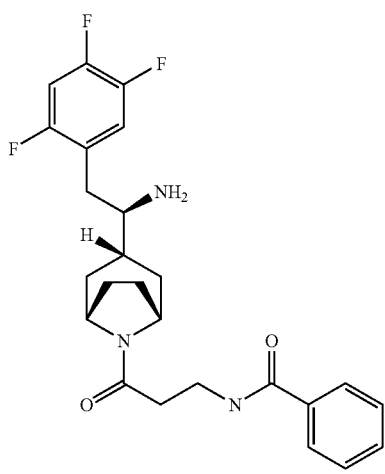

-continued
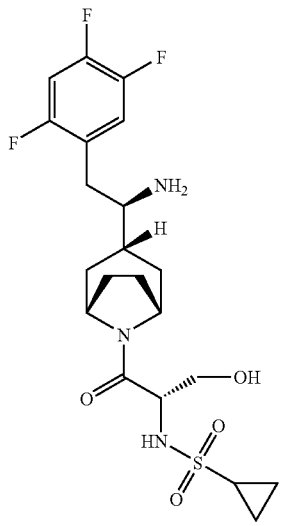
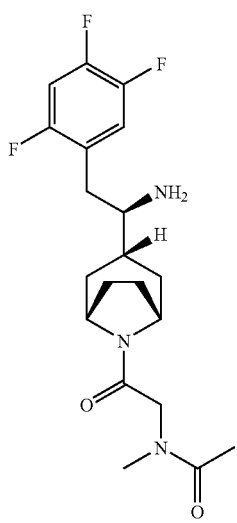
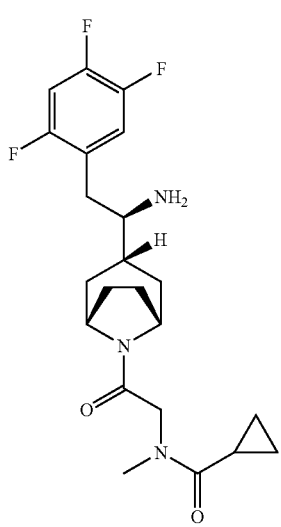
-continued
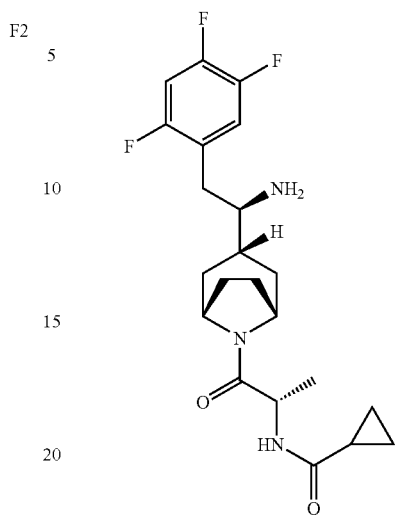
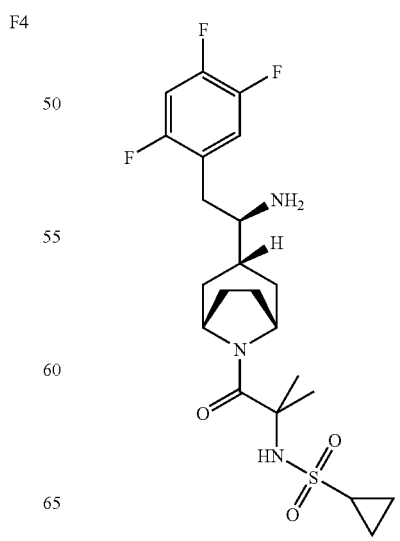

F8 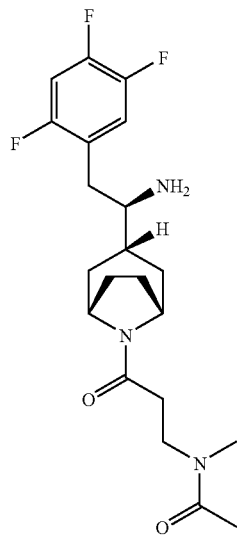
F9 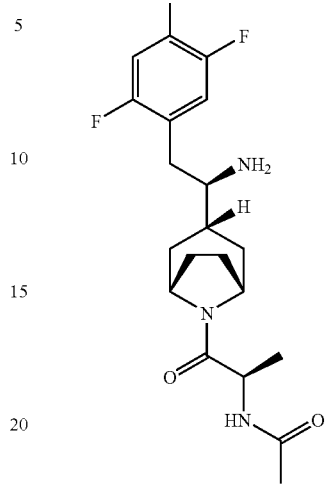
G1 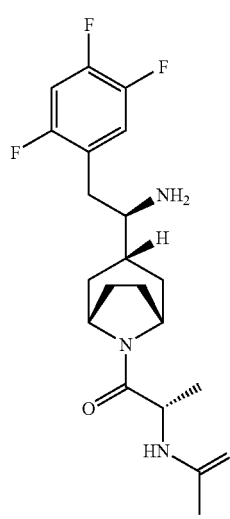
G2 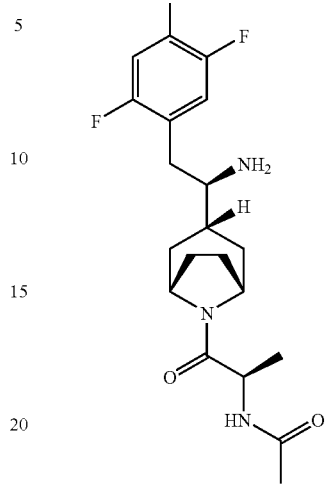
G3 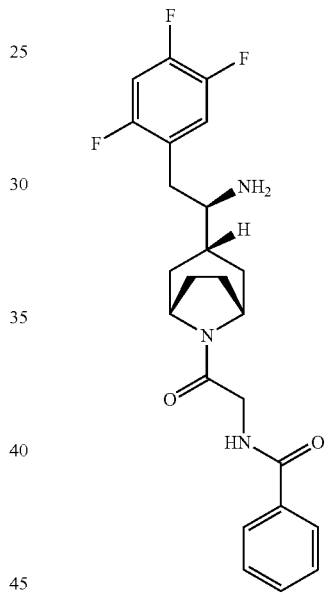
G4 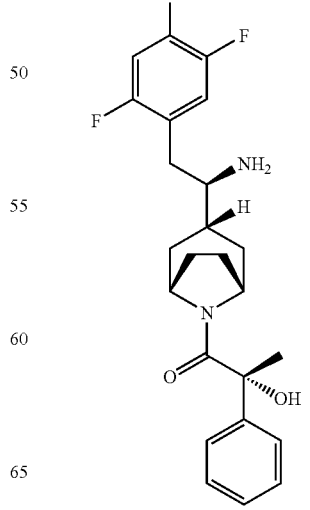

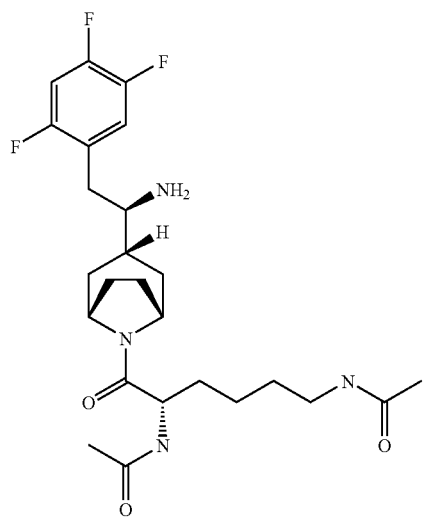
G5
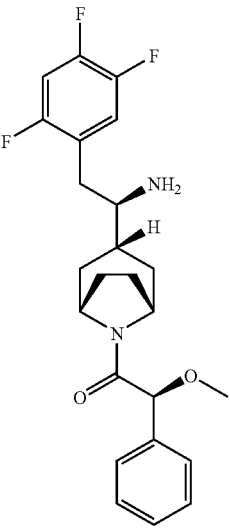
G8
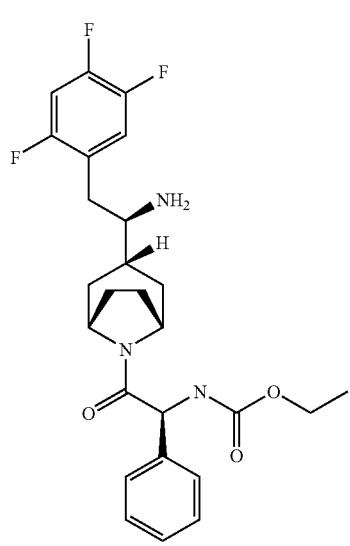
G6
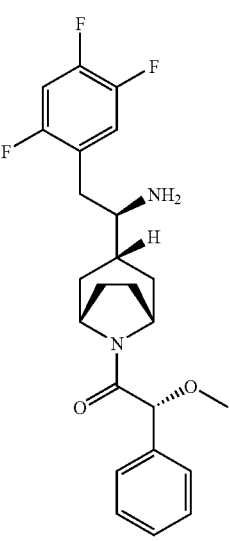
G9
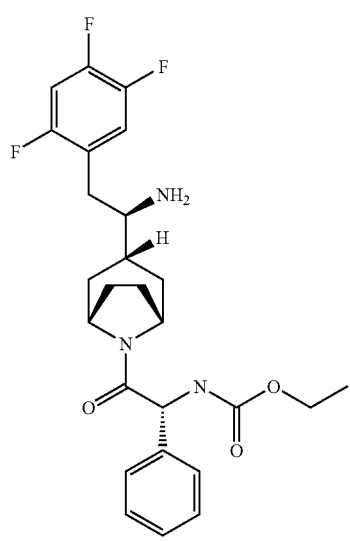
G7
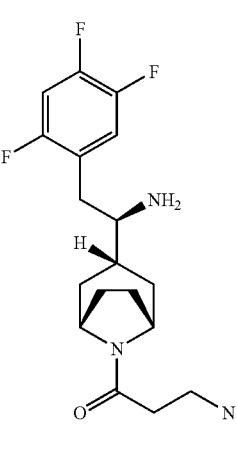
G10

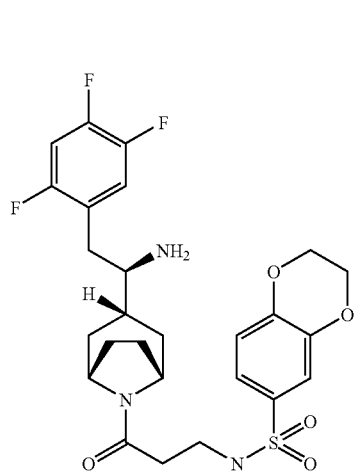
G11
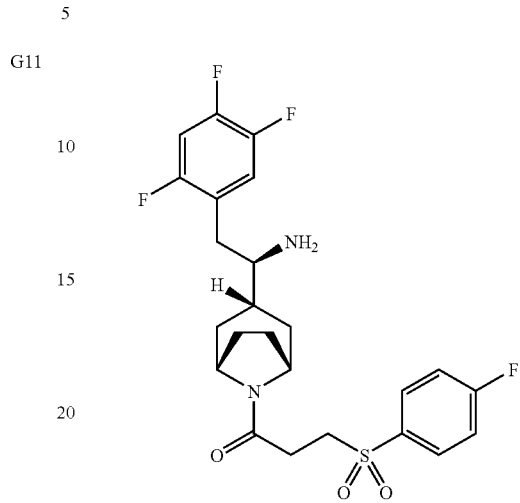
G14
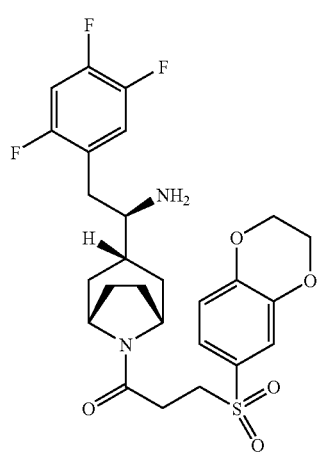
G12
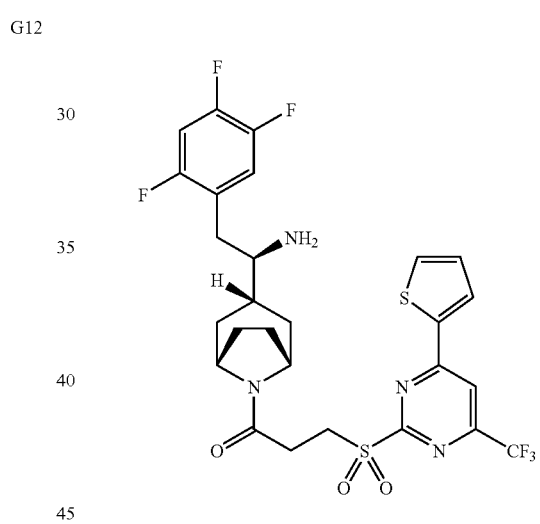
G15
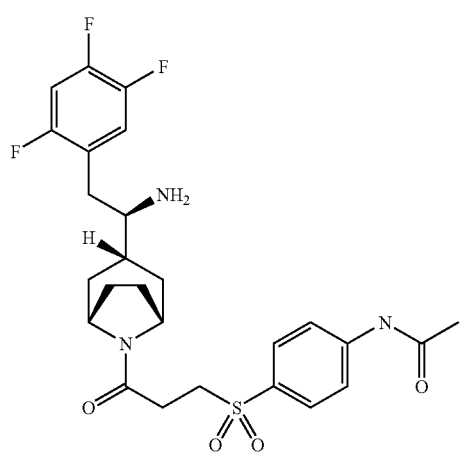
G13
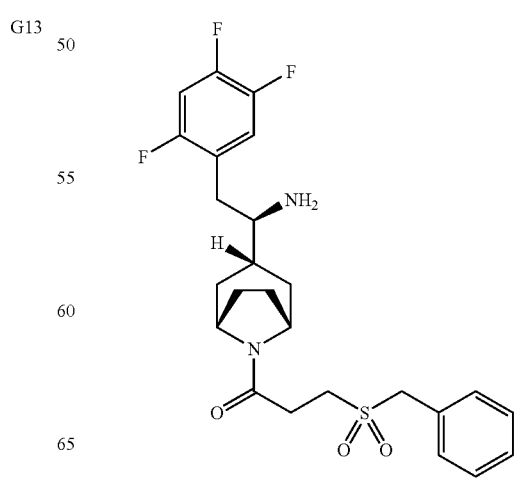
G16

| 51 | 52 |
|---|---|
| -continued | -continued |
| 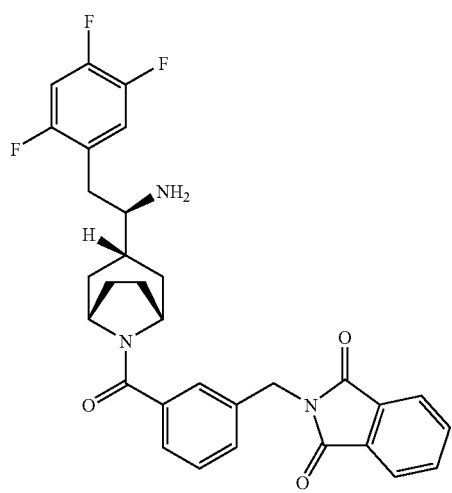 G17 | 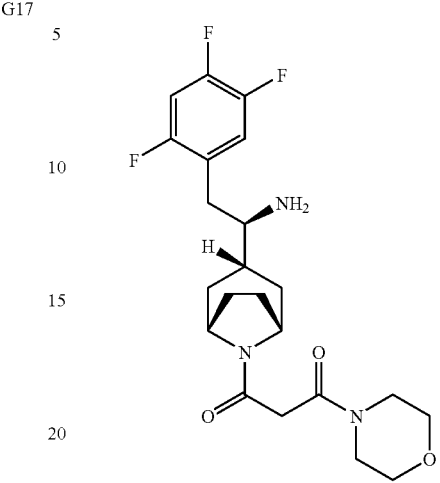 G20 |
| 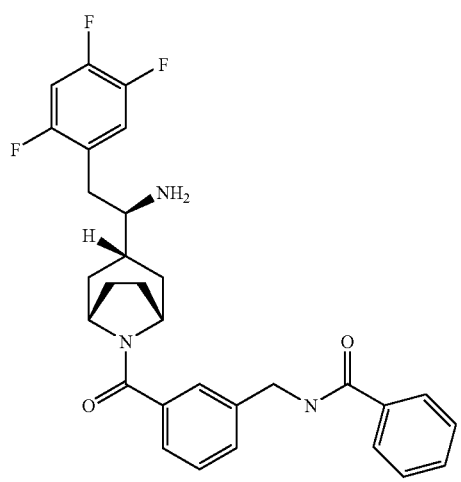 G18 | 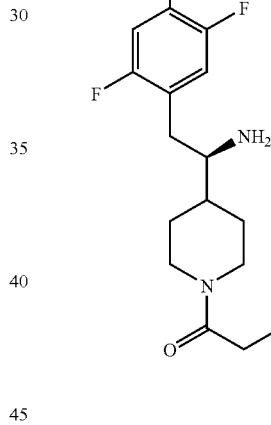 G21 |
| 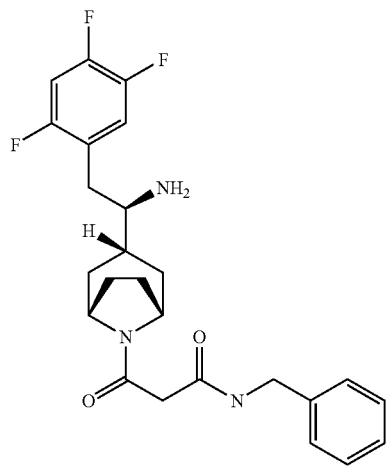 G19 | 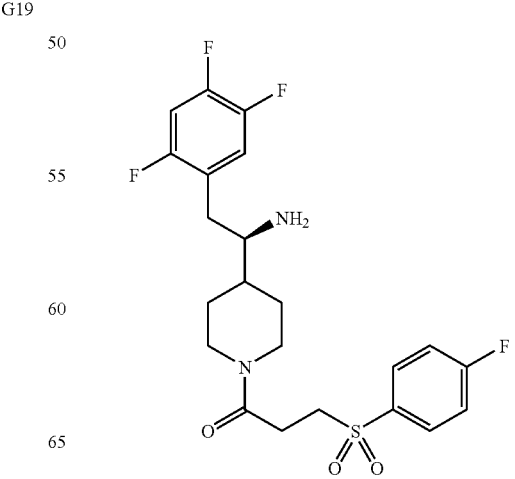 G22 |

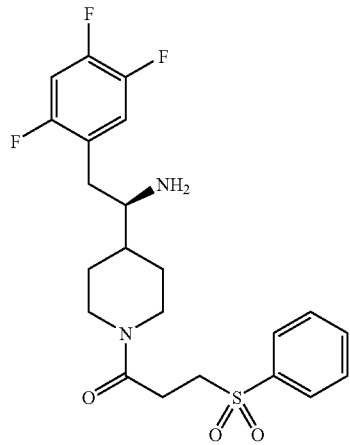
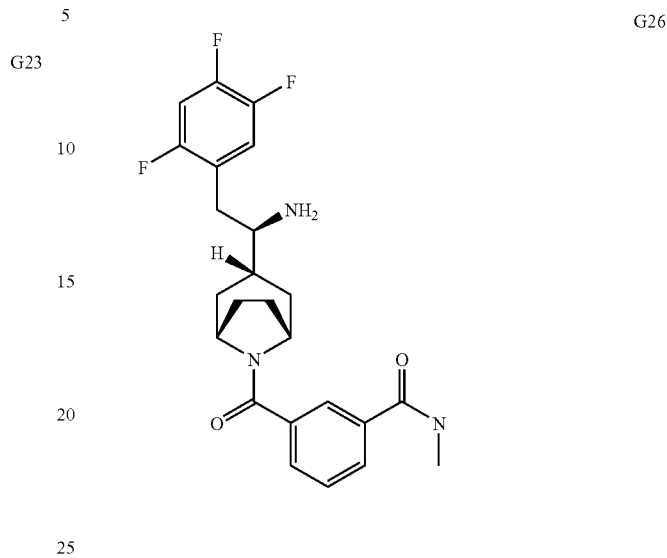
G23
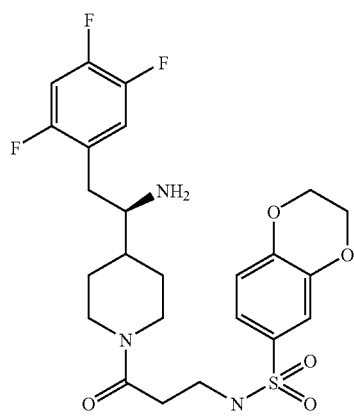
G24
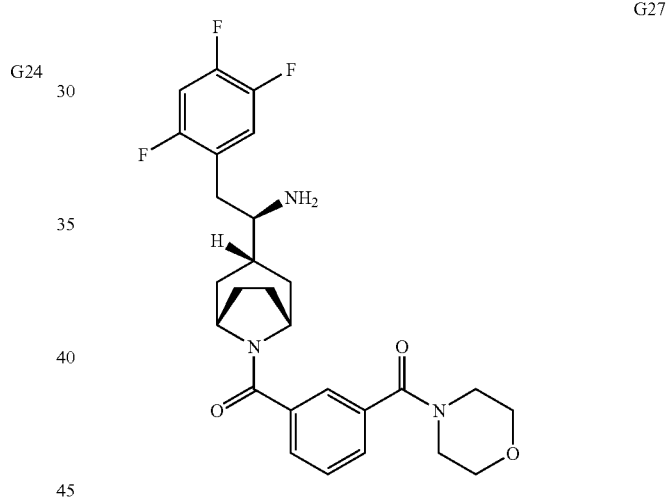
G27
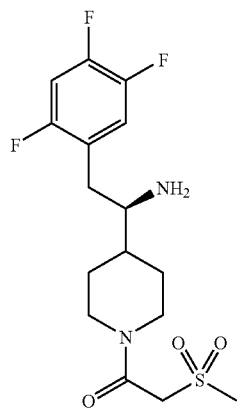
G25
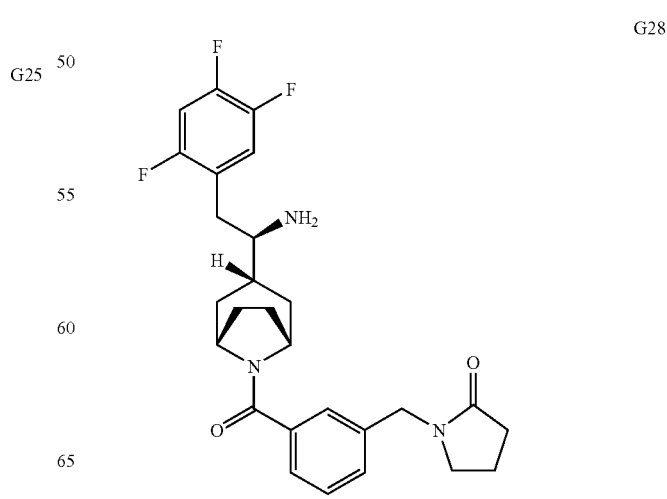
G28

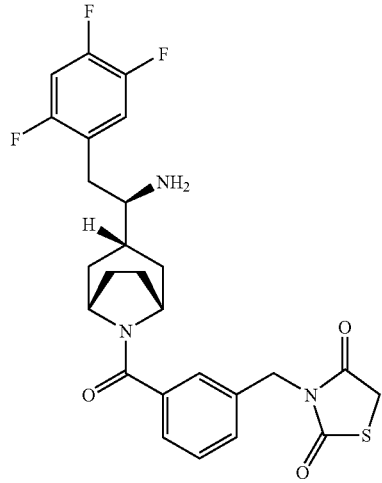
G29
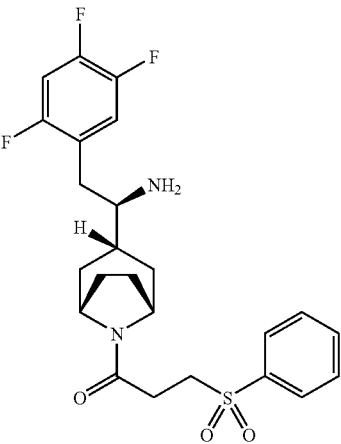
G30
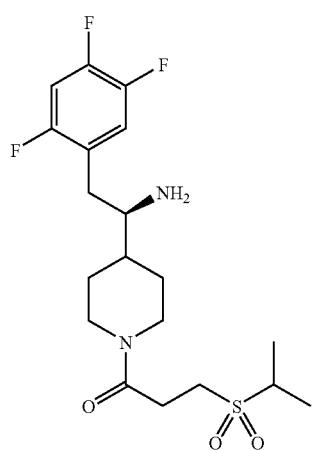
G32
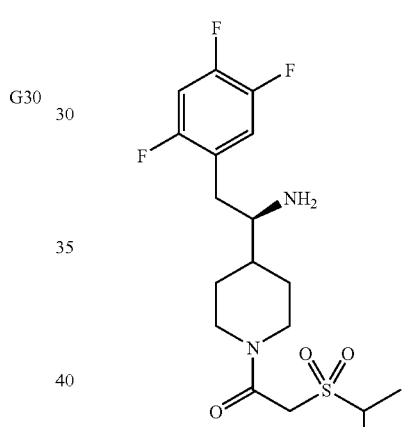
G33
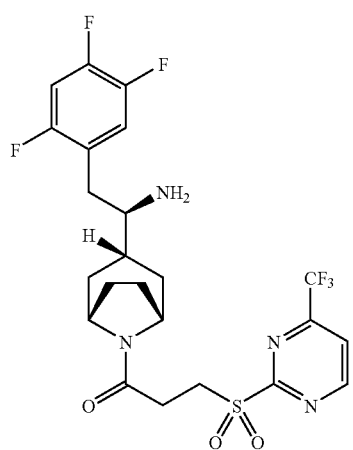
G31
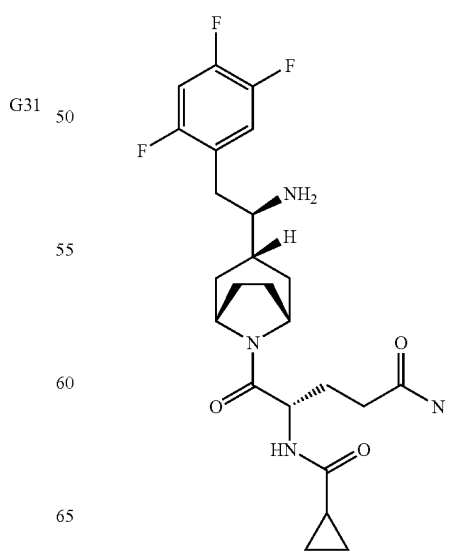
G34

H1
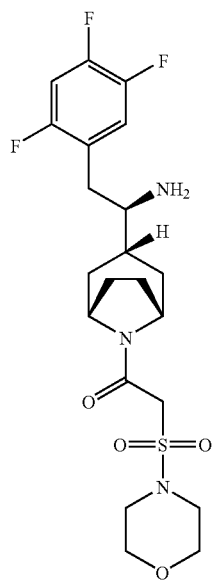
H2
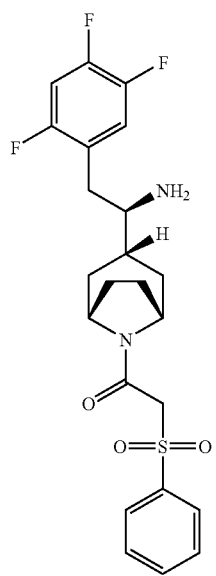
H3
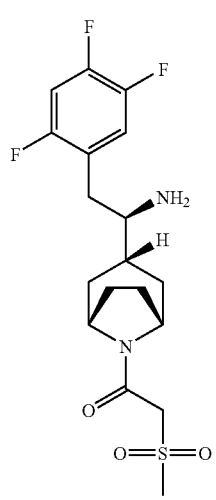
H4
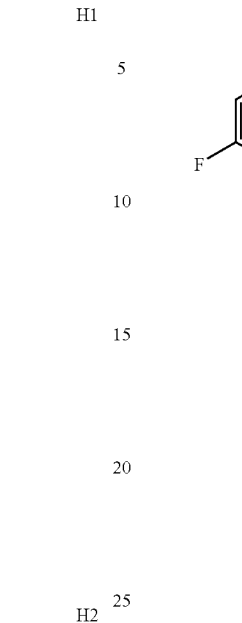
H5
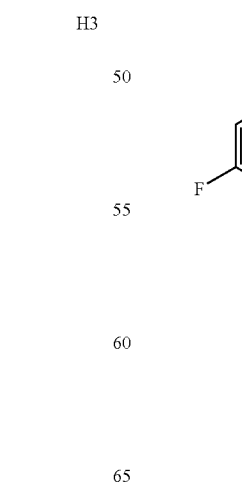
H6
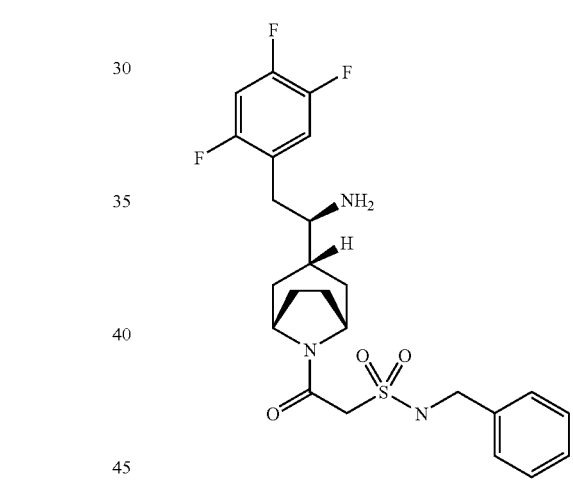

H7
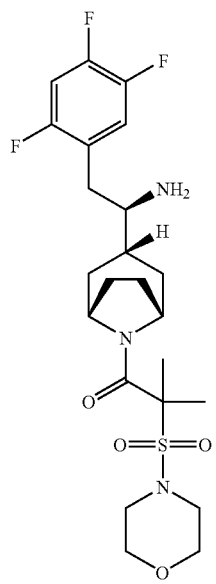
H8
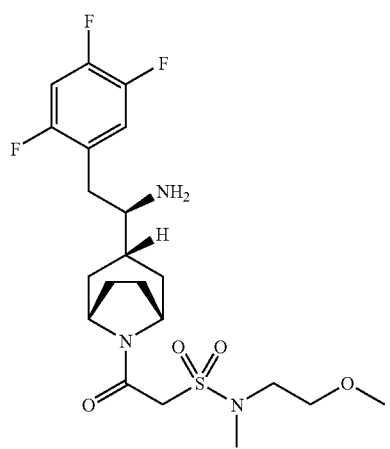
H9
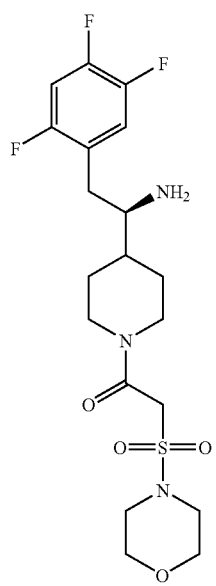
H10
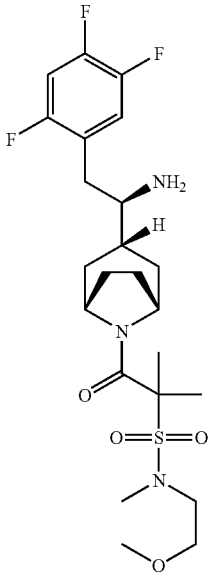
H11
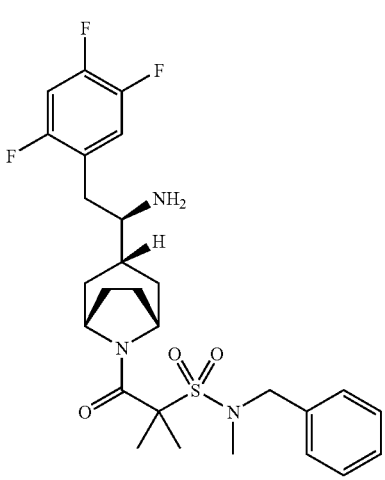
H12
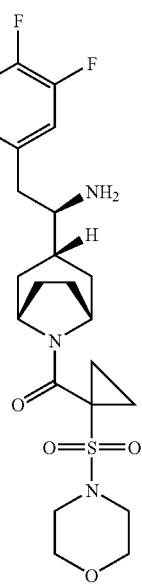

61 62
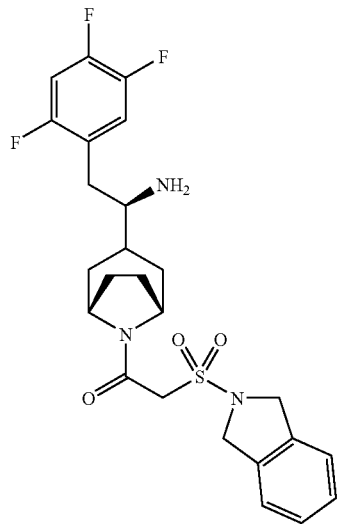
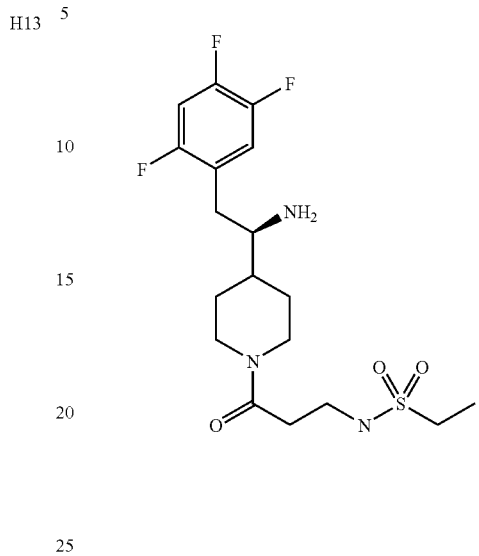 H13
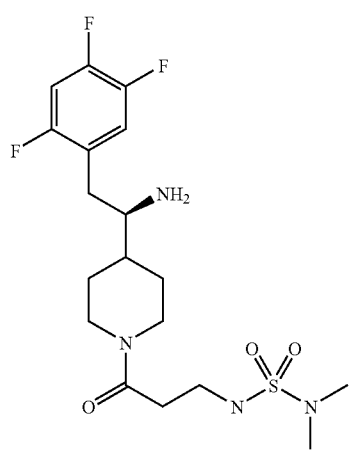 I1
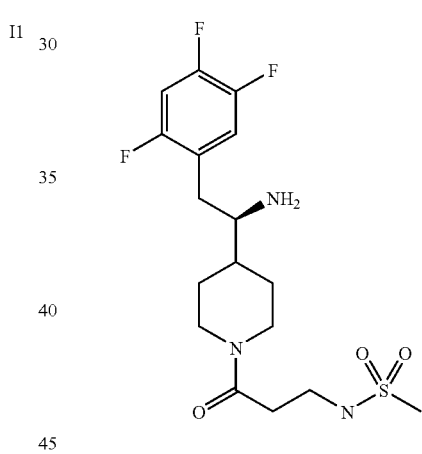 I4
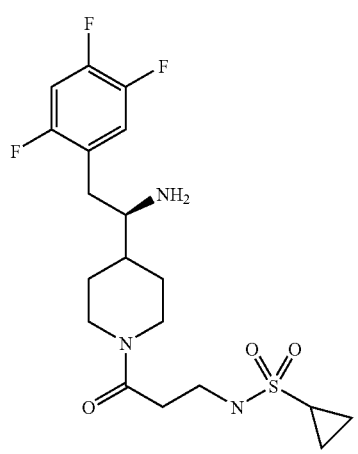 I2
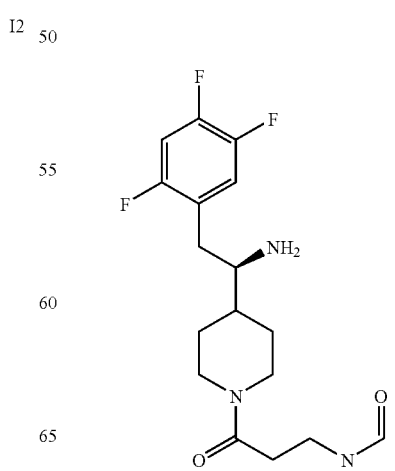 I5

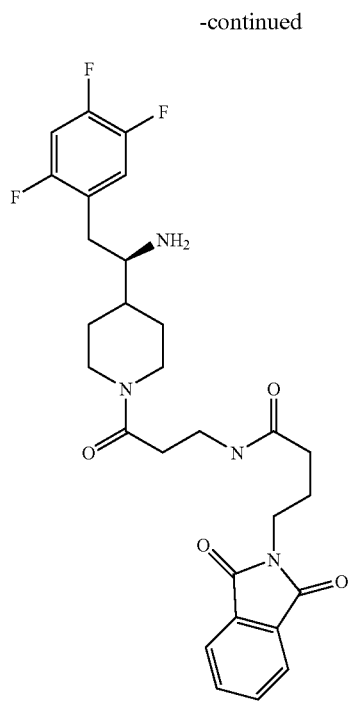
I6
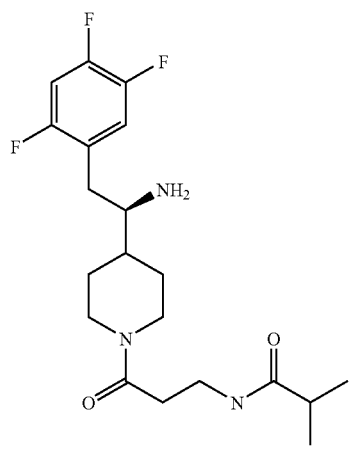
I7
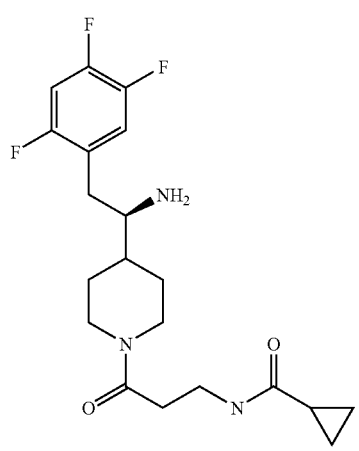
I8

65 66
K2
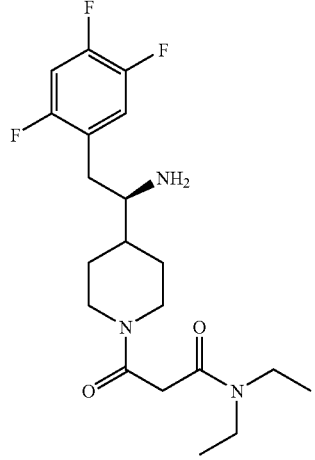
K5
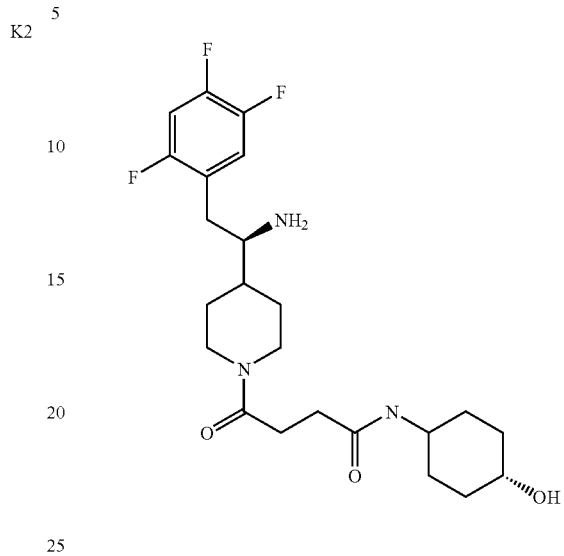
K3
K6
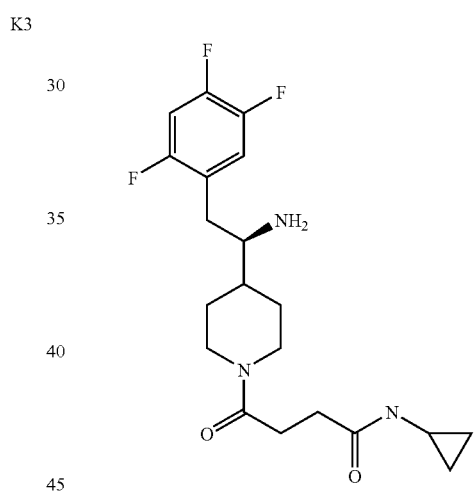
K4
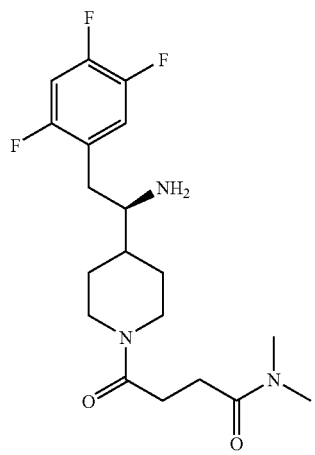
K7
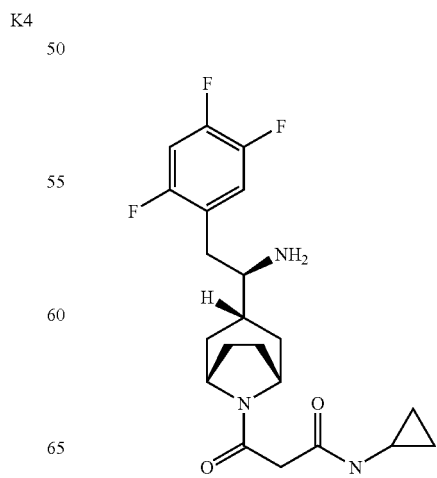

K8
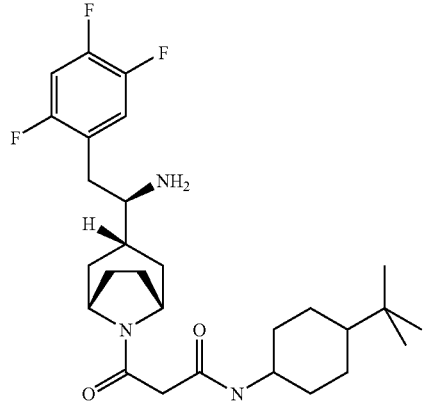
K9
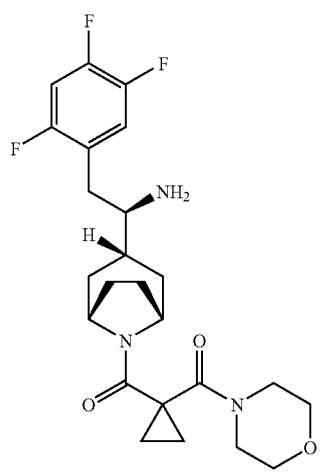
K10
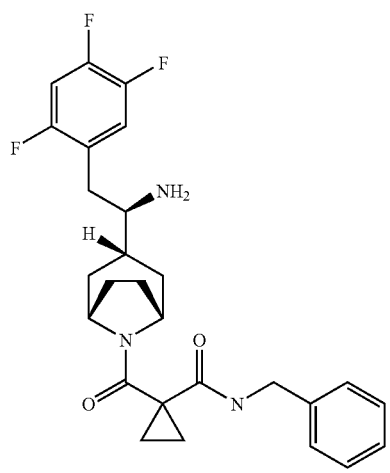
K11
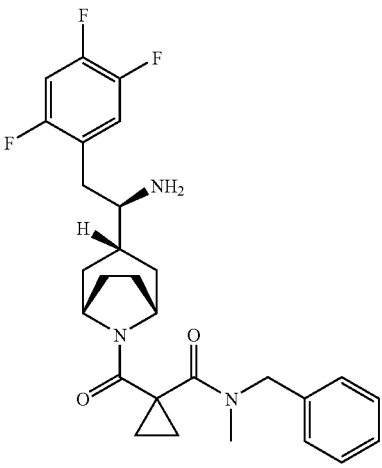
K12
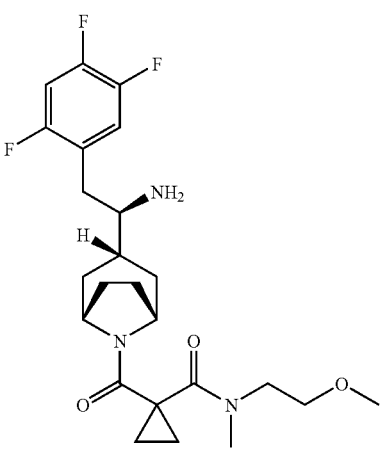
K13
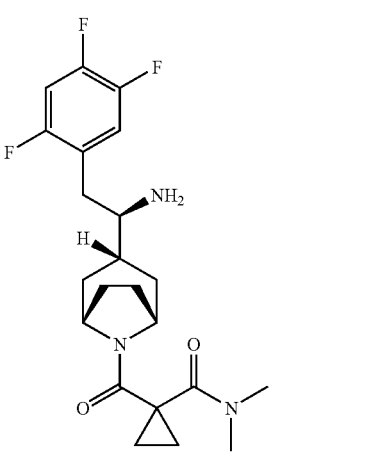

K14
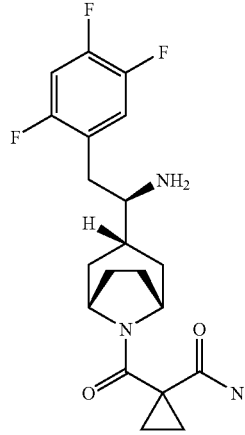
K15
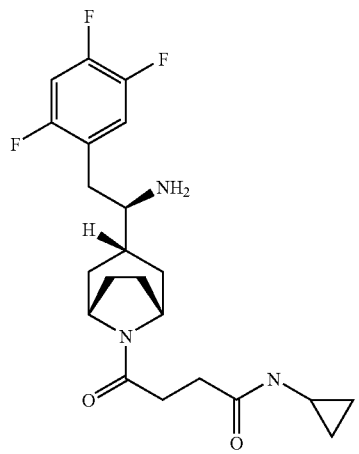
K16
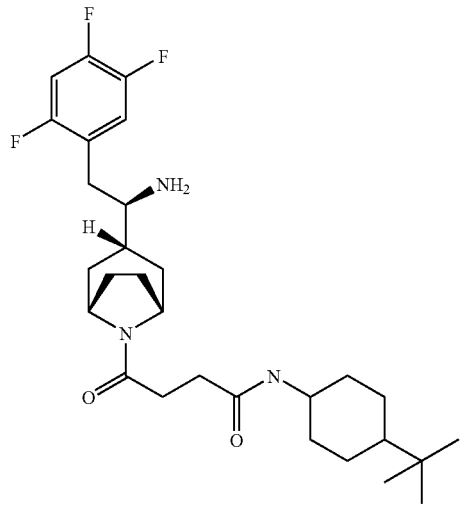
K17
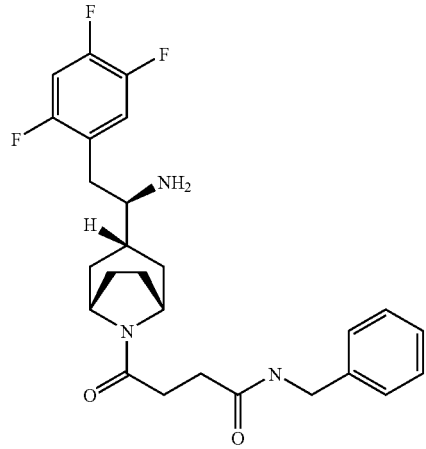
K18
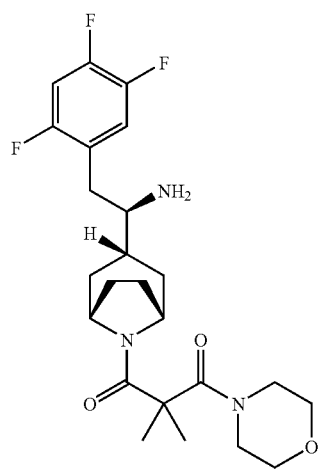
K19

-continued
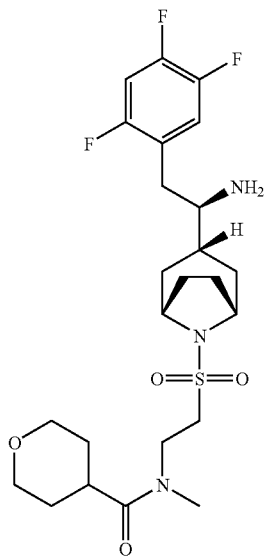
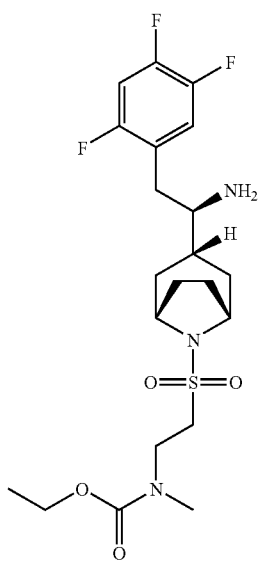
Further compounds of the invention include:
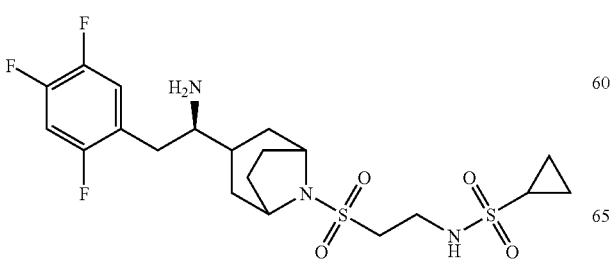
X1
-continued
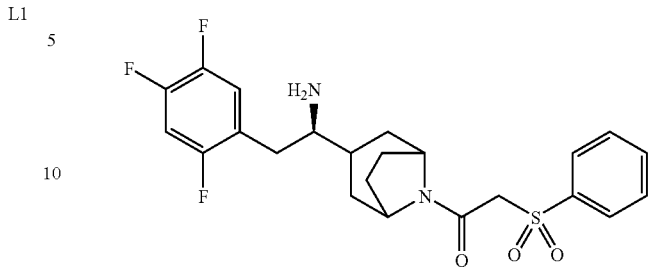
X2
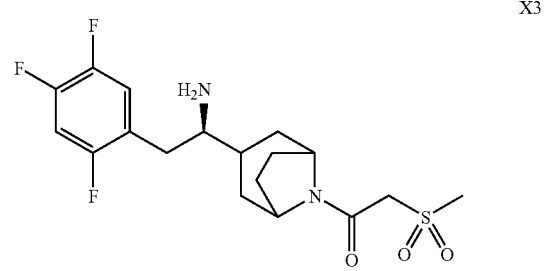
X3
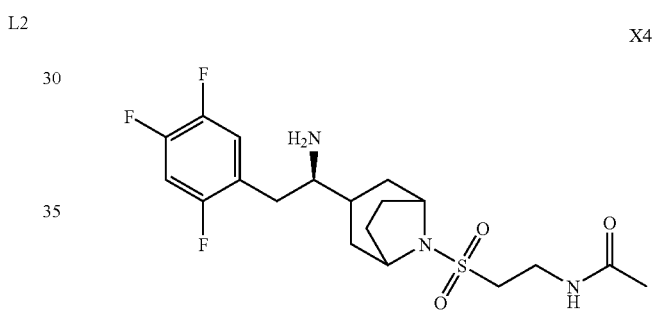
X4
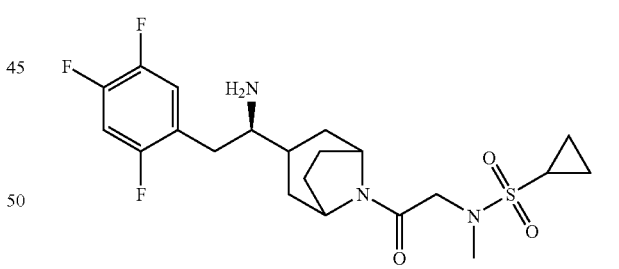
X5
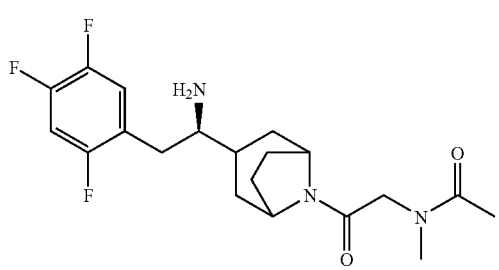
X6

-continued
X7
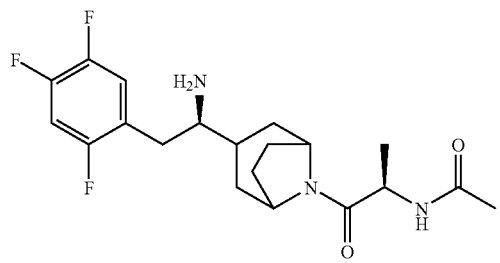
X8
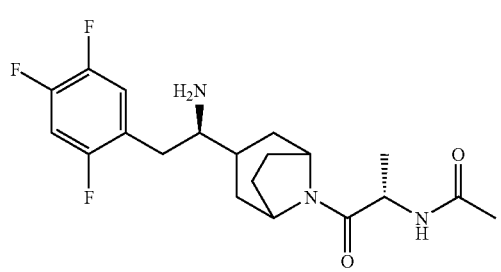
X9
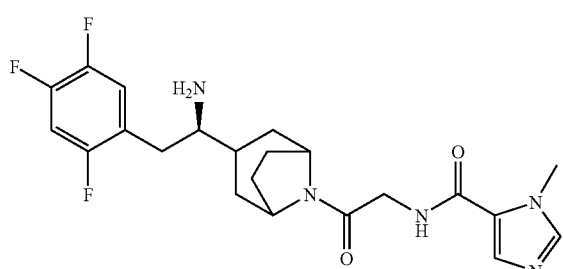
X10
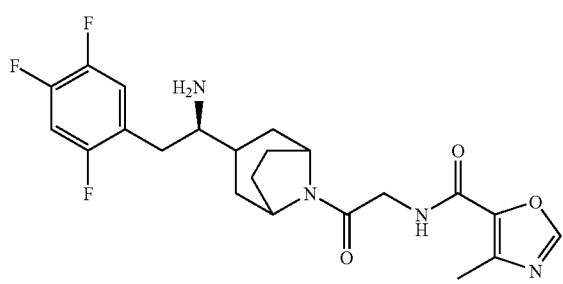
X11
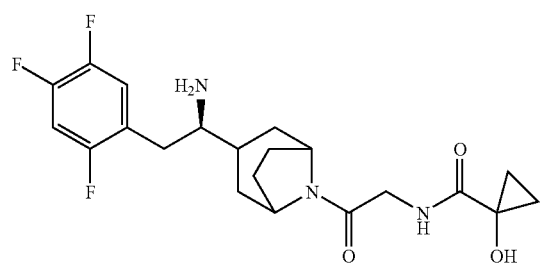
-continued
X12
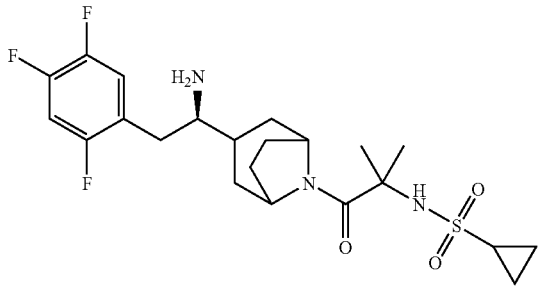
X13
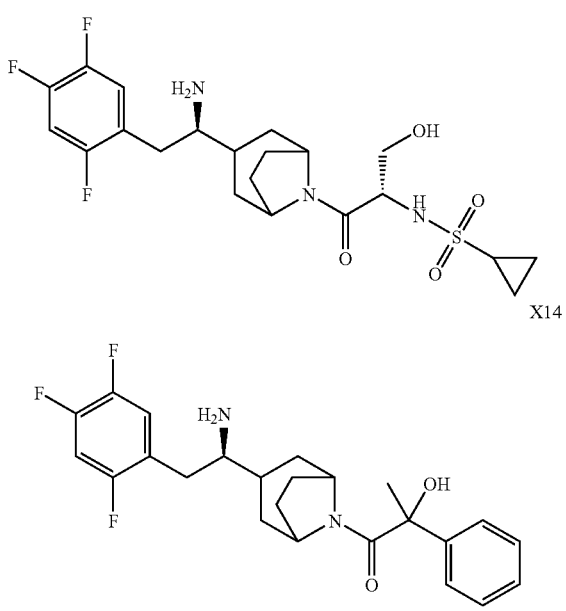
X14
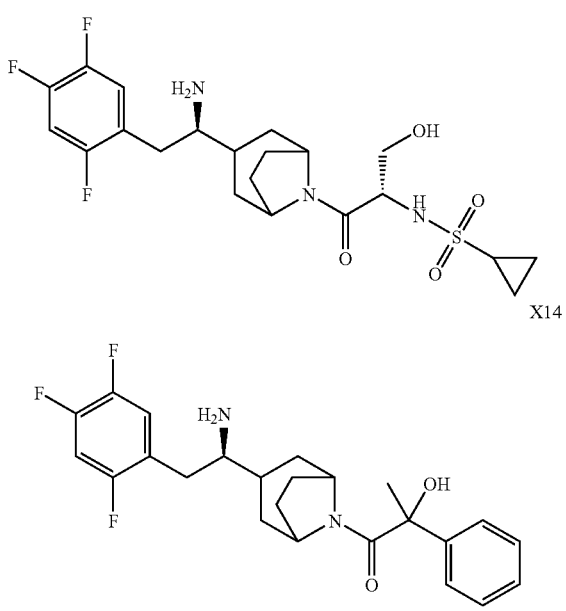
X15
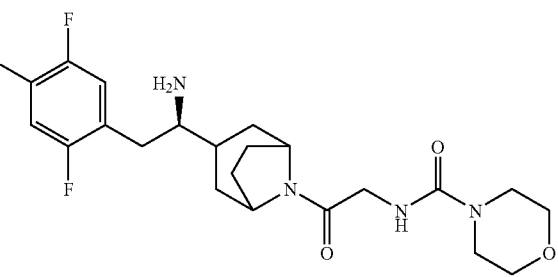
X16
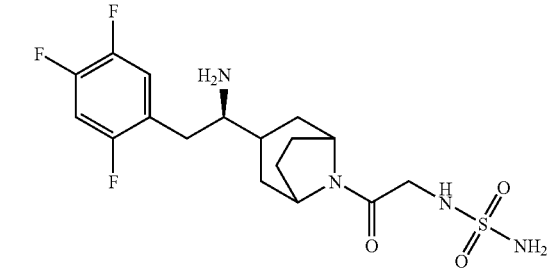

-continued

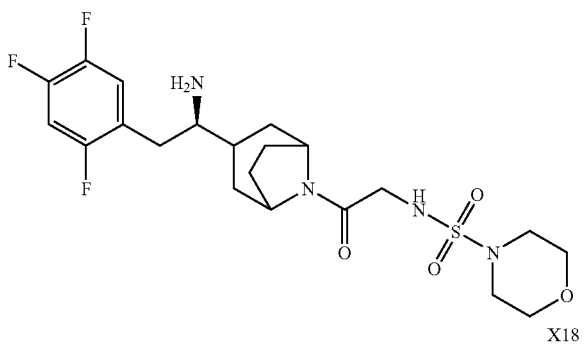

X17

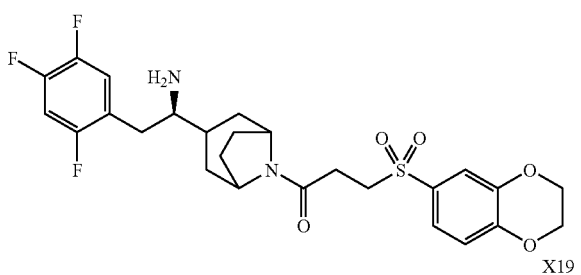

X18

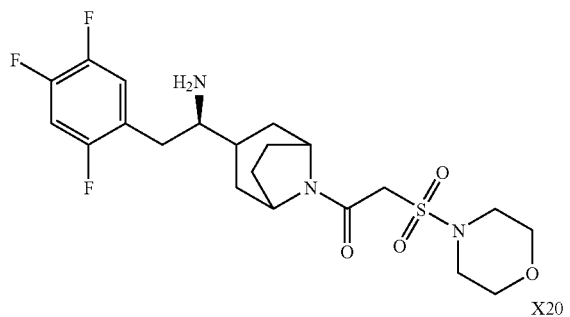

X19


X20

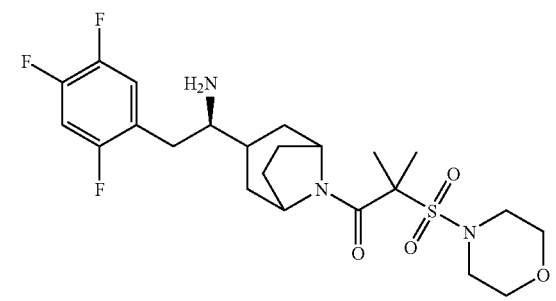

X21

Compounds of the invention may be in the form of pharmaceutically acceptable salts. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., US, 1985, p. 1418, the disclosure of which is hereby incorporated by reference; see also Stahl et al, Eds, *"Handbook of Pharmaceutical Salts Properties Selection and Use"*, Verlag Helvetica Chimica Acta and Wiley-VCH, 2002.

The disclosure thus includes pharmaceutically-acceptable salts of the disclosed compounds wherein the parent compound is modified by making acid or base salts thereof, for example the conventional non-toxic salts or the quaternary ammonium salts which are formed, e.g. from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention includes prodrugs for the active pharmaceutical species of the invention, for example in which one or more functional groups are protected or derivatised but can be converted in vivo to the functional group, as in the case of esters of carboxylic acids convertible in vivo to the free acid, or in the case of protected amines, to the free amino group. The term "prodrug," as used herein, represents in particular compounds which are rapidly transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), each of which is incorporated herein by reference.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. acyloxyalkyl esters, amides |
| Alcohol | Esters, including e.g. sulfates and phosphates as well as carboxylic acid esters |
| Amine | Amides, carbamates, imines, enamines, |
| Carbonyl (aldehyde, ketone) | Imines, oximes, acetals/ketals, enol esters, oxazolidines and thiazoxolidines |

Prodrugs also include compounds convertible to the active drug by an oxidative or reductive reaction. As examples may be mentioned:

Oxidative Activation
N- and O-dealkylation
Oxidative deamination
N-oxidation
Epoxidation
Reductive Activation
Azo reduction
Sulfoxide reduction
Disulfide reduction
Bioreductive alkylation
Nitro reduction.

Also to be mentioned as metabolic activations of prodrugs are nucleotide activation, phosphorylation activation and decarboxylation activation. For additional information, see "The Organic Chemistry of Drug Design and Drug Action", R B Silverman (particularly Chapter 8, pages 497 to 546), incorporated herein by reference.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the disclosure may not possess pharmacological activity as such, they may be administered, for example parenterally or orally, and thereafter metabolised in the body to form compounds of the invention which are pharmacologically active. Such derivatives are therefore examples of "prodrugs". All prodrugs of the described compounds are included within the scope of the disclosure.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the disclosure may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the disclosure. Where a single enantiomer or diasteromer is disclosed, the disclosure also covers the other enantiomers or diastereomers, and also racemates; in this regard, particular reference is made to the specific compounds listed herein. As mentioned above, the stereochemical configuration of the carbon atom to which the group —N($R^2$)($R^3$) is attached may be (R) or (S), especially (R).

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

The disclosure therefore includes all variant forms of the defined compounds, for example any tautomer or any pharmaceutically acceptable salt, ester, acid or other variant of the defined compounds and their tautomers as well as substances which, upon administration, are capable of providing directly or indirectly a compound as defined above or providing a species which is capable of existing in equilibrium with such a compound.

Synthesis

By way of illustration, a compound of the invention may be prepared according to the following Schemes, in which Scheme 1 shows the synthesis of an intermediate in the form of a racemate; Schemes 2 to 4 show synthesis of compounds of the invention in (S) form, and Schemes 5 and 6 show synthesis of compounds in (R) form. $R^x$, $R^y$ and $R^z$ may each be any suitable group. For example, $R^x$ and $R^y$ may be methyl and benzyl respectively, while —N($R^z$)$_2$ may form a phthalimido group.

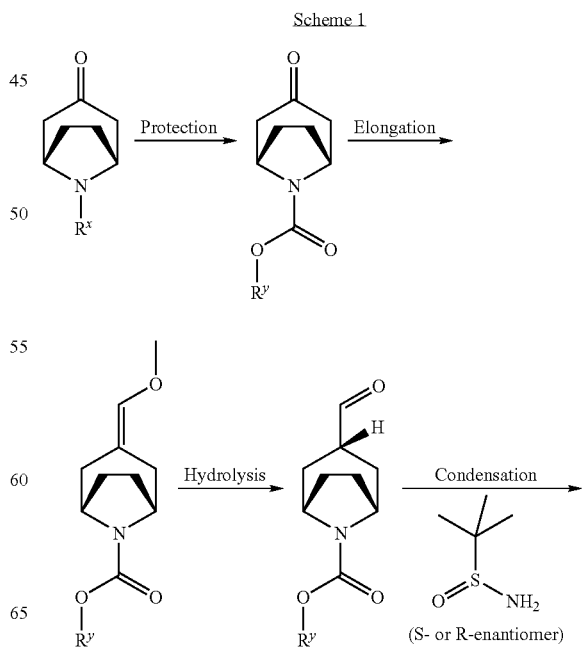

Scheme 1

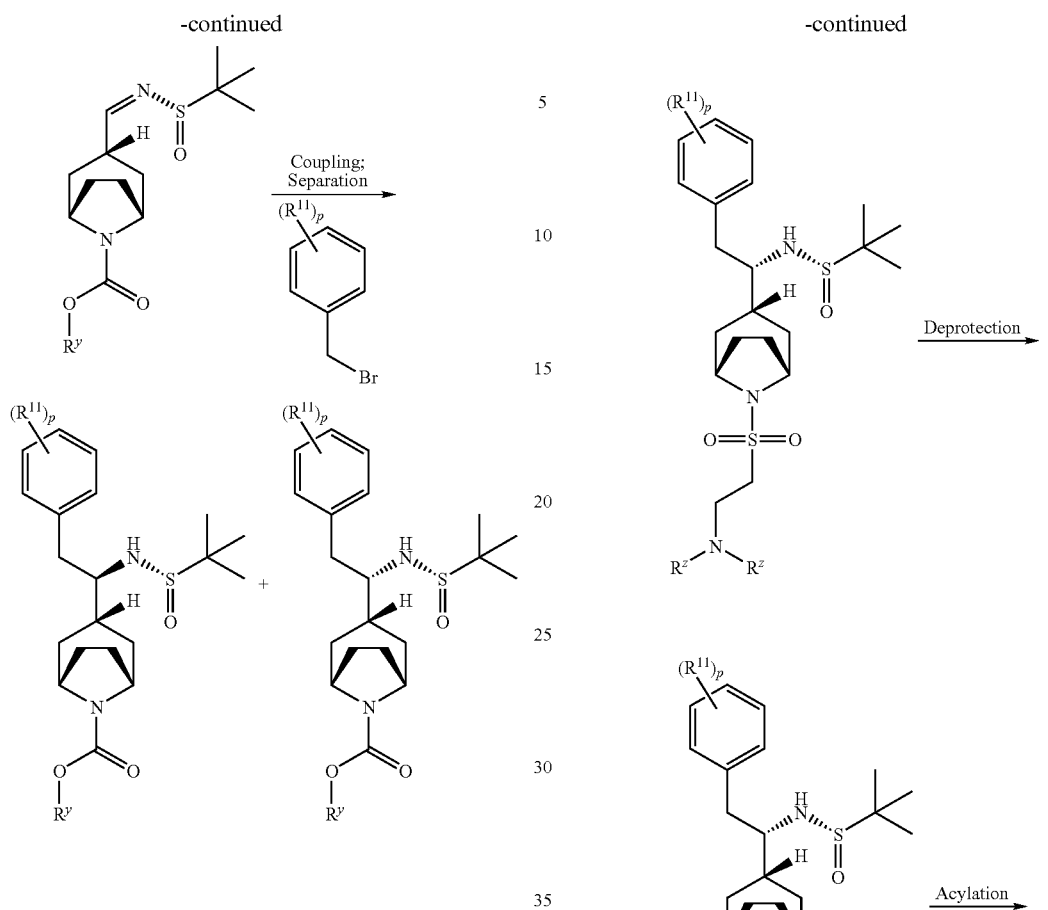
Scheme 2
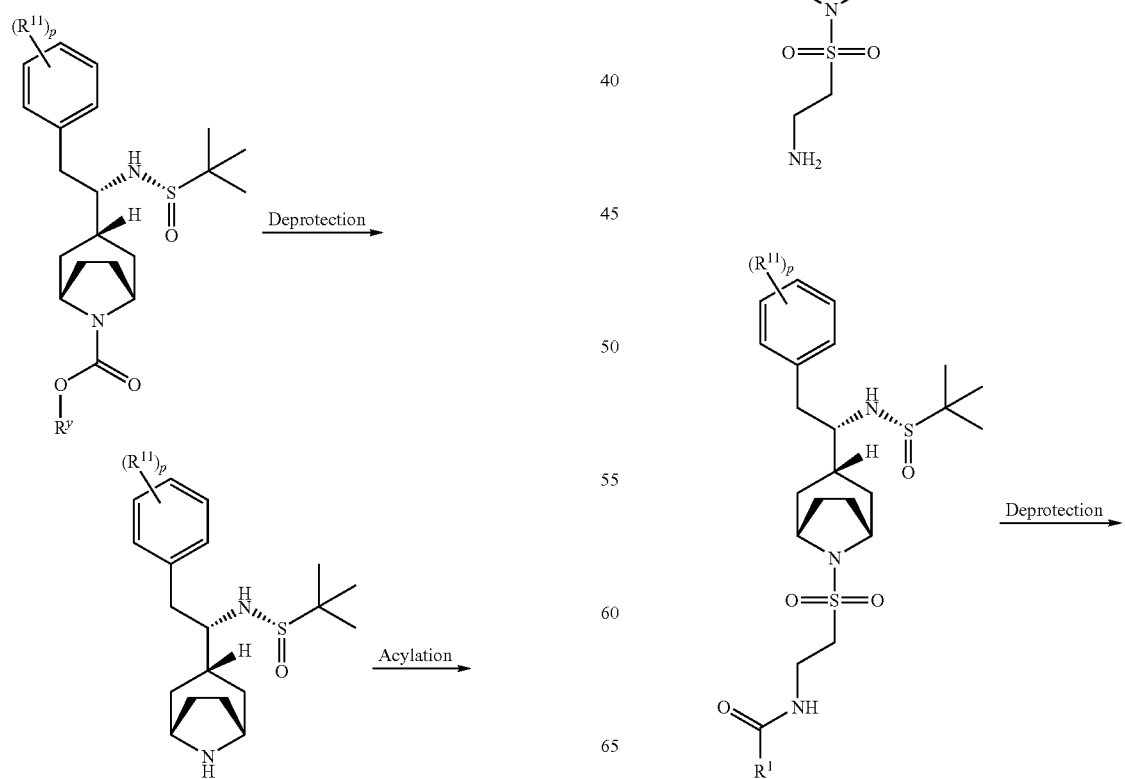

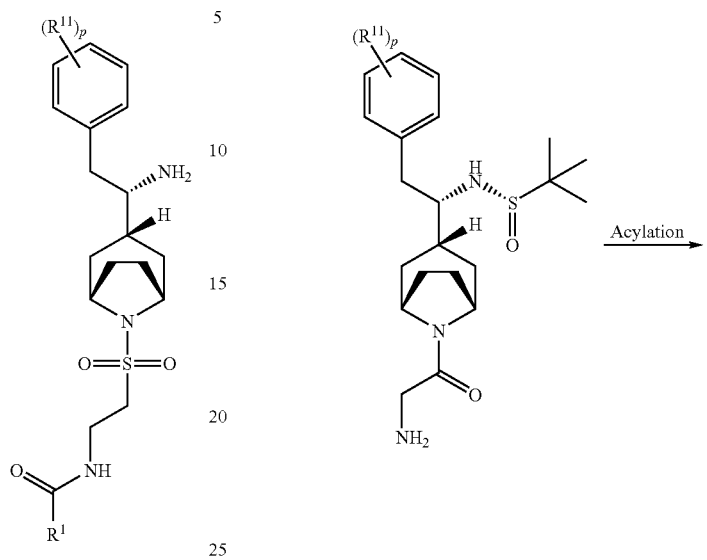
Scheme 3
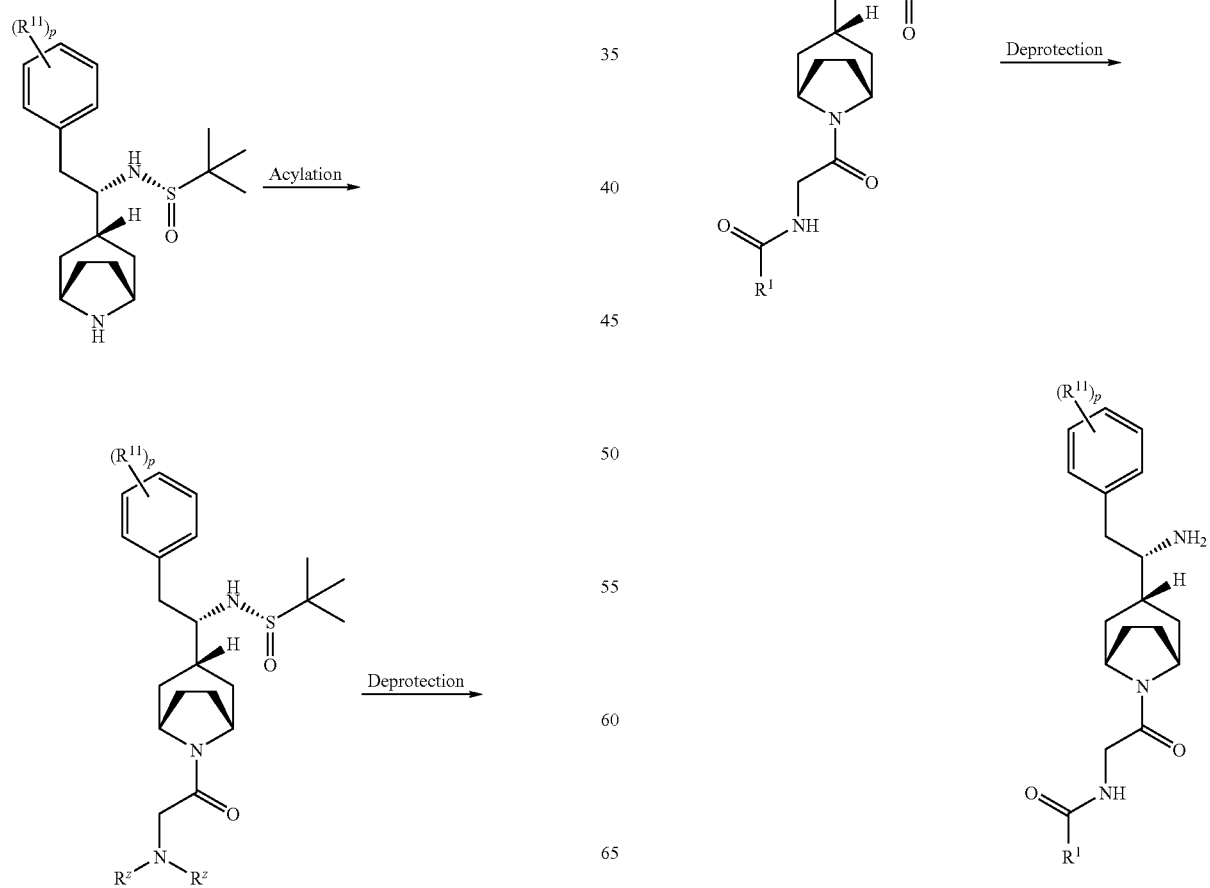

Scheme 4
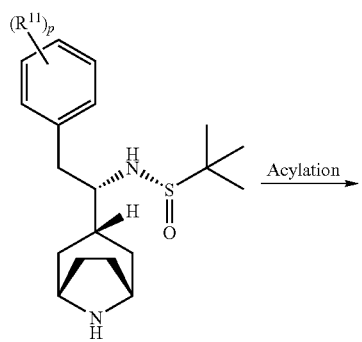
Acylation →
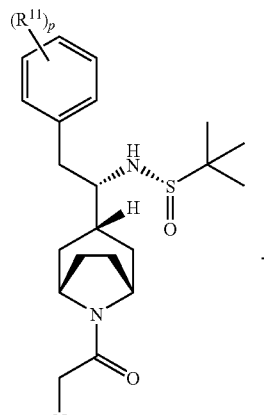
Deprotection →
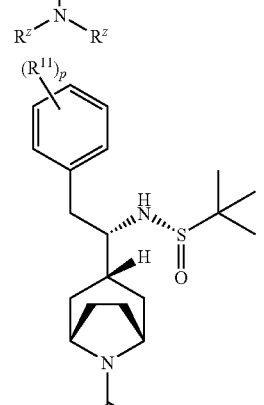
Acylation →
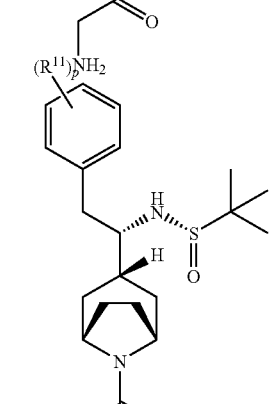
Deprotection →
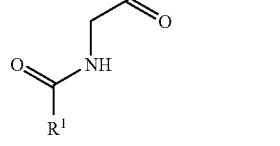
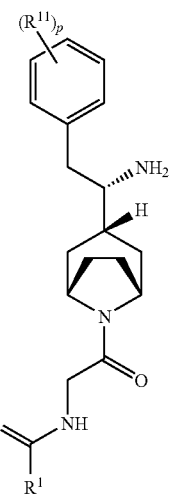
Scheme 5
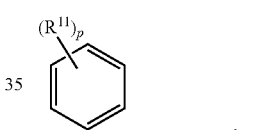
Deprotection →
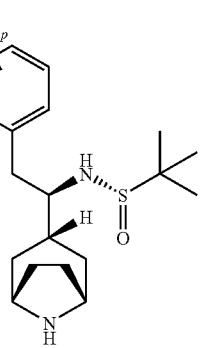
Acylation →

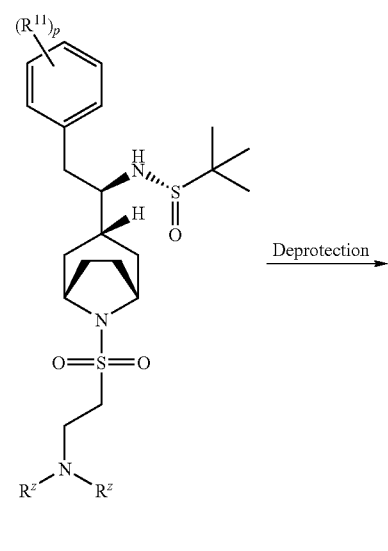
Deprotection →
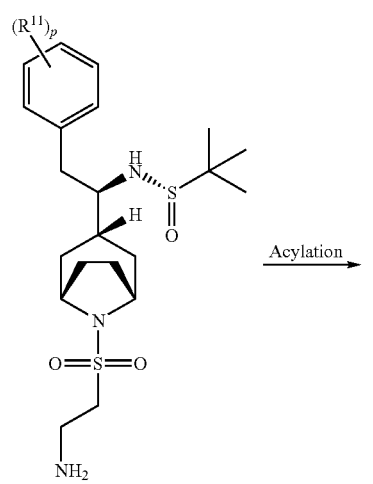
Acylation →
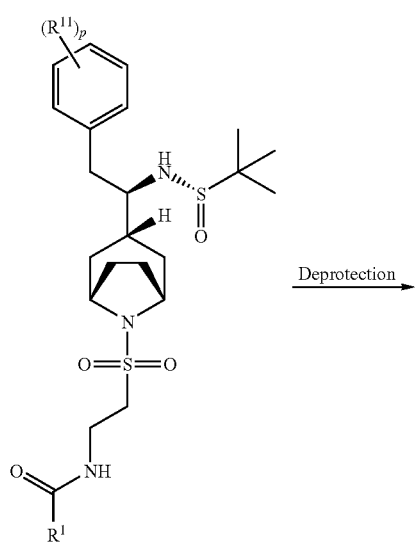
Deprotection →
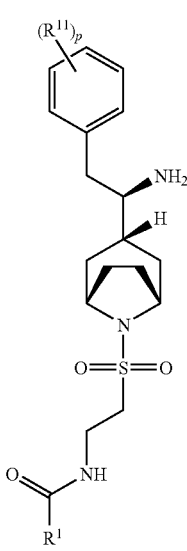
Scheme 6
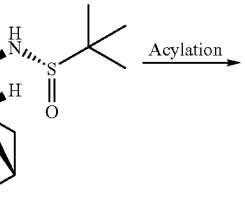
Acylation →
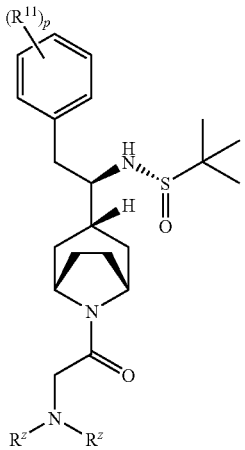
Deprotection →

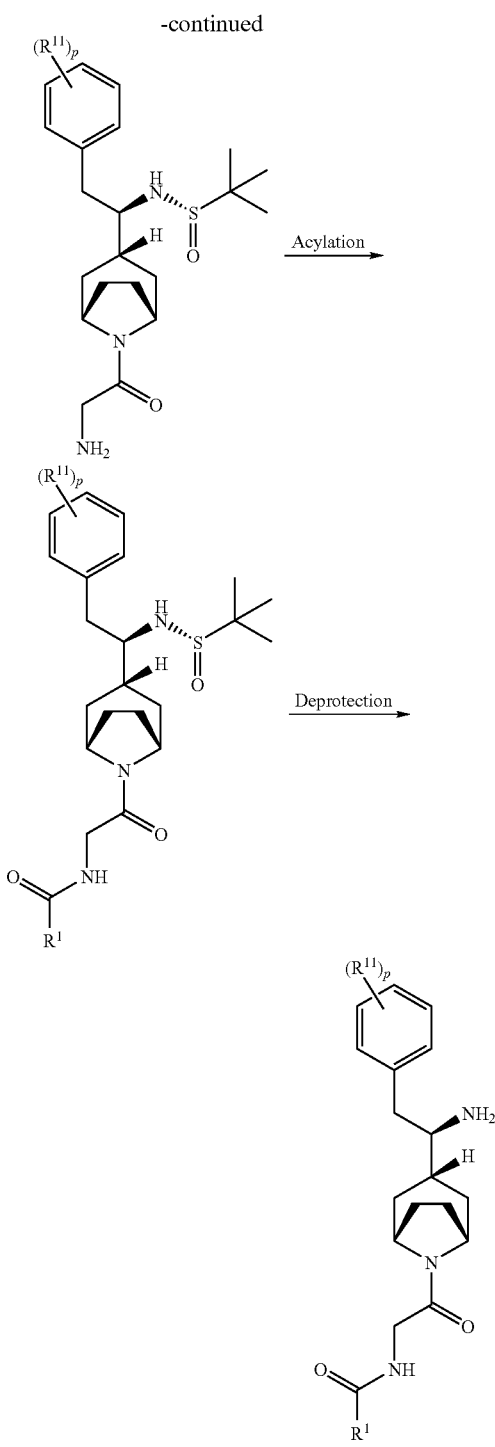

It will be understood that the processes detailed above are solely for the purpose of illustrating the invention and should not be construed as limiting. A process utilising similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Administration & Pharmaceutical Formulations

The compounds of the invention will normally be administered orally, intravenously, subcutaneously, buccally, rectally, dermally, nasally, tracheally, bronchially, by any other parenteral route, as an oral or nasal spray or via inhalation. The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion) to a host to obtain an protease-inhibitory effect. In the case of larger animals, such as humans, the compounds may be administered alone or as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

In the treatment, prevention, control, amelioration, or reduction of risk of conditions which require inhibition of DPP-IV enzyme activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, preferably once or twice per day. The dosage regimen may be adjusted to provide the optimal therapeutic response.

According to a further aspect of the invention there is thus provided a pharmaceutical composition including a compound of the invention, in admixture with a pharmaceutically acceptable adjuvant, diluent or carrier.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g. sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g. chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in micro-encapsulated form, if appropriate, with one or more of the above-mentioned excipients.

The active compounds may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Advantageously, the compounds of the invention may be orally active, have rapid onset of activity and low toxicity.

The compounds of the invention may have the advantage that they are more efficacious, less toxic, longer acting, have a broader range of activity, more potent, produce fewer side effects, more easily absorbed than, or have other useful pharmacological properties over, compounds known in the prior art.

Combination Therapies

Compounds of the invention may be administered in combination with one or more additional therapeutic agents. Accordingly, the invention provides a pharmaceutical composition comprising an additional agent. The invention also provides a product comprising a compound of the invention and an agent; as a combined preparation for simultaneous, separate or sequential use in therapy.

In particular, a composition or product of the invention may further comprise a therapeutic agent selected from anti-diabetic agents, hypolipidemic agents, anti-obesity or appetite-regulating agents, anti-hypertensive agents, HDL-increasing agents, cholesterol absorption modulators, Apo-A1 analogues and mimetics, thrombin inhibitors, aldosterone inhibitors, inhibitors of platelet aggregation, estrogen, testosterone, selective estrogen receptor modulators, selective androgen receptor modulators, chemotherapeutic agents, and 5-$HT_3$ or 5-$HT_4$ receptor modulators; or pharmaceutically acceptable salts or prodrugs thereof.

Examples of anti-diabetic agents include insulin, insulin derivatives and mimetics; insulin secretagogues, for example sulfonylureas (e.g. glipizide, glyburide or amaryl); insulinotropic sulfonylurea receptor ligands, for example meglitinides (e.g. nateglinide or repaglinide); insulin sensitisers, for example protein tyrosine phosphatase-1B (PTP-1B) inhibitors (e.g. PTP-112); GSK3 (glycogen synthase kinase-3) inhibitors, for example SB-517955, SB-4195052, SB-216763, N,N-57-05441 or N,N-57-05445; RXR ligands, for example GW-0791 or AGN-194204; sodium-dependent glucose cotransporter inhibitors, for example T-1095; glycogen phosphorylase A inhibitors, for example BAY R3401; biguanides, for example metformin; alpha-glucosidase inhibitors, for example acarbose; GLP-1 (glucagon like peptide-1), GLP-1 analogues and mimetics, for example exendin-4; DPPIV (dipeptidyl peptidase IV) inhibitors, for example DPP728, LAF237 (vildagliptin), MK-0431, saxagliptin or GSK23A; AGE breakers; and thiazolidone derivatives, for example glitazone, pioglitazone, rosiglitazone or (R)-1-{4-[5-methyl-2-(4-trifluoromethyl-phenyloxazol-4-ylmethoxy]-benzenesulfonyl}-2,3-dihydro-1H-indole-2-carboxylic acid (compound 4 of Example 19 of WO 03/043985) or a non-glitazone type PPAR-agonist (e.g. GI-262570); or pharmaceutically acceptable salts or prodrugs thereof.

Examples of hypolipidemic agents include 3-hydroxy-3-methyl-glutaryl coenzyme A (HMG-CoA) reductase inhibitors, for example lovastatin, pitavastatin, simvastatin, pravastatin, cerivastatin, mevastatin, velostatin, fluvastatin, dalvastatin, atorvastatin, rosuvastatin or rivastatin; squalene synthase inhibitors; FXR (farnesoid X receptor) ligands; LXR (liver X receptor) ligands; cholestyramine; fibrates; nicotinic acid; and aspirin; or pharmaceutically acceptable salts or prodrugs thereof.

Examples of anti-obesity/appetite-regulating agents include phentermine, leptin, bromocriptine, dexamphetamine, amphetamine, fenfluramine, dexfenfluramine, sibutramine, or list at, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine and cannabinoid receptor antagonists; or pharmaceutically acceptable salts or prodrugs thereof.

Examples of anti-hypertensive agents include loop diuretics, for example ethacrynic acid, furosemide or torsemide; diuretics, for example thiazide derivatives, chlorithiazide, hydrochlorothiazide or amiloride; angiotensin converting enzyme (ACE) inhibitors, for example benazepril, captopril, enalapril, fosinopril, lisinopril, moexipril, perinodopril, quinapril, ramipril or trandolapril; Na—K-ATPase membrane pump inhibitors, for example digoxin; neutralendopeptidase (NEP) inhibitors, for example thiorphan, terteo-thiorphan or SQ29072; ECE inhibitors, for example SLV306; dual ACE/NEP inhibitors, for example omapatrilat, sampatrilat or fasidotril; angiotensin II antagonists, for example candesartan, eprosartan, irbesartan, losartan, telmisartan or valsartan; renin inhibitors, for example aliskiren, terlakiren, ditekiren, RO-66-1132 or RO-66-1168; b-adrenergic receptor blockers, for example acebutolol, atenolol, betaxolol, bisoprolol, metoprolol, nadolol, propranolol, sotalol or timolol; inotropic agents, for example digoxin, dobutamine or milrinone; calcium channel blockers, for example amlodipine, bepridil, diltiazem, felodipine, nicardipine, nimodipine, nifedipine, nisoldipine or verapamil; aldosterone receptor antagonists; and aldosterone synthase inhibitors; or pharmaceutically acceptable salts or prodrugs thereof.

Examples of cholesterol absorption modulators include Zetia® and KT6-971, or pharmaceutically acceptable salts or prodrugs thereof.

Examples of aldosterone inhibitors include anastrazole, fadrazole and eplerenone, or pharmaceutically acceptable salts or prodrugs thereof.

Examples of inhibitors of platelet aggregation include aspirin or clopidogrel bisulfate, or pharmaceutically acceptable salts or prodrugs thereof.

Examples of chemotherapeutic agents include compounds decreasing the protein kinase activity, for example PDGF receptor tyrosine kinase inhibitors (e.g. imatinib or 4-methyl-N-[3-(4-methyl-imidazol-1-yl)-5-trifluoromethyl-phenyl]-3-(4-pyridin-3-yl-pyrimidin-2-ylamino)-benzamide), or pharmaceutically acceptable salts or prodrugs thereof.

Examples of 5-HT$_3$ or 5-HT$_4$ receptor modulators include tegaserod, tegaserod hydrogen maleate, cisapride or cilansetron, or pharmaceutically acceptable salts or prodrugs thereof.

The weight ratio of the compound of the present invention to the further active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200.

Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Use

Compounds of the invention may be useful in the therapy of a variety of diseases and conditions.

In particular, compounds of the invention may be useful in the treatment or prevention of a disease or condition selected from non-insulin-dependent diabetes mellitus, arthritis, obesity, allograft transplantation, osteoporosis, heart failure, impaired glucose metabolism or impaired glucose tolerance, neurodegenerative diseases (for example Alzheimer's disease or Parkinson disease), cardiovascular or renal diseases (for example diabetic cardiomyopathy, left or right ventricular hypertrophy, hypertrophic medial thickening in arteries and/or in large vessels, mesenteric vasculature hypertrophy or mesanglial hypertrophy), neurodegenerative or cognitive disorders, hyperglycemia, insulin resistance, lipid disorders, dyslipidemia, hyperlipidemia, hypertriglyceridemia, hypercholesterolemia, low HDL levels, high LDL levels, atherosclerosis, vascular restenosis, irritable bowel syndrome, inflammatory bowel disease (e.g. Crohn's disease or ulcerative colitis), pancreatitis, retinopathy, nephropathy, neuropathy, syndrome X, ovarian hyperandrogenism (polycystic ovarian syndrome), type 2 diabetes, growth hormone deficiency, neutropenia, neuronal disorders, tumor metastasis, benign prostatic hypertrophy, gingivitis, hypertension and osteoporosis.

The compounds may also be useful in producing a sedative or anxiolytic effect, attenuating post-surgical catabolic changes or hormonal responses to stress, reducing mortality and morbidity after myocardial infarction, modulating hyperlipidemia or associated conditions; and lowering VLDL, LDL or Lp(a) levels.

EXAMPLES

The following Examples illustrate the invention.
Terms used in the Examples:
ACN: acetonitrile
HPLC: high performance liquid chromatography
Cbz: carbobenzyloxy Intermediates A1 & A2

Intermediates A1 and A2 are prepared according to Scheme A:

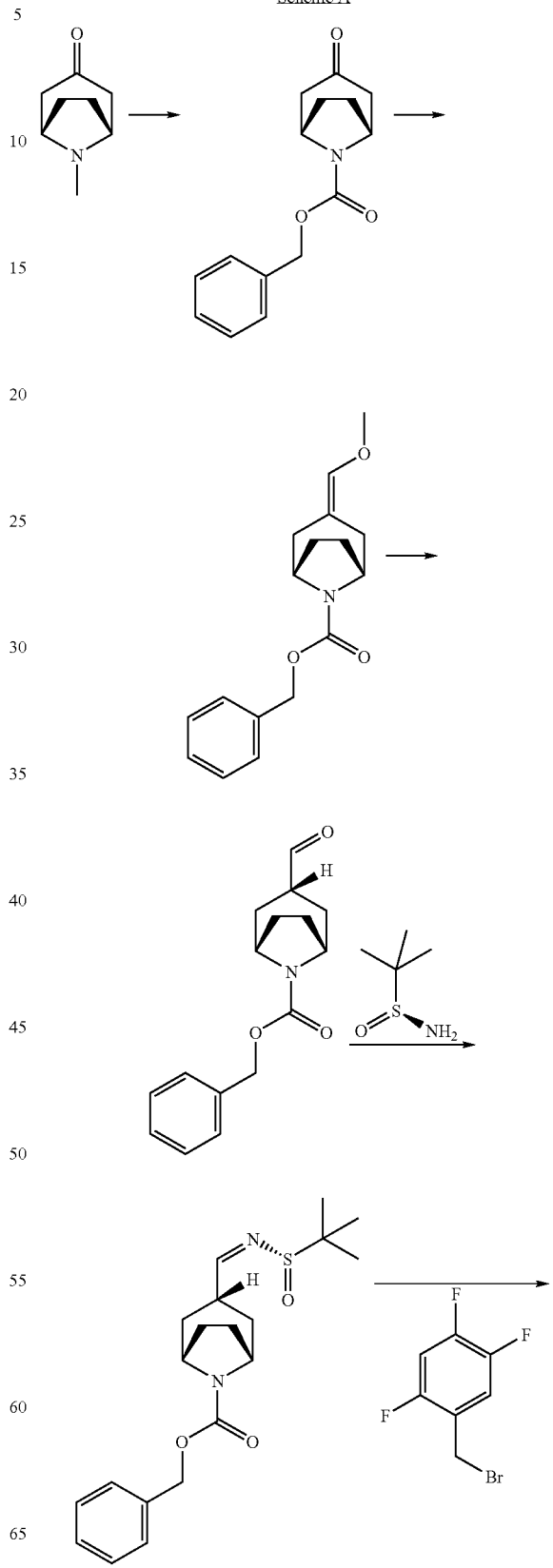

Scheme A

-continued

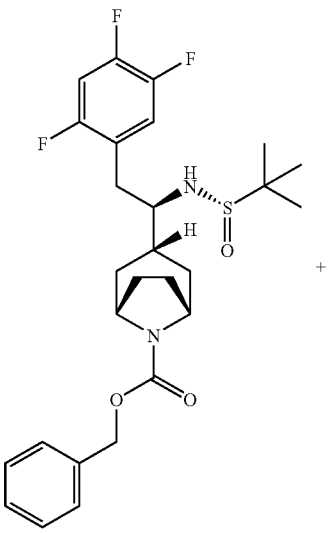

A) 3-Oxo-8-aza-bicyclo[3.2.1]octane-8-carboxylic acid benzyl ester

To tropinone (20 g, 142 mmol) in toluene (600 mL) are added benzyl chloroformate (42.2 mL, 284 mmol) and $K_2CO_3$ (118 mg, 0.853 mmol) and the resulting solution is stirred at reflux during 16 h. After evaporation of the solvent, the residue is treated with dichloromethane/aqueous saturated $NaHCO_3$, the organic phase is dried, filtered and evaporated to give a yellow oil.

MS: 260 [M+H]$^+$

TLC, Rf (cyclohexane/ethyl acetate 1/1)=0.7.

B) 3-[1-Methoxy-methylidene]-8-aza-bicyclo[3.2.1]octane-8-carboxylic acid benzyl ester To methoxymethyltriphenyl phosphonium chloride (46.6 g, 133 mmol) in tetrahydrofuran (900 mL) is added dropwise at −40° C. sodium bis(trimethylsilyl) amide in tetrahydrofuran (2M, 67 mL, 130 mmol) then the resulting red solution is stirred at −40° C. during 1 h and at 0° C. during 30 min. After cooling to −40° C., 3-oxo-8-aza-bicyclo[3.2.1]octane-8-carboxylic acid benzyl ester (27 g, 83 mmol) in tetrahydrofuran (100 mL) is added, The resulting mixture is warmed to 0° C. and stirred during 30 min. It is quenched with aqueous saturated $NH_4Cl$, extracted with dichloromethane and washed with aqueous saturated $NaHCO_3$. The organic phase is dried, filtered and evaporated to give a residue, which is purified by flash chromatography on silica gel (eluent: cyclohexane/ethyl acetate 100/0 to 7/3) to yield a yellow oil.

MS: 288 [M+H]$^+$

TLC, Rf (cyclohexane/ethyl acetate 1/1)=0.75.

C) 3-exo-Formyl-8-aza-bicyclo[3.2.1]octane-8-carboxylic acid benzyl ester

To 3-[1-methoxy-methylidene]-8-aza-bicyclo[3.2.1]octane-8-carboxylic acid benzyl ester (13 g, 40.7 mmol) in acetone (450 mL) and water (50 mL) is added 37% conc HCl in water (0.920 mL, 9.4 mmol). The resulting mixture is stirred at 50° C. during 24 h. After evaporation of the solvent, the residue is treated with dichloromethane/aqueous saturated $NaHCO_3$, the organic phase is dried, filtered and evaporated to give a residue, which is purified by flash chromatography on silica gel (eluent: cyclohexane/ethyl acetate 100/0 to 7/3) to yield a yellow oil.

MS: 274 [M+H]$^+$

TLC, Rf (cyclohexane/ethyl acetate 1/1)=0.42.

D) 3-exo-{[(S)-2-Methyl-propane-2-sulfinylimino]-methyl}-8-aza-bicyclo[3.2.1]octane-8-carboxylic acid benzyl ester (S)-2-methyl-2-propanesulfinamide (543 mg, 4.39 mmol), pyridinium toluene-4-sulfonate (46 mg, 0.183 mmol) and $MgSO_4$ (2.21 g, 18.3 mmol) are stirred in dichloroethane (15 mL) for 1 h, before the addition of 3-exo-formyl-8-aza-bicyclo[3.2.1]octane-8-carboxylic acid benzyl ester (1 g, 3.66 mmol) in dichloroethane (5 mL). The resulting mixture is stirred at 50° C. during 16 h, it is filtered and evaporated to give a residue, which is purified by flash chromatography on silica gel (eluent: cyclohexane/ethyl acetate 100/0 to 50/50) to yield a yellow oil.

MS: 377 [M+H]$^+$

TLC, Rf (cyclohexane/ethyl acetate 1/1)=0.37.

E) 3-exo-[(R)-1-((S-2-Methyl-propane-2-sulfonylamino)-2-(2,4,5-trifluoro-phenyl)-ethyl]-8-aza-bicyclo[3.2.1]octane-8-carboxylic acid benzyl ester (Intermediate A1); and 3-exo-[(S)-1-((S)-2-Methyl-propane-2-sulfinylamino)-2-(2,4,5-trifluoro-phenyl)-ethyl]-8-aza-bicyclo[3.2.1]octane-8-carboxylic acid benzyl ester (Intermediate A2)

To stirred magnesium turnings (18 mg, 0.75 mmol) in diethyl ether (0.5 mL) is added 2,4,5-trifluorobenzylbromide (112 mg, 0.499 mmol) in diethyl ether (0.5 mL). After stirring during 30 min at rt, the resulting suspension is added at 0° C. to a solution of 3-exo-{[(S)-2-methyl-propane-2-sulfinylimino]-methyl}-8-aza-bicyclo[3.2.1]octane-8-carboxylic acid benzyl ester (179 mg, 0.333 mmol) in dichloromethane (1 mL). The resulting mixture is stirred for 4 h at rt, before it is quenched at 0° C. with saturated aqueous NH₄Cl and extracted with dichloromethane. The organic phase is dried, filtered and evaporated to give a residue, which is purified by flash chromatography on silica gel (eluent: cyclohexane/ethyl acetate).

Intermediate A1: MS: 523 [M+H]⁺
  TLC, Rf (cyclohexane/ethyl acetate 1/1)=0.17

Intermediate A2: MS: 523 [M+H]⁺
  TLC, Rf (cyclohexane/ethyl acetate 1/1)=0.12

Intermediates A'1 & A'2
  Intermediates A'1 and A'2 are prepared according to Scheme A':

Scheme A'

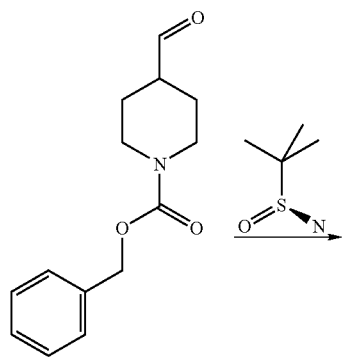

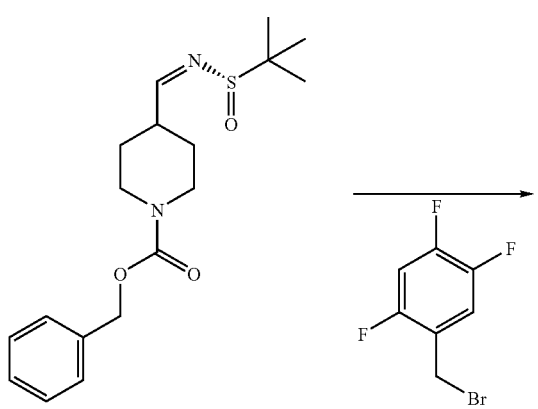

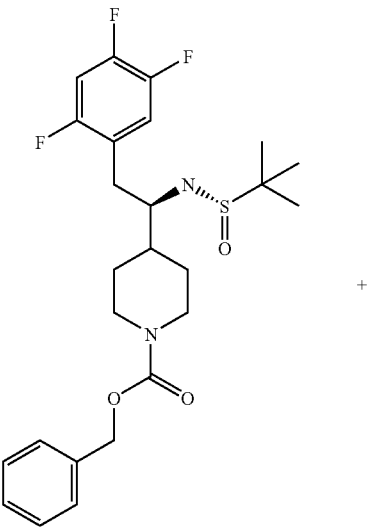

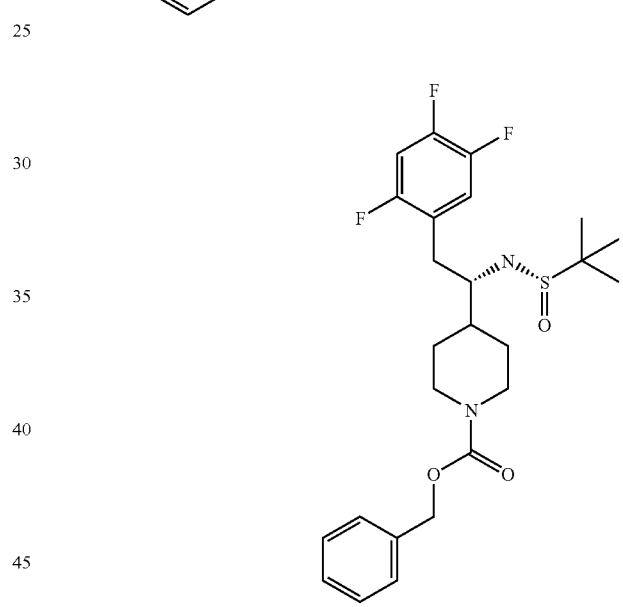

4-[(R)-1-((S)-2-Methyl-propane-2-sulfinylamino)-2-(2,4,5-trifluoro-phenyl)-ethyl]-piperidine-1-carboxylic acid benzyl ester (Intermediate A1); and 4-[(S)-1-((S)-2-Methyl-propane-2-sulfinylamino)-2-(2,4,5-trifluoro-phenyl)-ethyl]-piperidine-1-carboxylic acid benzyl ester (Intermediate A2)

The title compounds are prepared analogously as described in Scheme A using 4-Formyl-piperidine-1-carboxylic acid benzyl ester instead of 3-exo-formyl-8-aza-bicyclo[3.2.1]octane-8-carboxylic acid benzyl ester Intermediate A'1: MS: 497.1 [M+H]⁺
  TLC, Rf (cyclohexane/ethyl acetate 1/1)=0.23

Intermediate A'2: MS: 497.1 [M+H]⁺
  TLC, Rf (cyclohexane/ethyl acetate 1/1)=0.10

Example B1
N-(2-{3-exo-[(S)-1-Amino-2-(2,4,5-trifluoro-phenyl)-ethyl]-8-aza-bicyclo[3.2.1]octane-8-sulfonyl}-ethyl)-acetamide
This compound is prepared according to Scheme B:
Scheme B
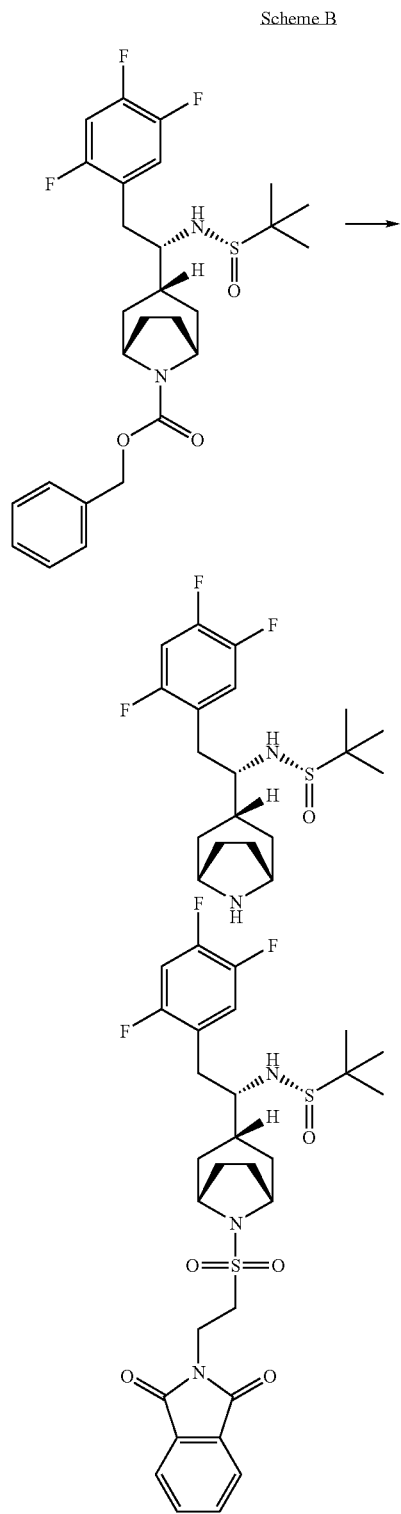
-continued
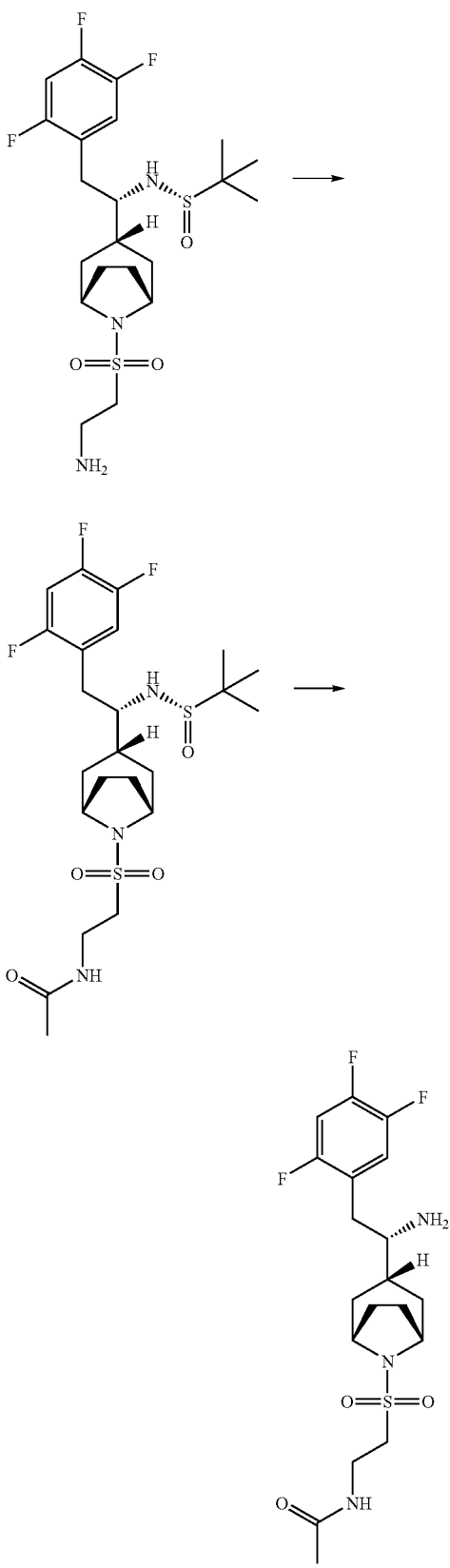

A) 3-exo-[(S)-1-((S)-2-Methyl-propane-2-sulfinylamino)-2-(2,4,5-trifluoro-phenyl)-ethyl]-8-aza-bicyclo[3.2.1]octane To 3-exo-[(S)-1-((S)-2-methyl-propane-2-sulfinylamino)-2-(2,4,5-trifluoro-phenyl)-ethyl]-8-aza-bicyclo[3.2.1]octane-8-carboxylic acid benzyl ester (Intermediate A2; 300 mg, 0.574 mmol) in ethylacetate (10 mL) is added 10% Pd/C (610 mg, 0.57 mmol). The resulting mixture is stirred and put under H$_2$-atmosphere. After 1 h of stirring, the suspension is filtered through celite and evaporated to give a residue, which is purified by preparative HPLC (Column Interchrom C18 ODB 10 μm 28×250, Gradient: 0-2.5 min 5% ACN, 2.5-25.5 min 5-100% ACN, 25.5-30 min 100% CAN) to yield the title compound.

MS: 389 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.06 min.

B) N-(2-{3-exo-[(S)-1-((S)-2-Methyl-propane-2-sulfinylamino)-2-(2,4,5-trifluoro-phenyl)-ethyl]-8-aza-bicyclo[3.2.1]octane-8-sulfonyl}-ethyl)-phthalimide To 3-exo-[(S)-1-((S)-2-methyl-propane-2-sulfinylamino)-2-(2,4,5-trifluoro-phenyl)-ethyl]-8-aza-bicyclo[3.2.1]octane (540 mg, 1.2 mmol) in dichloromethane/1M NaOH (1/1, 5 mL) is added 2-phthalimidoethane sulfonyl chloride (1.101 g, 3.59 mmol) then the resulting mixture is stirred at 50° C. during 16 h. It is extracted with dichloromethane, the organic phase is dried and evaporated to give a white solid.

MS: 626 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.44 min.

C) 2-{3-exo-[(S)-1-((S)-2-Methyl-propane-2-sulfinylamino)-2-(2,4,5-trifluoro-phenyl)-ethyl]-8-aza-bicyclo[3.2.1]octane-8-sulfonyl}-ethylamine To N-(2-{3-exo-[(S)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-phthalimide (100 mg, 0.160 mmol) in ethanol (2 mL) is added hydrazine monohydrate (0.396 mL, 8 mmol) and the resulting solution is stirred at rt during 12 h. After extraction with dichloromethane and aqueous saturated NaHCO$_3$, the organic phase is dried and evaporated to give a residue, which is purified by preparative HPLC (Column Waters C18 ODB 5 μm 19×50, Gradient: 0-2.5 min 5% ACN, 2.5-12.5 min 5-100% ACN, 12.5-15 min 100% ACN) to yield a white solid.

MS 496 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.05 min.

D) N-(2-{3-exo-[(S)-1-((S)-2-Methyl-propane-2-sulfinylamino)-2-(2,4,5-trifluoro-phenyl)-ethyl]-8-aza-bicyclo[3.2.1]octane-8-sulfonyl}-ethyl)-acetamide To 2-{3-exo-[(S)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (27 mg, 0.054 mmol) in acetic acid (1 mL) is added acetic anhydride (7.86 μL, 0.081 mmol) and the resulting solution is stirred at rt during 3 h. After extraction with dichloromethane and aqueous saturated NaHCO$_3$, the organic phase is dried and evaporated to give a colorless gum.

MS 538 [M+H]+

E) N-(2-{3-exo-[(S)-1-Amino-2-(2,4,5-trifluoro-phenyl)-ethyl]-8-aza-bicyclo[3.2.1]octane-8-sulfonyl}-ethyl)-acetamide To N-(2-{3-exo-[(S)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-acetamide (29.3 mg, 0.545 mmol) in dioxane (3 mL) is added 4N HCl in dioxane (2 mL). The resulting mixture is stirred at rt during 1 h. The solution is frozen and lyophilised to give a white solid.

MS: 435 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.95 min.

Example C1

N-(2-{3-exo-[(S)-1-Amino-2-(2,4,5-trifluoro-phenyl)-ethyl]-8-aza-bicyclo[3.2.1]oct-8-yl}-2-oxo-ethyl)-acetamide This compound is prepared according to Scheme C:

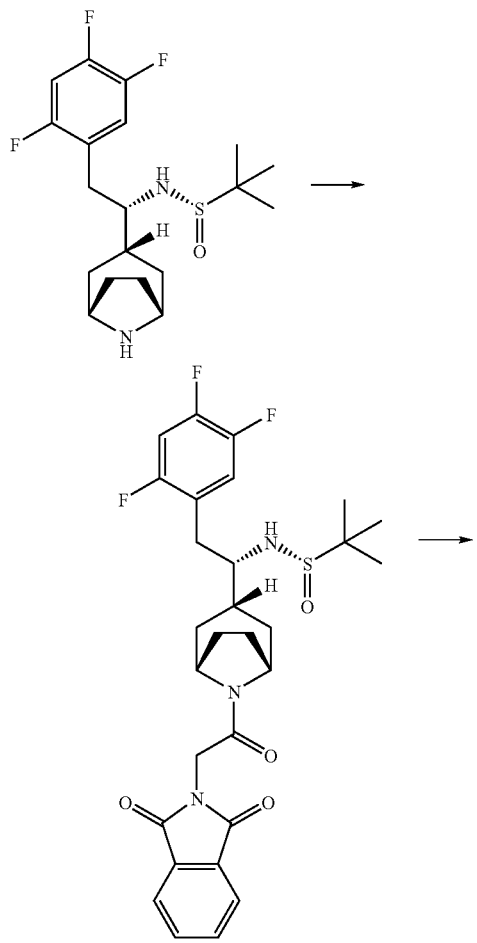

Scheme C

-continued

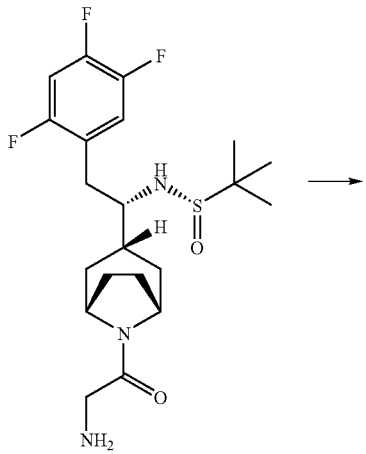

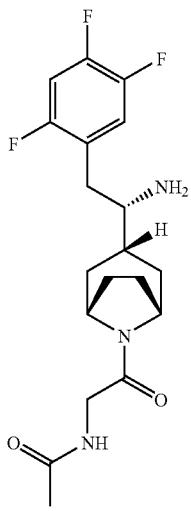

A) N-(2-{3-exo-[(S)-1-((S-2-Methyl-propane-2-sulfinylamino)-2-(2,4,5-trifluoro-phenyl)-ethyl]-8-aza-bicyclo[3.2.1]oct-8-yl}-2-oxo-ethyl)-phthalimide To a solution of N-phthaloylglycine (291 mg, 1.41 mmol) in acetonitrile (7 mL) is added benzotriazol-1-yloxytripyrrolidinophosphonium hexafluorophosphate (805 mg, 1.54 mmol) and the resulting mixture is stirred at rt during 1 h before addition of 3-exo-[(S)-1-((S)-2-methyl-propane-2-sulfinylamino)-2-(2,4,5-trifluoro-phenyl)-ethyl]-8-aza-bicyclo[3.2.1]octane (500 mg, 1.29 mmol) and triethylamine (720 µL, 5.16 mmol) in acetonitrile (5 mL). The resulting solution is stirred at rt during 16 h and is evaporated before purification by preparative HPLC (Column Interchrom C18 ODB 10 µm 28×250, Gradient: 0-2.5 min 5% ACN, 2.5-25.5 min 5-100% ACN, 25.5-30 min 100% ACN) to yield a yellow solid.

MS: 576 [M+H]+

B) N-(2-{3-exo-[(S)-1-Amino-2-(2,4,5-trifluoro-phenyl)-ethyl]-8-aza-bicyclo[3.2.1]oct-8-yl}-2-oxo-ethyl)-acetamide The title compound is prepared analogously as described in example B1 using N-(2-{3-exo-[(S)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-phthalimide instead of N-(2-{3-exo-[(S)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-phthalimide.

MS: 384 [M+H]

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.28 min.

Example C2

Cyclopropanesulfonic acid (2-{3-exo-[(S)-1-amino-2-(2,4,5-trifluoro-phenyl)-ethyl]-8-aza-bicyclo[3.2.1]oct-8-yl}-2-oxo-ethyl)-amide This compound is also prepared according to Scheme C.

A) Cyclopropanesulfonic acid (2-{3-exo-[(S)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide To a solution of 2-{3-exo-[(S)-1-((S)-2-methyl-propane-2-sulfinylamino)-2-(2,4,5-trifluoro-phenyl)-ethyl]-8-aza-bicyclo[3.2.1]oct-8-yl}-2-oxo-ethylamine (50 mg, 0.112 mmol) in dichloromethane (1 mL) are added triethylamine (32 µL, 0.224 mmol) and cyclopropanesulfonyl chloride (14 µL, 0.134 mmol). The resulting solution is stirred at rt during 16 h before evaporation and purification by preparative HPLC (Column Waters C18 ODB 5 µm 19×50, Gradient: 0-2.5 min 5% ACN, 2.5-12.5 min 5-100% ACN, 12.5-15 min 100% ACN) to yield a colorless gum.

MS 550 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

B) Cyclopropanesulfonic acid (2-{3-exo-[(S)-1-amino-2-(2,4,5-trifluoro-phenyl)-ethyl]-8-aza-bicyclo[3.2.1]oct-8-yl}-2-oxo-ethyl)-amide To cyclopropanesulfonic acid (2-{3-exo-[(S)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide (27 mg, 0.049 mmol) in dioxane (0.5 mL) is added 4N HCl in dioxane (0.5 mL). The resulting mixture is stirred at rt during 1 h. The solution is frozen and lyophilised to give a white solid before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield a colorless gum.

MS 446 [M+H]+

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.5 min.

Example D1

5-Methyl-pyrazine-2-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide This compound is prepared according to Scheme D:

Scheme D

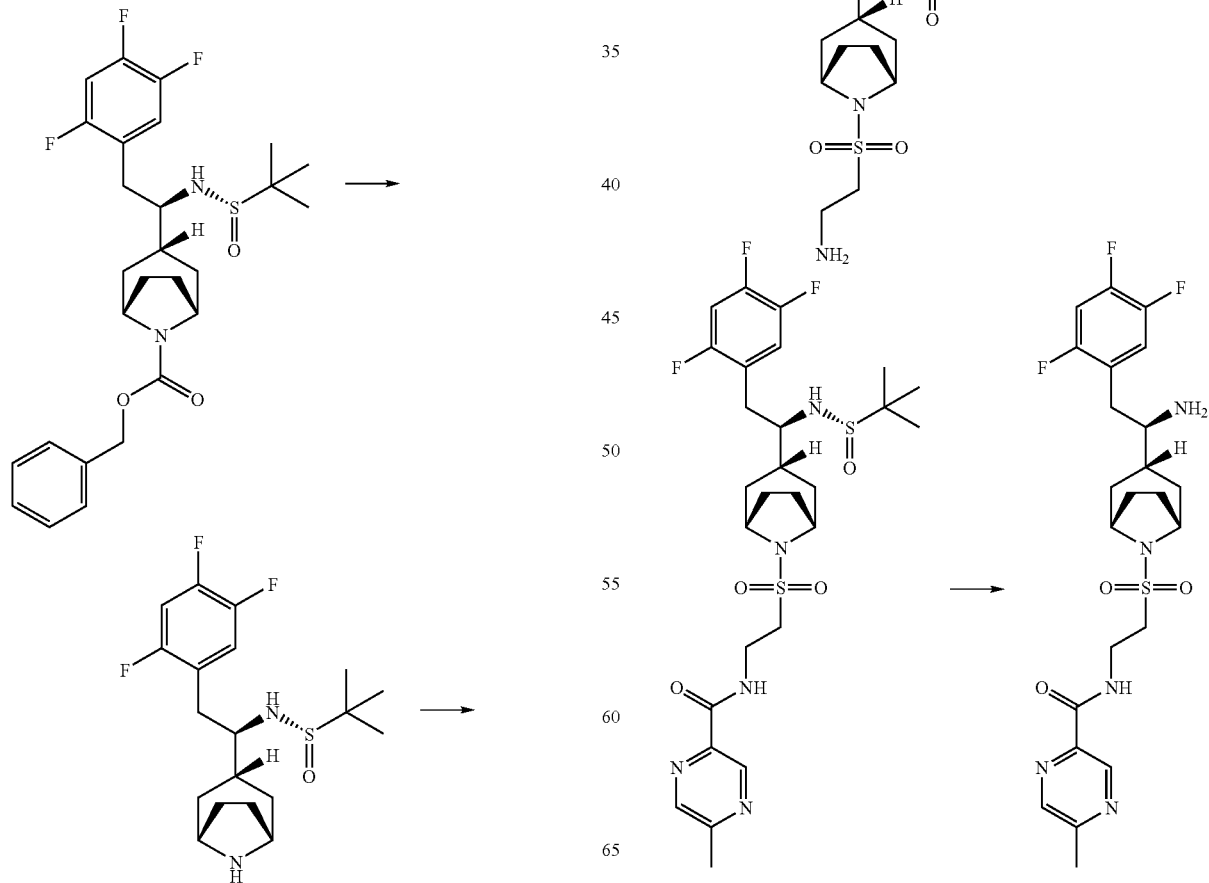

A) 3-exo-[(R)-1-((S)-2-Methyl-propane-2-sulfinylamino)-2-(2,4,5-trifluoro-phenyl)-ethyl]-8-aza-bicyclo[3.2.1]octane To 3-exo-[(R)-1-((S)-2-methyl-propane-2-sulfinylamino)-2-(2,4,5-trifluoro-phenyl ethyl]-8-aza-bicyclo[3.2.1]octane-8-carboxylic acid benzyl ester (Intermediate A1; 7.74 g, 14.8 mmol) in ethanol (200 mL) is added 10% Pd/C (16 g, 15 mmol), the resulting mixture is stirred and put under $H_2$-atmosphere. After 1 h of stirring, the suspension is filtered through celite and evaporated to yield the title compound.

MS: 389 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.91 min.

B) N-(2-{3-exo-[(R)-1-((S-2-Methyl-propane-2-sulfinylamino)-2-(2,4,5-trifluoro-phenyl)-ethyl]-8-aza-bicyclo[3.2.1]octane-8-sulfonyl}-ethyl)-phthalimide To 3-exo-[(R)-1-((S)-2-methyl-propane-2-sulfinylamino)-2-(2,4,5-trifluoro-phenyl)-ethyl]-8-aza-bicyclo[3.2.1]octane (265 mg, 0.68 mmol) in dichloromethane/1M NaOH (1/1, 5 mL) is added 2-phthalimidoethane sulfonyl chloride (577 mg, 2.05 mmol) then the resulting mixture is stirred at 50° C. during 16 h. It is extracted with dichloromethane, the organic phase is dried and evaporated to give a white solid.

MS: 626 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

C) 2-{3-exo-[(R)-1-((S)-2-Methyl-propane-2-sulfinylamino)-2-(2,4,5-trifluoro-phenyl)-ethyl]-8-aza-bicyclo[3.2.1]octane-8-sulfonyl}-ethylamine To N-(2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-phthalimide (256 mg, 0.409 mmol) in ethanol (3 mL) is added hydrazine monohydrate (1.01 mL, 20.5 mmol) and the resulting solution is stirred at rt during 12 h. After extraction with dichloromethane and aqueous saturated $NaHCO_3$, the organic phase is dried and evaporated to yield a colorless oil.

MS: 496 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.95 min.

D) 5-Methyl-pyrazine-2-carboxylic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide To 5-methylpyrazinecarboxylic acid (18.8 mg, 0.133 mmol) in acetonitrile (2 mL) is added benzotriazol-1-yloxytripyrrolidinophosphonium hexafluorophosphate (75.6 mg, 0.145 mmol) and the resulting mixture is stirred at rt during 1 h. After this time, 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (60 mg, 0.121) and triethylamine (50.5 µL, 0.363 mmol) in acetonitrile are added and the solution is shaken at rt during 16 h. The solution is purified by preparative HPLC (Column Waters C18 ODB 5 µm 19×50, Gradient: 0-2.5 min 5% ACN, 2.5-12.5 min 5-100% ACN, 12.5-15 min 100% CAN) to yield a white solid.

MS: 616 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

E) 5-Methyl-pyrazine-2-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide To 5-methyl-pyrazine-2-carboxylic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide (48.5 mg, 0.0788 mmol) in dioxane (3 mL) is added 4N HCl in dioxane (1 mL). The resulting mixture is stirred at rt during 1 h before it is purified by preparative HPLC (Column Waters C18 ODB 5 µm 19×50, Gradient: 0-2.5 min 5% ACN, 2.5-12.5 min 5-100% ACN, 12.5-15 min 100% CAN) to yield a white solid.

MS 513 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.95 min.

Example D2

Cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide This compound is prepared according to Scheme D.

A) Cyclopropanesulfonic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide To a solution of 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (40 mg, 0.078 mmol) in dichloroethane (2 mL) are added triethylamine (32.7 µL, 0.235 mmol), 4-dimethylaminopyridine (0.95 mg, 0.007 mmol) and cyclopropanesulfonyl chloride (16.8 µL, 0.157 mmol). The resulting solution is stirred at rt during 2 h before evaporation to yield the title compound.

MS: 600 [M+H]+

HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 3.28 min.

B) Cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide To Cyclopropanesulfonic acid (2-{3-exo-[(R)-1-((S-2-methyl-propane-2-sulfinylamino)-2-(2,4,5-trifluoro-phenyl)-ethyl]-8-aza-bicyclo[3.2.1]octane-8-sulfonyl}-ethyl)-amide (63 mg, 0.102 mmol) in dioxane (2 mL) is added 4N HCl in dioxane (3 mL). The resulting mixture is stirred at rt during 1 h. The solution is frozen and lyophilised to give a white solid before purification by preparative HPLC (Column Waters C18 ODB 5 µm 19×50, Gradient: 0-2.5 min 5% ACN, 2.5-12.5 min 5-100% ACN, 12.5-15 min 100% ACN) to yield title compound.

MS: 496 [M+H]+

HPLC (Waters Symmetry C18 3.5 µm 2.1×50 mm, 6 min method (0-3 min 5-95% ACN, 3.5-5.5 min 95% ACN, 5.5-5.55 min 95-5% ACN, 5.55-6 min 5% ACN): 2.56 min.

Example D2a

Cyclopropanesulfonic acid (2-{3-exo-[(R)-1-amino-2-(2,4,5-trifluoro-phenyl)-ethyl]-aza-bicyclo[3.2.1]octane-8-sulfonyl}-ethyl)-amide maleate This compound is prepared according to Scheme Da:

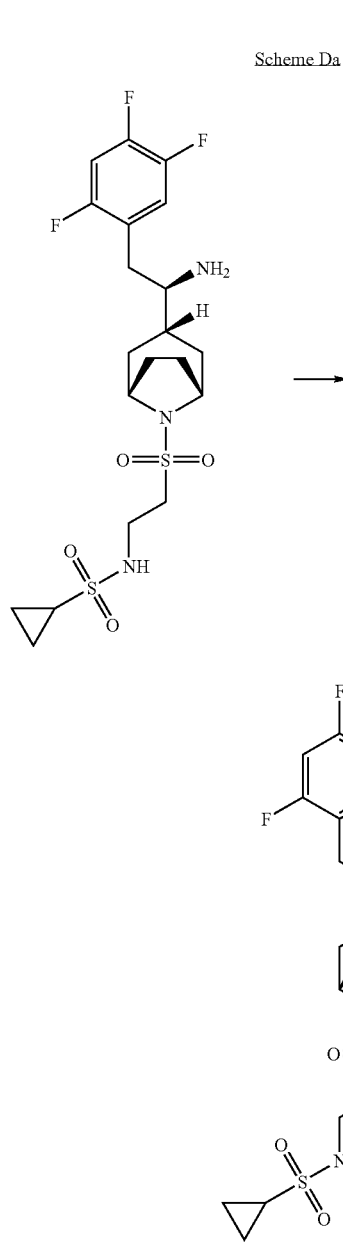

Example D2b

Cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide toluene-4-sulfonate This compound is prepared according to Scheme Db:

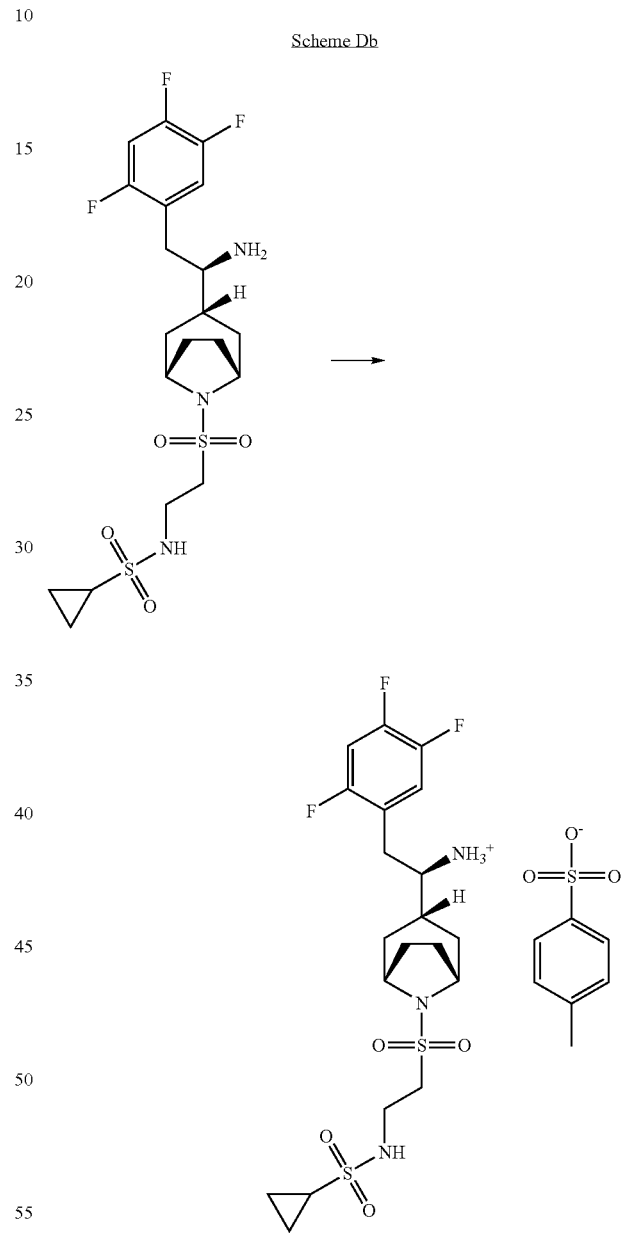

A solution of maleic acid in ethyl acetate (1 molequivalent; 0.1 M) is added to a solution of Cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide freebase (20 mg) in ethyl acetate (1 mL) under stirring. The obtained mixture is left to precipitate for one hour before it is stirred overnight. The resulting white suspension is filtered and the obtained solid is dried to yield the title compound.

A solution of toluene-4-sulfonic acid in ethyl acetate (1 molequivalent; 0.1 M) is added to a solution of Cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide freebase (50 mg) in ethyl acetate (1 mL) under stirring. The obtained mixture is left to precipitate for 2 hours before it is stirred overnight. The resulting white suspension is filtered and the obtained solid is dried to yield the title compound.

Example D3

N-(2-{3-exo-[(R)-1-Amino-2-(2,4,5-trifluoro-phenyl)-ethyl]-8-aza-bicyclo[3.2.1]octane-8-sulfonyl}-ethyl)-acetamide This compound is prepared according to Scheme D:

A) N-(2-{3-exo-[(R)-1-((S)-2-Methyl-propane-2-sulfinylamino)-2-(2,4,5-trifluoro-phenyl)-ethyl]-8-aza-bicyclo[3.2.1]octane-8-sulfonyl}-ethylacetamide To 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (100 mg, 0.202 mmol) in acetic acid (2 mL) is added acetic anhydride (29.1 µL, 0.303 mmol) and the resulting solution is stirred at rt during 3 h. After extraction with dichloromethane and aqueous saturated $NaHCO_3$, the organic phase is dried and evaporated to give the title compound.
MS: 538 [M+H]+

B) N-(2-{3-exo-[(R)-1-Amino-2-(2,4,5-trifluoro-phenyl)-ethyl]-8-aza-bicyclo[3.2.1]octane-8-sulfonyl}-ethyl)-acetamide To N-(2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-acetamide (108 mg, 0.199 mmol) in dioxane (2 mL) is added 4N HCl in dioxane (3 mL). The resulting mixture is stirred at rt during 1 h. The solution is frozen and lyophilised to give a white solid before purification by preparative HPLC (Column Waters C18 ODB 5 µm 19×50, Gradient: 0-2.5 min 5% ACN, 2.5-12.5 min 5-100% ACN, 12.5-15 min 100% ACN) to yield the title compound.
MS: 434 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.84 min.

Example D3a

N-(2-{3-exo-[(R)-1-Amino-2-(2,4,5-trifluoro-phenyl)-ethyl]-8-aza-bicyclo[3.2.1]octane-8-sulfonyl}-ethyl)-acetamide maleate The title compound is prepared analogously as described in example D2a using N-(2-{3-exo-[(R)-1-Amino-2-(2,4,5-trifluoro-phenyl)-ethyl]-8-aza-bicyclo[3.2.1]octane-8-sulfonyl}-ethyl)acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example D3b

N-(2-{3-exo-[(R)-1-Amino-2-(2,4,5-trifluoro-phenyl)-ethyl]-8-aza-bicyclo[3.2.1]octane-8-sulfonyl}-ethyl)-acetamide toluene-4-sulfonate The title compound is prepared analogously as described in example D2b using N-(2-{3-exo-[(R)-1-Amino-2-(2,4,5-trifluoro-phenyl)-ethyl]-8-aza-bicyclo[3.2.1]octane-8-sulfonyl}-ethyl)-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D4

Dimethylsulfamic acid (2-{3-exo-[(R)-1-amino-2-(2,4,5-trifluoro-phenyl)-ethyl]-8-aza-bicyclo[3.2.1]octane-8-sulfonyl}-ethyl)-amide The title compound is prepared analogously as described in example D2 using dimethylsulfamoyl chloride instead of cyclopropanesulfonyl chloride.
MS: 499 [M+H]
HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 0.94 min.

Example D4a

Dimethylsulfamic acid (2-{3-exo-[(R)-1-amino-2-(2,4,5-trifluoro-phenyl)-ethyl]-8-aza-bicyclo[3.2.1]octane-8-sulfonyl}-ethyl)-amide maleate The title compound is prepared analogously as described in example D2a using Dimethylsulfamic acid (2-{3-exo-[(R)-1-amino-2-(2,4,5-trifluoro-phenyl)-ethyl]-8-aza-bicyclo[3.2.1]octane-8-sulfonyl}-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D4b

Dimethylsulfamic acid (2-{3-exo-[(R)-1-amino-2-(2,4,5-trifluoro-phenyl)-ethyl]-8-aza-bicyclo[3.2.1]octane-8-sulfonyl}-ethyl)-amide toluene-4-sulfonate The title compound is prepared analogously as described in example D2b using Dimethylsulfamic acid (2-{3-exo-[(R)-1-amino-2-(2,4,5-trifluoro-phenyl)-ethyl]-8-aza-bicyclo[3.2.1]octane-8-sulfonyl}ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl)ethyl}-amide.

Example D5

N-(2-{3-exo-[(R)-1-Amino-2-(2,4,5-trifluoro-phenyl)-ethyl]-8-aza-bicyclo[3.2.1]octane-sulfonyl}-ethyl)-4-methoxy-benzenesulfonamide The title compound is prepared analogously as described in example D2 using 4-methoxyphenylsulfonyl chloride instead of cyclopropanesulfonyl chloride.
MS: 562 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.0 min.

Example D5a

N-(2-{3-exo-[(R)-1-Amino-2-(2,4,5-trifluoro-phenyl)-ethyl]-8-aza-bicyclo[3.2.1]octane-8-sulfonyl}-ethyl)-4-methoxy-benzenesulfonamide maleate The title compound is prepared analogously as described in example D2a using N-(2-{3-exo-[(R)-1-Amino-2-(2,4,5-trifluoro-phenyl)-ethyl]-8-aza-bicyclo[3.2.1]octane-8-sulfonyl}-ethyl)-4-methoxy-benzenesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D5b

N-(2-{3-exo-[(R)-1-Amino-2-(2,4,5-trifluoro-phenyl)-ethyl]-8-aza-bicyclo[3.2.1]octane-8-sulfonyl}-ethyl)-4-methoxy-benzenesulfonamide toluene-4-sulfonate The title compound is prepared analogously as described in example D2b using N-(2-{3-exo-[(R)-1-Amino-2-(2,4,5-trifluoro-phenyl)-ethyl]-8-aza-bicyclo[3.2.1]octane-8-sulfonyl}-ethyl)-4-methoxy-benzenesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D6

Tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide The title compound is prepared analogously as described in example D1 using tetrahydro-2H-pyran-4-carboxylic acid instead of 5-methylpyrazinecarboxylic acid.
MS: 505 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.92 min.

Example D7

Morpholine-4-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide The title compound is prepared analogously as described in example D2 using 4-morpholinesulfonyl chloride instead of cyclopropanesulfonyl chloride.
MS: 541 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.13 min.

Example D8

2-(1,3-Dioxo-1,3-dihydro-isoindol-2-yl)-ethanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide A) 2-(1,3-Dioxo-1,3-dihydro-isoindol-2-yl)-ethanesulfonic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide To a solution of 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (100 mg, 0.202 mmol) in dichloromethane/2N NaOH (2 mL, 1/1) are 2-phtalimidoethanesulfonyl chloride (167 mg, 0.605 mmol). The resulting solution is stirred at 50° C. during 2 h before extraction and evaporation of organic phase to yield the crude compound. It is purified by preparative HPLC (Column Waters C18 ODB 5 μm 19×50, Gradient: 0-2.5 min 5% ACN, 2.5-12.5 min 5-100% ACN, 12.5-15 min 100% ACN) to yield title compound.
MS: 734 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.43 min.

B) 2-(1,3-Dioxo-1,3-dihydro-isoindol-2-yl)-ethanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide To 2-(1,3-Dioxo-1,3-dihydroisoindol-2-yl)ethanesulfonic acid (2-{3-exo-[(R)-1-((S)-2-methyl-propane-2-sulfinylamino)-2-(2,4,5-trifluoro-phenyl-ethyl]-8-aza-bicyclo [3.2.1]octane-8-sulfonyl}-ethyl)-amide (49 mg, 0.057 mmol) in dioxane (3 mL) is added 4N HCl in dioxane (3 mL). The resulting mixture is stirred at rt during 1 h. The solution is frozen and lyophilised to give a white solid before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield title compound.
MS: 629 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example D9

N-(2-{3-exo-[(R)-1-Amino-2-(2,4,5-trifluoro-phenyl)-ethyl]-8-aza-bicyclo[3.2.1]octane-8-sulfonyl}-ethyl)-3-(1,3-dioxo-1,3-dihydro-isoindol-2-yl)-propionamide The title compound is prepared analogously as described in example D1 using 2-phtamilidoethanecarboxylic acid instead of 5-methylpyrazinecarboxylic acid.
MS: 593 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.8 min.

Example D10

(2-{3-exo-[(R)-1-Amino-2-(2,4,5-trifluoro-phenyl)-ethyl]-8-aza-bicyclo[3.2.1]octane-8-sulfonyl}-ethyl)-carbamic acid 2-methoxy-ethyl ester The title compound is prepared analogously as described in example D8 using chloroformic acid 2-methoxyethylester instead of 2-phtalimidoethanesulfonyl chloride.
MS: 494 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.14 min.

Example D10a (2-{3-exo-[(R)-1-Amino-2-(2,4,5-trifluoro-phenyl)-ethyl]-8-aza-bicyclo[3.2.1]octane-8-sulfonyl}-ethyl)-carbamic acid 2-methoxy-ethyl ester maleate The title compound is prepared analogously as described in example D2a using (2-{3-exo [(R)-1-Amino-2-(2,4,5-trifluoro-phenyl)-ethyl]-8-aza-bicyclo[3.2.1]octane-8-sulfonyl}-ethyl)-carbamic acid 2-methoxy-ethyl ester instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D10b (2-{3-exo-[(R)-1-Amino-2-(2,4,5-trifluoro-phenyl)-ethyl]-8-aza-bicyclo[3.2.1]octane-4-sulfonyl}-ethyl)-carbamic acid 2-methoxy-ethyl ester toluene-4-sulfonate The title compound is prepared analogously as described in example D2b using (2-{3-exo-[(R)-1-Amino-2-(2,4,5-trifluoro-phenyl)-ethyl]-8-aza-bicyclo[3.2.1]octane-8-sulfonyl}-ethyl)-carbamic acid 2-methoxy-ethyl ester instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D11

N-(2-{3-exo-[(R)-1-Amino-2-(2,4,5-trifluoro-phenyl)-ethyl]-8-aza-bicyclo[3.2.1]octane-8-sulfonyl}-ethyl)-4-methoxy-benzamide The title compound is prepared analogously as described in example D1 using p-anisic acid instead of 5-methylpyrazinecarboxylic acid.
MS: 526 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

Example D12

(2-{3-exo-[(R)-1-Amino-2-(2,4,5-trifluoro-phenyl)-ethyl]-8-aza-bicyclo[3.2.1]octane-8-sulfonyl}-ethyl)-carbamic acid 1,1-dioxo-benzothiophen-2-yl-methyl ester The title compound is prepared analogously as described in example D8 using 1,1-dioxobenzothiophen-2-yl-methylchloroformate instead of 2-phtalimidoethanesulfonyl chloride.
MS: 614 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.21 min.

Example D13

(2-{3-exo-[(R)-1-Amino-2-(2,4,5-trifluoro-phenyl)-ethyl]-8-aza-bicyclo[3.2.1]octane-8-sulfonyl}-ethyl)-carbamic acid ethyl ester The title compound is prepared analogously as described in example D2 using ethylchloroformate instead of cyclopropanesulfonyl chloride.
MS: 464 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.96 min.

Example D14

Pyrrolidine-1-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide The title compound is prepared analogously as described in example D2 using 1-pyrrolidinecarbonyl chloride instead of cyclopropanesulfonyl chloride.
MS: 489 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.97 min.

Example D15

Morpholine-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide The title compound is prepared analogously as described in example D2 using 4-morpholinecarbonyl chloride instead of cyclopropanesulfonyl chloride.
MS: 505 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.92 min.

Example D15a

Morpholine-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide maleate The title compound is prepared analogously as described in example D2a using morpholine-4-carboxylic acid (2-{3-exo-[(R)-1-amino-2-(2,4,5-trifluoro-phenyl)-ethyl]-8-aza-bicyclo[3.2.1]octane-8-sulfonyl}ethyl)-amide instead of cyclopropanesulfonic acid (2-{3-exo [(R)-1-amino-2-(2,4,5-trifluoro-phenyl)-ethyl]-8-aza-bicyclo[3.2.1]octane-8-sulfonyl}-ethyl)-amide.

Example D15b

Morpholine-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-amide toluene-4-sulfonate The title compound is prepared analogously as described in example D2b using morpholine-4-carboxylic acid (2-{3-ex-[(R)-1-amino-2-(2,4,5-trifluoro-phenyl)-ethyl]-8-aza-bicyclo[3.2.1]octane-8-sulfonyl}-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example D16

1-(2-{3-exo-[(R)-1-Amino-2-(2,4,5-trifluoro-phenyl)-ethyl]-8-aza-bicyclo[3.2.1]octane-8-sulfonyl}-ethyl)-3-(2-methoxy-ethyl)-urea A) (S)-2-Methyl-propane-2-sulfinic acid [(R)-1-(3-exo-8-{2-[3-(2-methoxy-ethyl)-ureido]-ethanesulfonyl}-8-aza-bicyclo[3.2.1]oct-3-yl)-2-(2,4,5-trifluoro-phenyl)-ethyl]-amide To a solution of 2-methoxyethylamine (29.8 uL, 0.344 mmol) in dimethyl formamide (2 mL) is added 1,1'-carbonyldiimidazole (58.6 mg). After stirring at rt, 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethylamine (180 mg, 0.312 mmol) is added. The resulting solution is stirred at 80° C. during 3 h before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield title compound.

MS: 597 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.32 min.

B) 1-(2-{3-exo-[(R)-1-Amino-2-(2,4,5-trifluoro-phenyl)-ethyl]-8-aza-bicyclo[3.2.1]octane-8-sulfonyl}-ethyl)-3-(2-methoxy-ethyl)-urea To (S)-2-methyl-propane-2-sulfinic acid [(R)-1-(3-exo-8-{2-[3-(2-methoxy-ethyl)ureido]-ethanesulfonyl}-8-aza-bicyclo[3.2.1]oct-3-yl)-2-(2,4,5-trifluoro-phenyl)-ethyl]-amide (143 mg, 0.206 mmol) in dioxane (3 mL) is added 4N HCl in dioxane (3 mL). The resulting mixture is stirred at rt during 1 h. The solution is frozen and lyophilised to give a white solid before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield title compound.

MS: 493 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.12 min.

Example D17

2-(1,3-Dioxo-1,3-dihydro-isoindol-2-yl)-ethane-sulfonic acid (2-{4-[(R)-1-amino-2-(2,4,5-trifluoro-phenyl)-ethyl]-piperidine-1-sulfonyl}-ethyl)-amide The title compound is prepared analogously as described in example D8 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.

MS: 603 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example D18

N-[2-(2-{3-exo-[(R)-1-Amino-2-(2,4,5-trifluoro-phenyl)-ethyl]-8-aza-bicyclo[3.2.1]octane-8-sulfonyl}-ethylsulfamoyl)-ethyl]-benzamide A) 2-Amino-ethanesulfonic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide The title compound is prepared analogously as described in example D1 using 2-(1,3-Dioxo-1,3-dihydro-isoindol-2-yl)-ethanesulfonic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide instead of N-(2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-phthalimide.

MS: 603 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

B) N-[2-(2-{3-exo-[(R)-1-Amino-2-(2,4,5-trifluoro-phenyl)-ethyl]-8-aza-bicyclo[3.2.1]octane-8-sulfonyl}-ethylsulfamoyl)-ethyl]-benzamide The title compound is prepared analogously as described in example D1 using 2-amino-ethanesulfonic acid (2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-amide instead of 2-{3-exo-[(R)-1-((S)-2-Methyl-propane-2-sulfinylamino)-2-(2,4,5-trifluoro-phenyl)-ethyl]-8-aza-bicyclo[3.2.1]octane-8-sulfonyl}-ethylamine and benzoic acid instead of 5-methyl-pyrazine-2-carboxylic acid.

MS: 601 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.16 min.

Example D19

Oxazole-5-carboxylic acid [2-(2-{3-exo-[(R)-1-amino-2-(2,4,5-trifluoro-phenyl)-ethyl]-8-aza-bicyclo[3.2.1]octane-8-sulfonyl}-ethylsulfamoyl)-ethyl]-amide The title compound is prepared analogously as described in example D1 using oxazole-5-carboxylic acid instead of 5-methylpyrazinecarboxylic acid.

MS: 488 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example E1

Cyclopropanecarboxylic acid (2-{3-exo-[(R)-1-amino-2-(2,4,5-trifluoro-phenyl)-ethyl]-8-aza-bicyclo[3.2.1]oct-4-yl}-2-oxo-ethyl)-amide This compound is prepared according to Scheme E:

Scheme E

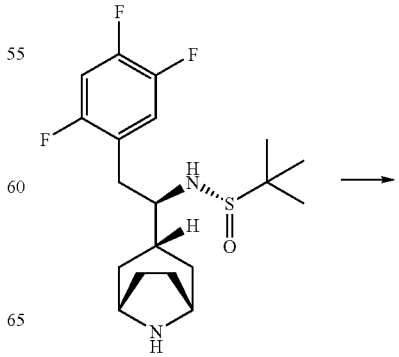

-continued

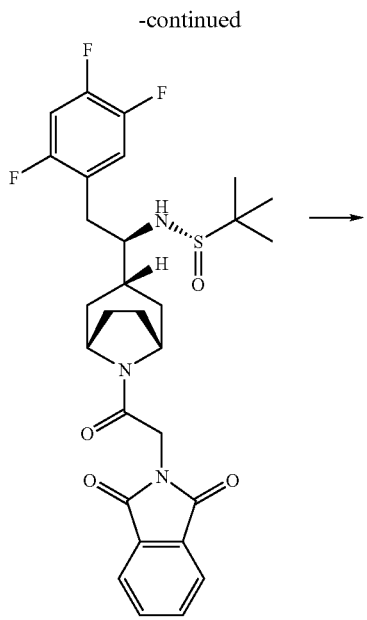

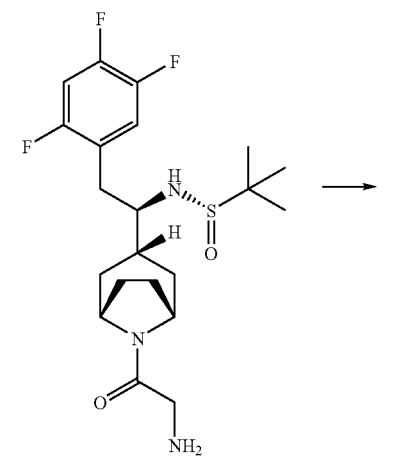

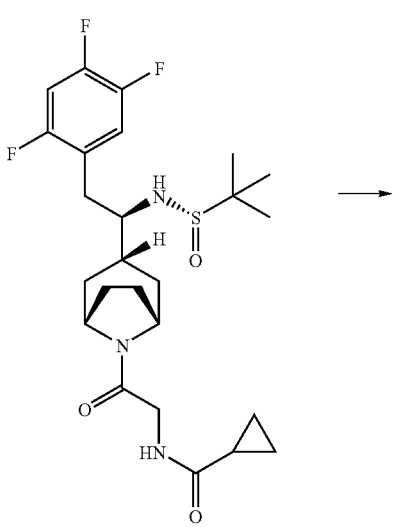

-continued

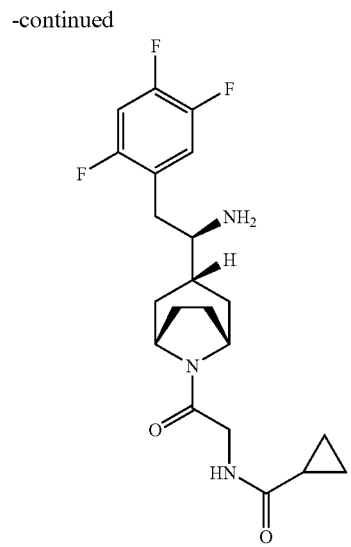

A) (S)-2-Methyl-propane-2-sulfinic acid [(R)-1-{3-exo-8-[2-(1,3-dioxo-1,3-dihydro-isoindol-2-yl)-acetyl]-8-aza-bicyclo[3.2.1]oct-3-yl}-2-(2,4,5-trifluoro-phenyl)-ethyl]-amide To a solution of N-phthaloylglycine (291 mg, 1.41 mmol) in acetonitrile (7 mL) is added benzotriazol-1-yloxytripyrrolidinophosphonium hexafluorophosphate (805 mg, 1.54 mmol) and the resulting mixture is stirred at rt during 1 h before addition of 3-exo-[(R)-1-((S)-2-methyl-propane-2-sulfinylamino)-2-(2,4,5-trifluoro-phenyl)-ethyl]-8-aza-bicyclo[3.2.1]octane (500 mg, 1.29 mmol) and triethylamine (720 μL, 5.16 mmol) in acetonitrile (5 mL). The resulting solution is stirred at rt during 16 h and is evaporated before purification by preparative HPLC (Column Interchrom C18 ODB 10 μm 28×250, Gradient: 0-2.5 min 5% ACN, 2.5-25.5 min 5-100% ACN, 25.5-30 min 100% ACN) to yield a yellow solid.

MS: 576 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

B) (S)-2-Methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide To (S)-2-methyl-propane-2-sulfinic acid [(R)-1-{3-exo-8-[2-(1,3-dioxo-1,3-dihydro-isoindol-2-yl)acetyl]-8-aza-bicyclo[3.2.1]oct-3-yl}-2-(2,4,5-trifluoro-phenyl)-ethyl]-amide (300 mg, 0.521 mmol) in ethanol (3.5 mL) is added hydrazine monohydrate (1.3 mL, 26.05 mmol) and the resulting solution is stirred at rt during 16 h. After extraction with dichloromethane and aqueous saturated NaHCO₃, the organic phase is dried and evaporated to yield a white solid.

MS: 446 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.96 min.

C) Cyclopropanecarboxylic acid (2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide To a solution of (S)-2-methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide (50 mg, 0.112 mmol) in dichloromethane (1 mL) are added triethylamine (32 µL, 0.224 mmol) and cyclopropanecarbonyl chloride (14 µL, 0.134 mmol). The resulting solution is stirred at rt during 2 h before evaporation and purification by preparative HPLC (Column Waters C18 ODB 5 µm 19×50, Gradient: 0-2.5 min 5% ACN, 2.5-12.5 min 5-100% ACN, 12.5-15 min 100% ACN) to yield a white solid.

MS: 514 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 2.87 min.

D) Cyclopropanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide To cyclopropanecarboxylic acid (2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide (26.4 mg, 0.052 mmol) in dioxane (0.5 mL) is added 4N HCl in dioxane (0.5 mL). The resulting mixture is stirred at rt during 1 h. The solution is frozen and lyophilised to give a white solid.

MS: 410 [M+H]+

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.55 min.

Example E1a

Cyclopropanecarboxylic acid (2-{3-exo-[(R)-1-amino-2-(2,4,5-trifluoro-phenyl)-ethyl]-8-aza-bicyclo[3.2.1]oct-4-yl}-2-oxo-ethyl)-amide maleate The title compound is prepared analogously as described in example D2a using Cyclopropanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E1b

Cyclopropanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide toluene-4-sulfonate The title compound is prepared analogously as described in example D2b using Cyclopropanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E2

5-Methyl-pyrazine-2-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is also prepared according to Scheme E and analogously to example D1 using 2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethylamine instead of 2-{3-exo-[(R)-1-((S)-2-methyl-propane-2-sulfinylamino-2-(2,4,5-trifluoro-phenyl)-ethyl]-8-aza-bicyclo[3.2.1]octane-8-sulfonyl}-ethylamine.

MS: 462 [M+H]

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.59 min.

Example E3

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is prepared analogously to example E1 using cyclopropanesulfonyl chloride instead of cyclopropanecarbonyl chloride.

MS: 446 [M+H]

HPLC (Nucleosil 100-5 C18, 10 min method (0-1 min 10% ACN, 14 min 10-100% ACN, 6-8.5 min 100% ACN, 8.5-9 min 100-10% ACN, 9-10 min 10% ACN): 3.56 min.

Example E3a

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide maleate The title compound is prepared analogously as described in example D2a using cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E3b

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide toluene-4-sulfonate The title compound is prepared analogously as described in example D2b using cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E4

N-(2-{3-exo-[(R)-1-Amino-2-(2,4,5-trifluoro-phenyl)-ethyl]-8-aza-bicyclo[3.2.1]oct-8-yl}-2-oxo-ethyl)-acetamide A) N-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-acetamide To 2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethylamine (50 mg, 0.112 mmol) in acetic acid (2 mL) is added acetic anhydride (16 µL, 0.168 mmol) and the resulting solution is stirred at rt during 3 h. After extraction with dichloromethane and aqueous saturated NaHCO$_3$, the organic phase is dried and evaporated to give a residue which is purified by preparative HPLC (Column Interchrom C18 ODB 10 µm 28×250, Gradient: 0-2.5 min 5% ACN, 2.5-25.5 min 5-100% ACN, 25.5-30 min 100% ACN) to yield a colorless gum.

MS: 488 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.09 min.

B) N-(2-{3-exo-[(R)-1-Amino-2-(2,4,5-trifluoro-phenyl)-ethyl]-8-aza-bicyclo[3.2.1]oct-8-yl}-2-oxo-ethyl)-acetamide To N-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-acetamide (38 mg, 0.078 mmol) in dioxane (0.5 mL) is added 4N HCl in dioxane (0.5 mL). The resulting mixture is stirred at rt during 1 h. The solution is frozen and lyophilised to give a white solid before purification by preparative HPLC (Column Waters C18 ODB 5 µm 19×50, Gradient: 0-2.5 min 5% ACN, 2.5-12.5 min 5-100% ACN, 12.5-15 min 100% ACN) to yield a light yellow solid.

MS 384 [M+H]+

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.28 min.

Example E5

Morpholine-4-sulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using morpholinesulfonyl chloride instead of cyclopropanecarbonyl chloride.

MS: 491 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.92 min.

Example E6

Morpholine-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using morpholinecarbonyl chloride instead of cyclopropanecarbonyl chloride.

MS: 455 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.87 min.

Example E6a

Morpholine-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide maleate The title compound is prepared analogously as described in example D2a using morpholine-4-carboxylic acid (2-{3-exo-[(R)-1-amino-2-(2,4,5-trifluoro-phenyl-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E6b

Morpholine-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide toluene-4-sulfonate The title compound is prepared analogously as described in example D2b using morpholine-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example E7

1-Hydroxy-cyclopropanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E2 using 1-hydroxycyclopropane-1-carboxylic acid instead of 4-methylpyrazinecarboxylic acid.

MS: 426 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.87 min.

Example E8

Tetrahydropyran-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E2 using tetrahydropyran-4-carboxylic acid instead of 4-methylpyrazinecarboxylic acid.

MS: 454 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

Example E9

Cyclobutanecarboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E2 using cyclobutanecarboxylic acid instead of 4-methylpyrazinecarboxylic acid.

MS: 424 [M+H]
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example E10

3-Methyl-3H-imidazole-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E2 using 3-methyl-3H-imidazole-4-carboxylic acid instead of 4-methylpyrazinecarboxylic acid.
MS: 449 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.76 min.

Example E11

N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-benzamide This compound is prepared analogously to example E1 using 4-fluorobenzoyl chloride instead of cyclopropanecarbonyl chloride.
MS: 464 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.13 min.

Example E11a

N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-benzamide maleate The title compound is prepared analogously as described in example D2a using N-(2-{3-exo [(R)-1-Amino-2-(2,4,5-trifluoro-phenyl)-ethyl]-8-aza-bicyclo[3.2.1]oct-8-yl}2-oxo-ethyl)-4-fluoro-benzamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E11b

N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-benzamide toluene-4-sulfonate The title compound is prepared analogously as described in example D2b using N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-benzamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example E12

3H-Imidazole-4-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is prepared analogously to example E2 using N-boc-3H-imidazole-4-carboxylic acid instead of 4-methylpyrazinecarboxylic acid.

MS: 436 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.81 min.

Example E13

Pyrazine-2-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is prepared analogously to example E2 using pyrazine-2-carboxylic acid instead of 4-methylpyrazinecarboxylic acid.
MS: 448 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.2 min.

Example E14

4-Methyl-oxazole-5-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is prepared analogously to example E2 using 4-methyl-oxazole-5-carboxylic acid instead of 4-methylpyrazinecarboxylic acid.
MS: 451 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.9 min.

Example E15

2-Amino-pyrimidine-5-carboxylic acid (2-{3-exo-[(R)-1-amino-2-(2,4,5-trifluoro-phenyl)-ethyl]-8-aza-bicyclo[3.2.1]oct-8-yl}-2-oxo-ethyl)-amide This compound is prepared analogously to example E2 using 2-amino-pyrimidine-5-carboxylic acid instead of 4-methylpyrazinecarboxylic acid.
MS: 463 [M−H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.11 min.

Example E16

N-(2-{3-exo-[(R)-1-Amino-2-(2,4,5-trifluoro-phenyl)-ethyl]-8-aza-bicyclo[3.2.1]oct-8-yl}-2-oxo-ethyl)-2-(1,3-dioxo-1,3-dihydro-isoindol-2-yl)-acetamide This compound is prepared analogously to example E2 using N-phthaloylglycine instead of 4-methylpyrazinecarboxylic acid.
MS: 530 [M−H]+
HPLC (waters symmetry C18, 6 min method (0-3.5 min 5-95% ACN, 3.5-5.5 min 95% ACN, 5.5-5.55 min 95-5% ACN, 5.55-6 min 5% ACN): 2.87 min.

127

Example E17

N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-benzenesulfonamide This compound is prepared analogously to example E1 using 4-fluorophenylsulfonyl chloride instead of cyclopropanecarbonyl chloride.

MS: 500 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.14 min.

Example E18

N-(3-{3-exo-[(R)-1-Amino-2-(2,4,5-trifluoro-phenyl)-ethyl]-8-aza-bicyclo[3.2.1]oct-8-yl}-3-oxo-propyl)-3-(1,3-dioxo-1,3-dihydro-isoindol-2-yl)-propionamide A) (S)-2-Methyl-propane-2-sulfinic acid [(R)-1-[3-exo-8-(3-amino-propionyl)-8-aza-bicyclo[3.2.1]oct-3-yl]-2-(2,4,5-trifluoro-phenyl)-ethyl]-amide This compound is prepared analogously to example E1 using N-phthaloyl-beta-glycine instead of N-phthaloylglycine.

MS: 460 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

B) N-(3-{3-exo-[(R-1-Amino-2-(2,4,5-trifluoro-phenyl)-ethyl]-8-aza-bicyclo[3.2.1]oct-8-yl}-3-oxo-propyl)-3-(1,3-dioxo-1,3-dihydro-isoindol-2-yl)-propionamide This compound is prepared analogously to example E2 using N-phthaloyl-beta-glycine instead of 4-methylpyrazinecarboxylic acid.

MS: 557 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example E19

Cyclopropanesulfonic acid (3-{3-exo-[(R)-1-amino-2-(2,4,5-trifluoro-phenyl)-ethyl]-8-aza-bicyclo[3.2.1]oct-8-yl}-3-oxo-propyl)-amide This compound is prepared analogously to example E3 using (S)-2-methyl-propane-2-sulfinic acid [(R)-1-[3-exo-8-(3-amino-propionyl)-8-aza-bicyclo[3.2.1]oct-3-yl]-2-(2,4,5-trifluoro-phenyl)-ethyl]-amide instead of (S)-2-methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide.

MS: 460 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.11 min.

128

Example E20

N-(3-{3-exo-[(R)-1-Amino-2-(2,4,5-trifluoro-phenyl)-ethyl]-8-aza-bicyclo[3.2.1]oct-8-yl}-3-oxo-propyl)-acetamide This compound is prepared analogously to example E4 using (S)-2-methyl-propane-2-sulfinic acid [(R)-1-[3-exo-8-(3-amino-propionyl)-8-aza-bicyclo[3.2.1]oct-3-yl]-2-(2,4,5-trifluoro-phenyl)-ethyl]-amide instead of (S)-2-methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide.

MS: 398 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.07 min.

Example E20a

N-(3-{3-exo-[(R)-1-Amino-2-(2,4,5-trifluoro-phenyl)-ethyl]-8-aza-bicyclo[3.2.1]oct-8-yl}-3-oxo-propyl)-acetamide maleate The title compound is prepared analogously as described in example D2a using N-(3-{3-exo-[(R)-1-Amino-2-(2,4,5-trifluoro-phenyl)-ethyl]-8-aza-bicyclo[3.2.1]oct-8-yl}-3-oxo-propyl)acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E20b

N-3-{3-exo-[(R)-1-Amino-2-(2,4,5-trifluoro-phenyl)-ethyl]-8-aza-bicyclo[3.2.1]oct-8-yl}-3-oxo-propyl)-acetamide toluene-4-sulfonate The title compound is prepared analogously as described in example D2b using N-(3-{3-exo-[(R)-1-Amino-2-(2,4,5-trifluoro-phenyl)-ethyl]-8-aza-bicyclo[3.2.1]oct-8-yl}-3-oxo-propyl)-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E21

N-(3-{3-exo-[(R)-1-Amino-2-(2,4,5-trifluoro-phenyl)-ethyl]-8-aza-bicyclo[3.2.1]oct-8-yl}-3-oxo-propyl)-benzamide This compound is prepared analogously to example E19 using benzoylchloride instead of cyclopropanesulfonyl chloride.

MS: 460 [M−H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.12 min.

Example E22

Cyclopropanecarboxylic acid (2-{4-[(R)-1-amino-2-(2,4,5-trifluoro-phenyl)-ethyl]-piperidin-1-yl}-2-oxo-ethyl)-amide The title compound is prepared analogously as described in example E1 (S)-2-methyl-propane-2-sulfinic acid [(R)-1-piperidin-4-yl-2-(2,4,5-trifluoro-phenyl)-ethyl]-amide instead of 3-exo-[(R1)-1-((S)-2-methyl-propane-2-sulfinylamino)-2-(2,4,5-trifluoro-phenyl)-ethyl]-8-aza-bicyclo[3.2.1]octane.

MS: 384 [M+H]

HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.6 min.

Example E23

N-(2-{4-[(R)-1-Amino-2-(2,4,5-trifluoro-phenyl)-ethyl]-piperidin-1-yl}-2-oxo-ethyl)-benzamide This compound is prepared analogously to example E22 using benzoylchloride instead of cyclopropanecarbonyl chloride.

MS: 420 [M+H]

HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.83 min.

Example E24

Cyclopropanecarboxylic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-isopropyl-amide A) (S)-2-Methyl-propane-2-sulfinic acid [(R)-1-[(1S,5R)-8-(2-isopropylamino-acetyl) bicyclo[3.2.1]oct-3-yl]-2-(2,4,5-trifluoro-phenyl)-ethyl]-amide To (S)-2-Methyl-propane-2-sulfinic acid [(R)-1-[(1S,5R)-8-(2-amino-acetyl)-bicyclo[3.2.1]oct-3-yl]-2-(2,4,5-trifluoro-phenyl)-ethyl]-amide (150 mg, 0.33 mmol) in methanol (3 mL) is added acetic acid until to have pH 5-5.5. After addition of acetone (124 uL, 1.68 mmol), the reaction is stirred at rt during 1 h and sodium cyanoborohydride (43 mg, 0.67 mmol) is added before stirring at rt during 16 h. The reaction is quenched with ethylacetate and an aqueous saturated NaHCO3 solution, the organic phase is dried and evaporated to afford the crude compound before purification onto a SCX-2 cartridge (5 g, DCM/MeOH 1:1, then 2N NH3 in MeOH) to yield the title compound.

MS: 488 [M+H]

HPLC (Luna 3 microns C18(2) 30×4.6 mm, 6 min method, 0-0.5 min 5% ACN, 0.5-5.5 min 5-95% ACN, 5.5-6 min 5% ACN): 2.17 min.

B) Cyclopropanecarboxylic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)isopropyl-amide This compound is prepared analogously to example E1 using (S)-2-Methyl-propane-2-sulfinic acid [(R)-1-[(1S,5R)-8-(2-isopropylamino-acetyl)-bicyclo[3.2.1]oct-3-yl]-2-(2,4,5-trifluoro-phenyl)-ethyl]-amide instead of (S)-2-Methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide.

MS: 452 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.39 min.

Example E25

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-3-phenyl-propionamide The title compound is prepared analogously as described in example E2 using 3-Phenylpropionic acid instead of 4-methylpyrazinecarboxylic acid.

MS: 474 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.74 min.

Example E25a

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-3-phenyl-propionamide maleate The title compound is prepared analogously as described in example D2a using N-(2-{(1S,3S,5R)-3-[(R)-1-Amino-2-(2,4,5-trifluoro-phenyl)-ethyl]-8-aza-bicyclo[3.2.1]-oct-8-yl}-2-oxo-ethyl)-3-phenyl-propionamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E25b

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-3-phenyl-propionamide toluene-4-sulfonate The title compound is prepared analogously as described in example D2b using N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-3-phenyl-propionamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E26

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-phenoxy-acetamide The title compound is prepared analogously as described in example E2 using 2-Phenoxyacetic acid instead of 4-methylpyrazinecarboxylic acid.

MS: 476 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.67 min.

Example E27

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-(3-methyl-isoxazol-5-yl)-acetamide The title compound is prepared analogously as described in example E2 using (3-Methyl-isoxazol-5-yl)-acetic acid instead of 4-methylpyrazinecarboxylic acid.
MS: 465 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.76 min.

Example E28

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-morpholin-4-yl-acetamide The title compound is prepared analogously as described in example E2 using Morpholin-4-yl-acetic acid instead of 4-methylpyrazinecarboxylic acid.
MS: 469 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 4.09 min.

Example E29

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-phenyl-acetamide The title compound is prepared analogously as described in example E2 using Phenylacetic acid instead of 4-methylpyrazinecarboxylic acid.
MS: 460 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.38 min.

Example E30

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-C-phenyl-methanesulfonamide The title compound is prepared analogously as described in example E1 using Phenylmethanesulfonyl chloride instead of cyclopropanecarbonyl chloride.
MS: 496 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.76 min.

Example E30a

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-C-phenyl-methanesulfonamide maleate The title compound is prepared analogously as described in example D2a using N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-C-phenyl-methanesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E30b

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-C-phenyl-methanesulfonamide toluene-4-sulfonate The title compound is prepared analogously as described in example D2b using N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-C-phenyl-methanesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E31

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-[1,2,4]triazol-1-yl-isobutyramide The title compound is prepared analogously as described in example E2 using 2-Methyl-2-[1,2,4]triazol-1-yl-propionic acid instead of 4-methylpyrazinecarboxylic acid.
MS: 479 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.53 min.

Example E32

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-(tetrahydro-pyran-4-yl)-acetamide The title compound is prepared analogously as described in example E2 using (Tetrahydro-pyran-4-yl)acetic acid instead of 4-methylpyrazinecarboxylic acid.
MS: 468 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95% CAN, 22-25 min 5% ACN): 5.56 min.

Example E33

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-methoxy-benzamide The title compound is prepared analogously as described in example E2 using 2-methoxybenzoic acid instead of 4-methylpyrazinecarboxylic acid.
MS: 476 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.62 min.

Example E34

2,3-Dihydro-benzo[1,4]dioxine-5-carboxylic acid (2-{(1S,3S,5R)-3-[(R)-1-amino-2-(2,4,5-trifluoro-phenyl)-ethyl]-8-aza-bicyclo[3.2.1]oct-8-yl})-2-oxo-ethyl)-amide The title compound is prepared analogously as described in example E2 using 2,3-Dihydro-benzo[1,4]dioxine-5-carboxylic acid instead of 4-methylpyrazinecarboxylic acid.

MS: 504 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.43 min.

Example E35

Pyridazine-3-carboxylic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E2 using Pyridazine-3-carboxylic acid instead of 4-methylpyrazinecarboxylic acid.

MS: 448 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.56 min.

Example E36

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-(3H-imidazol-4-yl)-acetamide The title compound is prepared analogously as described in example E2 using (3H-Imidazol-4-yl)acetic acid instead of 4-methylpyrazinecarboxylic acid.

MS: 450 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 0.84-3.14 min.

Example E37

2-Phenyl-ethanesulfonic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using Phenylethanesulfonyl chloride instead of cyclopropanecarbonyl chloride.

MS: 510 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.35 min.

Example E38

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-4-methyl-benzenesulfonamide The title compound is prepared analogously as described in example E1 using toluenesulfonyl chloride instead of cyclopropanecarbonyl chloride.

MS: 496 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 6.11 min.

Example E39

2,3-Dihydro-benzo[1,4]dioxine-6-sulfonic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using 2,3-Dihydro-benzo[1,4]dioxine-6-sulfonyl chloride instead of cyclopropanecarbonyl chloride.

MS: 540 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 955% CAN, 22-25 min 5% ACN): 5.87 min.

Example E40

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-methoxy-benzenesulfonamide The title compound is prepared analogously as described in example E1 using 2-Methoxybenzenesulfonyl chloride instead of cyclopropanecarbonyl chloride.

MS: 512 [M+H]

HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.74 min.

Example E40a

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-methoxy-benzenesulfonamide maleate The title compound is prepared analogously as described in example D2a using N-(2-{(1S,3S,5R)-3-[(R)-1-Amino-2-(2, 4,5-trifluoro-phenyl)-ethyl]-8-aza-bicyclo[3.2.1]oct-8-yl}-2-oxo-ethyl)-2-methoxy-benzenesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E40b

N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-methoxy-benzenesulfonamide toluene-4-sulfonate The title compound is prepared analogously as described in example D2b using N-(2-{(1S,3S,5R)-3-[(R)-1-Amino-2-(2,4,5-trifluoro-phenyl)-ethyl]-8-aza-bicyclo[3.2.1]oct-8-yl}-2-oxo-ethyl)-2-methoxy-benzenesulfonamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example E41

3,5-Dimethyl-isoxazole-4-sulfonic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using 3,5-Dimethyl-isoxazole-4-sulfonyl chloride instead of cyclopropanecarbonyl chloride.
MS: 501 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.55 min.

Example E42

1,3,5-Trimethyl-1H-pyrazole-4-sulfonic acid (2-{(1S,3S,5R)-3-[(R)-1-amino-2-(2,4,5-trifluoro-phenyl)-ethyl]-8-aza-bicyclo[3.2.1]oct-8-yl}-2-oxo-ethyl)-amide The title compound is prepared analogously as described in example E1 using 1,3,5-Trimethyl-1H-pyrazole-4-sulfonyl chloride instead of cyclopropanecarbonyl chloride.
MS: 514 [M+H]
HPLC (Higgins Clipeus 5 microns C18(2) 100×3 mm, 25 min method, 0-1 min 5% ACN, 1-15 min 5-95% ACN, 15-20 95% CAN, 20-22 min 95-5% CAN, 22-25 min 5% ACN): 5.15 min.

Example F1

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-methyl-amide This compound is prepared according to Scheme F, in which "Cbz" is carbobenzoxy:

Scheme F

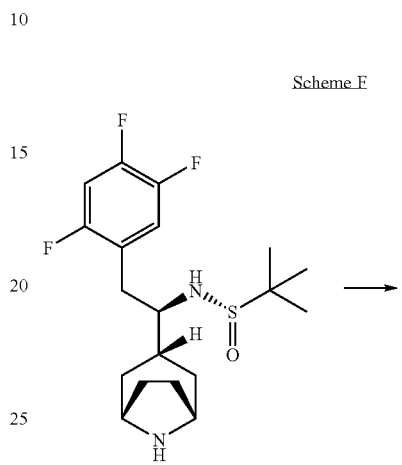

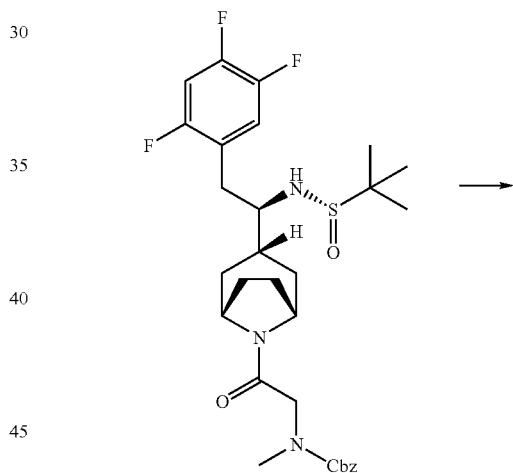

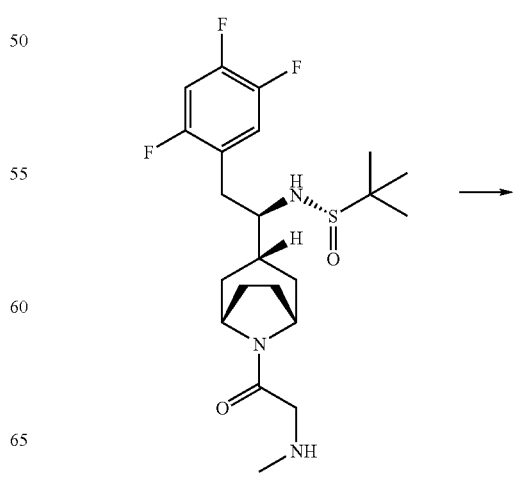

-continued

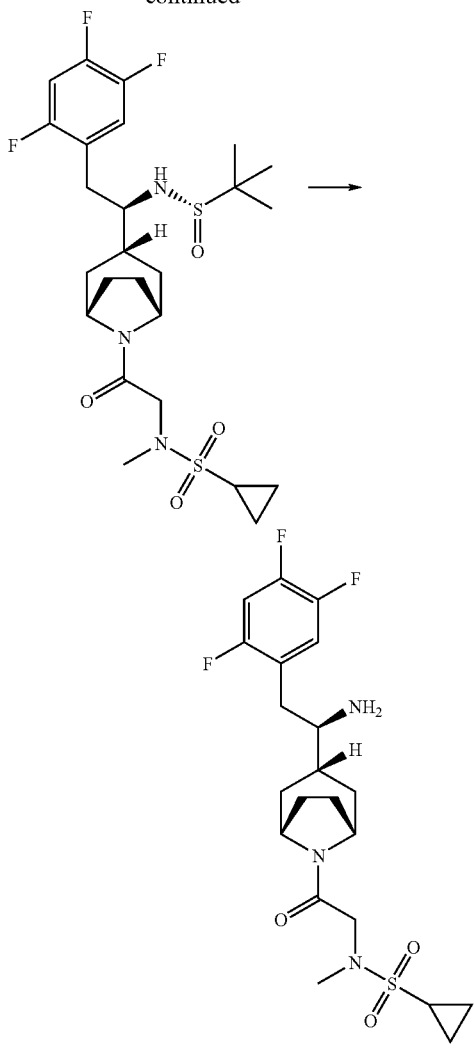

A) Methyl-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-carbamic acid benzyl ester The title compound is prepared analogously as described in example E1 using N-methyl-N-Cbz-glycine instead of N-phthaloylglycine.

MS: 594 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

B) Methyl-2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethylamine To methyl-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-carbamic acid benzyl ester (340 mg, 0.573 mmol) in ethanol (5 mL) is added palladium on charcoal (122 mg, 0.114 mmol) and the resulting mixture is stirred at rt during 4 h under $H_2$-atmosphere. The suspension is filtered through celite and the filtrate is evaporated to yield a grey solid.

MS: 460 [M+H]

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.97 min.

C) Cyclopropanesulfonic acid methyl-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide To a solution of methyl-2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethylamine (100 mg, 0.217 mmol) in dichloromethane (2 mL) are added triethylamine (91 µL, 0.651 mmol) and cyclopropanesulfonyl chloride (33 µL, 0.326 mmol). The resulting solution is stirred at rt during 3 h before evaporation and purification by preparative HPLC (Column Waters C18 ODB 5 µm 19×50, Gradient 0-2.5 min 5% ACN, 2.5-12.5 min 5-100% ACN, 12.5-15 min 100% ACN) to yield a white solid.

MS: 564 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

D) Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-methyl-amide To cyclopropanesulfonic acid methyl-(2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-amide (62 mg, 0.11 mmol) in dioxane (1 mL) is added 4N HCl in dioxane (1 mL). The resulting mixture is stirred at rt during 1 h. The solution is frozen and lyophilised to give a white solid.

MS 460 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.95 min.

Example F1a

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-methyl-amide maleate The title compound is prepared analogously as described in example D2a using cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F1b

Cyclopropanesulfonic acid (2-{3-exo-[(R)-1-amino-2-(2,4,5-trifluoro-phenyl)-ethyl]-8-aza-bicyclo[3.2.1]oct-8-yl}-2-oxo-ethyl)-methyl-amide toluene-4-sulfonate The title compound is prepared analogously as described in example D2b using cyclopropanesulfonic acid (2-{3-exo-

[(R)-1-amino-2-(2,4,5-trifluoro-phenyl)-ethyl]-8-aza-bicyclo[3.2.1]oct-8-yl}-2-oxo-ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F2

Cyclopropanesulfonic acid ((S)-2-{3-exo-[(R)-1-amino-2-(2,4,5-trifluoro-phenyl)-ethyl]-8-aza-bicyclo[3.2.1]oct-8-yl}-1-hydroxymethyl-2-oxo-ethyl)-amide The title compound is prepared analogously as described in example F1 using N-Cbz-serine(tBu)-OH instead of N-methyl-N-Cbz-glycine.

MS: 476 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.88 min.

Example F3

N-(2-{3-exo-[(R)-1-Amino-2-(2,4,5-trifluoro-phenyl)-ethyl]-8-aza-bicyclo[3.2.1]oct-8-yl}-2-oxo-ethyl)-N-methyl-acetamide The title compound is prepared analogously as described in example E4 using (S)-2-methyl-propane-2-sulfinic acid [(R)-1-[3-exo-8-(2-methylamino-acetyl)-8-aza-bicyclo[3.2.1]oct-3-yl]-2-(2,4,5-trifluoro-phenyl)-ethyl]-amide instead of (S)-2-methyl-propane-2-sulfinic acid [(R)-1-[3-exo-8-(2-amino-acetyl)-8-aza-bicyclo[3.2.1]oct-3-yl]-2-(2,4,5-trifluoro-phenyl)-ethyl]-amide.

MS: 398 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.86 min.

Example F3a

N-(2-{3-exo-[(R)-1-Amino-2-(2,4,5-trifluoro-phenyl)-ethyl]-8-aza-bicyclo[3.2.1]oct-8-yl}-2-oxo-ethyl)-N-methyl-acetamide maleate The title compound is prepared analogously as described in example D2a using N-(2-{3-exo-[(R)-1-Amino-2-(2,4,5-trifluoro-phenyl)-ethyl]-8-aza-bicyclo[3.2.1]oct-8-yl}-2-oxo-ethyl)-N-methyl-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F3b

N-(2-{3-exo-[(R)-1-Amino-2-(2,4,5-trifluoro-phenyl)-ethyl]-8-aza-bicyclo[3.2.1]oct-8-yl}-2-oxo-ethyl)-N-methyl-acetamide toluene-4-sulfonate The title compound is prepared analogously as described in example D2b using N-(2-{3-exo-[(R)-1-Amino-2-(2,4,5-trifluoro-phenyl)-ethyl]-8-aza-bicyclo[3.2.1]oct-8-yl}-2-oxo-ethyl)-N-methyl-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F4

Cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-hydroxymethyl-2-oxo-ethyl)-amide The title compound is prepared analogously as described in example F1 using cyclopropane carbonyl chloride instead of cyclopropane sulfonyl chloride.

MS: 424 [M+H]+

HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 2.74 min.

Example F5

Cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide The title compound is prepared analogously as described in example F4 using N-Cbz-(S)-alanine instead of N-methyl-N-Cbz-glycine.

MS: 460 [M+H]+

HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 2.80 min.

Example F5a

Cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide maleate The title compound is prepared analogously as described in example D2a using cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example F5b

Cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide toluene-4-sulfonate The title compound is prepared analogously as described in example D2b using cyclopropanecarboxylic acid ((S)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F6

N-(2-{3-exo-[(R)-1-Amino-2-(2,4,5-trifluoro-phenyl)-ethyl]-8-aza-bicyclo[3.2.1]oct-8-yl}-2-oxo-ethyl)-4-fluoro-N-methyl-benzenesulfonamide The title compound is prepared analogously as described in example F1 using 4-fluorophenylsulfonyl chloride instead of cyclopropane sulfonyl chloride.

MS: 514 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.13 min.

Example F7

Cyclopropanesulfonic acid (2-{3-exo-[(R)-1-amino-2-(2,4,5-trifluoro-phenyl)-ethyl]-8-aza-bicyclo[3.2.1]oct-8-yl}-1,1-dimethyl-2-oxo-ethyl)-amide The title compound is prepared analogously as described in example F4 using N-Cbz-methyl-alanine instead of N-methyl-N-Cbz-glycine.

MS: 474 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.93 min.

Example F7a

Cyclopropanesulfonic acid (2-{3-exo-[(R)-1-amino-2-(2,4,5-trifluoro-phenyl)-ethyl]-8-aza-bicyclo[3.2.1]oct-8-yl}-1,1-dimethyl-2-oxo-ethyl)-amide maleate The title compound is prepared analogously as described in example D2a using cyclopropanesulfonic acid (2-{3-exo-[(R)-1-amino-2-(2,4,5-trifluoro-phenyl)-ethyl]-8-aza-bicyclo[3.2.1]oct-8-yl}-1,1-dimethyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F7b

Cyclopropanesulfonic acid (2-{3-exo-[(R)-1-amino-2-(2,4,5-trifluoro-phenyl)-ethyl]-8-aza-bicyclo[3.2.1]oct-8-yl}-1,1-dimethyl-2-oxo-ethyl)-amide toluene-4-sulfonate The title compound is prepared analogously as described in example D2b using cyclopropanesulfonic acid (2-{3-exo-[(R)-1-amino-2-(2,4,5-trifluoro-phenyl)-ethyl]-8-aza-bicyclo[3.2.1]oct-8-yl}-1,1-dimethyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F8

N-(3-{3-exo-[(R)-1-Amino-2-(2,4,5-trifluoro-phenyl)-ethyl]-8-aza-bicyclo[3.2.1]oct-8-yl}-3-oxo-propyl)-N-methyl-acetamide The title compound is prepared analogously as described in example F3 using (S)-2-methyl-propane-2-sulfinic acid [(R)-1-[3-exo-8-(3-methylamino-propionyl)-8-aza-bicyclo[3.2.1]oct-3-yl]-2-(2,4,5-trifluoro-phenyl)-ethyl]-amide instead of (S)-2-methyl-propane-2-sulfinic acid [(R)-1-[3-exo-8-(2-methylamino-acetyl)-8-aza-bicyclo[3.2.1]oct-3-yl]-2-(2,4,5-trifluoro-phenyl)-ethyl]-amide.

MS: 412 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.09 min.

Example F9

Cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-1-hydroxymethyl-2-oxo-ethyl)-amide A) (R)-2-Benzyloxycarbonylamino-3-(tert-butyl-dimethyl-silanyloxy)propionic acid methyl ester To (R-2-Benzyloxycarbonylamino-3-hydroxy-propionic acid methyl ester (1 g, 4 mmol) in dimethyl formamide are added triethylamine (1.2 mL, 8 mmol), tert-butyldimethylsilyl chloride (895 mg, 6 mmol) and 4-dimethylaminopyridine (50 mg, 0.4 mmol). After stirring at rt during 16 h, the reaction is quenched with water and aqueous 1N HCl and extracted with ethyl acetate. The organic phase is dried and evaporated to give a residue, which is purified by flash chromatography (Silica gel, ethyl acetate/cyclohexane 1/9 to 1/4) to yield a light yellow gum.

MS: 368 [M+H]+

HPLC (waters symmetry C18, 6 min method (0-3.5 min 20-95% ACN, 3.5-5.5 min 95% ACN, 5.5-5.55 min 95-20% ACN, 5.55-6 min 20% ACN): 4.63 min.

B) (R)-2-Benzyloxycarbonylamino-3-(tert-butyl-dimethyl-silanyloxy)-propionic acid To (R)-2-Benzyloxycarbonylamino-3-(tert-butyl-dimethyl-silanyloxy)-propionic acid methyl ester (1.450 g, 3.95 mmol) in tetrahydrofuran/water (2/1) is added lithium hydroxide (250 mg, 5.92 mmol). After stirred at rt during 16 h, the solution is treated with ethyl acetate and the pH is decrease to 2 with aqueous 1N HCl. The organic phase is dried and evaporated to yield the title compound.

MS: 354 [M+H]+

HPLC (waters symmetry C18, 6 min method (0-3.5 min 20-95% ACN, 3.5-5.5 min 95% ACN, 5.5-5.55 min 95-20% ACN, 5.55-6 min 20% ACN): 4.25 min.

C) Cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-1-hydroxymethyl-2-oxo-ethyl)-amide The title compound is prepared analogously as described in example F2 using (R)-2-benzyloxycarbonylamino-3-(tert-butyl-dimethyl-silanyloxy)-propionic acid using instead of N-Cbz-serine(tBu)-OH and cyclopropylcarboxylic acid instead of cyclopropylsulfonyl chloride.

MS: 440 [M+H]+

HPLC (waters symmetry C18, 6 min method (0-3.5 min 5-95% ACN, 3.5-5.5 min 95% ACN, 5.5-5.55 min 95-5% ACN, 5.55-6 min 5% ACN): 2.65 min.

Example F10

N—((S)-2-{(1S,3S,5R)-3-[(R)-1-Amino-2-(2,4,5-trifluoro-phenyl)-ethyl]-8-aza-bicyclo[3.2.1]oct-8-yl}-1-methyl-2-oxo-ethyl)-isobutyramide The title compound is prepared analogously as described in example F5 using isobutyroyl chloride instead of cyclopropane carbonyl chloride.

MS: 426 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.239 min.

Example F11

N—((R)-2-{(1S,3S,5R)-3-[(R)-1-Amino-2-(2,4,5-trifluoro-phenyl)-ethyl]-8-aza-bicyclo[3.2.1]oct-8-yl}-1-methyl-2-oxo-ethyl)-isobutyramide The title compound is prepared analogously as described in example F10 using N-Cbz-(R)-alanine instead of N-Cbz-(S)-alanine.
MS: 426 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.236 min.

Example F12

Cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide The title compound is prepared analogously as described in example F5 using N-Cbz-(R)-alanine instead of N-Cbz-(S)-alanine.
MS: 424 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.224 min.

Example F12a

Cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide maleate The title compound is prepared analogously as described in example D2a using cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-methyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example F12b

Cyclopropanecarboxylic acid ((R)-2-{3-exo-[(R)-1-amino-2-(2,4,5-trifluoro-phenyl)-ethyl]-8-aza-bicyclo[3.2.1]oct-8-yl}-1-methyl-2-oxo-ethyl)-amide toluene-4-sulfonate The title compound is prepared analogously as described in example D2b using cyclopropanecarboxylic acid ((R)-2-{3-exo-[(R)-amino-2-(2,4,5-trifluoro-phenyl)-ethyl]-8-aza-bicyclo[3.2.1]oct-8-yl}-1-methyl-2-oxo-ethyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G1

N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide This compound is prepared according to Scheme G:

Scheme G

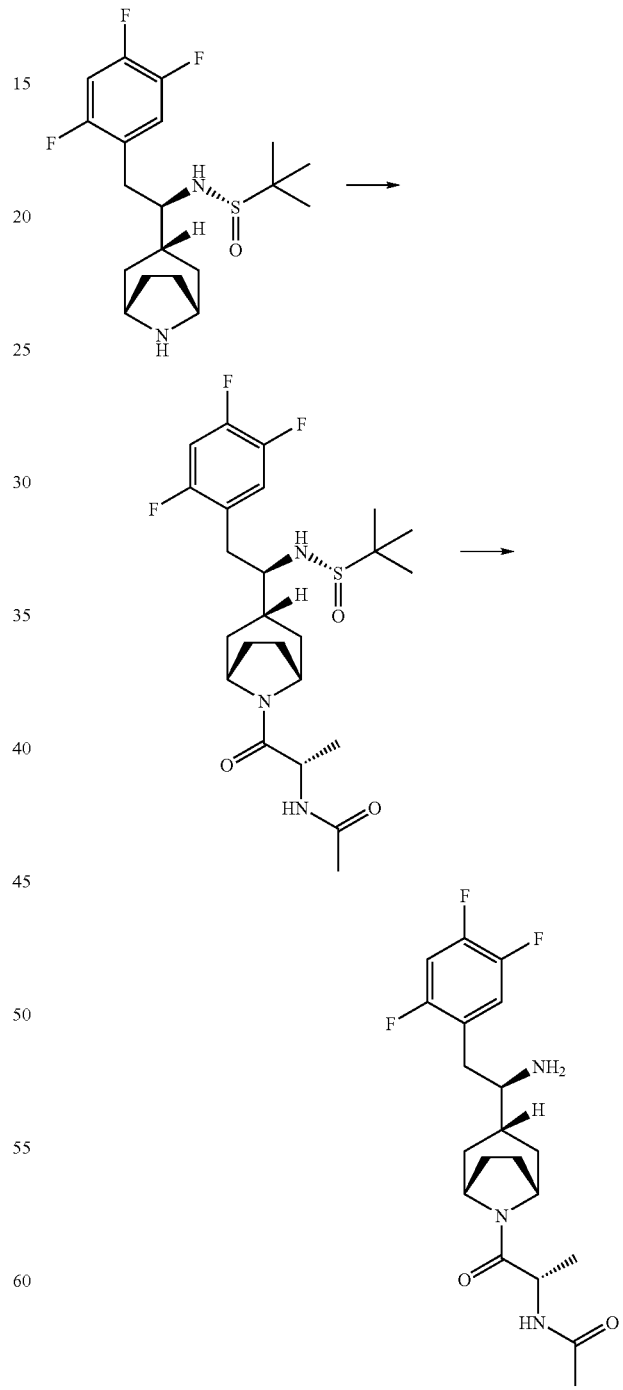

A) N—((S)-1-Methyl-2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)acetamide The title compound is prepared analogously as described in example E1 using N-acetyl-L-alanine instead of N-phtaloylglycine.

MS: 502 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.11 min.

B) N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide To N—((S)-1-Methyl-2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)acetamide (60 mg, 0.120 mmol) in dioxane (1 mL) is added 4N HCl in dioxane (1 mL). The resulting mixture is stirred at rt during 1 h. The solution is frozen and lyophilised to give a white solid before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield the title compound.

MS: 398 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.91 min.

Example G1a

N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide maleate The title compound is prepared analogously as described in example D2a using N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G1 b

N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide toluene-4-sulfonate The title compound is prepared analogously as described in example D2b using N—((S)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G2

N—((R)-2-{3-exo-[(R)-1-Amino-2-(2,4,5-trifluoro-phenyl)-ethyl]-8-aza-bicyclo[3.2.1]oct-8-yl}-1-methyl-2-oxo-ethyl)-acetamide The title compound is prepared analogously as described in example G1 using N-acetyl-D-alanine instead of N-acetyl-L-alanine.

MS: 398 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.88 min.

Example G3

N-(2-{3-exo-[(R)-1-Amino-2-(2,4,5-trifluoro-phenyl)-ethyl]-8-aza-bicyclo[3.2.1]oct-8-yl}-2-oxo-ethyl)-benzamide The title compound is prepared analogously as described in example G1 using N-benzoylglycine instead of N-acetyl-L-alanine.

MS: 446 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.94 min.

Example G4

(R)-1-{3-exo-[(R)-1-Amino-2-(2,4,5-trifluoro-phenyl)-ethyl]-8-aza-bicyclo[3.2.1]oct-8-yl}-2-hydroxy-2-phenyl-propan-1-one The title compound is prepared analogously as described in example G1 using (R)-2-hydroxy-2-phenyl-propionic acid instead of N-acetyl-L-alanine.

MS: 433 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.00 min.

Example G5

N—((S)-5-Acetylamino-1-{3-exo-[(R)-1-amino-2-(2,4,5-trifluoro-phenyl)-ethyl]-8-aza-bicyclo[3.2.1]octane-carbonyl}-pentyl)-acetamide The title compound is prepared analogously as described in example G1 using (S)-2,6-bis-acetylamino-hexanoic acid instead of N-acetyl-L-alanine.

MS: 497 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.10 min.

Example G6

((S)-2-{3-exo-[(R)-1-Amino-2-(2,4,5-trifluoro-phenyl)-ethyl]-8-aza-bicyclo[3.2.1]oct-8-yl}-2-oxo-1-phenyl-ethyl)-carbamic acid ethyl ester The title compound is prepared analogously as described in example G1 using (S)-ethoxycarbonylamino-phenyl-acetic acid instead of N-acetyl-L-alanine.

MS: 490 [M+H]+

HPLC (waters symmetry C18, 6 min method (0-3.5 min 5-95% ACN, 3.5-5.5 min 95% ACN, 5.5-5.55 min 95-5% ACN, 5.55-6 min 5% ACN): 3.14 min.

Example G7

((R)-2-{3-exo-[(R)-1-Amino-2-(2,4,5-trifluoro-phenyl)-ethyl]-8-aza-bicyclo[3.2.1]oct-8-yl}-2-oxo-1-phenyl-ethyl)-carbamic acid ethyl ester The title compound is prepared analogously as described in example G1 using (R) ethoxycarbonylamino-phenyl-acetic acid instead of N-acetyl-L-alanine.

MS: 490 [M+H]+

HPLC (waters symmetry C18, 6 min method (0-3.5 min 5-95% ACN, 3.5-5.5 min 95% ACN, 5.5-5.55 min 95-5% ACN, 5.55-6 min 5% ACN): 3.14 min.

Example G8

(S)-1-{3-exo-[(R)-1-Amino-2-(2,4,5-trifluoro-phenyl)-ethyl]-8-aza-bicyclo[3.2.1]oct-8-yl}-2-methoxy-2-phenyl-ethanone The title compound is prepared analogously as described in example G1 using (S) methoxyphenyl-acetic acid instead of N-acetyl-L-alanine.

MS: 433 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.556 min 20% ACN): 2.49 min.

Example G9

(R)-1-{-3-exo-[(R)-1-Amino-2-(2,4,5-trifluoro-phenyl)-ethyl]-8-aza-bicyclo[3.2.1]oct-8-yl}-2-methoxy-2-phenyl-ethanone The title compound is prepared analogously as described in example G1 using (R)-methoxyphenyl-acetic acid instead of N-acetyl-L-alanine.

MS: 433 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.47 min.

Example G10

N-(3-{3-exo-[(R)-1-Amino-2-(2,4,5-trifluoro-phenyl)-ethyl]-8-aza-bicyclo[3.2.1]oct-8-yl}-3-oxo-propyl)-benzenesulfonamide The title compound is prepared analogously as described in example G1 using 3-Benzenesulfonylamino-propionic acid instead of N-acetyl-L-alanine.

MS: 496 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example G10a

N-(3-{3-exo-[(R)-1-Amino-2-(2,4,5-trifluoro-phenyl)-ethyl]-8-aza-bicyclo[3.2.1]oct-8-yl}-3-oxo-propyl)-benzenesulfonamide maleate The title compound is prepared analogously as described in example D2a using N-(3-{3-exo-[(R)-1-Amino-2-(2,4,5-trifluoro-phenyl)-ethyl]-8-aza-bicyclo[3.2.1]oct-8-yl}-3-oxo-propyl)-benzenesulfonamide instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G10b

N-(3-{3-exo-[(R)-1-Amino-2-(2,4,5-trifluoro-phenyl)-ethyl]-8-aza-bicyclo[3.2.1]oct-8-yl}-3-oxo-propyl)-benzenesulfonamide toluene-4-sulfonate The title compound is prepared analogously as described in example D2b using N-(3-{3-exo [(R)-1-Amino-2-(2,4,5-trifluoro-phenyl)-ethyl]-8-aza-bicyclo[3.2.1]oct-8-yl}-3-oxo-propyl)-benzenesulfonamide instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example G11

2,3-Dihydro-benzo[1,4]dioxine-6-sulfonic acid (3-{3-exo-[(R)-1-amino-2-(2,4,5-trifluoro-phenyl)-ethyl]-8-aza-bicyclo[3.2.1]oct-8-yl}-3-oxo-propyl)-amide The title compound is prepared analogously as described in example G1 using 3-(2,3-dihydro-benzo[1,4]dioxine-6-sulfonylamino)-propionic acid instead of N-acetyl-L-alanine.

MS: 554 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

Example G12

1-(3-exo-[(R)-1-Amino-2-(2,4,5-trifluoro-phenyl)-ethyl]-8-aza-bicyclo[3.2.1]oct-8-yl)-3-(2,3-dihydro-benzo[1,4]dioxine-6-sulfonyl)-propan-1-one The title compound is prepared analogously as described in example G1 using 3-(2,3-dihydro-benzo[1,4]dioxine-6-sulfonyl)-propionic acid instead of N-acetyl-L-alanine.

MS: 539 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.97 min.

Example G13

N-[4-(3-{3-exo-[(R)-1-Amino-2-(2,4,5-trifluoro-phenyl)-ethyl]-8-aza-bicyclo[3.2.1]oct-8-yl}-3-oxo-propane-1-sulfonyl)-phenyl]-acetamide The title compound is prepared analogously as described in example G1 using 3-(4-acetylamino-benzenesulfonyl)-propionic acid instead of N-acetyl-L-alanine.

MS: 574 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.12 min.

Example G14

1-{3-exo-[(R)-1-Amino-2-(2,4,5-trifluoro-phenyl)-ethyl]-8-aza-bicyclo[3.2.1]oct-8-yl}-3-(4-fluoro-benzenesulfonyl)-propan-1-one The title compound is prepared analogously as described in example G1 using 3-(4-fluoro-benzenesulfonyl)-propionic acid instead of N-acetyl-L-alanine.

MS: 499 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.28 min.

Example G15

1-{3-exo-[(R)-1-Amino-2-(2,4,5-trifluoro-phenyl)-ethyl]-8-aza-bicyclo[3.2.1]oct-8-yl}-3-(4-thiophen-2-yl-6-trifluoromethyl-pyrimidine-2-sulfonyl)-propan-1-one The title compound is prepared analogously as described in example G1 using 3-(4-thiophen-2-yl-6-trifluoromethyl-pyrimidine-2-sulfonyl)propionic acid instead of N-acetyl-L-alanine.

MS: 663 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.21 min.

Example G16

1-{3-exo-[(R)-1-Amino-2-(2,4,5-trifluoro-phenyl)-ethyl]-8-aza-bicyclo[3.2.1]oct-8-yl}-3-phenyl-methanesulfonyl-propan-1-one The title compound is prepared analogously as described in example G1 using 3-phenylmethanesulfonyl-propionic acid instead of N-acetyl-L-alanine.

MS: 495 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.18 min.

Example G17

2-(3-{3-exo-[(R)-1-Amino-2-(2,4,5-trifluoro-phenyl)-ethyl]-8-aza-bicyclo[3.2.1]octane-8-carbonyl}-benzyl)-isoindole-1,3-dione The title compound is prepared analogously as described in example G1 using 3-(1,3-dioxo-1,3-dihydro-isoindol-2-ylmethyl)-benzoic acid instead of N-acetyl-L-alanine.

MS: 548 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.30 min.

Example G18

N-(3-{3-exo-[(R)-1-Amino-2-(2,4,5-trifluoro-phenyl)-ethyl]-8-aza-bicyclo[3.2.1]octane-8-carbonyl}-benzyl)-benzamide The title compound is prepared analogously as described in example E21 using (S)-2-methyl-propane-2-sulfinic acid [(R)-1-{3-exo-8-[3-(1,3-dioxo-1,3-dihydro-isoindol-2-ylmethyl)-benzoyl]-8-aza-bicyclo[3.2.1]oct-3-yl}-2-(2,4,5-trifluoro-phenyl)-ethyl]-amide instead of (S)-2-methyl-propane-2-sulfinic acid [(R)-1-{3-exo-8-[3-(1,3-dioxo-1,3-dihydro-isoindol-2-yl)-propionyl]-8-aza-bicyclo[3.2.1]oct-3-yl}-2-(2,4,5-trifluoro-phenyl)-ethyl]-amide.

MS: 522 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.28 min.

Example G19

3-{3-exo-[(R)-1-Amino-2-(2,4,5-trifluoro-phenyl)-ethyl]-8-aza-bicyclo[3.2.1]oct-8-yl}-N-benzyl-3-oxo-propionamide The title compound is prepared analogously as described in example G1 using N-benzyl-malonamic acid instead of N-acetyl-L-alanine.

MS: 462 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

Example G20

1-{3-exo-[(R)-1-Amino-2-(2,4,5-trifluoro-phenyl)-ethyl]-8-aza-bicyclo[3.2.1]oct-8-yl}-3-morpholin-4-yl-propane-1,3-dione The title compound is prepared analogously as described in example G1 using N-morpholin-malonamic acid instead of N-acetyl-L-alanine.

MS: 440 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.16 min.

Example G21

1-{4-[(R)-1-Amino-2-(2,4,5-trifluoro-phenyl)-ethyl]-piperidin-1-yl}-3-phenylmethanesulfonyl-propan-1-one The title compound is prepared analogously as described in example G16 using (S)-2-methyl-propane-2-sulfinic acid [(R)-1-piperidin-4-yl-2-(2,4,5-trifluoro-phenyl)-ethyl]-amide instead of 3-exo-[(R)-1-((S-2-methyl-propane-2-sulfinylamino)-2-(2,4,5-trifluoro-phenyl)-ethyl]-8-aza-bicyclo[3.2.1]octane.

MS: 469 [M+H]+

HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.98 min.

Example G21a

1-{4-[(R)-1-Amino-2-(2,4,5-trifluoro-phenyl)-ethyl]-piperidin-1-yl}-3-phenylmethanesulfonyl-propan-1-one maleate The title compound is prepared analogously as described in example D2a using 1-{4-[(R)-1-amino-2-(2,4,5-trifluoro-phenyl)-ethyl]-piperidin-1-yl}-3-phenylmethanesulfonyl-propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G21b

1-{4-[(R)-1-Amino-2-(2,4,5-trifluoro-phenyl)-ethyl]-piperidin-1-yl}-3-phenylmethanesulfonyl-propan-1-one toluene-4-sulfonate The title compound is prepared analogously as described in example D2b using 1-{4-[(R)-1-amino-2-(2,4,5-trifluoro-phenyl)-ethyl]-piperidin-1-yl}-3-phenylmethanesulfonyl-propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G22

1-(4-[(R)-1-Amino-2-{2,4,5-trifluoro-phenyl]-ethyl]-piperidin-1-yl}-3-(4-fluoro-benzenesulfonyl)-propan-1-one The title compound is prepared analogously as described in example G14 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.

MS: 473 [M+H]+

HPLC(YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.78 min.

Example G23

1-{4-[(R)-1-Amino-2-(2,4,5-trifluoro-phenyl)-ethyl]-piperidin-1-yl}-3-benzenesulfonyl-propan-1-one The title compound is prepared analogously as described in example G1 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane and 3-benzenesulfonyl-propionic acid instead of N-acetyl-L-alanine.

MS: 455 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.13 min.

Example G24

1-{4-[(R)-1-Amino-2-(2,4,5-trifluoro-phenyl)-ethyl]-piperidin-1-yl}-3-(2,3-dihydro-benzo[1,4]dioxine-6-sulfonyl)-propan-1-one The title compound is prepared analogously as described in example G12 using (S)-2-methyl-propane-2-sulfinic acid [(R)-1-piperidin-4-yl-2-(2,4,5-trifluoro-phenyl)-ethyl]-amide instead of 3-exo-[(R)-1-((S-2-methyl-propane-2-sulfinylamino)-2-(2,4,5-trifluoro-phenyl)-ethyl]-8-aza-bicyclo[3.2.1]octane.

MS: 513 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.15 min.

Example G25

1-{4-[(R)-1-Amino-2-(2,4,5-trifluoro-phenyl)-ethyl]-piperidin-1-yl}-2-methanesulfonyl-ethanone The title compound is prepared analogously as described in example G22 using methanesulfonyl-acetic acid instead of 3-(4-fluoro-benzenesulfonyl)-propionic acid.

MS: 401 [M+H]+

HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.48 min.

Example G26

3-{3-exo-[(R)-1-Amino-2-(2,4,5-trifluoro-phenyl)-ethyl]-8-aza-bicyclo[3.2.1]octane-8-carbonyl}-N-methyl-benzamide The title compound is prepared analogously as described in example G1 using N-methyl-isophthalamic acid instead of N-acetyl-L-alanine.

MS: 446 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example G26a

3-{3-exo-[(R)-1-Amino-2-(2,4,5-trifluoro-phenyl)-ethyl]-8-aza-bicyclo[3.2.1]octane-8-carbonyl}-N-methyl-benzamide maleate The title compound is prepared analogously as described in example D2a using 3-{3-exo-[(R)-1-Amino-2-(2,4,5-trifluoro-phenyl)-ethyl]-8-aza-bicyclo[3.2.1]octane-8-carbonyl}N-methyl-benzamide instead of cyclopropane-sulfonic acid (2-{3-exo-[(R)-amino-2-(2,4,5-trifluoro-phenyl)-ethyl]-8-aza-bicyclo[3.2.1]octane-8-sulfonyl}ethyl)-amide.

Example G26b

3-{3-exo-[(R)-1-Amino-2-(2,4,5-trifluoro-phenyl)-ethyl]-8-aza-bicyclo[3.2.1]octane-8-carbonyl}-N-methyl-benzamide toluene-4-sulfonate The title compound is prepared analogously as described in example D2b using 3-{3-exo [(R)-1-Amino-2-(2,4,5-trifluoro-phenyl)-ethyl]-8-aza-bicyclo[3.2.1]octane-8-carbonyl}-N-methyl-benzamide instead of cyclopropanesulfonic acid (2-(3-exo-[(R)-1-amino-2-(2,4,5-trifluoro-phenyl)-ethyl]-8-aza-bicyclo[3.2.1]octane-8-sulfonyl)ethyl)-amide.

Example G27

{3-exo-[(R)-1-Amino-2-(2,4,5-trifluoro-phenyl)-ethyl]-8-aza-bicyclo[3.2.1]oct-8-yl}-[3-morpholine-4-carbonyl)-phenyl]-methanone The title compound is prepared analogously as described in example G1 using 3-(morpholine-4-carbonyl)-benzoic acid instead of N-acetyl-L-alanine.
MS: 502 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.19 min.

Example G28

1-(3-{3-exo-[(R)-1-Amino-2-(2,4,5-trifluoro-phenyl)-ethyl]-8-aza-bicyclo[3.2.1]octane-8-carbonyl}-benzyl)-pyrrolidin-2-one The title compound is prepared analogously as described in example G1 using 3-(2-oxo-pyrrolidin-1-ylmethyl)-benzoic acid instead of N-acetyl-L-alanine.
MS: 486 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.23 min.

Example G29

3-(3-{3-exo-[(R)-1-Amino-2-(2,4,5-trifluoro-phenyl)-ethyl]-8-aza-bicyclo[3.2.1]octane-4-carbonyl}-benzyl)-thiazolidine-2,4-dione The title compound is prepared analogously as described in example G1 using 3-(2,4-dioxo-thiazolidin-3-ylmethyl)-benzoic acid instead of N-acetyl-L-alanine.
MS: 518 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

Example G30

1-{4-[(R)-1-Amino-2-(2,4,5-trifluoro-phenyl)-ethyl]-piperidin-1-yl}-3-(propane-2-sulfonyl)-propan-1-one A) 3-Isopropylsulfanyl-propionic acid benzyl ester To benzylacrylate (100 mg, 0.617 mmol) in ethanol (2 mL) are added triethylamine (95 uL, 0.679 mmol) and 2-propanethiol (58 uL, 0.617 mmol). After stirring at rt during 2 h, the solvent is evaporated to give a residue which is treated with dichloromethane and water. The organic phase is dried and evaporated to afford a colorless oil before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield the title compound.
MS: 239 [M+H]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.97 min.

B) 3-(Propane-2-sulfonyly propionic acid benzyl ester

To 3-isopropylsulfonyl-propionic acid benzyl ester (46 mg, 0.193 mmol) in acetic acid (500 uL) is added an aqueous 30% H2O2 solution (82 uL). After stirring at 80° C. during 2 h, the mixture is quenched with saturated NaHCO3 solution and extracted with dichloromethane. The organic phase is dried and evaporated to give the title compound.
MS: 271 [M+H]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.92 min.

C) 3-(Propane-2-sulfonyly propionic acid

To 3-(propane-2-sulfonyly propionic acid benzyl ester (49.3 mg, 0.182 mmol) in methanol (1 mL) is added Pd/C (5 mg) and the mixture is stirred at rt during 16 h under H2 atmosphere. The resulting suspension is filtered through celite and the filtrate is evaporated to yield the title compound.

D) 1-{4-[(R)-1-Amino-2-(2,4,5-trifluoro-phenyl)-ethyl]-piperidin-1-yl}-3-(propane-2-sulfonyl propan-1-one The title compound is prepared analogously as described in example G24 using 3-(propane-2-sulfonyl)propionic acid instead of 3-(2,3-dihydro-benzo[1,4]dioxine-6-sulfonylamino)-propionic acid.
MS: 421 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.6 min.

Example G31

1-{3-exo-[(R)-1-Amino-2-(2,4,5-trifluoro-phenyl)-ethyl]-8-aza-bicyclo[3.2.1]oct-8-yl}-3-(4-trifluoromethyl-pyrimidine-2-sulfonyl)-propan-1-one The title compound is prepared analogously as described in example G30 using 4-trifluoromethyl-pyrimidine-2-thiol instead of 2-propanethiol and 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 551 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

Example G32

1-{3-exo-[(R)-1-Amino-2-(2,4,5-trifluoro-phenyl)-ethyl]-8-aza-bicyclo[3.2.1]oct-8-yl}-3-benzenesulfonyl-propan-1-one The title compound is prepared analogously as described in example G1 using 3-benzenesulfonyl-propionic acid instead of N-acetyl-L-alanine.
MS: 481 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.2 min.

Example G33

1-{4-[1-Amino-2-(2,4,5-trifluoro-phenyl)-ethyl]-piperidin-1-yl}-2-(propane-2-sulfonyl)-ethanone A) Isopropylsulfanyl-acetic acid benzyl ester To benzyl bromoacetate (100 mg, 0.437 mmol) in dimethyl formamide (2 mL) is added triethylamine (67 uL, 0.481 mmol) and 2-propanethiol (41 uL, 0.437 mmol). After stirring at rt during 2 h, the solvent is evaporated, the residue is treated with dichloromethane and water. The organic phase is dried and evaporated to give a crude compound before purification by preparative HPLC (Column Waters C18 ODB 5 µm 19×50, Gradient: 0-2.5 min 5% ACN, 2.5-12.5 min 5-100% ACN, 12.5-15 min 100% ACN) to yield the title compound.
MS: 225 [M+H]+
HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 3.84 min.

B) 1-{4-[1-Amino-2-(2,4,5-trifluoro-phenyl)-ethyl]-piperidin-1-yl}-2-(propane-2-sulfonyl)-ethanone The title compound is prepared analogously as described in example G30 using isopropylsulfanyl-acetic acid benzyl ester instead of 3-isopropylsulfanyl-propionic acid benzyl ester.
MS: 551 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.25 min.

Example G34

Cyclopropanecarboxylic acid ((S)-1-{3-exo-[(R)-1-amino-2-(2,4,5-trifluoro-phenyl)-ethyl]-8-aza-bicyclo[3.2.1]octane-8-carbonyl}-3-carbamoyl-propyl)-amide A) (S)-4-Carbamoyl-2-(cyclopropanecarbonyl-amino)-butyric acid To (S)-2-Amino-4-carbamoyl-butyric acid (100 mg, 0.684 mmol) in water (16 mL) are added Na2CO3 (218 mg, 2.052 mmol) and a solution of cyclopropylcarboxylic acid (62.1 uL, 0.684 mmol) in tetrahydrofuran (8 mL). After stirring at rt during 2 h, ethyl acetate is added and the pH is decreased to 3 by addition of aqueous 1N HCl. The aqueous phase is evaporated, the residue is mixed with methanol and filtrated. The filtrate is evaporated to yield the title compound.
MS: 237 [M+H]+
HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 0.504 min.

B) Cyclopropanecarboxylic acid ((S)-1-{3-exo-[(R)-1-amino-2-(2,4,5-trifluoro-phenyl)-ethyl]-8-aza-bicyclo[3.2.1]octane-8-carbonyl}-3-carbamoyl-propyl)-amide The title compound is prepared analogously as described in example G1 using (S)-4-carbamoyl-2-(cyclopropanecarbonyl-amino)-butyric acid instead of N-acetyl-L-alanine.
MS: 482 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.13 min.

Example G35

N-[4-(3-{4-[(R)-1-Amino-2-(2,4,5-trifluoro-phenyl)-ethyl]-piperidin-1-yl}-3-oxo-propane-1-sulfonyl)-phenyl]-acetamide The title compound is prepared analogously as described in example G21 using 3-(4-acetylaminobenzenesulfonyl)-propionic acid instead of 3-phenylmethanesulfonyl-propionic acid.
MS: 512 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.19 min.

Example G35a

N-[4-(3-{4-[(R)-1-Amino-2-(2,4,5-trifluoro-phenyl)-ethyl]-piperidin-1-yl}-3-oxo-propane-1-sulfonyl)-phenyl]-acetamide maleate The title compound is prepared analogously as described in example D2a using N-[4-(3-{4-[(R)-1-Amino-2-(2,4,5-trifluoro-phenyl)-ethyl]-piperidin-1-yl}-3-oxo-propane-1-sulfonyl)-phenyl]-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example G35b

N-[4-(3-{4-[(R)-1-Amino-2-(2,4,5-trifluoro-phenyl)-ethyl]-piperidin-1-yl}-3-oxo-propane-1-sulfonyl)-phenyl]-acetamide toluene-4-sulfonate The title compound is prepared analogously as described in example D2b using N-[4-(3-{4-[(R)-1-Amino-2-(2,4,5-trifluoro-phenyl)-ethyl]-piperidin-1-yl}-3-oxo-propane-1-sulfonyl)-phenyl]-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G36

1-{4-[(R)-1-Amino-2-(2,4,5-trifluoro-phenyl)-ethyl]-piperidin-1-yl}-3-(tetrahydro-furan-2-ylmethane-sulfonyl)-propan-1-one A) 3-(2-Benzyloxycarbonyl-ethyldisulfanyl)-propionic acid benzyl ester To 3,3'-dithiodipropionic acid (1 g, 4.75 mmol) in DCM (6 mL) are added DIPEA (2.86 mL, 16.64 mmol), DMAP (76 mg, 0.618 mmol) and benzyl bromide (1.42 mL, 11.89 mmol). After stirring at rt during 16 h, the mixture is washed with water, brine, an aqueous 1N HCl solution and an aqueous 10% NaHCO3 solution. The organic phase is dried and evaporated to afford a orange oil before purification by flash chromatography on silica (cyclohexane/ethyl acetate 1/0 to 8/2) to yield a yellow oil.
MS: 391 [M+H]+
HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 4.206 min.

B) 3-Mercapto-propionic acid benzyl ester

A stirred solution of 3-(2-Benzyloxycarbonyl-ethyldisulfanyl)-propionic acid benzyl ester (1.73 g, 4.353 mmol) in THF (15 mL) and water (1.5 mL) is deoxygenated during 15 min using a stream of N2. After addition of tributylphosphine (2.15 mL, 8.706 mmol), the mixture is stirred at rt during 6 h and the solvent is evaporated. The aqueous phase is treated with DCM and an aqueous 1N HCl solution, the aqueous phase is extracted with DCM and the combined organic phases are dried and evaporated to afford a yellow oil before purification by flash chromatography on silica (cyclohexane/ethyl acetate 1/0 to 8/2) to yield a yellow oil.
MS: 219 [M+Na]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.365 min.

C) 3-(Tetrahydro-furan-2-ylmethylsulfanyl)propionic acid benzyl ester

To 3-Mercapto-propionic acid benzyl ester (200 mg, 1.019 mmol) are added tetrahydrofurfuryl bromide (505 mg, 3.057 mmol) and sodium methoxide (55 mg, 1.019 mmol). After stirring at rt during 2 h, the mixture is quenched with ethyl acetate and water, the organic phase is washed with water and brine, dried and evaporated to afford a yellow oil before purification by preparative HPLC (Column interchim C18 ODB 5 μm 19×50, Gradient: 0-5 min 20% ACN, 5-15 min 20-100% ACN, 15-20 min 100% ACN) to yield a colorless oil.
MS: 281 [M+H]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.522 min.

D) 3-(Tetrahydro-furan-2-ylmethanesulfonyl)-propionic acid

The title compound is prepared analogously as described in example G30 using 3-(Tetrahydro-furan-2-ylmethylsulfonyl)-propionic acid benzyl ester instead of 3-isopropylsulfonyl-propionic acid benzyl ester. MS: 245 [M+Na]+

E) 1-{4-[(R)-1-Amino-2-(2,4,5-trifluoro-phenyl)-ethyl]-piperidin-1-yl}3-(tetrahydro-furan-2-yl-methanesulfonyl)-propan-1-one The title compound is prepared analogously as described in example G24 using 3-(Tetrahydro-furan-2-ylmethanesulfonyl)-propionic acid instead of 3-(2,3-dihydro-benzo[1,4]dioxine-6-sulfonylamino)-propionic acid.
MS: 463 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.469 min.

Example G37

1-{4-[(R)-1-Amino-2-(2,4,5-trifluoro-phenyl)-ethyl]-piperidin-1-yl}-3-cyclopentanesulfonyl-propan-1-one The title compound is prepared analogously as described in example G30 using cyclopentyl mercaptan instead of 2-propanethiol.
MS: 447 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.641 min.

Example G38

1-{4-[(R)-1-Amino-2-(2,4,5-trifluoro-phenyl)-ethyl]-piperidin-1-yl}-3-ethanesulfonyl-propan-1-one The title compound is prepared analogously as described in example G30 using ethanthiol instead of 2-propanethiol.
MS: 407 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.43 min.

Example G39

1-{4-[(R)-1-Amino-2-(2,4,5-trifluoro-phenyl)-ethyl]-piperidin-1-yl}-3-(2-methyl-propane-2-sulfonyl)-propan-1-one The title compound is prepared analogously as described in example G30 using terbutylthiol instead of 2-propanethiol.
MS: 435 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.63 min.

Example G40

1-{4-[(R)-1-Amino-2-(2,4,5-trifluoro-phenyl)-ethyl]-piperidin-1-yl}-3-(tetrahydro-pyran-2-ylmethane-sulfonyl)-propan-1-one The title compound is prepared analogously as described in example G36 using 2-(Bromomethyl)tetrahydro-2H-pyran instead of tetrahydrofurfuryl bromide.
MS: 477 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.585 min.

Example G41

1-{4-[(R)-1-Amino-2-(2,4,5-trifluoro-phenyl)-ethyl]-piperidin-1-yl}-3-(2-methoxy-ethanesulfonyl)-propan-1-one The title compound is prepared analogously as described in example G36 using 2-bromoethyl-methyl ether instead of tetrahydrofurfuryl bromide.
MS: 437 [M+H]+
HPLC (YMC Pack ODS-AQ 3 μm 2.1×50 mm, 6 min method (0-3.5 min 5-95% ACN, 3.5-5.5 min 95% ACN, 5.5-5.55 min 95-20% ACN, 5.55-6 min 5% ACN): 2.295 min.

Example G41a

1-{4-[(R)-1-Amino-2-(2,4,5-trifluoro-phenyl)-ethyl]-piperidin-1-yl}-3-(2-methoxy-ethanesulfonyl)-propan-1-one maleate The title compound is prepared analogously as described in example D2a using 1-{4-[(R)-1-Amino-2-(2,4,5-trifluoro-phenyl)-ethyl]-piperidin-1-yl}-(2-methoxy-ethanesulfonyl)- propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G41b

1-{4-[(R)-1-Amino-2-(2,4,5-trifluoro-phenyl)-ethyl]-piperidin-1-yl}-3-(2-methoxy-ethanesulfonyl)-propan-1-one toluene-4-sulfonate The title compound is prepared analogously as described in example D2b using 1-{4-[(R)-1-Amino-2-(2,4,5-trifluoro-phenyl)-ethyl]-piperidin-1-yl}-3-(2-methoxy-ethanesulfonyl)propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G42

1-{4-[(R)-1-Amino-2-(2,4,5-trifluoro-phenyl)-ethyl]-piperidin-1-yl}-2-(2-methyl-propane-2-sulfonyl)-ethanone The title compound is prepared analogously as described in example G33 using terbutylthiol instead of 2-propanethiol.
MS: 421 [M+H]+
HPLC (YMC Pack ODS-AQ 3 µm 2.1×50 mm, 6 min method (0-3.5 min 5-95% ACN, 3.5-5.5 min 95% ACN, 5.5-5.55 min 95-20% ACN, 5.55-6 min 5% ACN): 2.56 min.

Example G43

1-{4-[(R)-1-Amino-2-(2,4,5-trifluoro-phenyl)-ethyl]-piperidin-1-yl}-2-cyclopentanesulfonyl-ethanone The title compound is prepared analogously as described in example G33 using cyclopentyl mercaptan instead of 2-propanethiol.
MS: 433 [M+H]+
HPLC (YMC Pack ODS-AQ 3 µm 2.1×50 mm, 6 min method (0-3.5 min 5-95% ACN, 3.5-5.5 min 95% ACN, 5.5-5.55 min 95-20% ACN, 5.55-6 min 5% ACN): 2.68 min.

Example G44

1-{(1S,3S,5R)-3-[(R)-1-Amino-2-(2,4,5-trifluoro-phenyl)-ethyl]-8-aza-bicyclo[3.2.1]oct-8-yl}-2-(2-methyl-propane-2-sulfonyl)-ethanone The title compound is prepared analogously as described in example G42 using 3-exo-[(R) 1-((S-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 447 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.659 min.

Example G45

1-{(1S,3S,5R)-3-[(R)-1-Amino-2-(2,4,5-trifluoro-phenyl)-ethyl]-8-aza-bicyclo[3.2.1]oct-8-yl}-2-cyclopentanesulfonyl-ethanone The title compound is prepared analogously as described in example G43 using 3-exo-[(R)-1-((S-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 459 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.755 min.

Example G46

1-(1S,3S,5R)-3-[(R)-1-Amino-2-(2,4,5-trifluoro-phenyl)-ethyl]-8-aza-bicyclo[3.2.1]oct-8-yl)-2-(propane-2-sulfonyl)-ethanone The title compound is prepared analogously as described in example G33 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 433 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.601 min.

Example G47

N-[4-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-phenyl]-acetamide The title compound is prepared analogously as described in example G35 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 574 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.12 min.

Example G48

1-{(1S,3S,5R)-3-[(R)-1-Amino-2-(2,4,5-trifluoro-phenyl)-ethyl]-8-aza-bicyclo[3.2.1]oct-8-yl}-3-(3-methoxy-benzenesulfonyl)-propan-1-one The title compound is prepared analogously as described in example G44 using 3-methoxythiophenol instead of terbutylthiol.
MS: 511 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.26 min.

Example G49

1-{(1S,3S,5R)-3-[(R)-1-Amino-2-(2,4,5-trifluoro-phenyl)-ethyl]-8-aza-bicyclo[3.2.1]oct-8-yl}-3-(toluene-3-sulfonyl)-propan-1-one The title compound is prepared analogously as described in example G44 using 3-thiocresol instead of terbutylthiol.
MS: 495 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.27 min.

Example G50

1-((1S,3S,5R)-3-[(R)-1-Amino-2-(2,4,5-trifluoro-phenyl)-ethyl]-8-aza-bicyclo[3.2.1]oct-8-yl)-3-(pyrimidine-2-sulfonyl)-propan-1-one The title compound is prepared analogously as described in example G44 using Pyrimidine-2-thiol instead of terbutylthiol.
MS: 483 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example G51

1-{(1S,3S,5R)-3-[(R)-1-Amino-2-(2,4,5-trifluoro-phenyl)-ethyl]-8-aza-bicyclo[3.2.1]oct-8-yl}-3-(6-methyl-pyridine-2-sulfonyl)-propan-1-one The title compound is prepared analogously as described in example G44 using 6-Methyl-pyridine-2-thiol instead of ter-butylthiol.
MS: 498 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.24 min.

Example G52

7-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-3,4-dihydro-2H-isoquinolin-1-one The title compound is prepared analogously as described in example G44 using 7-Mercapto-3,4-dihydro-2H-isoquinolin-1-one instead of terbutylthiol.
MS: 550 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.20 min.

Example G53

3-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-benzamide The title compound is prepared analogously as described in example G44 using 3-Mercapto-benzamide instead of terbutylthiol.
MS: 525 [M+H]+

Example G53a 3-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-benzamide maleate The title compound is prepared analogously as described in example D2a using 3-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-benzamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G53b 3-(3-{(1S,3S,5R)-3-[(R)-1-Amino-2-(2,4,5-trifluoro-phenyl)-ethyl]-8-aza-bicyclo[3.2.1]oct-8-yl}-oxo-propane-1-sulfonyl)-benzamide toluene-4-sulfonate The title compound is prepared analogously as described in example D2b using 3-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)benzamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G54

1-{(1S,3S,5R)-3-[(R)-1-Amino-2-(2,4,5-trifluoro-phenyl)-ethyl]-8-aza-bicyclo[3.2.1]oct-8-yl}-3-cyclopentanesulfonyl-propan-1-one The title compound is prepared analogously as described in example G37 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 473 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.731 min.

Example G55

1-{(1S,3S,5R)-3-[(R)-1-Amino-2-(2,4,5-trifluoro-phenyl)-ethyl]-8-aza-bicyclo[3.2.1]oct-8-yl}-3-(tetrahydro-furan-2-ylmethanesulfonyl)-propan-1-one The title compound is prepared analogously as described in example G36 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 489 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.565 min.

Example G56

1-{(1S,3S,5R)-3-[(R)-1-Amino-2-(2,4,5-trifluoro-phenyl)-ethyl]-8-aza-bicyclo[3.2.1]oct-8-yl}-3-(2-methyl-propane-2-sulfonyl)-propan-1-one The title compound is prepared analogously as described in example G39 using 3-exo-[(R)-1-((S-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 461 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.700 min.

Example G57

1-{(1S,3S,5R)-3-[(R)-1-Amino-2-(2,4,5-trifluoro-phenyl)-ethyl]-8-aza-bicyclo[3.2.1]oct-8-yl}-3-ethanesulfonyl-propan-1-one The title compound is prepared analogously as described in example G38 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 433 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.572 min.

Example G58

1-{(1S,3S,5R)-3-[(R)-1-Amino-2-(2,4,5-trifluoro-phenyl)-ethyl]-8-aza-bicyclo[3.2.1]oct-8-yl}-3-(tetrahydro-pyran-2-ylmethanesulfonyl)-propan-1-one The title compound is prepared analogously as described in example G40 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 503 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.666 min.

Example G59

1-{(1S,3S,5R)-3-[(R)-1-Amino-2-(2,4,5-trifluoro-phenyl)-ethyl]-8-aza-bicyclo[3.2.1]oct-8-yl}-3-(2-methoxy-ethanesulfonyl)-propan-1-one The title compound is prepared analogously as described in example G41 using 3-exo-[(R)-1-((S-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 463 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.435 min.

Example G60

3-(3-{(1S,3S,5R)-3-[(R)-1-Amino-2-(2,4,5-trifluoro-phenyl)-ethyl]-8-aza-bicyclo[3.2.1]octane-8-arbonyl}-benzyl)-1-methyl-imidazolidine-2,4-dione A) 3-(3-Methyl-2,5-dioxo-imidazolidin-1-ylmethyl) benzoic acid methyl ester To methylhydantoine (50 mg, 0.438 mmol) in DMF (2 mL) is added at 0° C. sodium hydride (23 mg, 0.525 mmol). After stirring at 0° C. during 1 h, methyl 2-bromomethylphenylcarboxylate (121 mg, 0.525 mmol) is added and the mixture is stirred at rt during 2 h before quenching with an aqueous saturated NaHCO3 solution and DCM. The organic phase is dried and evaporated to give a crude compound before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield the title compound.
MS: 285 [M+Na]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.216 min.

B) 3-(3-Methyl-2,5-dioxo-imidazolidin-1-ylmethyl)-benzoic acid

To 3-(3-Methyl-2,5-dioxo-imidazolidin-1-ylmethyl)benzoic acid methyl ester (100 mg, 0.381 mmol) in THF/water (2/1, 2 mL) is added lithium hydroxyde monohydrate (24 mg, 0.572 mmol) and the reaction is stirred at rt during 16 h before quenching with water and ethylacetate. The separated aqueous phase is acidified to pH 2 with an aqueous 1N HCl solution, extracted with ethylacetate and the organic phase is dried and evaporated to give the title compound.
MS: 267 [M+H2O+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.25 min.

C) 3-(3-{(1S,3S,5R)-3-[(R)-1-Amino-2-(2,4,5-trifluoro-phenyl)-ethyl]-8-aza-bicyclo[3.2.1]octane-8-carbonyl}benzyl)-1-methyl-imidazolidine-2,4-dione The title compound is prepared analogously as described in example G17 using 3-(3-Methyl-2,5-dioxo-imidazolidin-1-ylmethyl)-benzoic acid instead of 3-(1,3-dioxo-1,3-dihydro-isoindol-2-yl-methyl)-benzoic acid.
MS: 515 [M+H]+
HPLC (Waters Symmetry C18 3.5 μm 2.1×50 mm, 6 min method (0-3 min 595% ACN, 3.5-5.5 min 95% ACN, 5.5-5.55 min 95-5% ACN, 5.55-6 min 5% ACN): 2.91 min.

Example G61

3-(4-{(1S,3S,5R)-3-[(R)-1-Amino-2-(2,4,5-trifluoro-phenyl)-ethyl]-8-aza-bicyclo[3.2.1]octane-8-carbonyl}-benzyl)-thiazolidine-2,4-dione The title compound is prepared analogously as described in example G1 using 4-(2,4-Dioxo-thiazolidin-3-ylmethyl)-benzoic acid instead of N-acetyl-L-alanine.
MS: 518 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.245 min.

Example G62

1-(4-{(1S,3S,5R)-3-[(R)-1-Amino-2-(2,4,5-trifluoro-phenyl)-ethyl]-8-aza-bicyclo[3.2.1]octane-8-carbo-nyl}-benzyl)-pyrrolidine-2,5-dione A) 2-Methyl-propane-2-sulfinic acid [(R)-1-{(1S,3S,5R)-8-[3-(2,5-dioxo-pyrrolidin-1-ylmethyl)-benzoyl]-8-aza-bicyclo[3.2.1]oct-3-yl}-2-(2,4,5-trifluoro-phenyl)-ethyl]-amide To 2-Methyl-propane-2-sulfinic acid [(R)-1-[(1S,3S,5R)-8-(3-aminomethyl-benzoyl)-8-aza-bicyclo[3.2.1]oct-3-yl]-2-(2,4,5-trifluoro-phenyl)-ethyl]-amide (228 mg, 0.437 mmol) in toluene (10 ml) are added succinic anhydride (53 mg, 0.524 mmol) and molecular sieves (200 mg). After stirring at 110° C. during 6 h, CDI (107 mg, 0.655 mmol) and triethylamine (183 uL, 1.311 mmol) are added and the mixture is stirred at 110° C. during 24 h. After filtration and evaporation of the solvent, the residue is treated with DCM and an aqueous saturated NaHCO3 solution, the organic phase is dried and evaporated to give a crude compound before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield the title compound.

MS: 604 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.370 min.

B) 1-(4-{(1S,3S,5R)$_3$-[(R)-1-Amino-2-(2,4,5-trifluoro-phenyl)-ethyl]-8-aza-bicyclo[3.2.1]octane-8-carbonyl}-benzyl)-pyrrolidine-2,5-dione The title compound is prepared analogously as described in example G1 using (S)-2-Methyl-propane-2-sulfinic acid [(R)-1-{(1S,3S,5R)-8-[3-(2,5-dioxo-pyrrolidin-1-ylmethyl) benzoyl]-8-aza-bicyclo[3.2.1]oct-3-yl}-2-(2,4,5-trifluoro-phenyl)-ethyl]-amide instead of N—((S)-1-Methyl-2-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-2-oxo-ethyl)-acetamide.

MS: 500 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.212 min.

Example G63

1-{(4-[(R)-1-Amino-2-(2,4,5-trifluoro-phenyl)-ethyl]-piperidin-1-yl}-3-[2-(1,1-dioxo-1lambda*6*-thiomorpholin 4-yl)-2-oxo-ethanesulfonyl]-propan-1-one A) 3-Carboxymethylsulfanyl-propionic acid benzyl ester The title compound is prepared analogously as described in example G36 using Bromoacetic acid instead of tetrahydrofurfuryl bromide.
MS: 255 [M+H]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.841 min.

B) 3-(2-Oxo-2-thiomorpholin-4-yl-ethylsulfanyl)-propionic acid benzyl ester

To 3-Carboxymethylsulfanyl-propionic acid benzyl ester (763 mg, 3 mmol), HBTU (1.71 g, 4.5 mmol) and DIPEA (2.05 mL, 12 mmol) in DCM (10 mL) is added thiomorpholine (283 uL, 3 mmol). After stirring at rt during 2 h and evaporation of the solvent, the residue is dissolved with ethylacetate and washed with an aqueous 1N HCl solution and an aqueous saturated NaHCO3 solution. The organic phase is dried and evaporated to afford the title compound.
MS: 340 [M+H]+
HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.529 min.

C) 1-{4-[(R)-1-Amino-2-(2,4,5-trifluoro-phenyl)-ethyl]-piperidin-1-yl}-3-[2-(1,1-dioxo-1lambda*6*-thiomorpholin-4-yl)-2-oxo-ethanesulfonyl]-propan-1-one The title compound is prepared analogously as described in example G36 using 3-(2-Oxo-2-thiomorpholin-4-yl-ethylsulfanyl)-propionic acid benzyl ester instead of 3-(Tetrahydro-furan-2-ylmethylsulfonyl)-propionic acid benzyl ester.
MS: 554 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.214 min.

Example G63a

1-{4-[(R)-1-Amino-2-(2,4,5-trifluoro-phenyl)-ethyl]-piperidin-1-yl}-3-[2-(1,1-dioxo-1 lambda*6*-thiomorpholin-4-yl)-2-oxo-ethanesulfonyl]-propan-1-one maleate The title compound is prepared analogously as described in example D2a using 1-{4-[(R)-1-Amino-2-(2,4,5-trifluoro-phenyl)-ethyl]-piperidin-1-yl}-3-[2-(1,1-dioxo-1 lambda*6*-thiomorpholin-4-yl)-2-oxo-ethanesulfonyl]-propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G63b

1-{4-[(R)-1-Amino-2-(2,4,5-trifluoro-phenyl)-ethyl]-piperidin-1-yl}-3-[2-(1,1-dioxo-1lambda*6*-thiomorpholin-4-yl)-2-oxo-ethanesulfonyl]-propan-1-one toluene-4-sulfonate The title compound is prepared analogously as described in example D2b using 1-{4-[(R)-1-Amino-2-(2,4,5-trifluoro-phenyl)-ethyl]-piperidin-1-yl}-3-[2-(1,1-dioxo-1 lambda*6*-thiomorpholin-4-yl)-2-oxo-ethanesulfonyl]-propan-1-one instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example G64

1-{4-[(R)-1-Amino-2-(2,4,5-trifluoro-phenyl)-ethyl]-piperidin-1-yl}-3-(2-morpholin-4-yl-2-oxo-ethanesulfonyl)-propan-1-one The title compound is prepared analogously as described in example G63 using morpholine instead of thiomorpholine.

MS: 506 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.296 min.

Example G65

1-{4-[(R)-1-Amino-2-(2,4,5-trifluoro-phenyl)-ethyl]-piperidin-1-yl}-3-(tetrahydro-pyran-2-ylmethane-sulfonyl)-propan-1-one The title compound is prepared analogously as described in example G58 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.

MS: 477 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.372 min.

Example G66

1-{(1S,3S,5R)-3-[(R)-1-Amino-2-(2,4,5-trifluoro-phenyl)-ethyl]-8-aza-bicyclo[3.2.1]oct-8-yl}-3-[2-(1,1-dioxo-1 lambda*6*-thiomorpholin-4-yl)-2-oxo-ethanesulfonyl]-propan-1-one The title compound is prepared analogously as described in example G63 using 3-exo-[(R)-1-((S)-2-methyl-propane-2-sufinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 580 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.352 min.

Example G67

1-{(1S,3S,5R)-3-[(R)-1-Amino-2-(2,4,5-trifluoro-phenyl)-ethyl]-8-aza-bicyclo[3.2.1]oct-8-yl}-3-(2-morpholin-4-yl-2-oxo-ethanesulfonyl)-propan-1-one The title compound is prepared analogously as described in example G64 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 532 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.379 min.

Example H1

1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone This compound is prepared according to Scheme H:

Scheme H

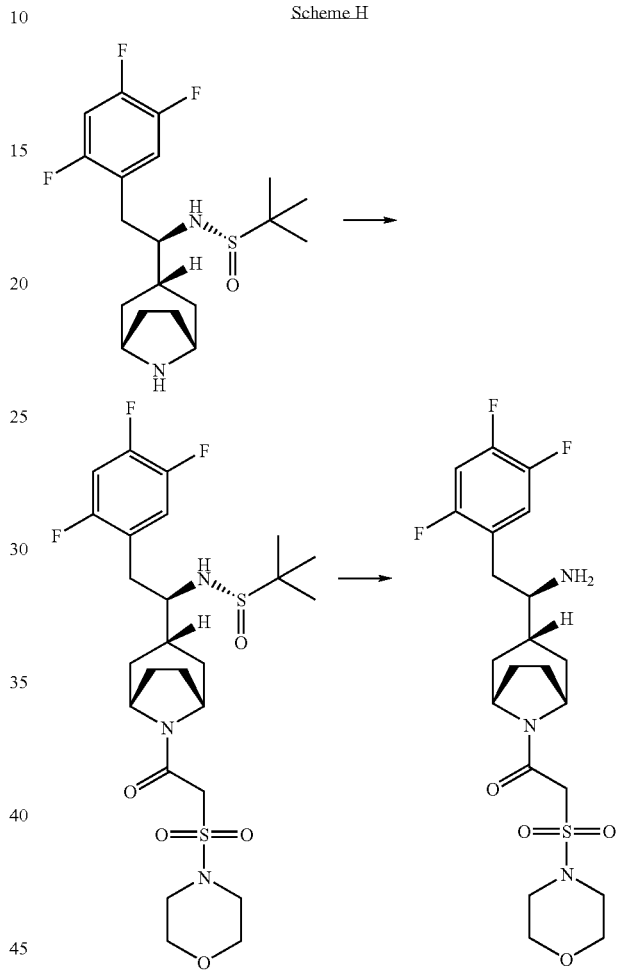

A) Chlorosulfonyl-acetic acid methyl ester

To chlorosulfonyl chloride (3.34 g, 17.9 mmol) in diethyl ether (30 mL) is added at 0° C. methanol (800 μL, 19.7 mmol). The resulting mixture is stirred at 0° C. during 1 h and the solvent is evaporated to give the title compound.

B) (Morpholine-4-sulfonyl)acetic acid methyl ester

To chlorosulfonyl-acetic acid methyl ester (3.39 g, 19.6 mmol) in dichloromethane (50 mL) is added morpholine (8.6 mL, 98 mmol). The resulting mixture is stirred at rt during 2 h and the solvent is evaporated to yield the title compound.

MS: 223 [M−H]+

C) (Morpholine-4-sulfonyl)-acetic acid (Morpholine-4-sulfonyl)acetic acid methyl ester (0.5 g, 2.24 mmol) is dissolved in 0.66 N KOH aqueous ethanol solution (1/1, 150 mL) and the mixture is heated at reflux during 16 h. The solvent is evaporated and residue is extracted with dichloromethane/methanol 4:1 to yield the title compound.

MS: 232 [M+Na]

D) 1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone The title compound is prepared analogously as described in example G1 using (morpholine-4-sulfonyl)-acetic acid instead of N-acetyl-L-alanine. MS: 476 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.94 min.

Example H1a

1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone maleate The title compound is prepared analogously as described in example D2a using 1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example H1b

1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone toluene-4-sulfonate The title compound is prepared analogously as described in example D2b using 1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example H2

1-{3-exo-[(R)-1-Amino-2-(2,4,5-trifluoro-phenyl)-ethyl]-8-aza-bicyclo[3.2.1]oct-8-yl}-2-benzenesulfonyl-ethanone The title compound is prepared analogously as described in example H1 using phenylsulfonylacetic acid instead of (Morpholine-4-sulfonyl)acetic acid.

MS: 466 [M+H]+

HPLC (Nucleosil 100-5 C18, 10 min method (0-1 min 10% ACN, 1-6 min 10-100% ACN, 6-8.5 min 100% ACN, 8.5-9 min 100-10% ACN, 9-10 min 10% ACN): 3.88 min.

Example H3

1-{3-exo-[(R)-1-Amino-2-(2,4,5-trifluoro-phenyl)-ethyl]-8-aza-bicyclo[3.2.1]oct-8-yl}-2-methanesulfonyl-ethanone The title compound is prepared analogously as described in example H1 using methanesulfonylacetic acid instead of (Morpholine-4-sulfonylyacetic acid.

MS: 405 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 0.87 min.

Example H4

1-{3-exo-[(R)-1-Amino-2-(2,4,5-trifluoro-phenyl)-ethyl]-8-aza-bicyclo[3.2.1]oct-8-yl}-2-(piperidine-1-sulfonyl)-ethanone The title compound is prepared analogously as described in example H1 using piperidine instead of morpholine.

MS: 474 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.28 min.

Example H5

2-{3-exo-[(R)-1-Amino-2-(2,4,5-trifluoro-phenyl)-ethyl]-8-aza-bicyclo[3.2.1]oct-8-yl}-2-oxo-ethanesulfonic acid benzylamide The title compound is prepared analogously as described in example H1 using benzylamine instead of morpholine.

MS: 496 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.28 min.

Example H6

2-{3-exo-[(R)-1-Amino-2-(2,4,5-trifluoro-phenyl)-ethyl]-8-aza-bicyclo[3.2.1]oct-8-yl}-2-oxo-ethanesulfonic acid benzyl-methyl-amide The title compound is prepared analogously as described in example H1 using N-methylbenzylamine instead of morpholine.

MS: 510 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.30 min.

Example H7

1-{3-exo-[(R)-1-Amino-2-(2,4,5-trifluoro-phenyl)-ethyl]-8-aza-bicyclo[3.2.1]oct-8-yl}-2-methyl-2-(morpholine-4-sulfonyl)-propan-1-one A) 2-Methyl-2-(morpholine-4-sulfonyl)-propionic acid methyl ester To a solution of (Morpholine-4-sulfonylyacetic acid methyl ester (500 mg, 2.24 mmol) in tetrahydrofuran (10 mL) is added potassium bis(trimethylsilyl) amide (1.18 g, 5.6 mmol). After stirring at rt during 1 h, methyliodide (349 uL, 5.6 mmol) is added and the resulting mixture is stirred at rt during 1 h and at 50° C. during the weekend. The solution is purified by flash chromatography on silica gel (eluent: cyclohexane/ethyl acetate 100/0 to 0/100) to yield a yellow solid.

MS: 252 [M+H]+

B) 1-{3-exo-[(R)-1-Amino-2-(2,4,5-trifluoro-phenyl)-ethyl]-8-aza-bicyclo[3.2.1]oct-8-yl}-2-methyl-2-(morpholine-4-sulfonyl)-propan-1-one The title compound is prepared analogously as described in example H1 using 2-methyl-2-(morpholine-4-sulfonyl)-propionic acid methyl ester instead of (Morpholine-4-sulfonyl)-acetic acid methyl ester.

MS: 504 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.26 min.

Example H8

2-{3-exo-[(R)-1-Amino-2-(2,4,5-trifluoro-phenyl)-ethyl]-8-aza-bicyclo[3.2.1]oct-8-yl}-2-oxo-ethanesulfonic acid (2-methoxy-ethyl)-methyl-amide The title compound is prepared analogously as described in example H1 using N-methyl-2-methoxyethylamine instead of morpholine.

MS: 478 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example H8a

2-{3-exo-[(R)-1-Amino-2-(2,4,5-trifluoro-phenyl)-ethyl]-8-aza-bicyclo[3.2.1]oct-8-yl}-2-oxo-ethanesulfonic acid (2-methoxy-ethyl)-methyl-amide maleate The title compound is prepared analogously as described in example D2a using 2-{3-exo [(R)-1-Amino-2-(2,4,5-trifluoro-phenyl)-ethyl]-8-aza-bicyclo[3.2.1]oct-8-yl}-2-oxo-ethanesulfonic acid (2-methoxy-ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example H8b

2-{3-exo-[(R)-1-Amino-2-(2,4,5-trifluoro-phenyl)-ethyl]-8-aza-bicyclo[3.2.1]oct-8-yl}-2-oxo-ethanesulfonic acid (2-methoxy-ethyl)-methyl-amide toluene-4-sulfonate The title compound is prepared analogously as described in example D2b using 2-{3-exo [(R)-1-Amino-2-(2,4,5-trifluoro-phenyl)-ethyl]-8-aza-bicyclo[3.2.1]oct-8-yl}-2-oxo-ethanesulfonic acid (2-methoxy-ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example H9

1-{4-[(R)-1-Amino-2-(2,4,5-trifluoro-phenyl)-ethyl]-piperidin-1-yl}-2-(morpholine-4-sulfonyl)-ethanone The title compound is prepared analogously as described in example H1 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.

MS: 450 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.70 min.

Example H10

1-{3-exo-[(R)-1-Amino-2-(2,4,5-trifluoro-phenyl)-ethyl]-8-aza-bicyclo[3.2.1]oct-8-yl}-2-methyl-1-oxo-propane-2-sulfonic acid (2-methoxy-ethyl)-methyl-amide The title compound is prepared analogously as described in example H7 using N-methyl-2-methoxyethylamine instead of morpholine.

MS: 506 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.29 min.

Example H11

1-{3-exo-[(R)-1-Amino-2-(2,4,5-trifluoro-phenyl)-ethyl]-8-aza-bicyclo[3.2.1]oct-8-yl}-2-methyl-1-oxo-propane-2-sulfonic acid benzyl-methyl-amide The title compound is prepared analogously as described in example H7 using N-methyl-benzylamine instead of morpholine.

MS: 538 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.36 min.

Example H12

{3-exo-[(R)-1-Amino-2-(2,4,5-trifluoro-phenyl)-ethyl]-8-aza-bicyclo[3.2.1]oct-8-yl}-[1-(morpholine-4-sulfonyl)-cyclopropyl]-methanone The title compound is prepared analogously as described in example H7 using 1,2-dibromoethane instead of methyliodide.

MS: 502 [M+H]+

Example H13

1-{3-exo-[(R)-1-Amino-2-(2,4,5-trifluoro-phenyl)-ethyl]-8-aza-bicyclo[3.2.1]oct-8-yl}-2-(1,3-dihydro-isoindole-2-sulfonyl)-ethanone The title compound is prepared analogously as described in example H1 using isoindoline instead of morpholine.

MS: 508 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.26 min.

Example H14

1-{(1S,3S,5R)-3-[(R)-1-Amino-2-(2,4,5-trifluoro-phenyl)-ethyl]-8-aza-bicyclo[3.2.1]oct-8-yl}-2-(4,4-difluoro-piperidine-1-sulfonyl)-ethanone The title compound is prepared analogously as described in example H1 using 4,4-Difluoropiperidine instead of morpholine.

MS: 510 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.23 min.

Example I1

N-(3-{3-exo-[(R)-1-Amino-2-(2,4,5-trifluoro-phenyl)-ethyl]-8-aza-bicyclo[3.2.1]oct-8-yl}-3-oxo-propyl)-3-(1,3-dioxo-1,3-dihydro-isoindol-2-yl)-propionamide This compound is prepared according to Scheme I:

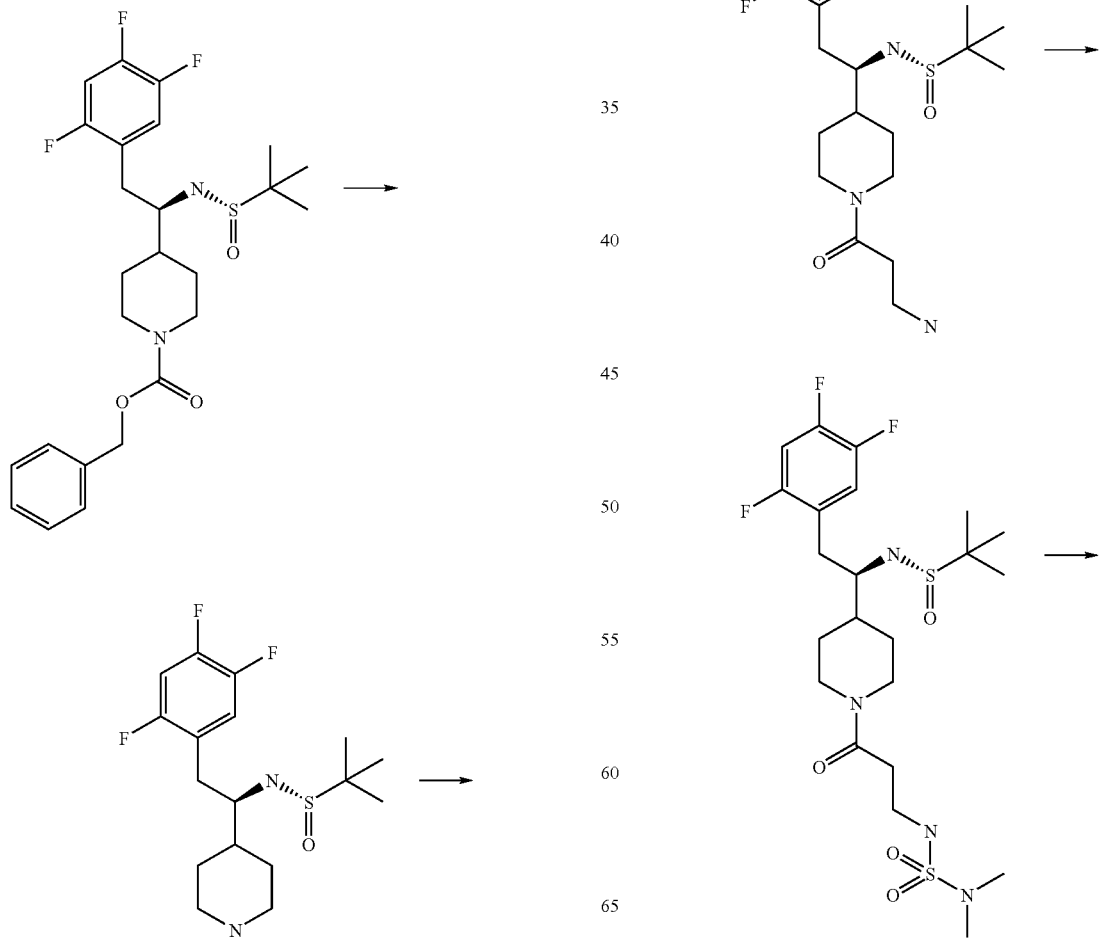

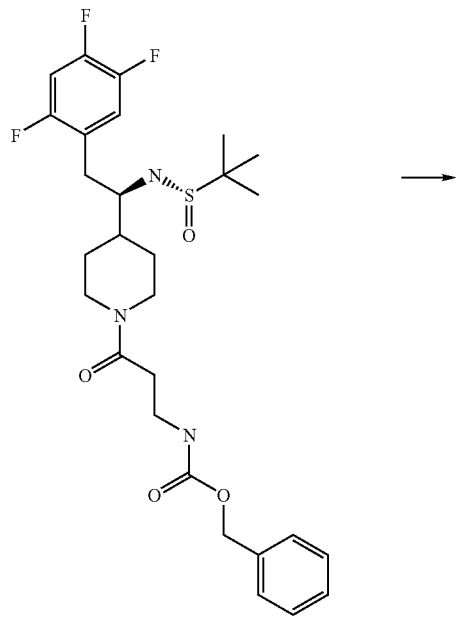

-continued

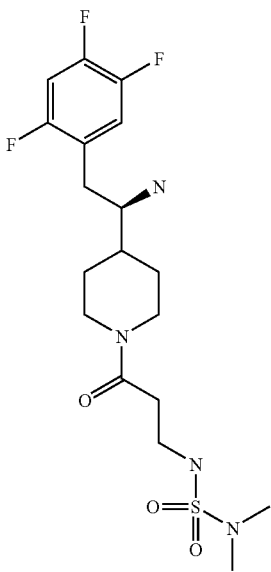

A) (S)-2-Methyl-propane-2-sulfinic acid [(R)-1-piperidin-4-yl-2-(2,4,5-trifluoro-phenyl)-ethyl]-amide The title compound is prepared analogously as described in example B1 using 4-[(R)-1-((S)-2-methyl-propane-2-sulfinylamino)-2-(2,4,5-trifluoro-phenyl)-ethyl]-piperidine-1-carboxylic acid benzyl ester instead of 3-exo-[(S)-1-((S)-2-methyl-propane-2-sulfinylamino)-2-(2,4,5-trifluoro-phenyl)-ethyl]-8-aza-bicyclo[3.2.1]octane-8-carboxylic acid benzyl ester.

MS: 363 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.45 min.

B) (3-{4-[(R)-1-((S)-2-Methyl-propane-2-sulfinylamino)-2-(2,4,5-trifluoro-phenyl)-ethyl]-piperidin-1-yl}-3-oxo-propyl)-carbamic acid benzyl ester To a solution of Cbz-beta-alanine (339 mg, 1.52 mmol) in dichloromethane (10 mL) are added O-benzotriazol-1-yl-tetramethyluronium hexafluorophosphate (785 mg, 2.07 mmol) and diisopropylethylamine (960 uL, 5.52 mmol) before addition of (S)-2-methyl-propane-2-sulfinic acid [(R)-1-piperidin-4-yl-2-(2,4,5-trifluoro-phenyl)-ethyl]-amide (500 mg, 1.379 mmol). The resulting solution is stirred at rt during 2 h and washed with water and brine. The organic phase is dried and evaporated before purification by preparative HPLC (Column Interchrom C18 ODB 10 μm 28×250, Gradient: 0-2.5 min 5% ACN, 2.5-25.5 min 5-100% ACN, 25.5-30 min 100% ACN) to yield a yellow solid.

MS: 568 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.41 min.

C) (S)-2-Methyl-propane-2-sulfinic acid [(R)-1-[1-(3-amino-propionyl)piperidin-4-yl]-2-(2,4,5-trifluoro-phenyl)-ethyl]-amide To (3-{4-[(R)-1-((S)-2-methyl-propane-2-sulfinylamino)-2-(2,4,5-trifluoro-phenyl)-ethyl]-piperidin-1-yl}-oxo-propyl)-carbamic acid benzyl ester (684 mg, 1.205 mmol) in methanol (10 mL) are added ammonium formiate (379 mg, 6.025 mmol) and Pd/C (171 mg). After stirring at rt during 72 h, the solution is filtered through celite and evaporated to yield a yellow solid.

MS: 434 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

D) 3-(1,3-Dioxo-1,3-dihydro-isoindol-2-yl)-N-(3-{4-[(R)-1-((S)-2-methyl-propane-2-sulfinylamino)-2-(2,4,5-trifluoro-phenyl)-ethyl]-piperidin-1-yl}-3-oxo-propyl)-propionamide To 2-methyl-propane-2-sulfinic acid [(R)-1-[1-(3-amino-propionyl)-piperidin-4-yl]-2-(2,4,5-trifluoro-phenyl)-ethyl]-amide (104 mg, 0.241 mmol) in dichloromethane (3 mL) are added triethylamine (101 uL, 0.723), N,N-dimethylamidosulfonyl chloride (28.5 uL, 0.265 mmol) and 4-dimethylaminopyridine (6 mg, 0.05 mmol). After stirring during 4 h at rt, the mixture is washed with saturated NaHCO3 solution, the organic phase is dried and evaporated to give a residue which is purified by preparative HPLC (Column Interchrom C18 ODB 5 μm 19×50, Gradient: 0-5 min 10% ACN, 5-15 min 10-90% ACN, 15-20 min 90% ACN) to yield a yellow oil.

MS: [M+H]+ 541

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.309 min.

E) N-(3-{4-[(R)-1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide To 3-(1,3-Dioxo-1,3-dihydro-isoindol-2-yl)-N-(3-{4-[(R)-1-((S)-2-methyl-propane-2-sulfinylamino)-2-(2,4,5-trifluoro-phenyl)-ethyl]-piperidin-1-yl}-3-oxo-propyl)propionamide (22.3 mg, 0.041 mmol) is added 4N HCl in dioxane (2 mL). The resulting mixture is stirred at rt during 1 h before it is frozen, lyophilized and purified by preparative HPLC (Column YMC ODS-AQ 20×50 5 uM, Gradient: 0-2.5 min 5% ACN, 2.5-12.5 min 5-100% ACN, 12.5-15 min 100% CAN) to yield a white solid.

MS 437 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.09 min.

Example I1a

N-(3-{4-[(R)-1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide maleate The title compound is prepared analogously as described in example D2a using N-(3-{4-[(R)-1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example I1b

N-(3-{4-[(R)-1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide toluene-4-sulfonate The title compound is prepared analogously as described in example D2b using N-(3-{4-[(R) 1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example I2

Cyclopropanesulfonic acid (3-{4-[(R)-1-amino-2-(2,4,5-trifluoro-phenyl)-ethyl]-piperidin-1-yl}-3-oxo-propyl)-amide The title compound is prepared analogously as described in example I1 using cyclopropanesulfonyl chloride instead of N,N-dimethylamidosulfonyl chloride.

MS: 434 [M+H]+

HPLC (Nucleosil C18 HD CC70, 6 min method (0-3.5 min 5-95% ACN, 3.5-5.5 min 95% ACN, 5.5-5.55 min 95-5% ACN, 5.55-6 min 5% ACN): 4.008 min.

Example I3

Ethylsulfonic acid (3-{4-[(R)-1-amino-2-(2,4,5-trifluoro-phenyl)-ethyl]-piperidin-1-yl}-3-oxo-propyl)-amide The title compound is prepared analogously as described in example I1 using ethylsulfonyl chloride instead of N,N-dimethylamidosulfonyl chloride.

MS: 422 [M+H]+

HPLC (Nucleosil C18 HD CC70, 6 min method (0-3.5 min 5-95% ACN, 3.5-5.5 min 95% ACN, 5.5-5.55 min 95-5% ACN, 5.55-6 min 5% ACN): 3.957 min.

Example I4 methylsulfonic acid (3-{4-[(R)-1-amino-2-(2,4,5-trifluoro-phenyl)-ethyl]-piperidin-1-yl}-3-oxo-propyl)-amide The title compound is prepared analogously as described in example I1 using methylsulfonyl chloride instead of N,N-dimethylamidosulfonyl chloride.

MS: 408 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.58 min.

Example I5

N-(3-{4-[(R)-1-Amino-2-(2,4,5-trifluoro-phenyl)-ethyl]-piperidin-1-yl}-3-oxo-propyl)-formamide The title compound is prepared analogously as described in example I1 using 3-formylamino-propionic acid instead of Cbz-beta-alanine.

MS: 358 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.45 min.

Example I6

A) 3-(1,3-Dioxo-1,3-dihydro-isoindol-2-yl)-N-(3-{4-[(R)-1-((S)-2-methyl-propane-2-sulfinylamino)-2-(2,4,5-trifluoro-phenyl)-ethyl]-piperidin-1-yl}3-oxo-propylypropionamide To a solution of 3-(1,3-dioxo-1,3-dihydro-isoindol-2-yl)-propionic acid (83 mg, 0.381 mmol) in dichloromethane (2 mL) are added O-benzotriazol-1-yl-tetramethyluronium hexafluorophosphate (196 mg, 0.519 mmol) and diisopropylethylamine (237 uL, 1.384 mmol) before addition of (S)-2-methyl-propane-2-sulfinic acid [(R)-1-[1-(3-amino-propionyl)piperidin-4-yl]-2-(2,4,5-trifluoro-phenyl)-ethyl]-amide (150 mg, 0.346 mmol). The resulting solution is stirred at rt during 16 h and washed with aqueous 1N HCl and saturated aqueous NaHCO3. The organic phase is dried and evaporated before purification by preparative HPLC (Column Interchrom C18 ODB 10 μm 50×28, Gradient: 0-10 min 5% ACN, 10-20 min 5-90% ACN, 20-25 min 90% ACN) to yield an orange solid.

MS: 635 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.14 min.

B) N-(3-{4-[(R)-1-Amino-2-(2,4,5-trifluoro-phenyl)-ethyl]-piperidin-1-yl}-3-oxo-propyl)-3-(1,3-dioxo-1,3-dihydro-isoindol-2-yl)-propionamide To 3-(1,3-Dioxo-1,3-dihydro-isoindol-2-yl)-N-(3-{4-[(R)-1-((S)-2-methyl-propane-2-sulfinylamino)-2-(2,4,5-trifluoro-phenyl)-ethyl]-piperidin-1-yl}-3-oxo-propyl)-propionamide (137 mg, 0.216 mmol) is added 4N HCl in dioxane (2 mL). The resulting mixture is stirred at rt during 1 h before it is frozen, lyophilized and purified by preparative HPLC (Column Interchrom C18 ODS-AQ 10 μm 50×20, Gradient: 0-2.5 min 2% ACN, 2.5-12.5 min 2-90% ACN, 12.5-15 min 90% ACN) to yield a light yellow solid.

MS: 553 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.87 min.

Example I7

N-(3-{4-[(R)-1-Amino-2-(2,4,5-trifluoro-phenyl)-ethyl]-piperidin-1-yl}-3-oxo-propyl)-isobutyramide The title compound is prepared analogously as described in example I6 using isobutyric acid instead of 3-(1,3-Dioxo-1,3-dihydro-isoindol-2-yl)-propionic acid.

MS: 400 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.096 min.

Example I8

Cyclopropanecarboxylic acid (3-{4-[(R)-1-amino-2-(2,4,5-trifluoro-phenyl)-ethyl]-piperidin-1-yl}-3-oxo-propyl)-amide The title compound is prepared analogously as described in example I6 using cyclopropanecarboxylic acid instead of 3-(1,3-Dioxo-1,3-dihydro-isoindol-2-yl)-propionic acid.
MS: 398 [M+H]+
HPLC (Waters Symmetry C18 3.5 µm 2.1×50 mm, 6 min method (0-3 min 20-95% ACN, 3.5-5.5 min 95% ACN, 5.5-5.55 min 95-20% ACN, 5.55-6 min 20% ACN): 1.75 min.

Example I9

5-Oxo-pyrrolidine-2-carboxylic acid (3-{4-[(R)-1-amino-2-(2,4,5-trifluoro-phenyl)-ethyl]-piperidin-1-yl}-3-oxo-propyl)-amide The title compound is prepared analogously as described in example I6 using 5-oxo-pyrrolidine-2-carboxylic acid instead of 3-(1,3-Dioxo-1,3-dihydro-isoindol-2-yl)-propionic acid.
MS: 441 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.40 min.

Example I9a

5-Oxo-pyrrolidine-2-carboxylic acid (3-{4-[(R)-1-amino-2-(2,4,5-trifluoro-phenyl)-ethyl]-piperidin-1-yl}-3-oxo-propyl)-amide maleate The title compound is prepared analogously as described in example D2a using 5-Oxo-pyrrolidine-2-carboxylic acid (3-{4-[(R)-1-amino-2-(2,4,5-trifluoro-phenyl)-ethyl]-piperidin-1-yl}3-oxo-propyl)amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example I9b

5-Oxo-pyrrolidine-2-carboxylic acid (3-{4-[(R)-1-amino-2-(2,4,5-trifluoro-phenyl)-ethyl]-piperidin-1-yl}-3-oxo-propyl)-amide toluene-4-sulfonate The title compound is prepared analogously as described in example D2b using 5-Oxo-pyrrolidine-2-carboxylic acid (3-{4-[(R)-1-amino-2-(2,4,5-trifluoro-phenyl)-ethyl]-piperidin-1-yl}-3-oxo-propyl)-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example I10

Pyridazine-4-carboxylic acid (3-{4-[(R)-1-amino-2-(2,4,5-trifluoro-phenyl)-ethyl]-piperidin-1-yl}-3-oxo-propyl)-amide The title compound is prepared analogously as described in example I6 using pyridazine-4-carboxylic acid instead of 3-(1,3-Dioxo-1,3-dihydro-isoindol-2-yl)-propionic acid.

MS: 436 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.49 min.

Example K1

3-{4-[(R)-1-Amino-2-(2,4,5-trifluoro-phenyl)-ethyl]-piperidin-1-yl}-N-cyclopropyl-3-oxo-propionamide This compound is prepared according to Scheme I:

Scheme K

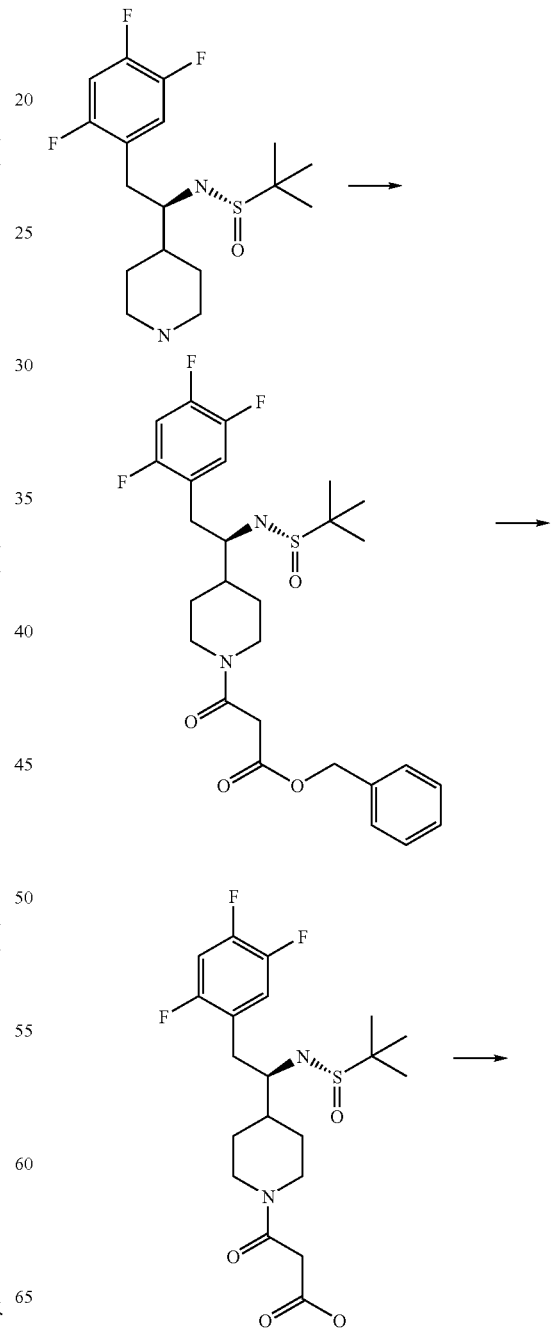

-continued

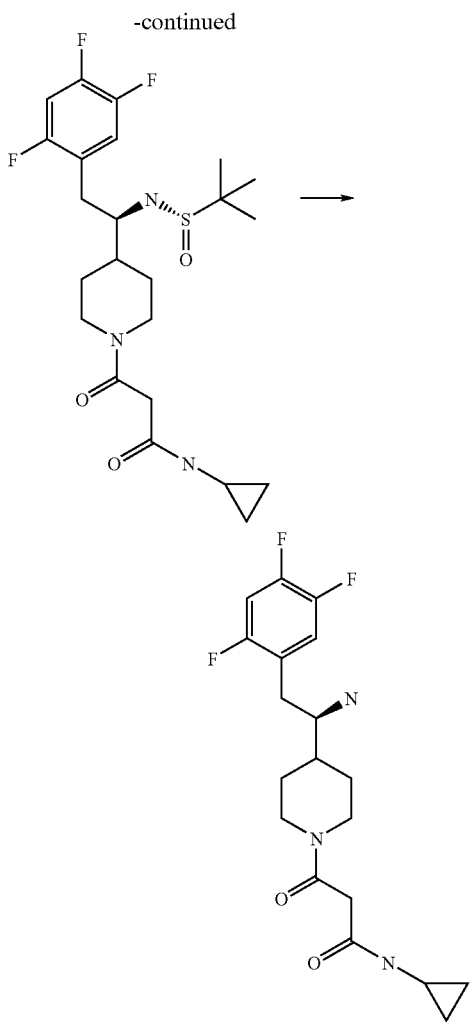

A) 3-{4-[(R)-1-((S-2-Methyl-propane-2-sulfinylamino)-2-(2,4,5-trifluoro-phenyl)-ethyl]-piperidin-1-yl}-3-oxo-propionic acid benzyl ester The title compound is prepared analogously as described in example I1 using malonic acid monobenzyl ester instead of Cbz-beta-alanine.

MS: 539 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.44 min.

B) 3-{4-[(R)-1-((S-2-Methyl-propane-2-sulfinylamino)-2-(2,4,5-trifluoro-phenyl)-ethyl]-piperidin-1-yl}-3-oxo-propionic acid The title compound is prepared analogously as described in example I1 using 3-{4-[(R)-1-((S)-2-methyl-propane-2-sulfinylamino)-2-(2,4,5-trifluoro-phenyl)-ethyl]-piperidin-1-yl}-3-oxo-propionic acid benzyl ester instead of (3-{4-[(R)-1-((S)-2-methyl-propane-2-sulfinylamino)-2-(2,4,5-trifluoro-phenyl)-ethyl]-piperidin-1-yl}-3-oxo-propyl)-carbamic acid benzyl ester.

MS: 449 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.24 min.

C) N-Cyclopropyl-3-{4-[(R)-1-((S)-2-methyl-propane-2-sulfinylamino)-2-(2,4,5-trifluoro-phenyl)-ethyl]-piperidin-1-yl}-3-oxo-propionamide To a solution of 3-{4-[(R)-1-((S)-2-methyl-propane-2-sulfinylamino)-2-(2,4,5-trifluoro-phenyl)-ethyl]-piperidin-1-yl}-3-oxo-propionic acid (45 mg, 0.0.1 mmol) in dichloromethane (2 mL) are added O-benzotriazol-1-yl-tetramethyluronium hexafluorophosphate (57 mg, 0.15 mmol) and diisopropylethylamine (69 uL, 0.4 mmol) before addition of cyclopropylamine (8 uL, 0.11 mmol). The resulting solution is stirred at rt during 3 h and washed with water and brine. The organic phase is dried and evaporated before purification by preparative HPLC (Column Interchrom C18 ODB 110 μm 50×28, Gradient: 0-2 min 10% ACN, 2-12 min 10-100% ACN, 12-15 min 100% ACN) to yield a colorless oil.

MS: 488 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.27 min.

D) 3-{4-[(R)-1-Amino-2-(2,4,5-trifluoro-phenyl)-ethyl]-piperidin-1-yl}-N-cyclopropyl-3-oxo-propionamide To N-cyclopropyl-3-{4-[(R)-1-((S)-2-methylpropane-2-sulfinylamino)-2-(2,4,5-trifluoro-phenyl)-ethyl]-piperidin-1-yl}-3-oxo-propionamide (40 mg, 0.082 mmol) is added 4N HCl in dioxane (2 mL). The resulting mixture is stirred at rt during 1 h before it is frozen, lyophilized and purified by preparative HPLC (Column nucleosil C18HD 5 um 50×21, Gradient: 0-2.5 min 5% ACN, 2.5-12.5 min 5-100% ACN, 12.5-15 min 100% ACN) to yield a white solid.

MS: 384 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.57 min.

Example K1a

3-{4-[(R)-1-Amino-2-(2,4,5-trifluoro-phenyl)-ethyl]-piperidin-1-yl}-N-cyclopropyl-3-oxo-propionamide maleate The title compound is prepared analogously as described in example D2a using 3-{4-[(R)-1-Amino-2-(2,4,5-trifluoro-phenyl)-ethyl]-piperidin-1-yl}-N-cyclopropyl-3-oxo-propionamide instead of cyclopropanesulfonic acid (2-{3-exo-[(R)-1-amino-2-(2,4,5-trifluoro-phenyl)-ethyl]-8-azabicyclo[3.2.1]octane-8-sulfonyl}-ethyl)-amide.

Example K1b

3-{4-[(R)-1-Amino-2-(2,4,5-trifluoro-phenyl)-ethyl]-piperidin-1-yl}-N-cyclopropyl-3-oxo-propionamide toluene-4-sulfonate The title compound is prepared analogously as described in example D2b using 3-{4-[(R)-1-Amino-2-(2,4,5-trifluoro-phenyl)-ethyl]-piperidin-1-yl}-N-cyclopropyl-3-oxo-propionamide instead of cyclopropanesulfonic acid (2-{3-exo-

[(R)-1-amino-2-(2,4,5-trifluoro-phenyl)-ethyl]-8-aza-bicyclo[3.2.1]octane-8-sulfonyl}-ethyl)-amide.

Example K2

3-{4-[(R)-1-Amino-2-(2,4,5-trifluoro-phenyl)-ethyl]-piperidin-1-yl}-N,N-diethyl-3-oxo-propionamide The title compound is prepared analogously as described in example K1 using diethylamine instead of cyclopropylamine.
MS: 400 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.75 min.

Example K3

3-{4-[(R)-1-Amino-2-(2,4,5-trifluoro-phenyl)-ethyl]-piperidin-1-yl}-N—((R)-2-hydroxy-propyl)-3-oxo-propionamide The title compound is prepared analogously as described in example K1 using (R)-1-Amino-propan-2-ol instead of cyclopropylamine.
MS: 402 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.39 min.

Example K4

4-{4-[(R)-1-Amino-2-(2,4,5-trifluoro-phenyl)-ethyl]-piperidin-1-yl}-N,N-dimethyl-4-oxo-butyramide The title compound is prepared analogously as described in example K1 using succinic acid monobenzyl ester instead malonic acid monobenzyl ester and dimethylamine instead of cyclopropylamine.
MS: 386 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.260 min.

Example K5

4-{4-[(R)-1-Amino-2-(2,4,5-trifluoro-phenyl)-ethyl]-piperidin-1-yl}-N-4-hydroxy-cyclohexyl)-4-oxo-butyramide The title compound is prepared analogously as described in example K4 using 4-amino-cyclohexanol instead of dimethylamine.
MS: 456 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.46 min.

Example K6

4-{4-[(R)-1-Amino-2-(2,4,5-trifluoro-phenyl)-ethyl]-piperidin-1-yl}-N-cyclopropyl-4-oxo-butyramide The title compound is prepared analogously as described in example K1 using succinic acid monobenzyl ester instead malonic acid monobenzyl ester.

MS: 398 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.56 min.

Example K7

3-{3-exo-[(R)-1-Amino-2-(2,4,5-trifluoro-phenyl)-ethyl]-8-aza-bicyclo[3.2.1]oct-8-yl}-N-cyclopropyl-3-oxo-propionamide The title compound is prepared analogously as described in example K1 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 412 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.56 min.

Example K8

3-{3-exo-[(R)-1-Amino-2-(2,4,5-trifluoro-phenyl)-ethyl]-8-aza-bicyclo[3.2.1]oct-8-yl}-N-(4-tert-butyl-cyclohexyl)-3-oxo-propionamide The title compound is prepared analogously as described in example K7 using 4-terbutylcyclohexylamine instead of cyclopropylamine.
MS: 508 [M+H]+
HPLC (YMC, 6 min method (0-3 min 5-95% ACN, 3.5-5.5 min 95% ACN, 5.5-5.55 min 95-5% ACN, 5.55-6 min 20% ACN): 3.38 min.

Example K9

{3-exo-[(R)-1-Amino-2-(2,4,5-trifluoro-phenyl)-ethyl]-8-aza-bicyclo[3.2.1]oct-8-yl}-[1-(morpholine-4-carbonyl)-cyclopropyl]-methanone A) 1-{3-exo-[(R)-1-((S)-2-methyl-propane-2-sulfinylamino)-2-(2,4,5-trifluoro-phenyl)-ethyl]-8-aza-bicyclo[3.2.1]octane-8-carbonyl}-cyclopropanecarboxylic acid benzyl ester The title compound is prepared analogously as described in example K7 using cyclopropane-1,1-dicarboxylic acid benzyl ester instead of malonic acid monobenzyl ester.
MS: 591 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.5 min.

B) 1-(3-exo-[(R)-1-((S)-2-Methyl-propane-2-sulfinylamino)-2-(2,4,5-trifluoro-phenyl)-ethyl]-8-aza-bicyclo[3.2.1]octane-8-carbonyl)cyclopropanecarboxylic acid To 1-{3-exo-[(R)-1-((S)-2-methyl-propane-2-sulfinylamino)-2-(2,4,5-trifluoro-phenyl)-ethyl]-8-aza-bicyclo [3.2.1]octane-8-carbonyl}-cyclopropanecarboxylic acid benzyl ester (50 mg, 0.085 mmol) in MeOH (0.425 mL) is adde an aqueous 1N LiOH solution (93.5 uL, 0.093 mmol).
After stirring at rt during 16 h, the pH is adjusted to 3 with aqueous 1N HCl, the mixture is extracted with chloroform and the organic phase is dried and evaporated to give a crude compound which is and purified by preparative HPLC (Column Waters ODB 19×50 5 uM, Gradient: 0-2.5 min 5% ACN, 2.5-12.5 min 5-100% ACN, 12.5-15 min 100% ACN) to yield a white solid.

MS 501 [M+H]+

LCMS (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 3.3 min.

C) {3-exo-[(R)-1-Amino-2-(2,4,5-trifluoro-phenyl)-ethyl]-8-aza-bicyclo[3.2.1]oct-8-yl}-[1-(morpholine-4-carbonyl)-cyclopropyl]-methanone The title compound is prepared analogously as described in example K7 using 1-{3-exo-[(R)-1-((S)-2-methyl-propane-2-sulfinylamino)-2-(2,4,5-trifluoro-phenyl)-ethyl]-8-aza-bicyclo[3.2.1]octane-8-carbonyl}-cyclopropanecarboxylic acid instead of 3-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-3-oxo-propionic acid and morpholine instead of cyclopropylamine.

MS: 466 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.23 min.

Example K10

1-{3-exo-[(R)-1-Amino-2-(2,4,5-trifluoro-phenyl)-ethyl]-8-aza-bicyclo[3.2.1]octane-8-carbonyl}-cyclopropanecarboxylic acid benzylamide The title compound is prepared analogously as described in example K9 using benzylamine instead of morpholine.

MS: 487 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.17 min.

Example K10a

1-{3-exo-[(R)-1-Amino-2-(2,4,5-trifluoro-phenyl)-ethyl]-8-aza-bicyclo[3.2.1]octane-8-carbonyl})-clopropanecarboxylic acid benzylamide maleate The title compound is prepared analogously as described in example D2a using 1-{3-exo-[(R)-1-Amino-2-(2,4,5-trifluoro-phenyl)-ethyl]-8-aza-bicyclo[3.2.1]octane-8-carbonyl}-cyclopropanecarboxylic acid benzylamide instead of cyclopropanesulfonic acid (2-{3-exo-[(R1-amino-2-(2,4,5-trifluoro-phenyl)-ethyl]-8-aza-bicyclo[3.2.1]octane-8-sulfonyl}-ethyl)-amide.

Example K10b

1-{3-exo-[(R)-1-Amino-2-(2,4,5-trifluoro-phenyl)-ethyl]-8-aza-bicyclo[3.2.1]octane-8-carbonyl}-cyclopropanecarboxylic acid benzylamide toluene-4-sulfonate The title compound is prepared analogously as described in example D2b using 1-{3-exo-[(R)-1-Amino-2-(2,4,5-trifluoro-phenyl)-ethyl]-8-aza-bicyclo[3.2.1]octane-8-carbonyl}cyclopropanecarboxylic acid benzylamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl) amide.

Example K11

1-{3-exo-[(R)-1-Amino-2-(2,4,5-trifluoro-phenyl)-ethyl]-8-aza-bicyclo[3.2.1]octane-8-carbonyl}-cyclopropanecarboxylic acid benzyl-methyl-amide The title compound is prepared analogously as described in example K9 using N-methylbenzylamine instead of morpholine.

MS: 500 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.27 min.

Example K12

1-{3-exo-[(R)-1-Amino-2-(2,4,5-trifluoro-phenyl)-ethyl]-8-aza-bicyclo[3.2.1]octane-8-carbonyl}-cyclopropanecarboxylic acid (2-methoxy-ethyl)-methyl-amide The title compound is prepared analogously as described in example K9 using N-methyl-2-methoxyethylamine instead of morpholine.

MS: 468 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example K13

1-{3-exo-[(R)-1-Amino-2-(2,4,5-trifluoro-phenyl)-ethyl]-8-aza-bicyclo[3.2.1]octane-8-carbonyl}-cyclopropanecarboxylic acid dimethylamide The title compound is prepared analogously as described in example K9 using dimethylamine instead of morpholine.

MS: 424 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example K14

1-{3-exo-[(R)-1-((S)-2-Methylpropane-2-sulfinylamino)-2-(2,4,5-trifluoro-phenyl)-ethyl]-8-aza-bicyclo[3.2.1]octane-8-carbonyl}-cyclopropanecarboxylic acid amide The title compound is prepared analogously as described in example K9 using ammonium carbonate instead of morpholine.

MS: 396 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.11 min.

Example K15

4-{4-[(R)-1-Amino-2-(2,4,5-trifluoro-phenyl)-ethyl]-piperidin-1-yl}-N-cyclopropyl-4-oxo-butyramide The title compound is prepared analogously as described in example K6 using 4-{3-exo-[(R)-1-((S)-2-methyl-propane-2-sulfinylamino)-2-(2,4,5-trifluoro-phenyl)-ethyl]-8-aza-bicyclo[3.2.1]oct-8-yl}-4-oxo-butyric acid instead of 4-{4-[(R)-1-Amino-2-(2,4,5-trifluoro-phenyl)-ethyl]-piperidin-1-yl}-4-oxo-butyric acid.
MS: 424 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.61 min.

Example K16

4-{3-exo-[(R)-1-Amino-2-(2,4,5-trifluoro-phenyl)-ethyl]-8-aza-bicyclo[3.2.1]oct-8-yl}-N-(4-tert-butyl-cyclohexyl)-4-oxo-butyramide The title compound is prepared analogously as described in example K15 using 4-tert-butylcyclohexylamine instead of cyclopropylamine.
MS: 522 [M+H]+
HPLC (YMC, 6 min method (0-3 min 5-95% ACN, 3.5-5.5 min 95% ACN, 5.5-5.55 min 95-5% ACN, 5.55-6 min 20% ACN): 3.36 min.

Example K17

4-{3-exo-[(R)-1-Amino-2-(2,4,5-trifluoro-phenyl)-ethyl]-8-aza-bicyclo[3.2.1]oct-8-yl}-N-benzyl-4-oxo-butyramide The title compound is prepared analogously as described in example K15 using benzylamine instead of cyclopropylamine.
MS: 473 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.89 min.

Example K18

3-{3-exo-[(R)-1-Amino-2-(2,4,5-trifluoro-phenyl)-ethyl]-8-aza-bicyclo[3.2.1]oct-8-yl}-N-benzyl-2,2-dimethyl-3-oxo-propionamide The title compound is prepared analogously as described in example K7 using dimethyl-1,1-dicarboxylic acid benzyl ester instead of cyclopropane-1,1-dicarboxylic acid benzyl ester and benzyl amine instead of morpholine.
MS: 489 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.29 min.

Example K19

1-{3-exo-[(R)-1-Amino-2-(2,4,5-trifluoro-phenyl)-ethyl]-8-aza-bicyclo[3.2.1]oct-8-yl}-2,2-dimethyl-3-morpholin-4-yl-propane-1,3-dione The title compound is prepared analogously as described in example K18 using morpholine instead of benzylamine.
MS: 468 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.22 min.

Example K20

{4-[(R)-1-Amino-2-(2,4,5-trifluoro-phenyl)-ethyl]-piperidin-1-yl}-[1-(morpholine-4-carbonyl)-cyclopropyl]-methanone The title compound is prepared analogously as described in example K9 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.
MS: 440 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.594 min.

Example K20a

{4-[(R)-1-Amino-2-(2,4,5-trifluoro-phenyl)-ethyl]-piperidin-1-yl}-[1-(morpholine-4-carbonyl)-cyclopropyl]-methanone maleate The title compound is prepared analogously as described in example D2a using {4-[(R)-1-Amino-2-(2,4,5-trifluoro-phenyl)-ethyl]-piperidin-1-yl}-[1-(morpholine-4-carbonyl)-cyclopropyl]-methanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}ethyl)-amide.

Example K20b

{4-[(R)-1-Amino-2-(2,4,5-trifluoro-phenyl)-ethyl]-piperidin-1-yl}-[1-(morpholine-4-carbonyl)-cyclopropyl]-methanone toluene-4-sulfonate The title compound is prepared analogously as described in example D2b using {4-[(R)-1-Amino-2-(2,4,5-trifluoro-phenyl)-ethyl]-piperidin-1-yl}-[1-(morpholine-4-carbonyl)-cyclopropyl]-methanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example K21

1-{4-[(R)-1-Amino-2-(2,4,5-trifluoro-phenyl)-ethyl]-piperidine-1-carbonyl}-cyclopropanecarboxylic acid benzyl-methyl-amide The title compound is prepared analogously as described in example K11 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.
MS: 474 [M+H]+
HPLC (YMC, 6 min method (0-3 min 5-95% ACN, 3.5-5.5 min 95% ACN, 5.5-5.55 min 95-5% ACN, 5.55-6 min 20% ACN): 3.00 min.

Example K22

1-(4-[(R)-1-Amino-2-(2,4,5-trifluoro-phenyl)-ethyl]-piperidine-1-carbonyl)-cyclopropanecarboxylic acid benzylamide The title compound is prepared analogously as described in example K10 using (S)-2-methyl-propane-2-sulfinic acid [(R)-1-piperidin-4-yl-2-(2,4,5-trifluoro-phenyl)-ethyl]-amide instead of 3-exo-[(R)-1-((S)-2-methyl-propane-2-sulfinylamino)-2-(2,4,5-trifluoro-phenyl)-ethyl]-8-aza-bicyclo[3.2.1]octane.

MS: 457 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.881 min.

Example K23

3-{(1S,3S,5R)-3-[(R)-1-Amino-2-(2,4,5-trifluoro-phenyl)-ethyl]-8-aza-bicyclo[3.2.1]oct-8-yl}-N-(4-hydroxy-cyclohexyl)-3-oxo-propionamide The title compound is prepared analogously as described in example K7 using 4-Aminocyclohexanol instead of cyclopropylamine.

MS: 468 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.500 min.

Example K24

3-{(1S,3S,5R)-3-[(R)-1-Amino-2-(2,4,5-trifluoro-phenyl)-ethyl]-8-aza-bicyclo[3.2.1]oct-8-yl}-N,N-dimethyl-3-oxo-propionamide The title compound is prepared analogously as described in example K7 using dimethylamine instead of cyclopropylamine.

MS: 398 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.413 min.

Example K25

{(1S,3S,5R)-3-[(R)-1-Amino-2-(2,4,5-trifluoro-phenyl)-ethyl]-8-aza-bicyclo[3.2.1]oct-8-yl}-(1-{(1S,3S,5R)-3-[(R)-1-amino-2-(2,4,5-trifluoro-phenyl)-ethyl]-bicyclo[3.2.1]octane-8-carbonyl}-cyclopropyl)-methanone The title compound is prepared analogously as described in example K9 using 3-exo-[(R)-1-((S)-2-methyl-propane-2-sulfinylamino)-2-(2,4,5-trifluoro-phenyl)-ethyl]-8-aza-bicyclo[3.2.1]octane instead of morpholine.

MS: 663 [M+H]+

HPLC (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 2.974 min.

Example K26

4-{(1S,3S,5R)-3-[(R)-1-Amino-2-(2,4,5-trifluoro-phenyl)-ethyl]-8-aza-bicyclo[3.2.1]oct-8-yl}-N,N-dimethyl-4-oxo-butyramide The title compound is prepared analogously as described in example K4 using 3-exo-[(R)-1-((S-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 412 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.643 min.

Example K27

4-{(1S,3S,5R)-3-[(R)-1-Amino-2-(2,4,5-trifluoro-phenyl)-ethyl]8-aza-bicyclo[3.2.1]oct-8-yl}-N-(4-hydroxy-cyclohexyl)-4-oxo-butyramide The title compound is prepared analogously as described in example K5 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 482 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.559 min.

Example L1

Tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-methyl-amide This compound is prepared according to Scheme L:

Scheme L

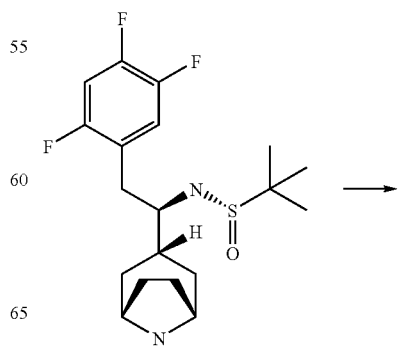

-continued

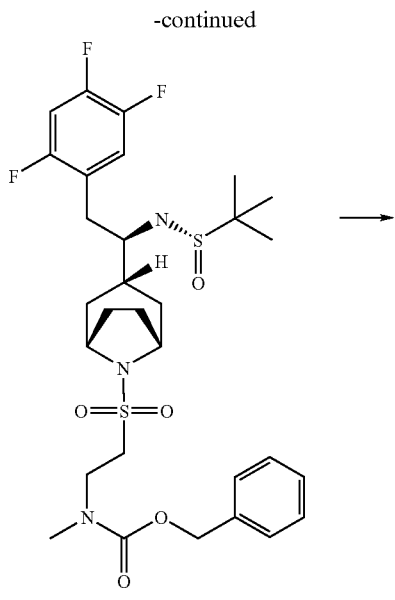

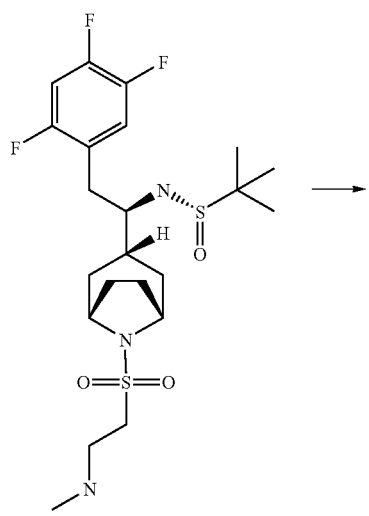

-continued

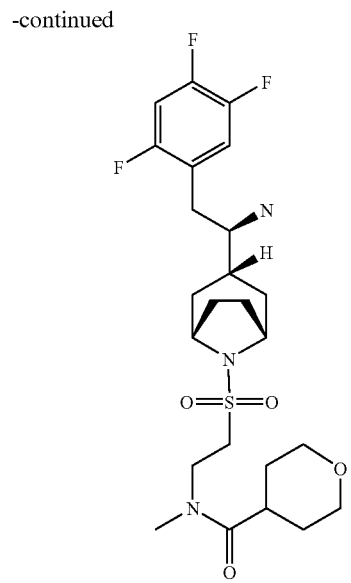

A) Methyl-(2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-carbamic acid benzyl ester The title compound is prepared analogously as described in example D1 using (2-chlorosulfonyl-ethyl)-methyl-carbamic acid benzyl ester instead of 2-phthalimidoethane sulfonyl chloride.

MS: 644 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.53 min.

P B) (S)-2-Methyl-propane-2-sulfinic acid [(R)-1-[3-exo-8-(2-methylamino-ethanesulfonyl)-8-aza-bicyclo[3.2.1]oct-3-yl]-2-(2,4,5-trifluoro-phenyl)-ethyl]-amide To methyl-(2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}-ethyl)-carbamic acid benzyl ester (530 mg, 0.799 mmol) in ethanol (20 mL) is added Pd/C (85 mg, 0.799 mmol). After stirring at rt during 2 h under H2 atmosphere, the solution is filtered through celite and evaporated to yield a yellow solid.

MS: 510 [M+H]+

C) Tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-methyl-amide The title compound is prepared analogously as described in example D6 using (S)-2-methyl-propane-2-sulfinic acid [(R)-1-[3-exo-8-(2-methylamino-ethanesulfonyl)-8-aza-bicyclo[3.2.1]oct-3-yl]-2-(2,4,5-trifluoro-phenyl)-ethyl]-amide instead of 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}ethylamine.

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.13 min.

Example L1a

Tetrahydropyran-4-carboxylic acid (2-(3-exo-[(R)-1-amino-2-(2,4,5-trifluoro-phenyl)-ethyl]-8-aza-bicyclo[3.2.1]octane-8-sulfonyl)-ethyl)-methyl-amide maleate The title compound is prepared analogously as described in example D2a using tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example L2b

Tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}-ethyl)-methyl-amide toluene-4-sulfonate The title compound is prepared analogously as described in example D2b using tetrahydropyran-4-carboxylic acid (2-{3-exo-[(R)-1-amino-2-(2,4,5-trifluoro-phenyl)-ethyl]-8-aza-bicyclo[3.2.1]octane-8-sulfonyl}ethyl)-methyl-amide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example L2

(2-{3-exo-[(R)-1-Amino-2-(2,4,5-trifluoro-phenyl)-ethyl]-8-aza-bicyclo[3.2.1]octane-8-sulfonyl}-ethyl)-methyl-carbamic acid ethyl ester The title compound is prepared analogously as described in example D13 using (S)-2-methyl-propane-2-sulfinic acid [(R)-1-[3-exo-8-(2-methylamino-ethanesulfonyl)-8-aza-bicyclo[3.2.1]oct-3-yl]-2-(2,4,5-trifluoro-phenyl)-ethyl]-amide instead of 2-{3-exo-[(R)-1-((S)-2-methyl-propane-2-sulfinylamino)-2-(2,4,5-trifluoro-phenyl)-ethyl]-8-aza-bicyclo[3.2.1]octane-8-sulfonyl}ethylamine.

MS: 478 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.21 min.

Example M1

1-{3-exo-[(R)-1-Amino-2-(2,4,5-trifluoro-phenyl)-ethyl]-8-aza-bicyclo[3.2.1]oct-8-yl}-2-(morpholine-4-sulfonyl)-ethanone This compound is prepared according to Scheme M:

Scheme M

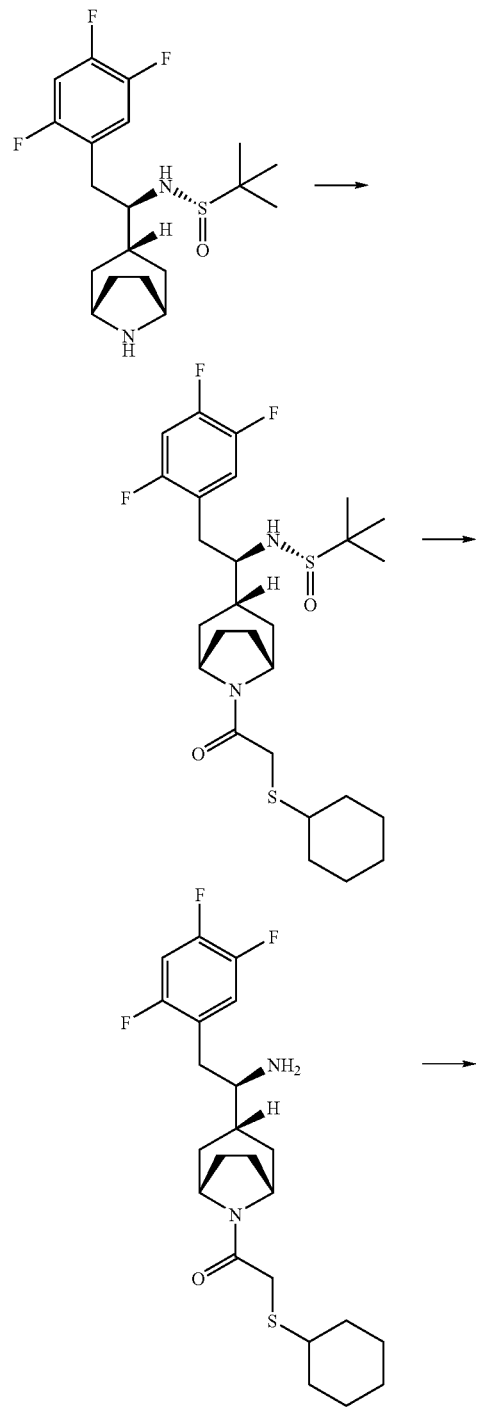

-continued

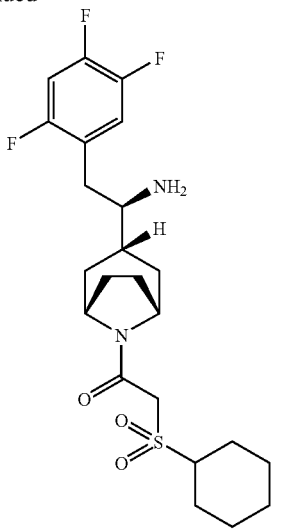

A) Cyclohexylsulfanyl-acetic acid

To cyclohexylmercaptane (147 uL, 1.2 mmol) in DMF (1 mL) are added bromoacetic acid (167 mg, 1.2 mmol) and DIPEA (616 uL, 3.6 mmol). The resulting mixture is stirred at rt during 2 h and used such as in the next step.

B) (S)-2-Methyl-propane-2-sulfinic acid [(R)-1-[1-(2-cyclohexylsulfanyl-acetyl)piperidin-4-yl]-2-(2,4,5-trifluoro-phenyl)-ethyl]-amide To (S)-2-Methyl-propane-2-sulfinic acid [(R)-1-piperidin-4-yl-2-(2,4,5-trifluoro-phenyl)-ethyl]-amide (200 mg, 0.552 mmol) in dichloromethane (1 mL) are added EDC (127 mg, 0.662 mmol), HOBt (97 mg, 0.718 mmol), DIPEA (283 uL, 1.656 mmol) and cyclohexylsulfanyl-acetic acid in DMF (2 mL, 1.2 mmol). After stirring at rt during 3 days, the mixture is washed with an aqueous 1N HCl solution, the organic phase is dried and evaporated to give the title compound.

MS 519 [M+H]+

LCMS (Waters Symmetry C18 3.5 μm 2.1×50 mm, 6 min method (0-3 min 20-95% ACN, 3.5-5.5 min 95% ACN, 5.5-5.55 min 95-20% ACN, 5.55-6 min 20% ACN): 4.236 min.

C) 1-{4-[(R)-1-Amino-2-(2,4,5-trifluoro-phenyl)-ethyl]-piperidin-1-yl}-2-cyclohexylsulfanyl-ethanone To (S)-2-Methyl-propane-2-sulfinic acid [(R)-1-[1-(2-cyclohexylsulfanyl-acetyl)-piperidin-4-yl]-2-(2,4,5-trifluoro-phenyl)-ethyl]-amide (367 mg, 0.552 mmol) is added 4N HCl in dioxane (2 mL). The resulting mixture is stirred at rt during 20 min. The solution is frozen and lyophilised to give a yellow oil before purification by preparative HPLC (Column YMC ODS-AQ 20×50 5 uM, Gradient: 0-2.5 min 5% ACN, 2.5-12.5 min 5-100% ACN, 12.5-15 min 100% ACN) to yield a colorless oil.

MS 415 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.287 min.

D) 1-{4-[(R)-1-Amino-2-(2,4,5-trifluoro-phenyl)-ethyl]-piperidin-1-yl-2-cyclohexanesulfonyl-ethanone To 1-(4-[(R)-1-Amino-2-(2,4,5-trifluoro-phenyl)-ethyl]-piperidin-1-yl}-2-cyclohexylsulfanyl-ethanone (84 mg, 0.203 mmol) in acetic acid (465 uL) is added an aqueous 30% H2O2 solution (83 uL, 0.812 mmol). The resulting mixture is stirred at 80° C. during 30 min. The solution is frozen and lyophilised to give a colorless oil

MS: 447 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.219 min.

Example M1a

1-{4-[(R)-1-Amino-2-(2,4,5-trifluoro-phenyl)-ethyl]-piperidin-1-yl}-2-cyclohexanesulfonyl-ethanone maleate The title compound is prepared analogously as described in example D2a using 1-{4-[(R)-1-amino-2-(2,4,5-trifluoro-phenyl)-ethyl]-piperidin-1-yl}-2-cyclohexanesulfonyl-ethanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example M1b

1-{4-[(R)-1-Amino-2-(2,4,5-trifluoro-phenyl)-ethyl]-piperidin-1-yl}-2-cyclohexanesulfonyl-ethanone toluene-4-sulfonate The title compound is prepared analogously as described in example D2b using 1-{4-[(R)-1-amino-2-(2,4,5-trifluoro-phenyl)-ethyl]-piperidin-1-yl}-2-cyclohexanesulfonyl-ethanone instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example M2

2-(3-{4-[(R)-1-Amino-2-(2,4,5-trifluoro-phenyl)-ethyl]-piperidin-1-yl}-3-oxo-propane-1-sulfonyl)-N,N-diethyl-acetamide A) 3-Diethylcarbamoylmethylsulfanyl-propionic acid To 3-mercaptopropionic acid (200 mg, 1.884 mmol) in methanol (3 mL) are added sodium methoxide (204 mg, 3.768 mmol) and 2-Bromo-N,N-diethyl-acetamide (402 mg, 2.070 mmol). After stirring at 80° C. during 4 h and evaporation of solvent, the residue is treated with ethyl acetate and water, the pH is adjusted to 10 with an aqueous NaHCO3 solution and the aqueous phase is extracted with ethyl acetate. After acidification of the aqueous phase to pH 2 with an aqueous 1N HCl solution, it is extracted with ethyl acetate, then the organic phase is dried and evaporated to give the title compound.

MS: 220 [M+H]+

HPLC (YMC, 6 min method (0-3 min 5-95% ACN, 3.5-5.5 min 95% ACN, 5.5-5.55 min 95-5% ACN, 5.55-6 min 20% ACN): 0.9 min.

B) 2-(3-{4-[(R)-1-Amino-2-(2,4,5-trifluoro-phenyl)-ethyl]-piperidin-1-yl}-3-oxo-propane-1-sulfonyl)-N,N-diethyl-acetamide The title compound is prepared analogously as described in example M1 using 3-Diethylcarbamoylmethylsulfanyl-propionic acid instead of Cyclohexylsulfanyl-acetic acid.
MS: 492 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.548 min.

Example M3

1-{4-[(R)-1-Amino-2-(2,4,5-trifluoro-phenyl)-ethyl]-piperidin-1-yl}-3-cyclopropylmethanesulfonyl-propan-1-one The title compound is prepared analogously as described in example M2 using Bromomethylcyclopropane instead of 2-Bromo-N,N-diethyl-acetamide.
MS: 433 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.48 min.

Example M4

1-{4-[(R)-1-Amino-2-(2,4,5-trifluoro-phenyl)-ethyl]-piperidin-1-yl}-3-methanesulfonyl-propan-1-one The title compound is prepared analogously as described in example M1 using 3-Methylthiopropionic acid instead of Cyclohexylsulfanyl-acetic acid.
MS: 392 [M+H]+

Example M5

1-{4-[(R)-1-Amino-2-(2,4,5-trifluoro-phenyl)-ethyl]-piperidin-1-yl}-3-cyclohexanesulfonyl-propan-1-one The title compound is prepared analogously as described in example M1 using 3-bromopropionic acid instead of bromoacetic acid.
MS: 461 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.221 min.

Example M6

7-(3-{4-[(R)-1-Amino-2-(2,4,5-trifluoro-phenyl)-ethyl]-piperidin-1-yl}-3-oxo-propane-1-sulfonyl)-3,4-dihydro-2H-isoquinolin-1-one

A) 1-Oxo-1,2,3,4-tetrahydro-isoquinoline-7-sulfonyl chloride

To Chlorosulfonic acid (30 mL) is added 3,4-Dihydro-2H-isoquinolin-1-one (5 g, 34 mmol) at 0° C. After stirring at rt during 1 h, the mixture is heated at 50° C. during 16 h, then it is poured carefully into an ice bath and stirred at 0° C. during 30 min. The precipitate is filtered and dried in oven at 60° C. to give the title compound.
MS: 246 [M+H]+

B) 7-Mercapto-3,4-dihydro-2H-isoquinolin-1-one

To a zinc powder (2.79 g, 42.7 mmol) and Dichlorodimethylsilane (5.15 mL, 42.7 mmol) in DCE (45 mL) is added a solution of 1-Oxo-1,2,3,4-tetrahydro-isoquinoline-7-sulfonyl chloride (3 g, 12.2 mmol) and 1,3-dimethylimidazolidin-2-one (3.96 mL, 36.6 mmol) in DCE (5 mL). After stirring at rt during 2 h, the mixture is concentrated.
MS: 180 [M+H]+

C) 7-(3-{4-[(R)-1-Amino-2-(2,4,5-trifluoro-phenyl)-ethyl]-piperidin-1-yl}-3-oxo-propane-1-sulfonyl)-3,4-dihydro-2H-isoquinolin-1-one The title compound is prepared analogously as described in example M1 using 7-Mercapto-3,4-dihydro-2H-isoquinolin-1-one instead of cyclohexylmercaptane.
MS: 510 [M+H]+
HPLC (Waters Symmetry C18 3.5 µm 2.1×50 mm, 6 min method (0-3 min 5-95% ACN, 3.5-5.5 min 95% ACN, 5.5-5.55 min 95-5% ACN, 5.55-6 min 5% ACN): 2.776 min.

Example M7

1-{(1S,3S,5R)-3-[(R)-1-Amino-2-(2,4,5-trifluoro-phenyl)-ethyl]-8-aza-bicyclo[3.2.1]oct-8-yl}-2-cyclohexanesulfonyl-ethanone The title compound is prepared analogously as described in example Ml using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 473 [M+H]+
HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.239 min.

Example M8

2-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-N,N-diethyl-acetamide The title compound is prepared analogously as described in example M2 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.
MS: 518 [M+H]+
HPLC (YMC, 6 min method (0-3 min 5-95% ACN, 3.5-5.5 min 95% ACN, 5.5-5.55 min 95-5% ACN, 5.55-6 min 20% ACN): 2.648 min.

Example M8a 2-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-N,N-diethyl-acetamide maleate The title compound is prepared analogously as described in example D2a using 2-(3-{(1S,3S,5R)-3-[(R)-1-Amino-2-(2,4,5-trifluoro-phenyl)-ethyl]-8-aza-bicyclo[3.2.1]oct-8-yl}-

3-oxo-propane-1-sulfonyl)-N,N-diethyl-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example M8b 2-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-N,N-diethyl-acetamide toluene-4-sulfonate The title compound is prepared analogously as described in example D2b using 2-(3-{(1S,3S,5R)-3-[(R)-1-Amino-2-(2,4,5-trifluoro-phenyl)-ethyl]-8-aza-bicyclo[3.2.1]oct-8-yl}-3-oxo-propane-1-sulfonyl)-N,N-diethyl-acetamide instead of cyclopropanesulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example M9

1-{(1S,3S,5R)-3-[(R)-1-Amino-2-(2,4,5-trifluoro-phenyl)-ethyl]-8-aza-bicyclo[3.2.1]oct-8-yl}-3-cyclopropylmethanesulfonyl-propan-1-one The title compound is prepared analogously as described in example M3 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 459 [M+H]+

HPLC (YMC, 6 min method (0-3 min 5-95% ACN, 3.5-5.5 min 95% ACN, 5.5-5.55 min 95-5% ACN, 5.55-6 min 20% ACN): 2.573 min.

Example M10

1-{(1S,3S,5R)-3-[(R)-1-Amino-2-(2,4,5-trifluoro-phenyl)-ethyl]-8-aza-bicyclo[3.2.1]oct-8-yl}-3-cyclohexanesulfonyl-propan-1-one The title compound is prepared analogously as described in example M5 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

MS: 487 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.241 min.

Example M11

1-{(1S,3S,5R)-3-[(R)-1-Amino-2-(2,4,5-trifluoro-phenyl)-ethyl]-8-aza-bicyclo[3.2.1]oct-8-yl}-3-methanesulfonyl-propan-1-one The title compound is prepared analogously as described in example M4 using 3-exo-[(R)-1-((S)-2-methyl-propane-2-sulfinylamino)-2-(2,4,5-trifluoro-phenyl)-ethyl]-8-aza-bicyclo[3.2.1]octane instead of (S)-2-methyl-propane-2-sulfinic acid [(R)-1-piperidin-4-yl-2-(2,4,5-trifluoro-phenyl)-ethyl]-amide.

Example N1

2-(3-{(1S,3S,5R)-3-[(R)-1-Amino-2-(2,4,5-trifluoro-phenyl)-ethyl]8-aza-bicyclo[3.2.1]oct-8-ylmethyl}-benzyl)-isoindole-1,3-dione This compound is prepared according to Scheme N:

Scheme N

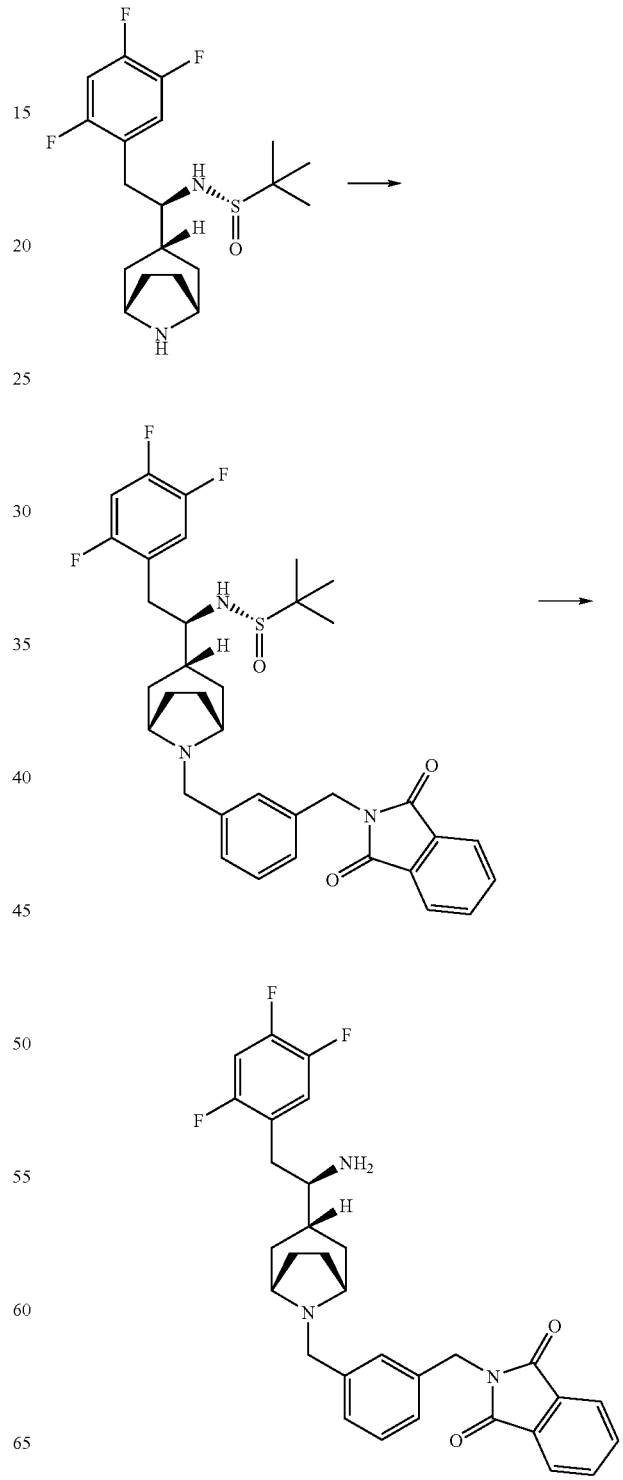

A) 2-(3-Hydroxymethyl-benzyl)isoindole-1,3-dione

To 3-(1,3-Dioxo-1,3-dihydro-isoindol-2-ylmethyl)-benzoic acid (300 mg, 1.066 mmol) in DCM (1 mL9 are added at 0° C. triethylamine (164 uL, 1.173 mmol) and ethylchloroformate (112 uL, 1.173 mmol). After stirring at 0° C. during 15 min and filtration, the obtained solution is added at 0° C. to NaBH4 (61 mg, 1.599 mmol) in water (400 uL) before stirring at 0° C. during 30 min and at rt during 2 h. The solution is acidified to pH 3 with an aqueous 1N HCl solution, extracted with ethylacetate, the organic phase is dried and evaporated to give a crude compound before purification by flash chromatography on silica gel (eluent: cyclohexane/ethyl acetate 9/1 to 1/1) to yield a colorless gum. TLC, Rf (cyclohexane/ethyl acetate 1/1)=0.15.

B) 3-(1,3-Dioxo-1,3-dihydro-isoindol-2-ylmethyl)-benzaldehyde

To oxalylchloride (43 uL, 0.449 mmol) in DCM (400 uL) is added at −78° C. DMSO (43 uL, 0.598 mmol). After stirring at −78° C. during 15 min, 2-(3-Hydroxymethyl-benzyl)isoindole-1,3-dione (80 mg, 0.299 mmol) in DCM (600 uL) is added and the mixture is stirred at −78° C. during 45 min before addition of triethylamine (210 uL, 1.495 mmol). After stirring at rt during 4 h, the reaction is quenched with water, extracted with DCM, the organic phase is washed with an aqueous 10% NaHSO4 solution and an aqueous saturated NaHCO3 solution. The organic phase is dried and evaporated to give a crude compound before purification by flash chromatography on silica gel (eluent: cyclohexane/ethyl acetate 9/1 to 2/1) to yield a colorless gum.

MS: 266 [M+H]+

TLC, Rf (cyclohexane/ethyl acetate 1/1)=0.7.

C) (S)-2-Methyl-propane-2-sulfinic acid [(R)-1-{(1S,3S,5R)-8-[3-(1,3-dioxo-1,3-dihydro-isoindol-2-ylmethyl)-benzyl]-8-aza-bicyclo[3.2.1]oct-3-yl}-2-(2,4,5-trifluoro-phenyl)-ethyl]-amide 3-(1,3-Dioxo-1,3-dihydro-isoindol-2-ylmethyl)-benzaldehyde (44 mg, 0.166 mmol) and 3-exo-[(R)-1-((S)-2-methyl-propane-2-sulfinylamino)-2-(2,4,5-trifluoro-phenyl)-ethyl]-aza-bicyclo[3.2.1]octane (54 mg, 0.138 mmol) in DCE (500 uL) are stirred at rt during 1 h before added of sodium triacetoxyborohydride (74 mg, 0.345 mmol). The mixture is stirred at rt during 16 h and the solvent is evaporated to give a crude compound before purification by preparative HPLC (Column Waters C18 ODB 5 μm 19×50, Gradient: 0-2.5 min 5% ACN, 2.5-12.5 min 5-100% ACN, 12.5-15 min 100% ACN) to yield the title compound.

MS: 638 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.361 min.

D) 2-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-isoindole-1,3-dione The title compound is prepared analogously as described in example G17 using S)-2-Methyl-propane-2-sulfinic acid [(R)-1-{(1S,3S,5R)-8-[3-(1,3-dioxo-1,3-dihydro-isoindol-2-ylmethyl)-benzyl]-8-aza-bicyclo[3.2.1]oct-3-yl}-2-(2,4,5-trifluoro-phenyl)-ethyl]-amide instead of (S)-2-Methyl-propane-2-sulfinic acid [(R)-1-{(1S,3S,5R)-8-[3-(1,3-dioxo-1,3-dihydro-isoindol-2-ylmethyl)-benzoyl]-8-aza-bicyclo[3.2.1]oct-3-yl}-2-(2,4,5-trifluoro-phenyl)-ethyl]-amide.

MS: 534 [M+H]+

HPLC (Zorbax SB C18, 2 min method (0-0.8 min 10-95% ACN, 0.8-1.5 min 95% ACN, 1.5-1.6 min 95-10% ACN, 1.6-2 min 10% ACN): 1.228 min.

Example N1a 2-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-isoindole-1,3-dione maleate The title compound is prepared analogously as described in example D2a using 2-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-isoindole-1,3-dione instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example N1b 2-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-isoindole-1,3-dione toluene-4-sulfonate The title compound is prepared analogously as described in example D2b using 2-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-isoindole-1,3-dione instead of cyclopropane-sulfonic acid (2-{3-exo-[(R)-1-amino-2-(2,4,5-trifluoro-phenyl)-ethyl]-8-aza-bicyclo[3.2.1]octane-8-sulfonyl}-ethyl)-amide.

Example N2

N-(3-{(1S,3S,5R)-3-[(R)-1-Amino-2-(2,4,5-trifluoro-phenyl)-ethyl]-8-aza-bicyclo[3.2.1]oct-8-ylmethyl}-benzyl)-benzamide The title compound is prepared analogously as described in example G18 using (S)-2-Methyl-propane-2-sulfinic acid [(R)-1{(1S,3S,5R)-8-[3-(1,3-dioxo-1,3-dihydro-isoindol-2-ylmethyl)-benzyl]-8-aza-bicyclo[3.2.1]oct-3-yl}-2-(2,4,5-trifluoro-phenyl)-ethyl]-amide instead of (S)-2-methyl-propane-2-sulfinic acid [(R)-1-{3-exo-8-[3-(1,3-dioxo-1,3-dihydro-isoindol-2-ylmethyl)-benzoyl]-8-aza-bicyclo[3.2.1]oct-3-yl}-2-(2,4,5-trifluoro-phenyl)-ethyl]-amide.

MS: 508 [M+H]+

HPLC (Waters Symmetry C18 3.5 μm 2.1×50 mm, 6 min method (0-3 min 5-95% ACN, 3.5-5.5 min 95% ACN, 5.5-5.55 min 95-5% ACN, 5.55-6 min 5% ACN): 2.863 min.

Example P

Activity Assay

Various compounds of the invention were tested for their inhibitory activity to human DPP-IV.

Materials

Human DPP-IV consisting of amino acids 39 to 766 followed by a C-terminal Streptavidin-tag was expressed using the baculovirus system and purified to >80% purity. The enzyme was stored in 25 mM Tris buffer, pH 9.0, containing 300 mM NaCl at −80° C. The fluorogenic substrates H-Gly-Pro-AMC was purchased from Bachem AG (Bubendorf, Switzerland). The substrate was kept as a 5 mM stock solution in DMSO at −20° C. All other chemicals were purchased from Sigma (Buchs, Switzerland).

The assay buffer for the DPP-IV reaction was 25 mM Tris/HCl, pH 7.5, containing 140 mM NaCl, 10 mM KCl and 0.05% (w/v) CHAPS.

Compound and Liquid Handling

The test compounds were dissolved in 90% DMSO/10% H2O (v/v). Serial dilutions of the compounds from 3 mM to 0.03 μM in 90% DMSO/10% H2O (v/v) followed by a 1:33.3 dilution in assay buffer was done in 96-well polypropylene plates using a CyBio Dilus 8-channel pipetter (CyBio AG, Jena, Germany) with tip change after each pipetting step. The compound solutions as well as the substrate and the enzyme solutions were transferred to the assay plates (384-well black Cliniplate; cat. no. 95040020 Labsystems Oy, Finland) by means of a CyBi-Well 96-channel pipetter (CyBio AG, Jena, Germany).

Kinetic Measurements

Enzyme kinetics were measured by mixing 10 μl of a 3-fold concentrated substrate solution in assay buffer (final substrate concentration was 10 μM) with 10 μl of the corresponding compound solution. The reactions were initiated by addition of 10 μl of a 3-fold concentrated solution of the enzyme in assay buffer. Final enzyme (active site) concentrations in the assay was 10 pM for DPP-IV. Fluorescence product (AMC) formation was monitored for 1 hour at room temperature at 35 second intervals by measuring the fluorescence emission at 500 nm using an exitation wavelength of 350 nm in a TECAN Ultra fluorescence reader (TECAN, Maennedorf, Switzerland). The fluorescence in each well was excited by one flash per measurement. The Origin software package (Origin 7.5 Mircocal, Northampton, Mass., USA) was used to generate all graphs and to perform the IC50 calculations.

Results

The inhibitory activities (IC50 values) of the compounds to human DPP-IV were found to be 4.7 μM or less and in many cases 0.01 μM or less. In the case of exemplary compounds, their IC50 values were found to be between 4.7 and 0.0001 μM or between 4.7 μM and 0.0053 μM.

Representative Examples

| Examples | hDPPIV IC50 (μM) |
|---|---|
| D1 | 0.0077 |
| E7 | 0.0006 |
| G4 | 0.01 |
| H13 | 0.007 |

We claim:

1. A compound of Formula (I):

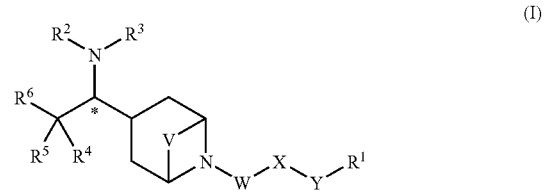

wherein
the asterisk * designates a chiral centre of (R) or (S) configuration;
V is absent or is ethylene;
W is —C(O)— or —S(O)$_t$—;
X is a linker having 1 to 12 in-chain atoms and comprising one or more linkages selected from —O—, —C(O)—, —S(O)$_t$—, —N(R$^9$)— and hydrocarbylene optionally substituted with 1, 2, 3, 4 or 5 R$^{11}$;
Y is a linker selected from —O—, —N(R$^9$)—, —C(O)—, —C(O)O—, —C(O)N(R$^9$)—, —S(O)$_t$— and S(O)$_t$N(R$^9$)—;
R$^1$ is selected from hydrogen; —N(R$^9$)(R$^{10}$) hydrocarbyl optionally substituted with 1, 2, 3, 4 or 5 R$^{11}$; hydrocarbyloxy optionally substituted with 1, 2, 3, 4 or 5 R$^{11}$; and —(CH$_2$)$_k$-heterocyclyl optionally substituted with 1, 2, 3, 4 or 5 R$^{11}$;
or, when Y is —N(R$^9$)—, R$^1$ and R$^9$ taken together with the nitrogen atom to which they are attached may form a heterocycle, wherein said heterocycle is bound to X via said nitrogen atom and is optionally substituted with 1, 2, 3, 4 or 5 R$^{11}$;
R$^2$ and R$^3$ are each independently selected from R$^8$, —OR$^8$; —C(O)R$^8$; —C(O)OR$^8$ and —S(O)$_t$R$^9$;
R$^4$ and R$^5$ are each independently selected from hydrogen, hydroxy, halogen and C$_{1-6}$ alkyl optionally substituted with 1, 2, 3, 4 or 5 R$^{11}$;
R$^6$ is aryl or heteroaryl, either of which is optionally-substituted with 1, 2, 3, 4 or 5 R$^{11}$;
R$^8$ is selected from hydrogen; hydrocarbyl optionally substituted with 1, 2, 3, 4 or 5 R$^{11}$;
and —(CH$_2$)$_k$-heterocyclyl optionally substituted with 1, 2, 3, 4 or 5 R$^{11}$;
R$^9$ and R$^{10}$ are each independently selected from R$^8$, —OR$^8$, —C(O)R$^8$, —C(O)OR$^8$ and —S(O)$_t$R$^8$;
or R$^9$ and R$^{10}$ taken together with a nitrogen atom to which they are attached form heterocyclyl optionally substituted with 1, 2, 3, 4 or 5 R$^{11}$;
each R$^{11}$ is independently selected from R$^{12}$; hydrocarbyl optionally substituted with 1, 2, 3, 4 or 5 R$^{12}$; and —(CH$_2$)$_k$-heterocyclyl optionally substituted with 1, 2, 3, 4 or 5 R$^{12}$;
R$^{12}$ is independently selected from halogen, trifluoromethyl, cyano, nitro, oxo, =NR$^{13}$, —OR$^{13}$, —C(O)R$^{13}$, —C(O)N(R$^{13}$)R$^{14}$, C(O)OR$^{13}$, —OC(O)R$^{13}$, —S(O)$_t$R$^{13}$, —S(O)$_t$N(R$^{13}$)R$^{14}$, —N(R$^{13}$)R$^{14}$, —N(R$^{13}$)N(R$^{13}$)R$^{14}$, —N(R$^{13}$)C(O)R$^{14}$ and —N(R$^{13}$)S(O)$_t$R$^{13}$;
R$^{13}$ and R$^{14}$ are each independently hydrogen or selected from hydrocarbyl and —(CH$_2$)$_k$-heterocyclyl, either of which is optionally substituted with 1, 2, 3, 4 or 5 substituents independently selected from oxo, halogen, cyano, amino, hydroxy, C$_{1-6}$ alkyl and C$_{1-6}$ alkoxy;

k is 0, 1, 2, 3, 4, 5 or 6; and l is 0, 1 or 2;

or a pharmaceutically acceptable salt or prodrug thereof.

2. The compound according to claim 1, which is of the Formula (II):

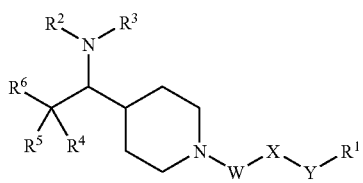

(II)

or a pharmaceutically acceptable salt or prodrug thereof.

3. The compound according to claim 1, which is of the Formula (III):

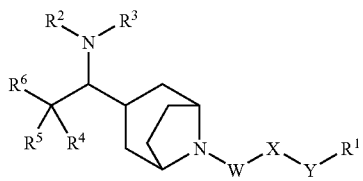

(III)

or a pharmaceutically acceptable salt or prodrug thereof.

4. The compound according to claim 1, wherein X is —$X^1$— and wherein $X^1$ is selected from —O—, —C(O)—, —S(O)$_l$—, —N(R$^9$)— and hydrocarbylene optionally substituted with 1, 2, 3, 4 or 5 R$^{11}$.

5. The compound according to claim 4, which is of the Formula (IV):

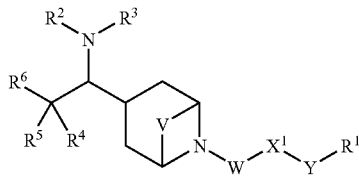

(IV)

wherein $X^1$ is —N(R$^9$)— or hydrocarbylene optionally substituted with 1, 2, 3, 4 or 5 R$^{11}$;

or a pharmaceutically acceptable salt or prodrug thereof.

6. The compound according to claim 5, wherein $X^1$ is $C_{1-6}$ alkylene optionally substituted with 1, 2, 3, 4 or 5 R$^{11}$.

7. The compound according to claim 6, wherein —W—$X^1$—Y— is one of the following linkers:

| No. | W | $X^1$ | Y |
|---|---|---|---|
| 1 | —C(O)— | $C_{1-6}$ alkylene | —S(O)$_2$— |
| 2 | —S(O)$_l$— | $C_{1-6}$ alkylene | —C(O)— | wherein $X^1$ is optionally substituted with 1, 2, 3, 4 or 5 R$^{11}$.

8. The compound according to claim 7, wherein —W—$X^1$—Y— is one of the following linkers:

| No. | W | $X^1$ | Y |
|---|---|---|---|
| 1 | —C(O)— | —CH$_2$— | —S(O)$_2$— |
| 2 | —C(O)— | —CH(CH$_3$)— | —S(O)$_2$— |
| 3 | —C(O)— | —C(CH$_3$)$_2$— | —S(O)$_2$— |
| 4 | —C(O)— | —CH$_2$CH$_2$— | —S(O)$_2$— |
| 5 | —S(O)$_2$— | —CH$_2$— | —C(O)— |
| 6 | —S(O)$_2$— | —CH(CH$_3$)— | —C(O)— |
| 7 | —S(O)$_2$— | —C(CH$_3$)$_2$— | —C(O)— |
| 8 | —S(O)$_2$— | —CH$_2$CH$_2$— | —C(O)— | wherein $X^1$ is optionally substituted with 1, 2, 3, 4 or 5 R$^{11}$.

9. The compound according to claim 1, wherein R$^1$ is heterocyclyl optionally substituted with 1, 2, 3, 4 or 5 R$^{11}$.

10. The compound according to claim 1, wherein V is ethylene, and which is in an "exo" configuration, or, in each case, a pharmaceutically, acceptable salt or prodrug thereof.

11. The compound according to claim 1, selected from:

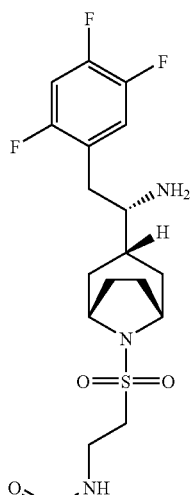

B1

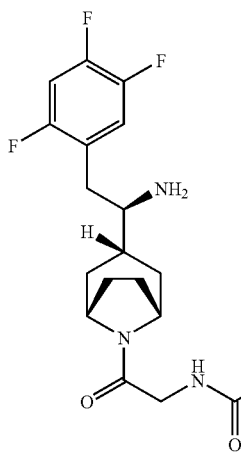

C1

207
-continued
C2
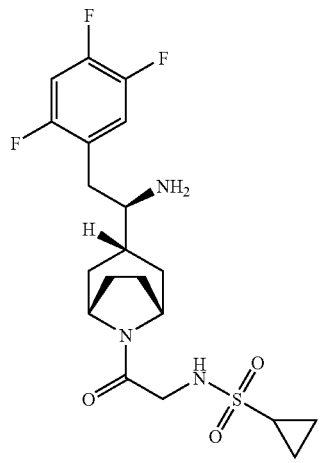
D1
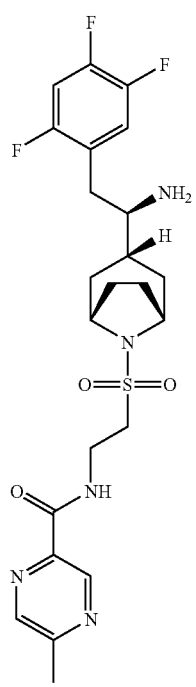
208
-continued
D2
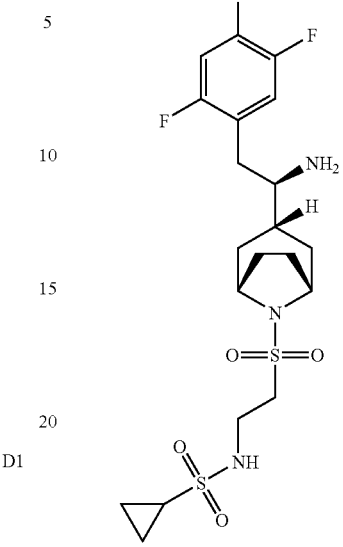
D3
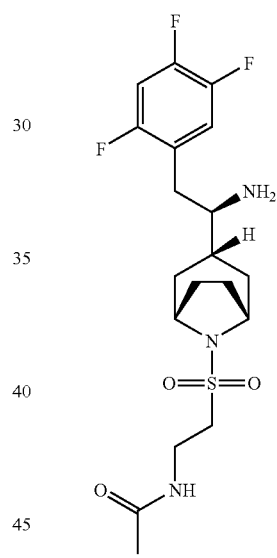

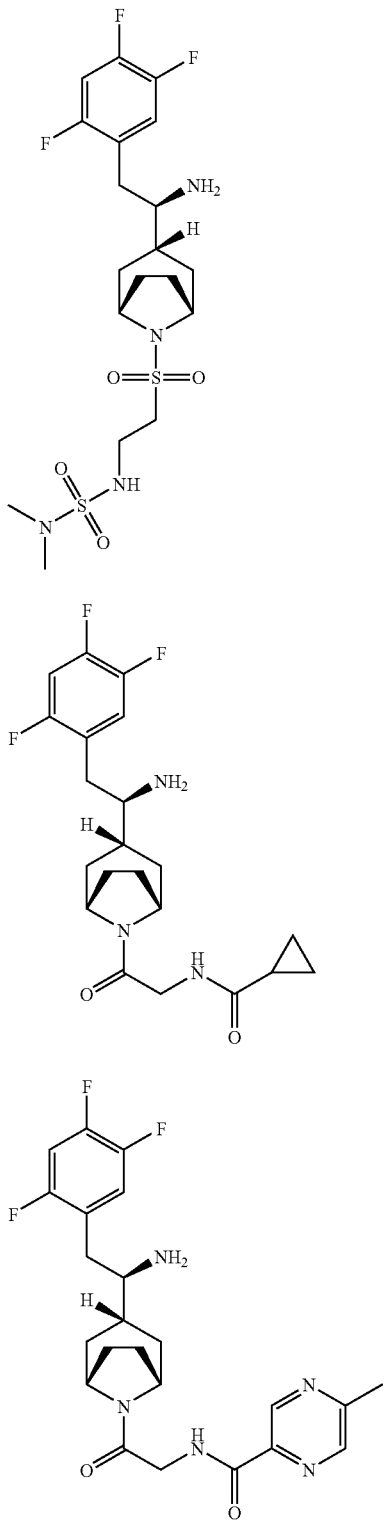
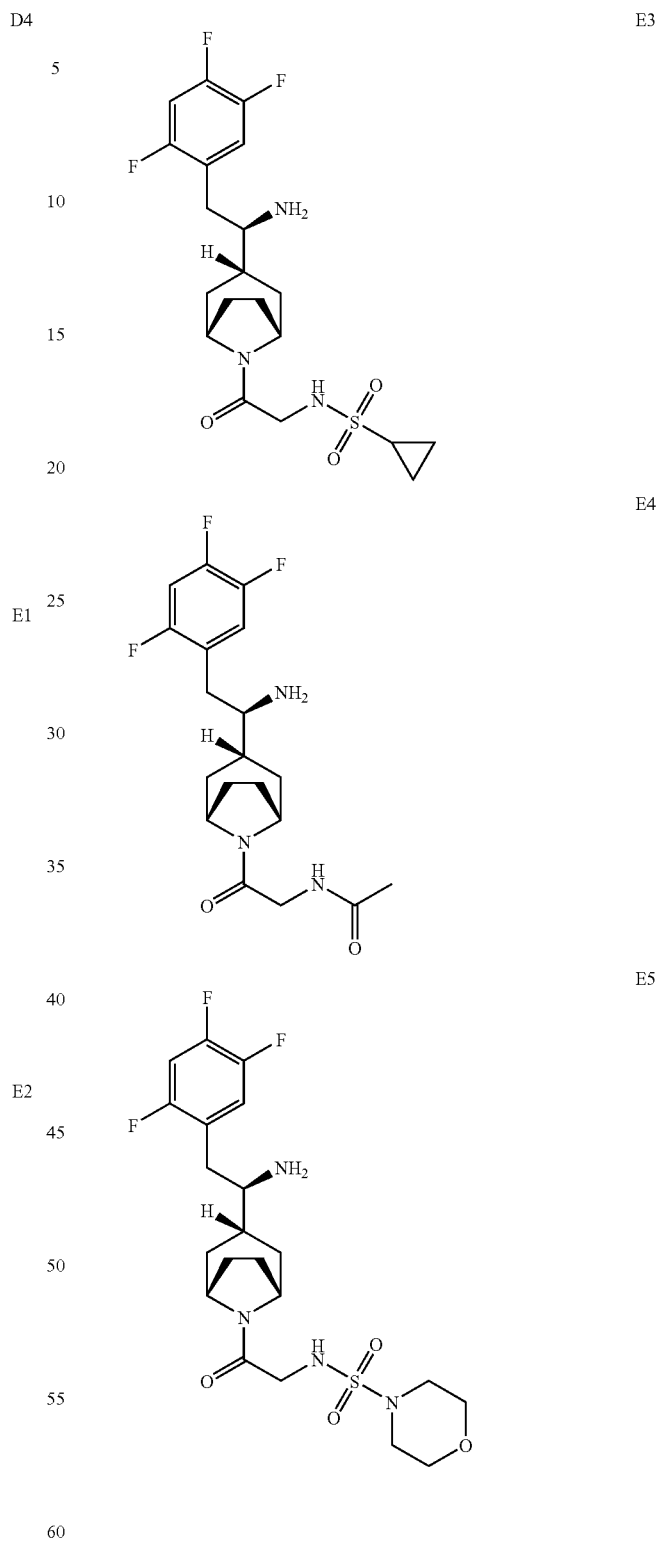

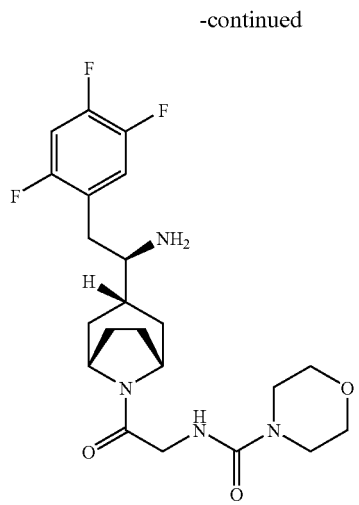
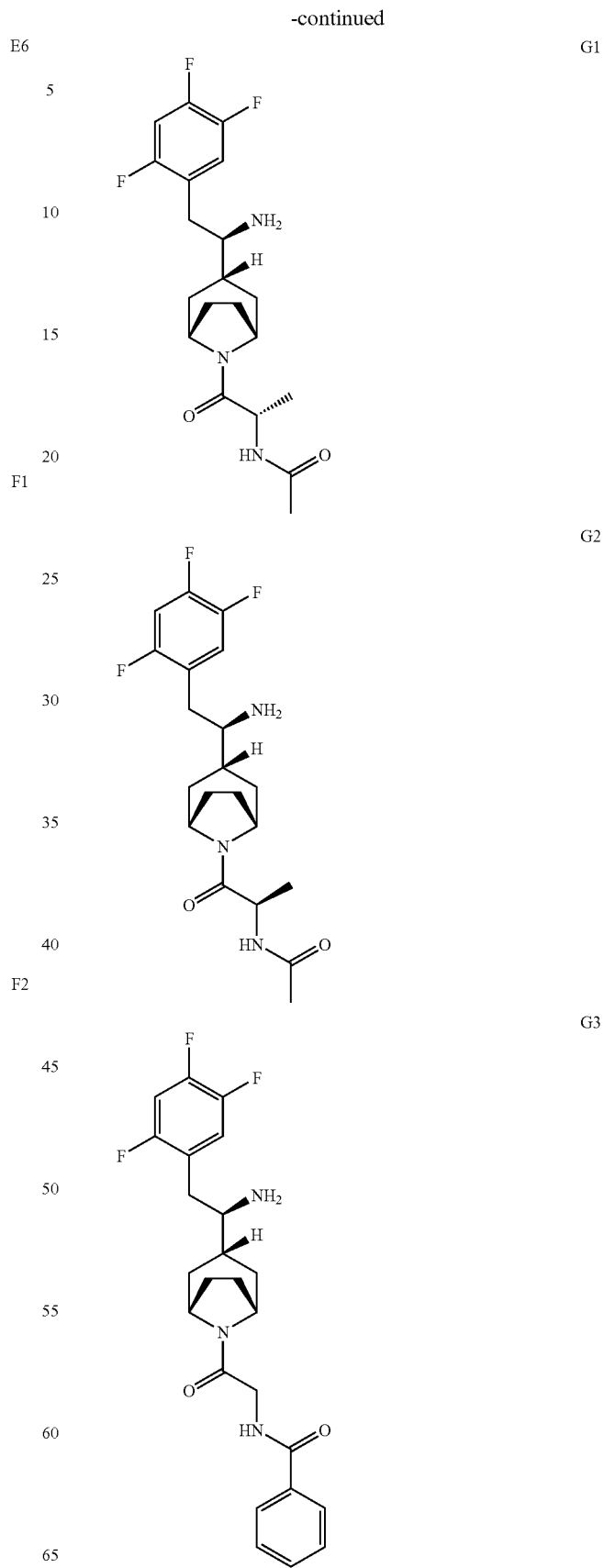

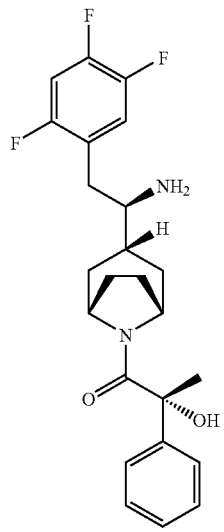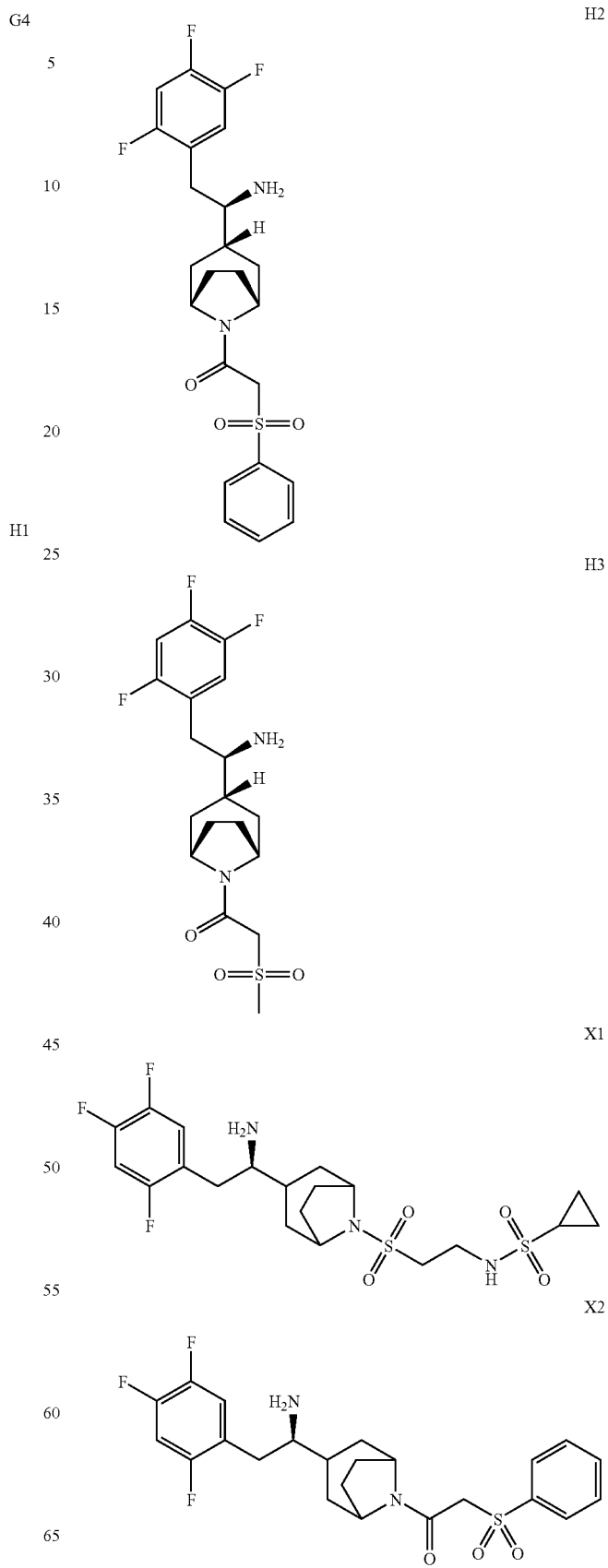

215                                                             216
-continued                                                       -continued
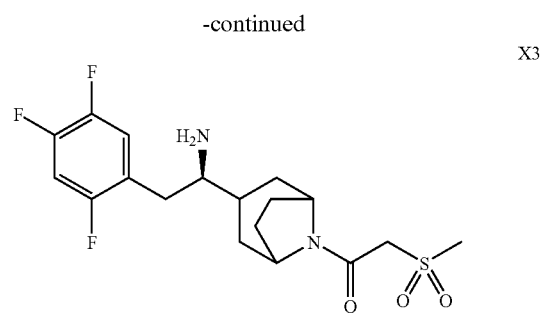
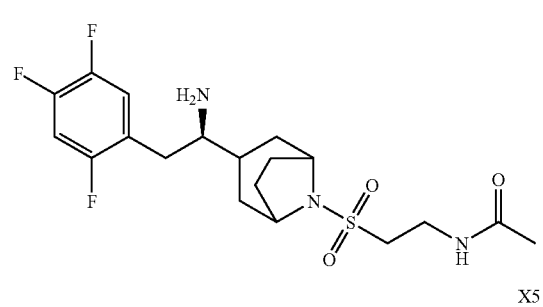
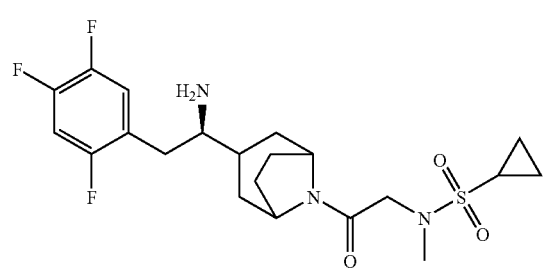
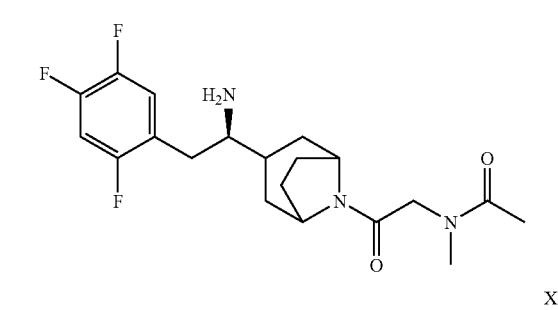
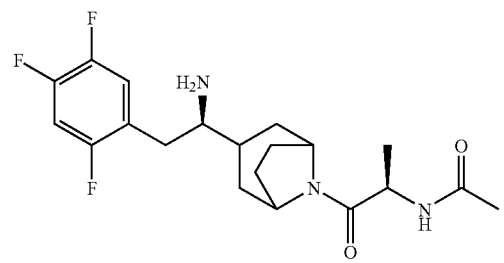

X13
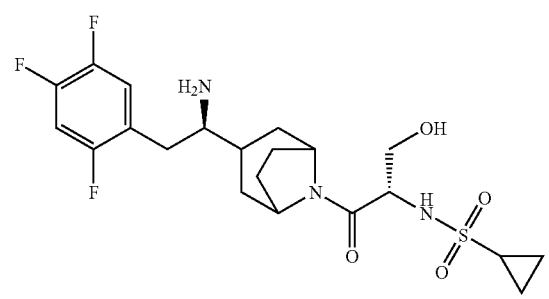
X14
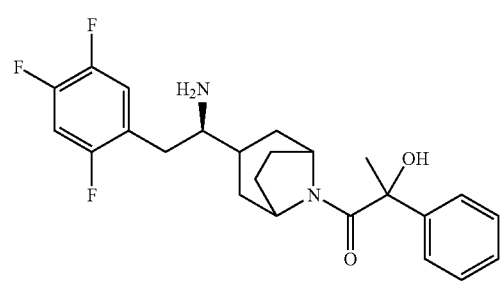
X15
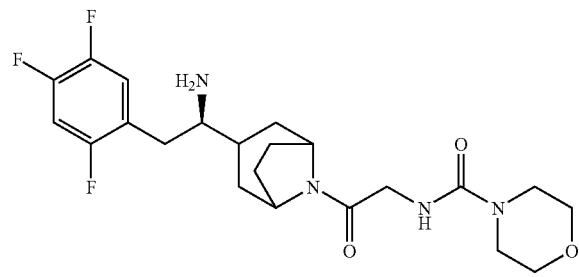
X16
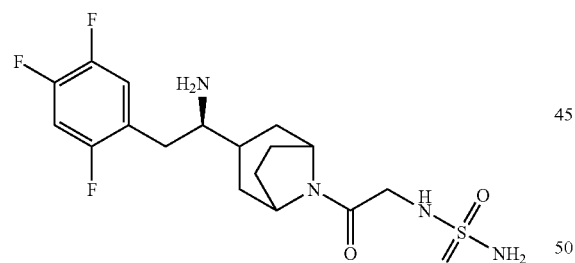
X17
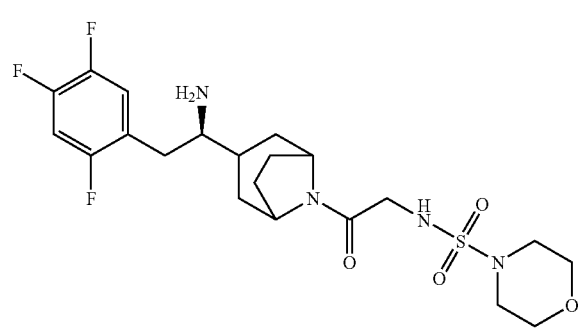
X18
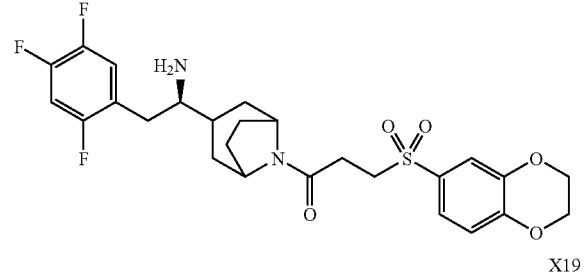
X19
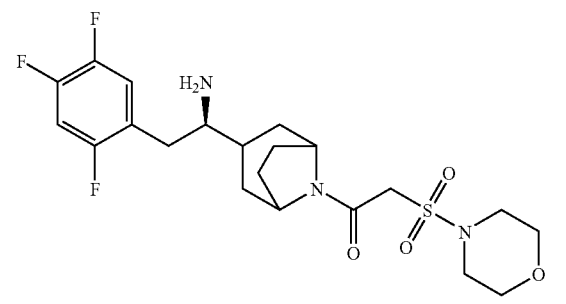
X20
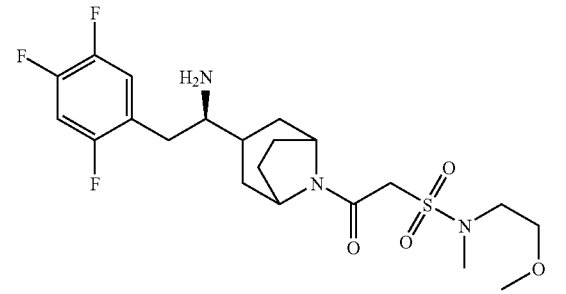
X21
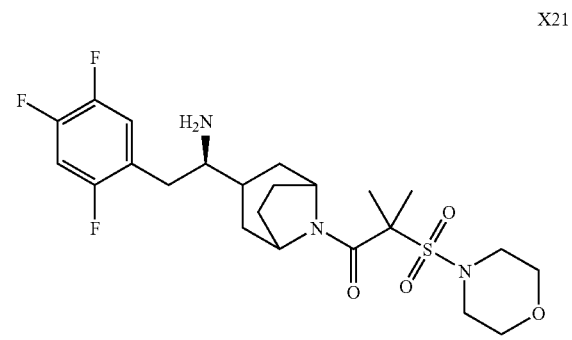
or, in each case a pharmaceutically acceptable salt or prodrug thereof.
12. The compound according to claim 1, selected from:

219
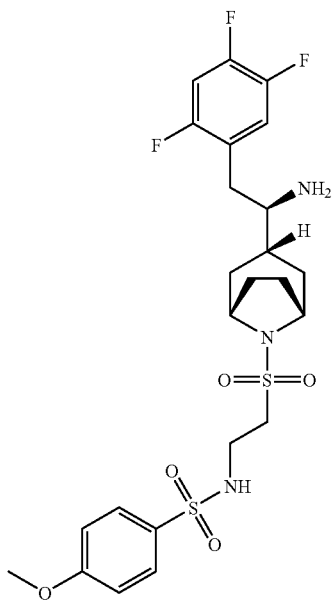
220
-continued
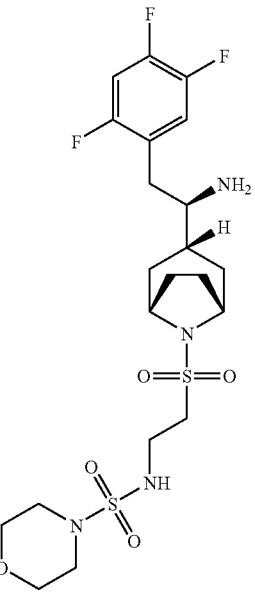
D5
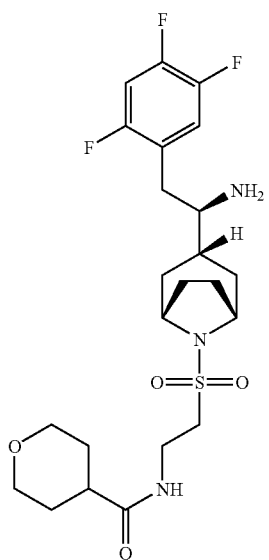
D7
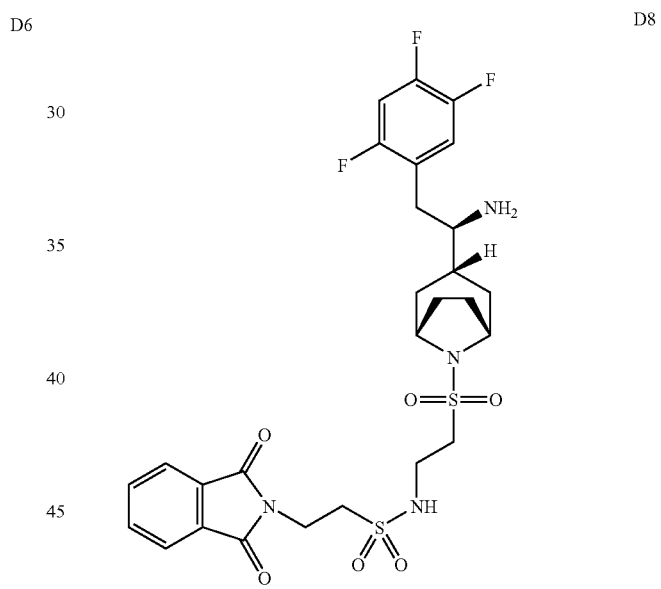
D6
D8

-continued
D9
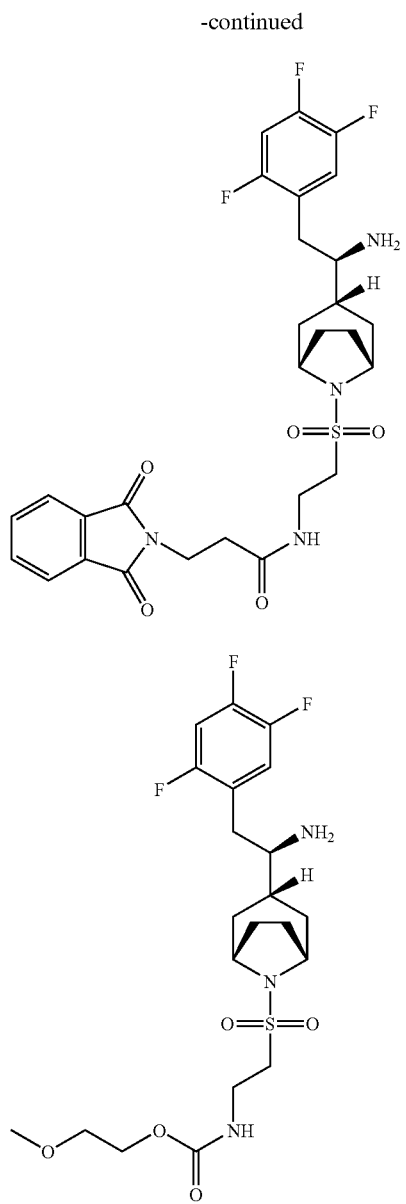
D10
D11
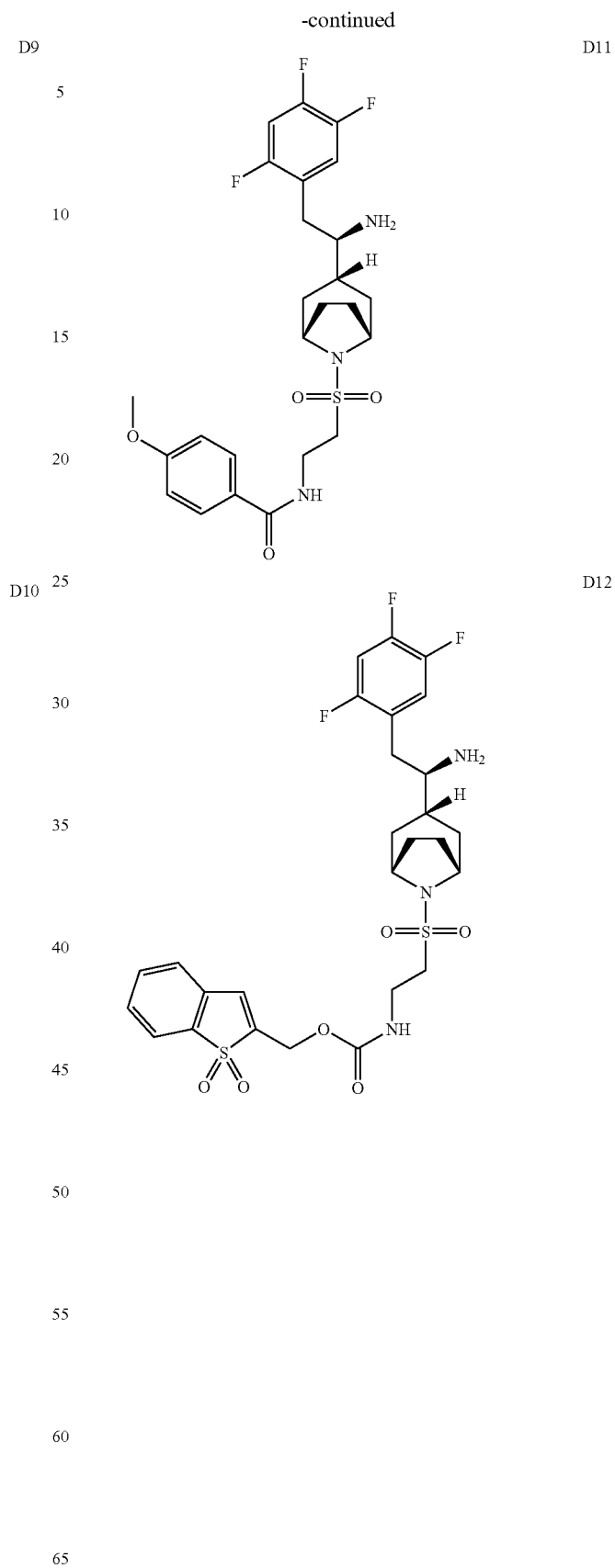
D12

-continued
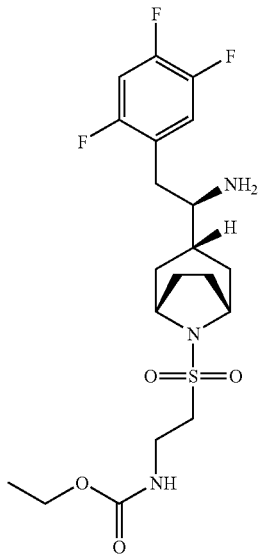
D13
D14
-continued
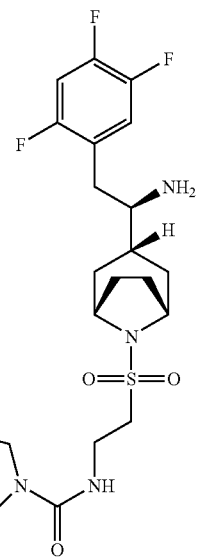
D15
D16

225 226
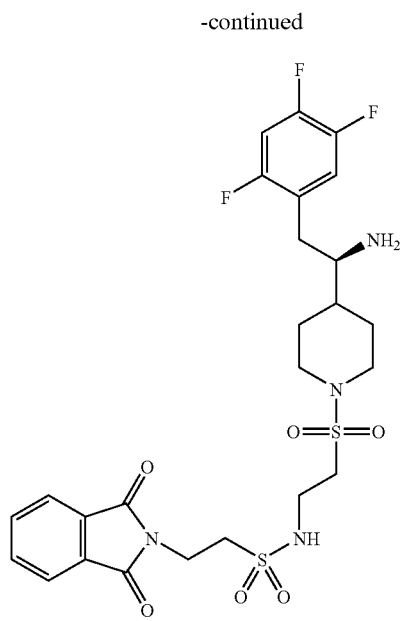
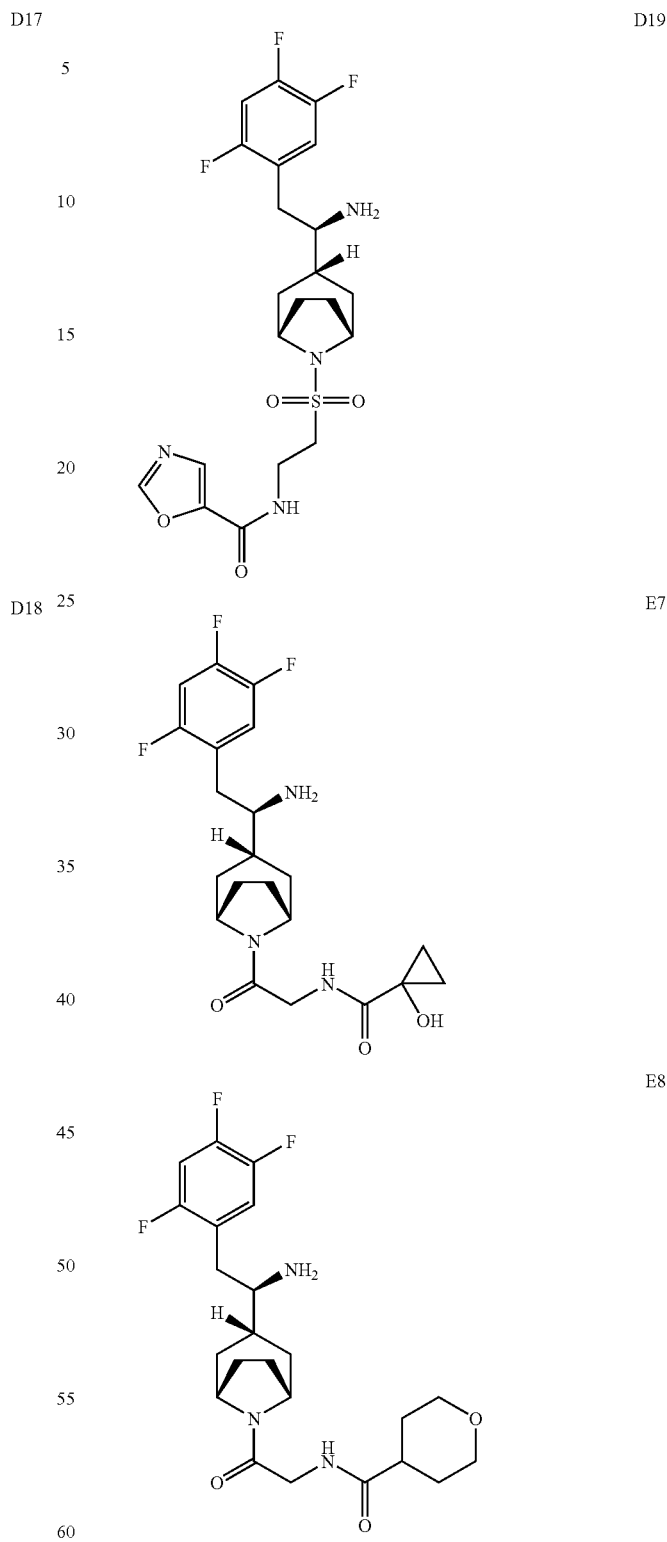

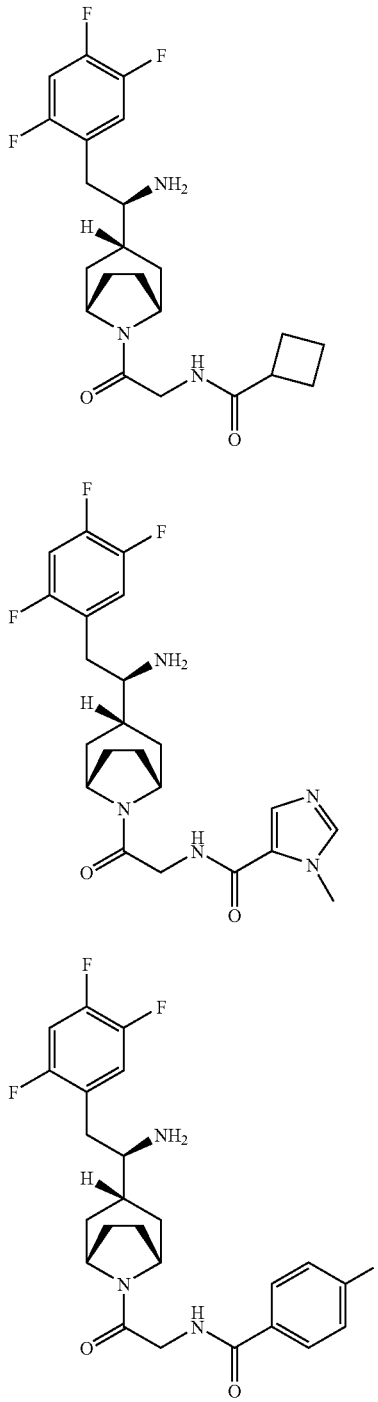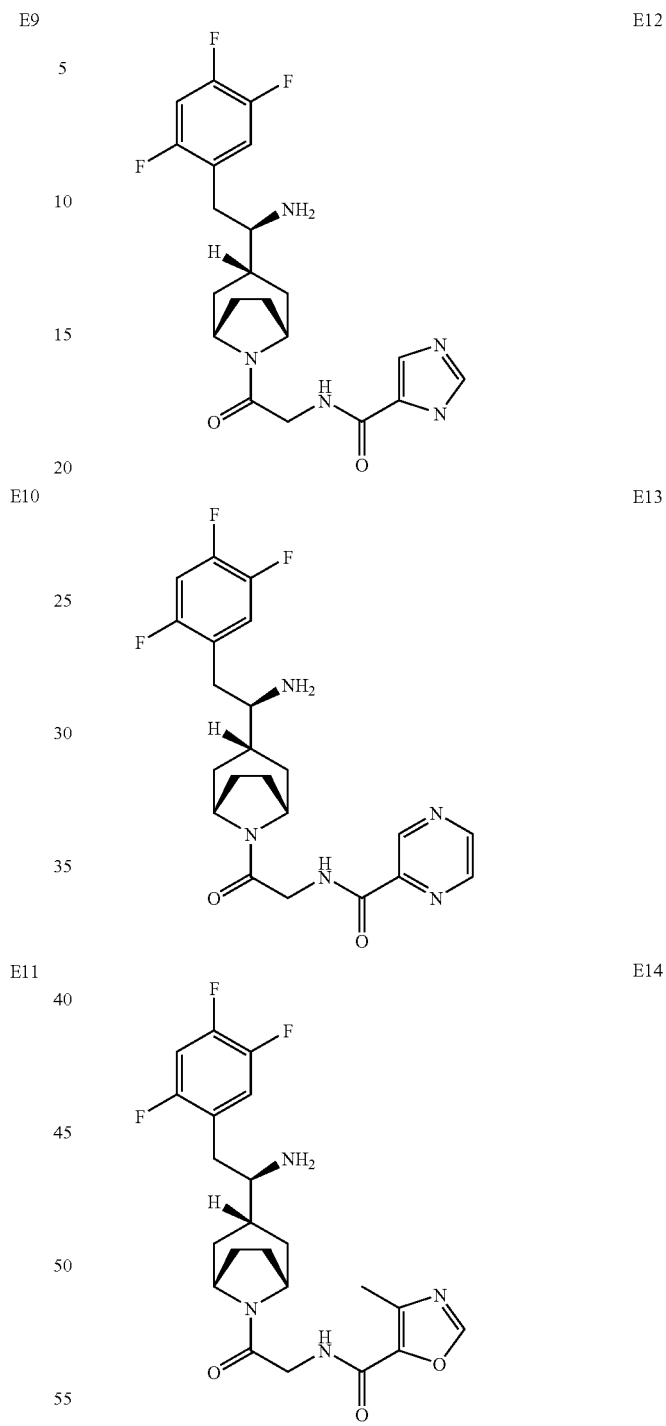

-continued
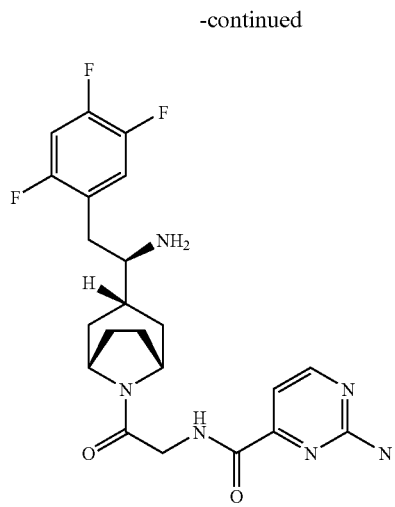
E15
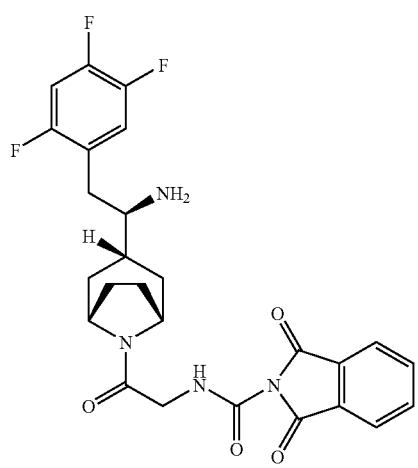
E16
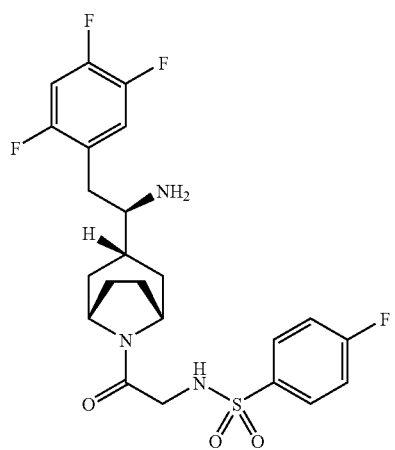
E17
-continued
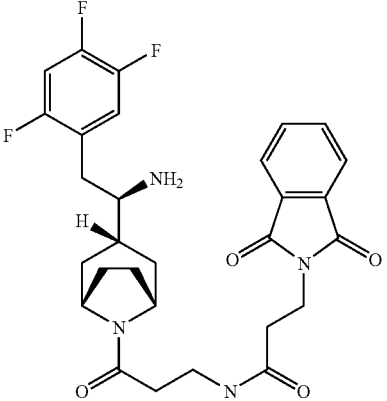
E18
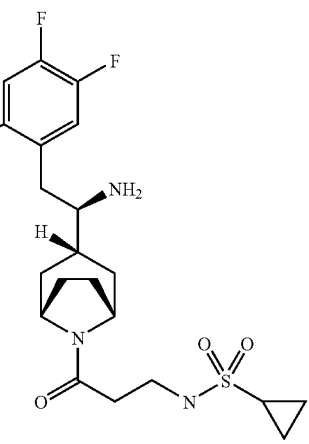
E19
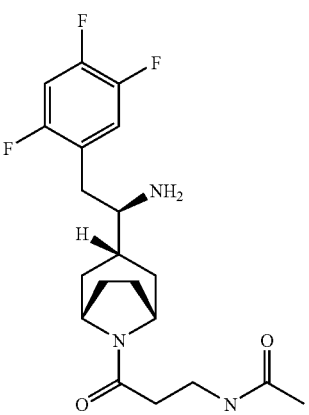
E20

-continued
E21
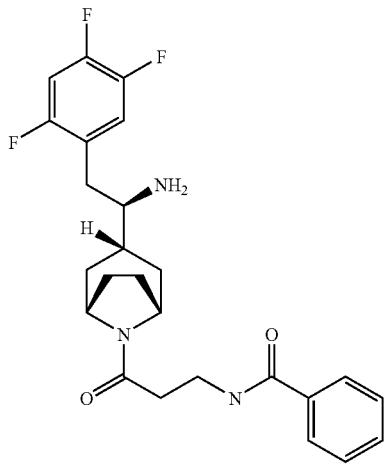
E22
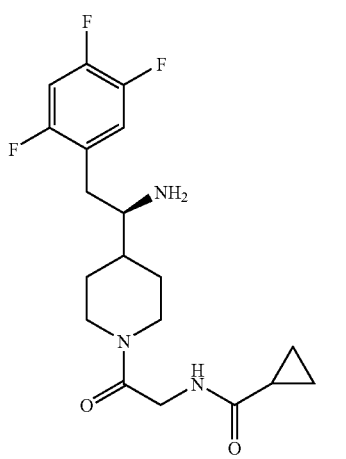
E23
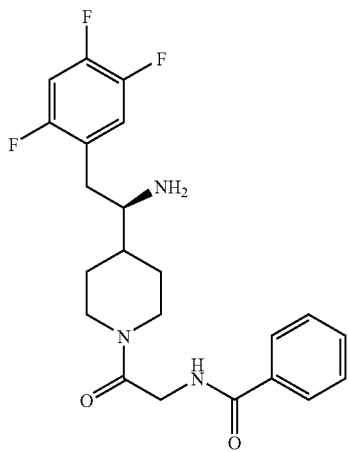
-continued
E24
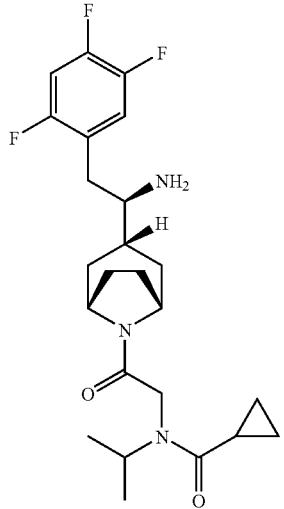
E25
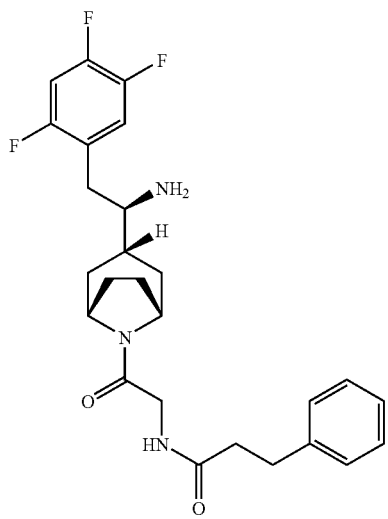
E26
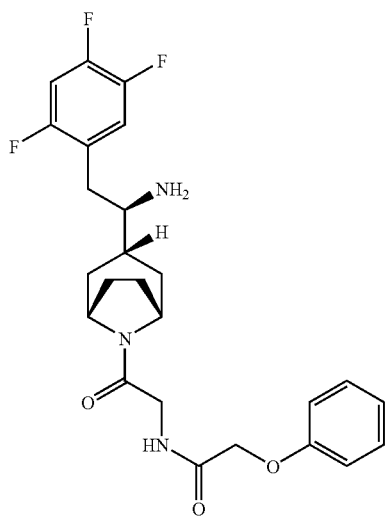

-continued
E27
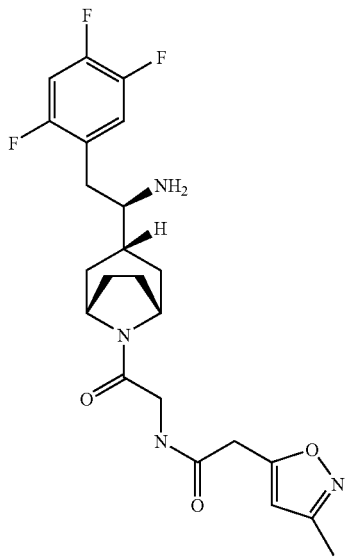
E28
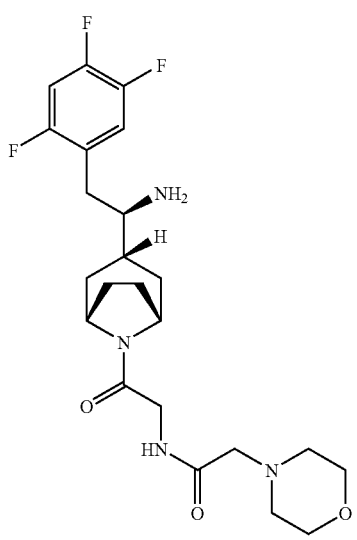
E29
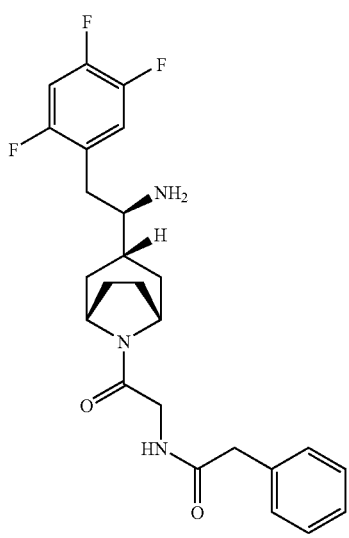
-continued
E30
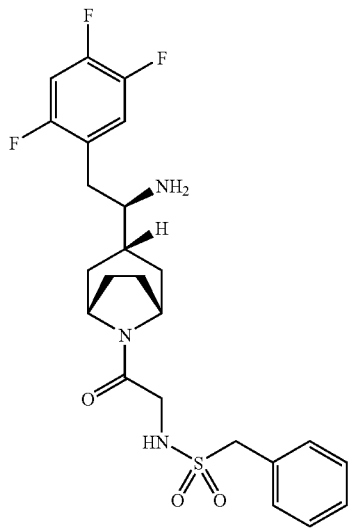
E31
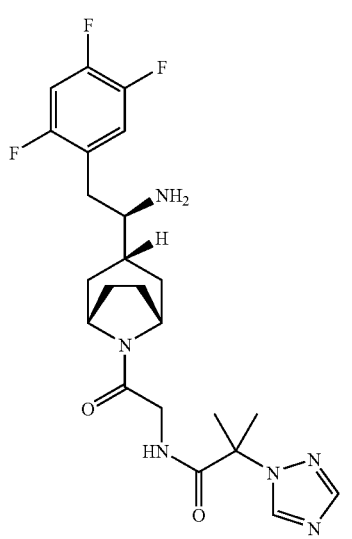
E32
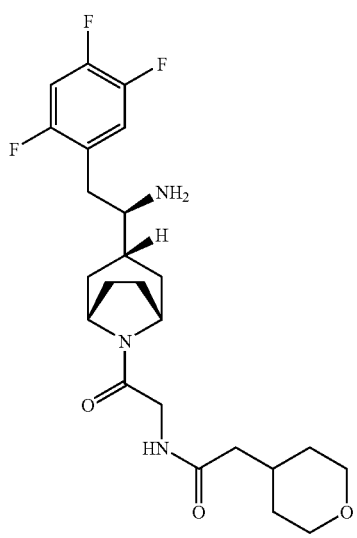

-continued
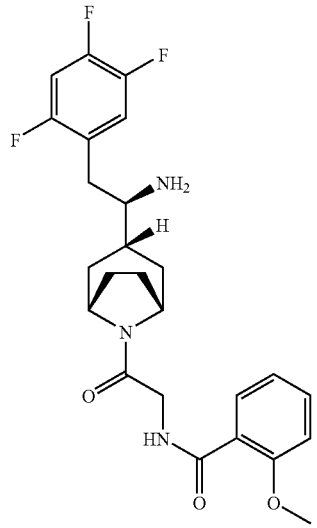
E33
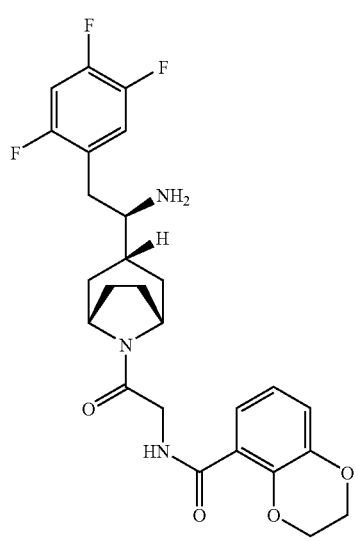
E34
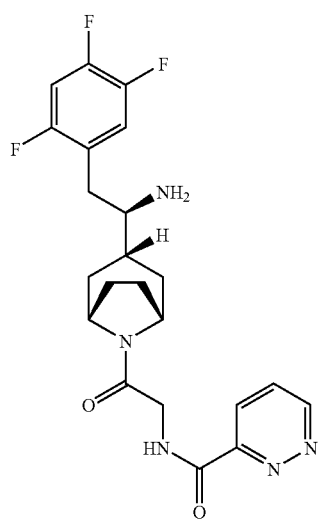
E35
-continued
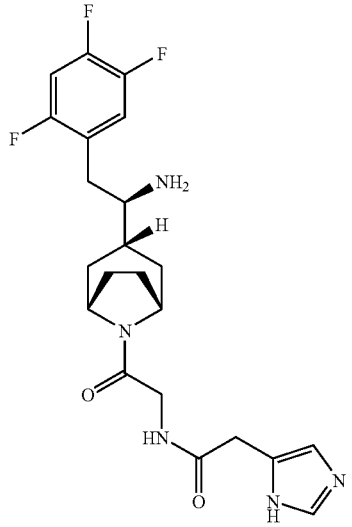
E36
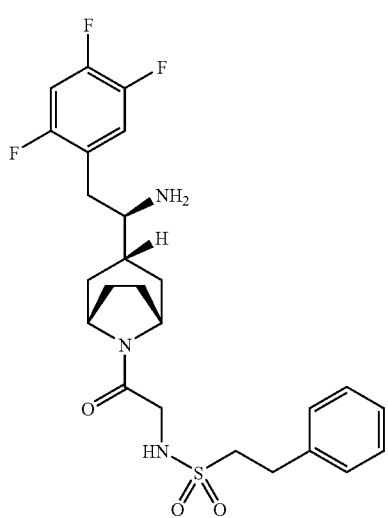
E37
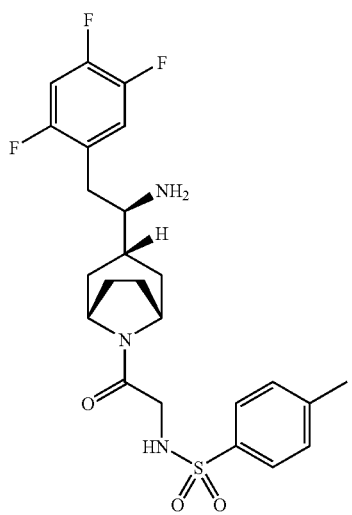
E38

E39
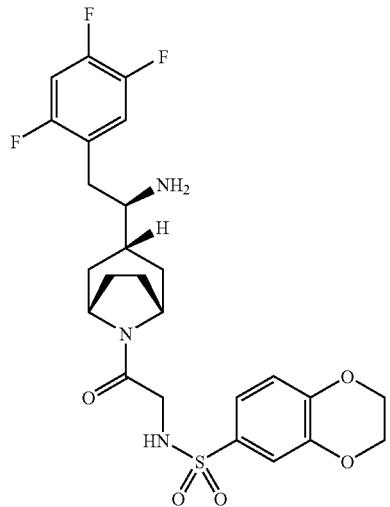
E40
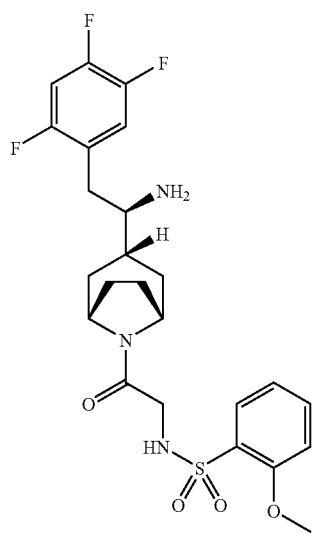
E41
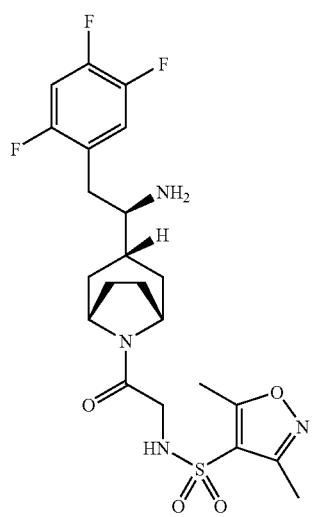
E42
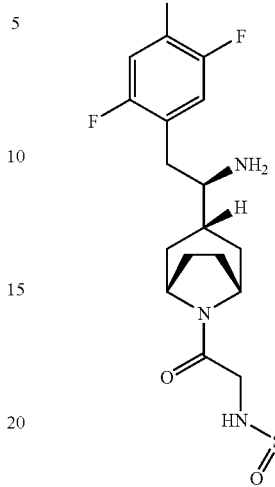
F3
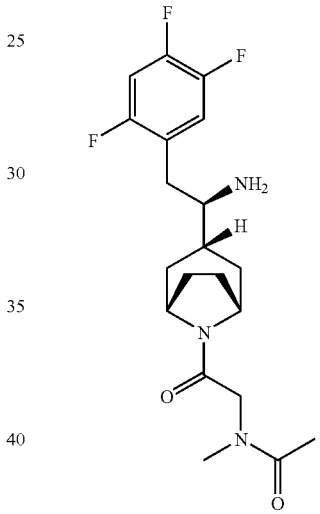
F4
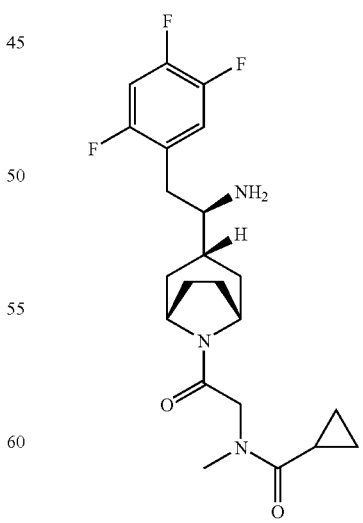

-continued
F5
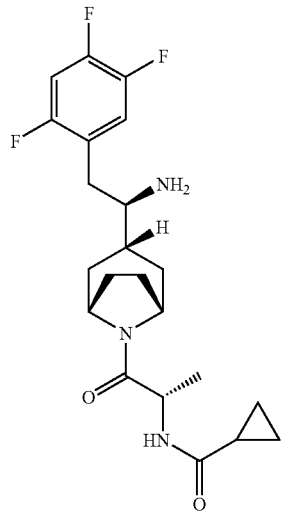
F6
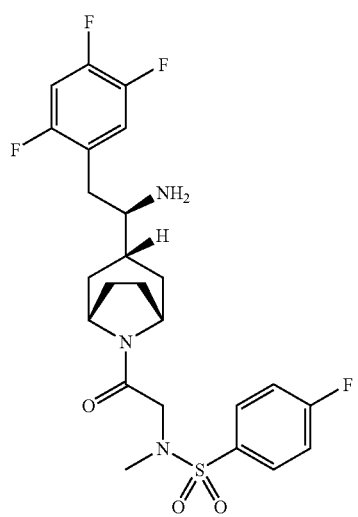
F7
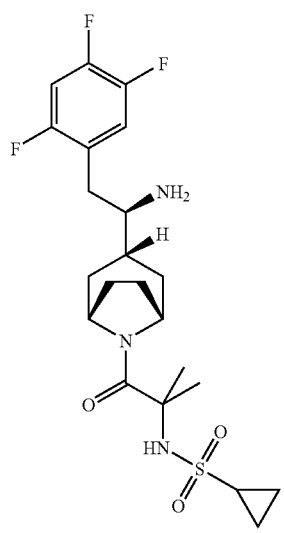
-continued
F8
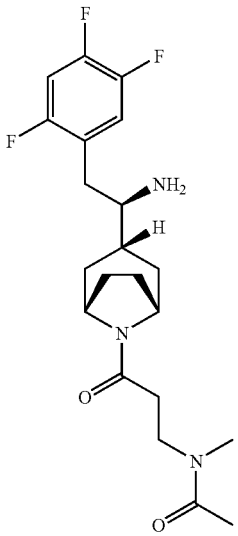
F9
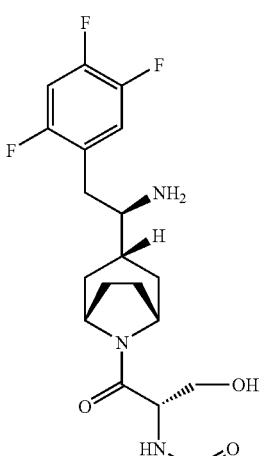
F10
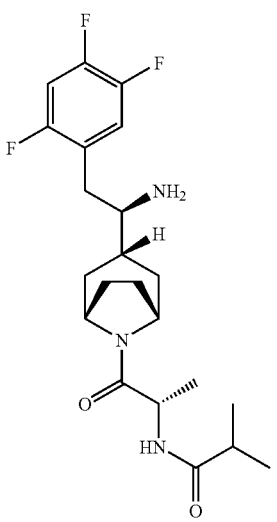

241
-continued
F11 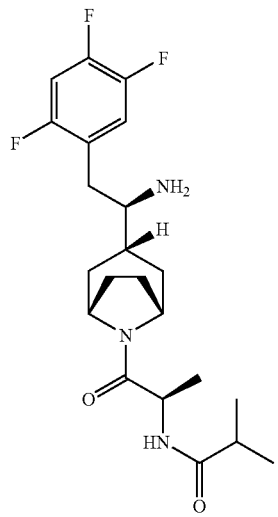
F12 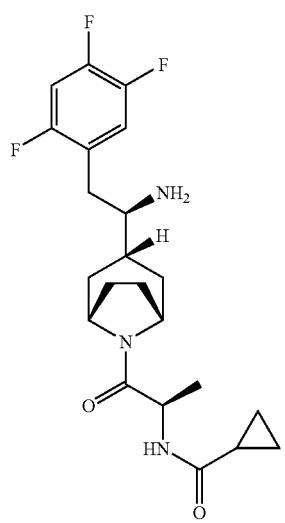
G5 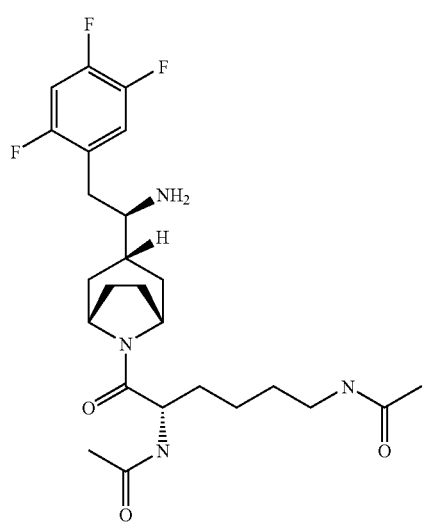
242
-continued
G6 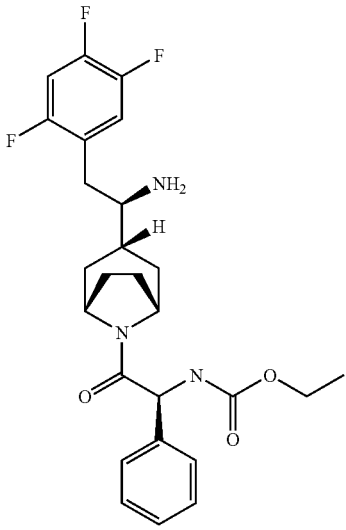
G7 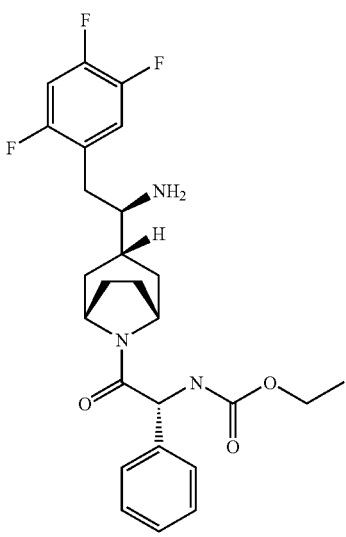
G8 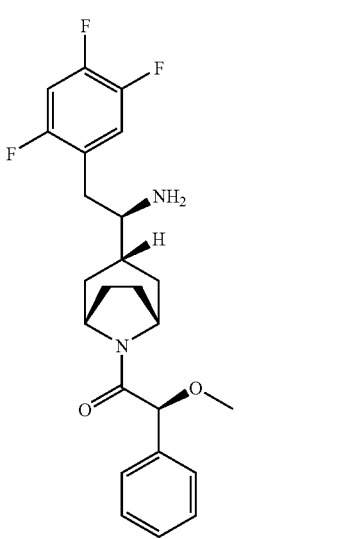

243 244
-continued
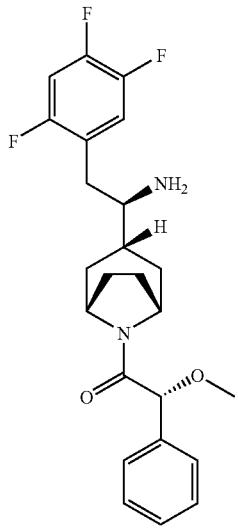
G9
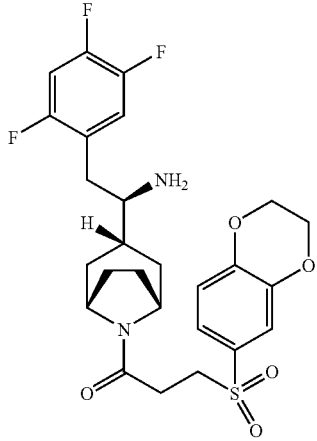
G12
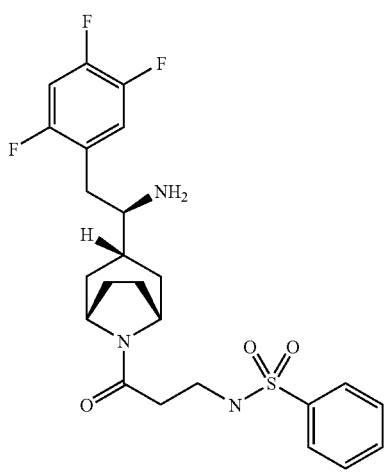
G10
G13
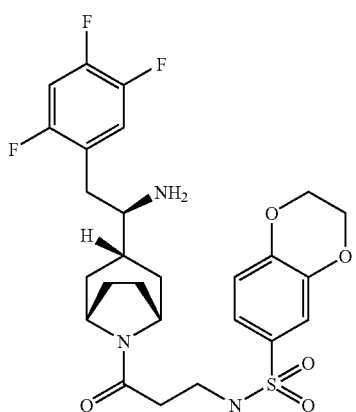
G11
G14

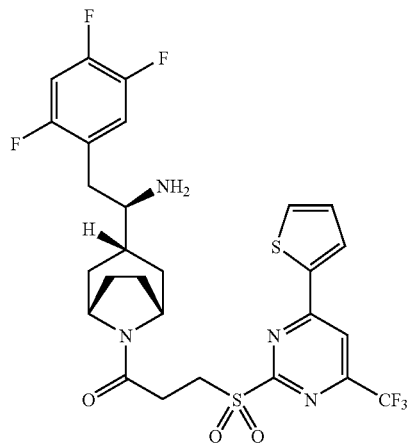
G15
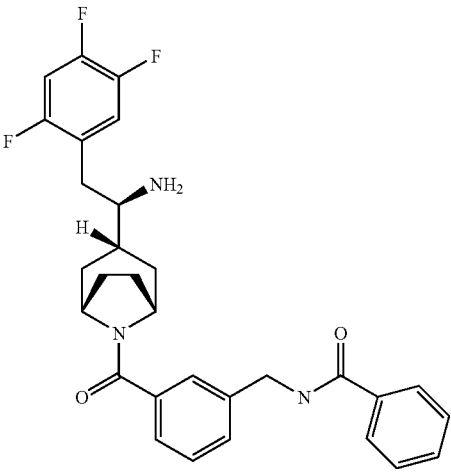
G18
G16
G19
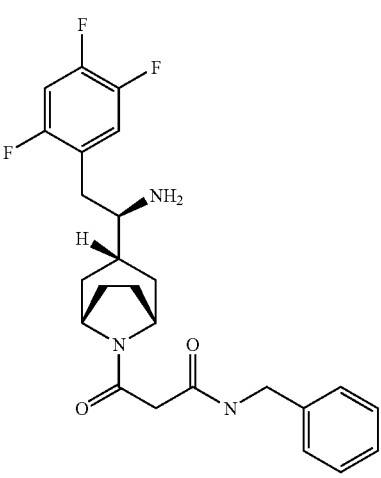
G17
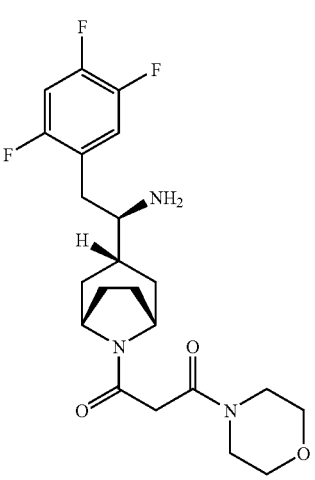
G20

-continued
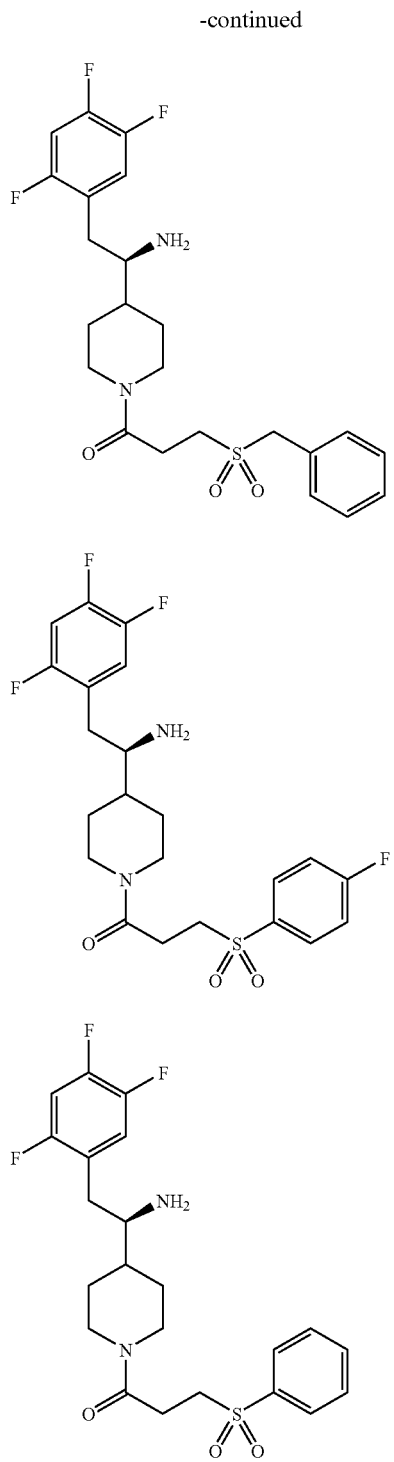
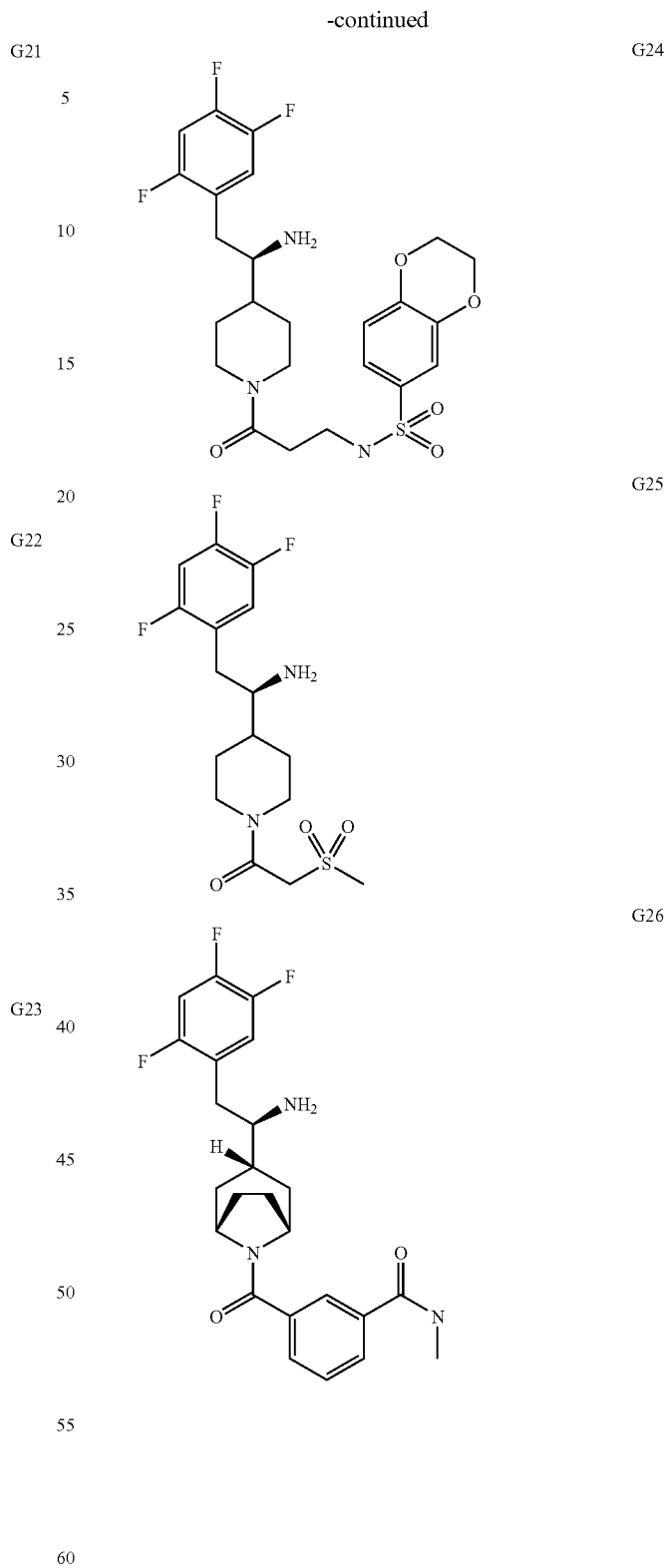

-continued
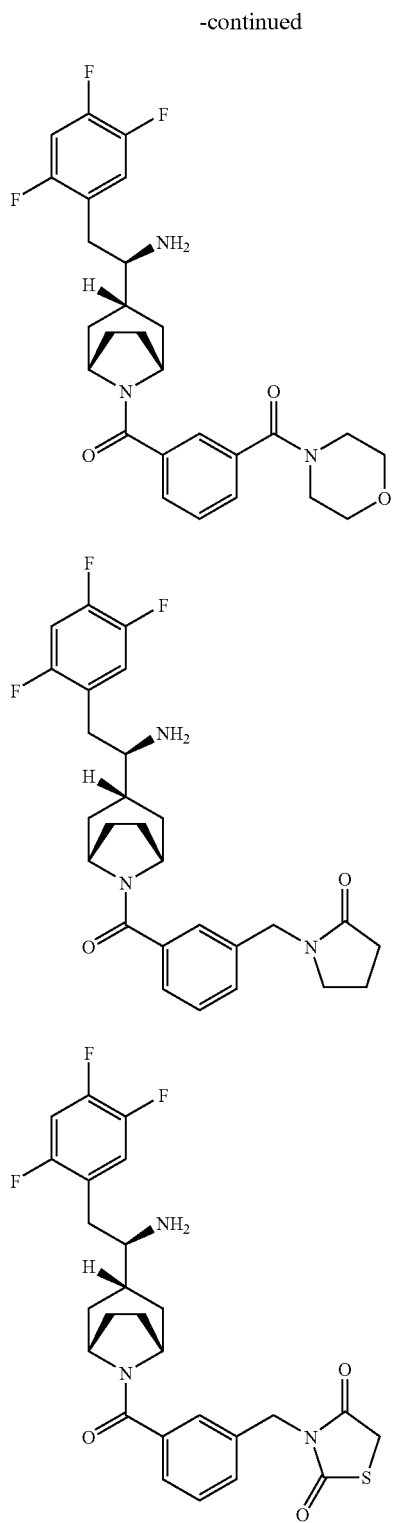
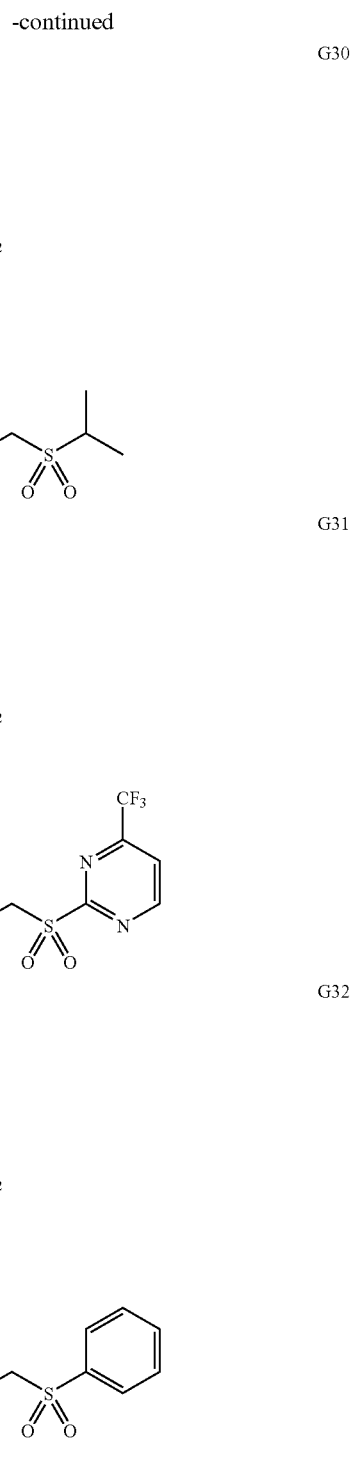

-continued
G33
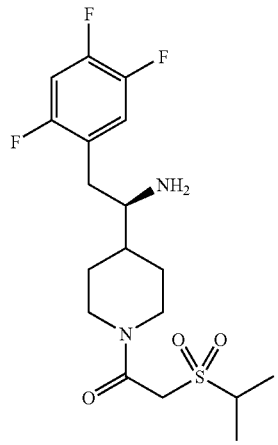
G34
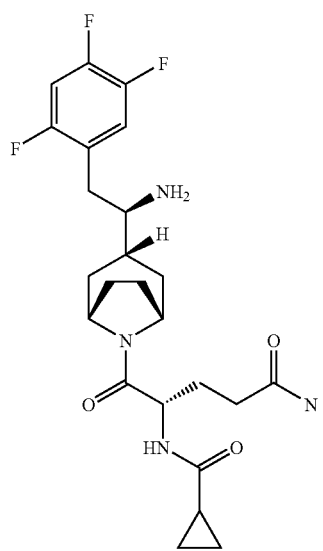
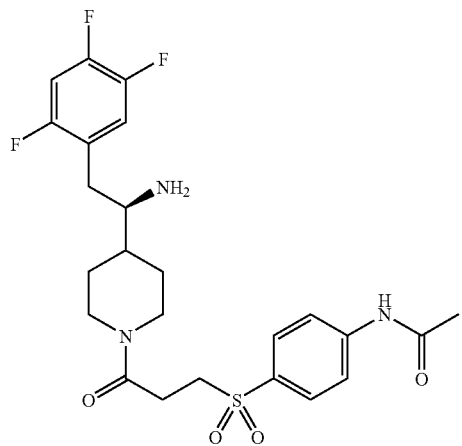
-continued
G36
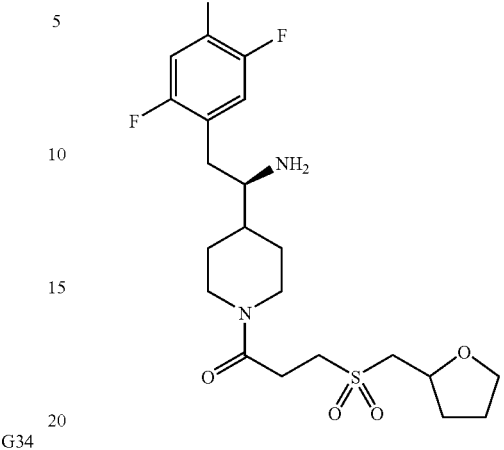
G37
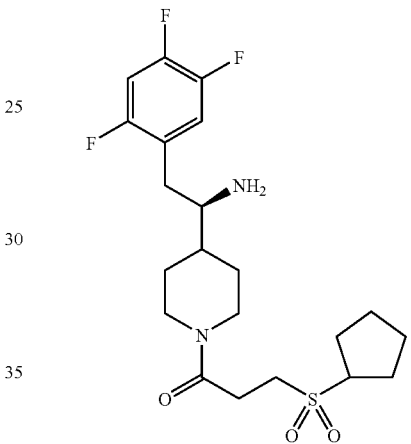
G38
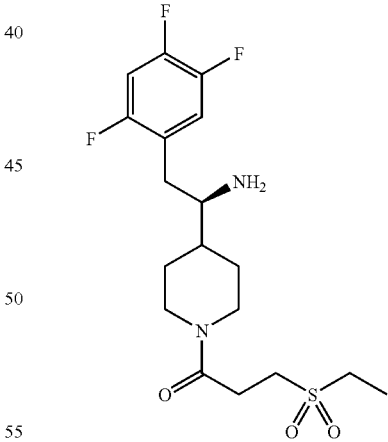

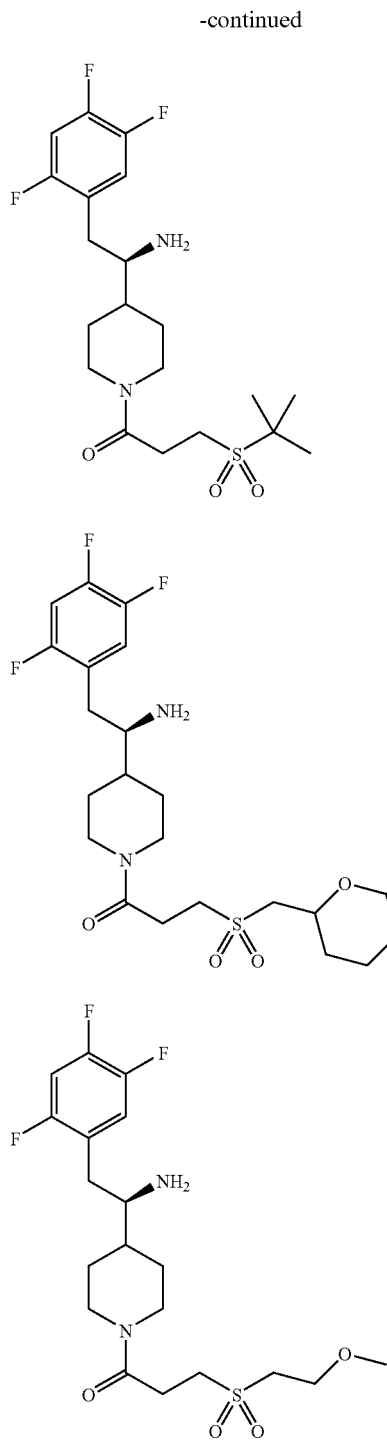
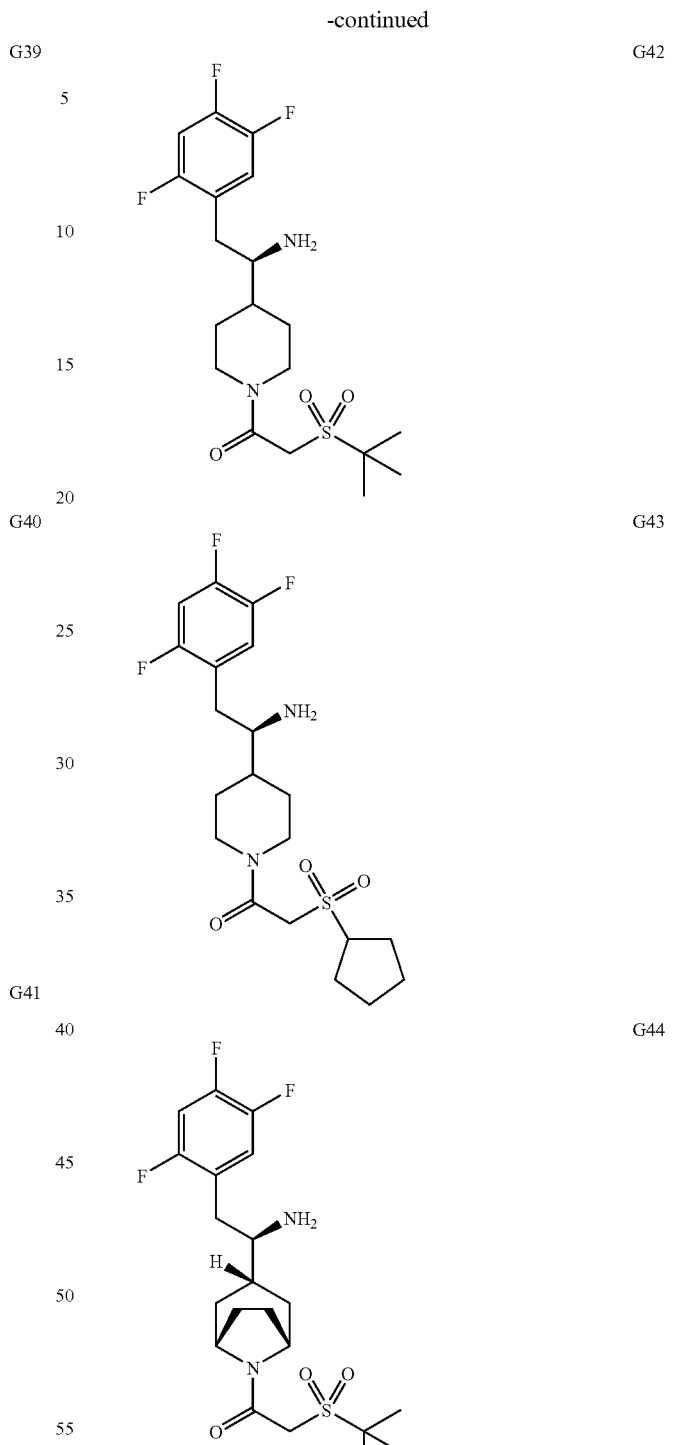

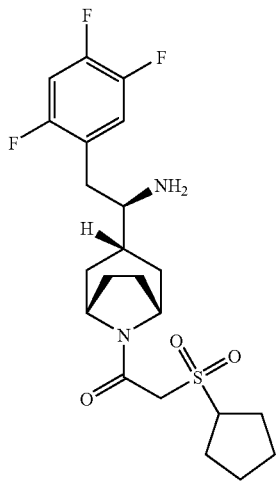
G45
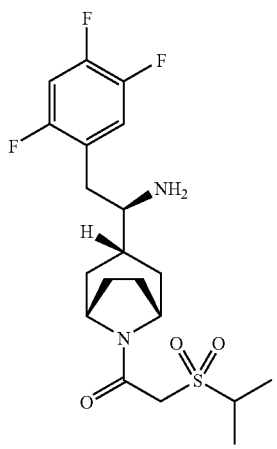
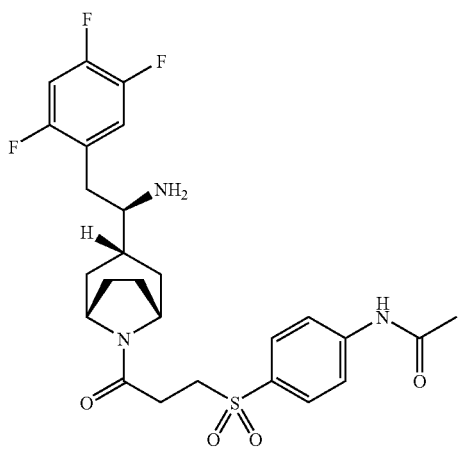
G47
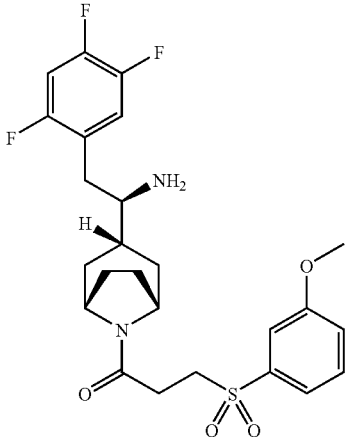
G48
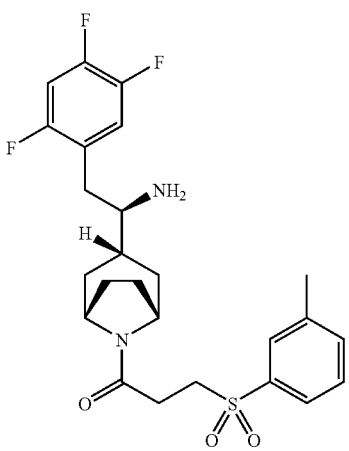
G49
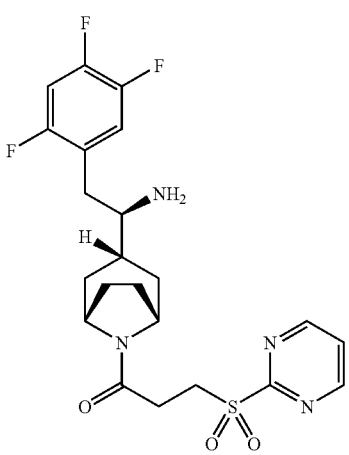
G50

G51 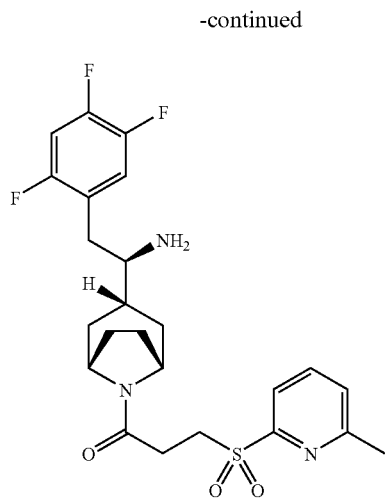
G52 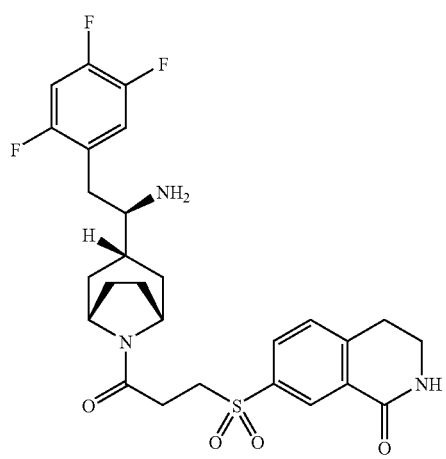
G53 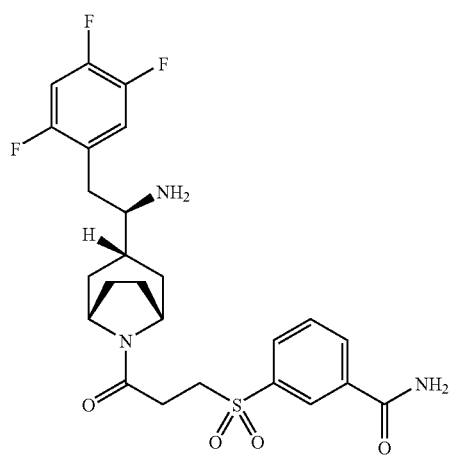
G54 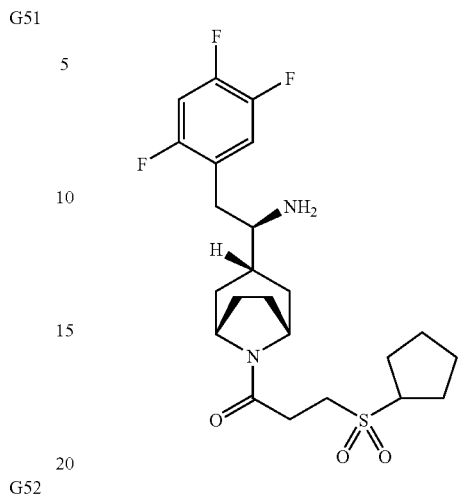
G55 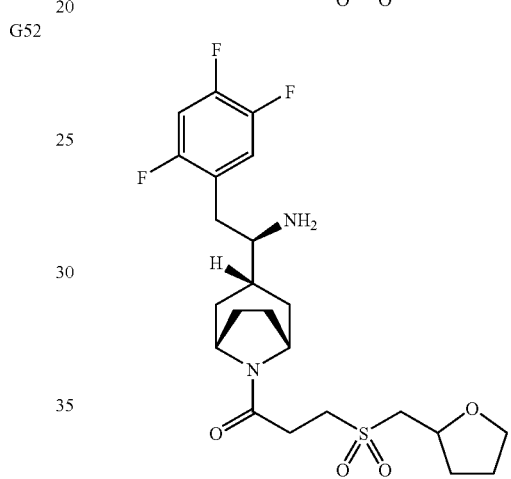
G56 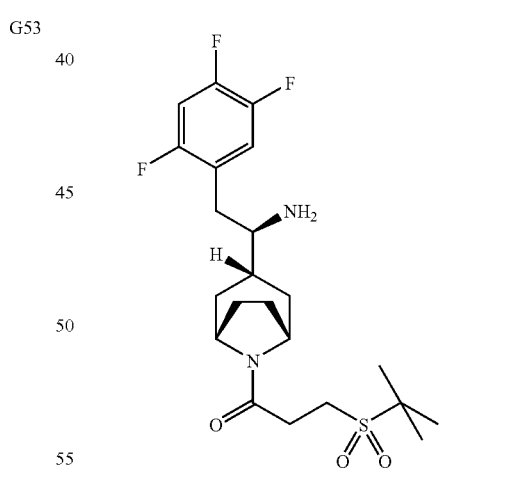

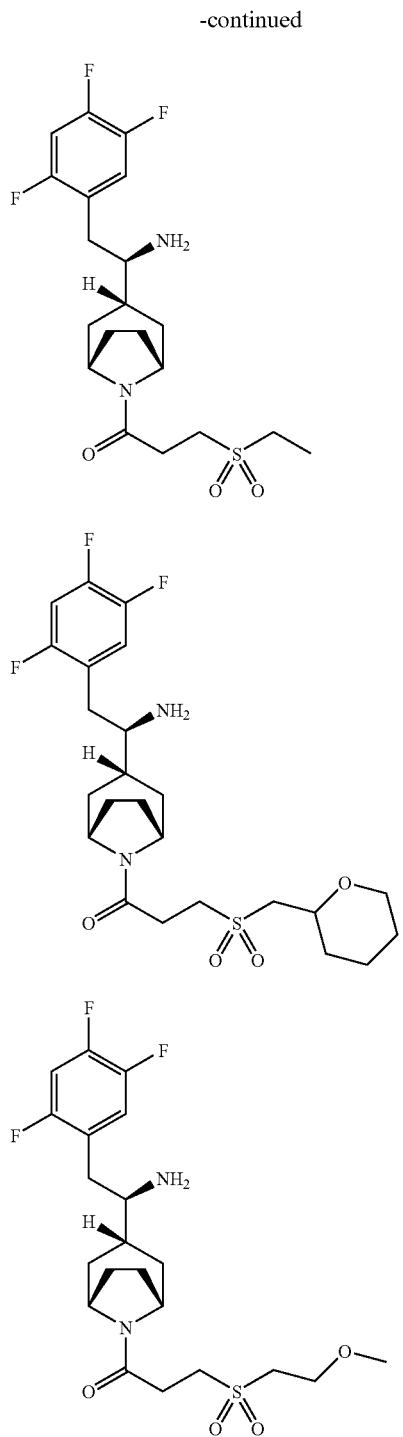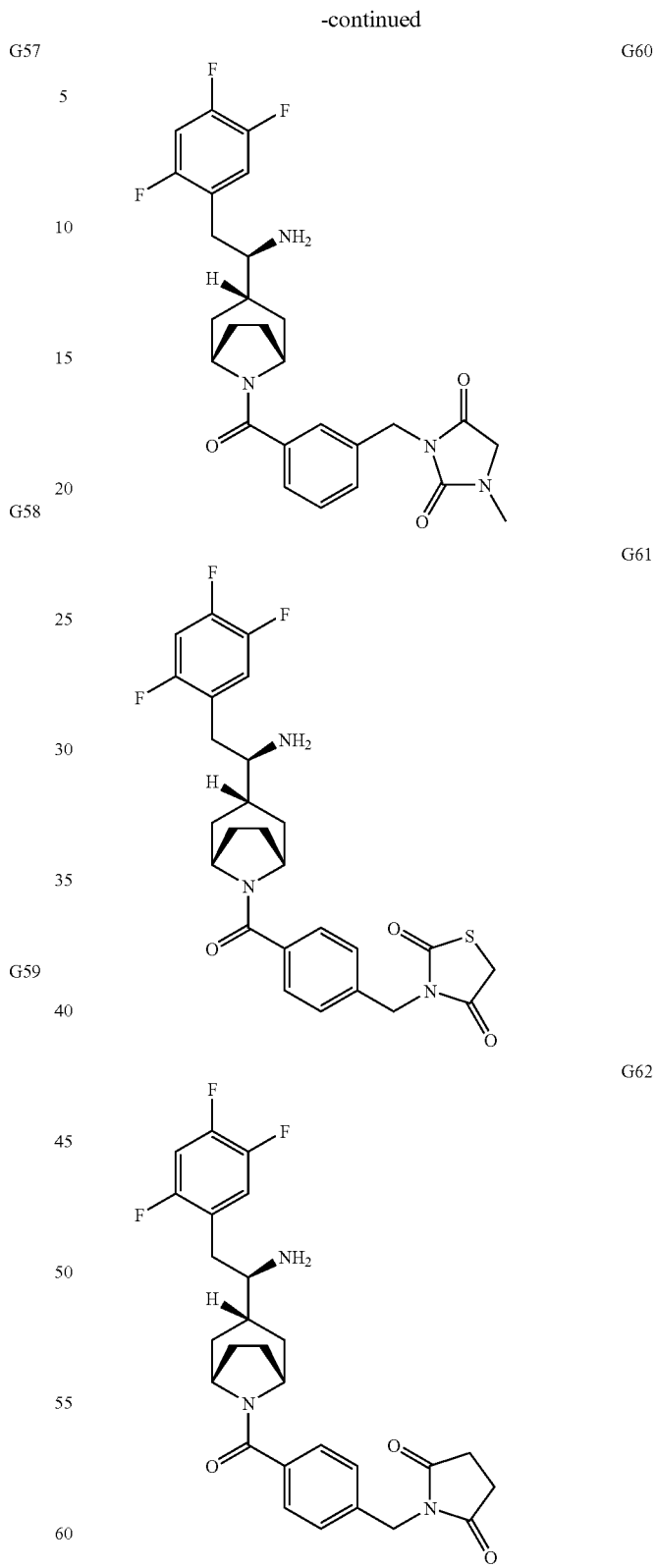

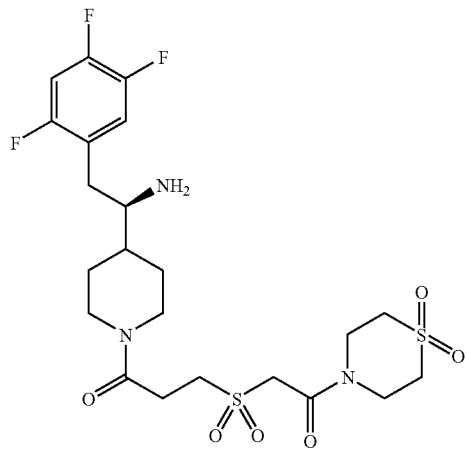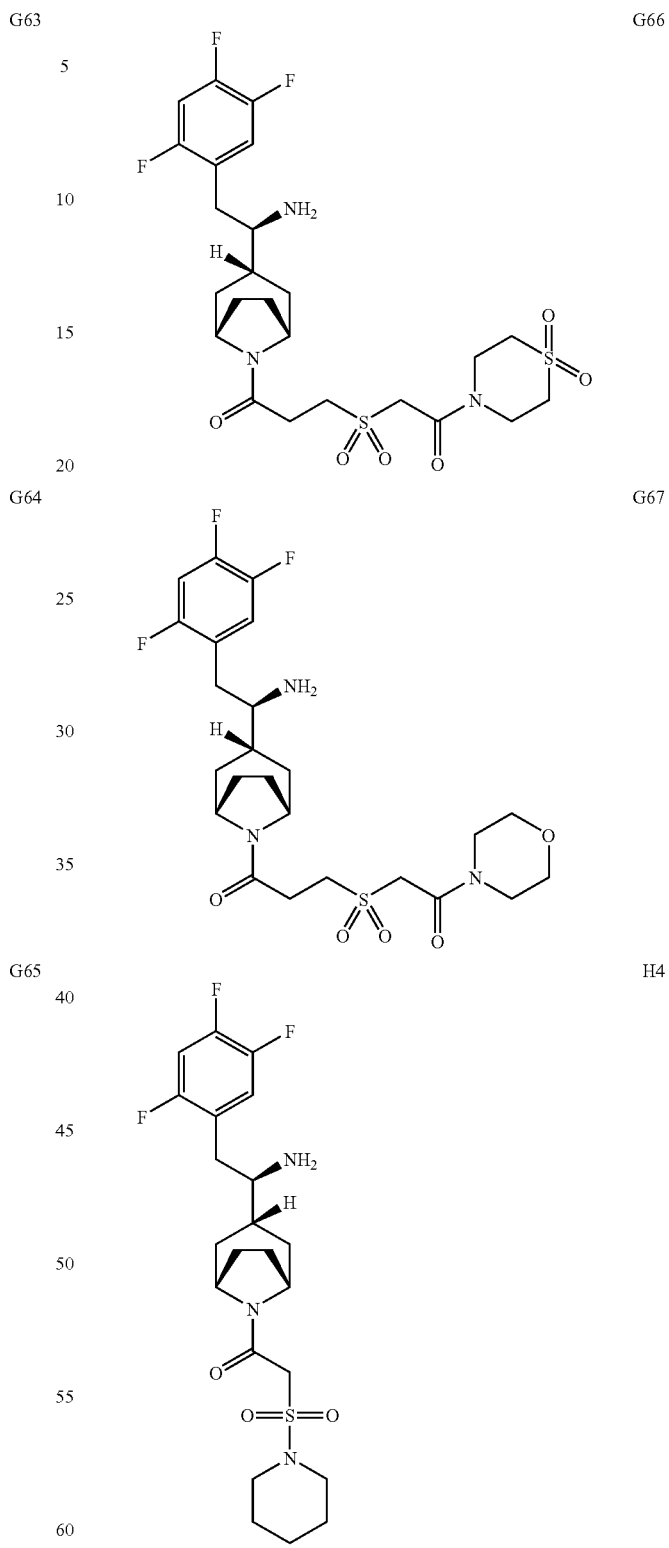

263
-continued
H5
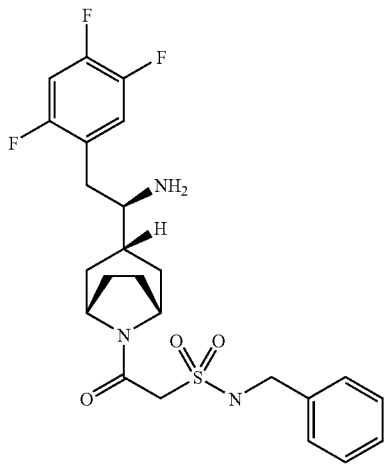
H6
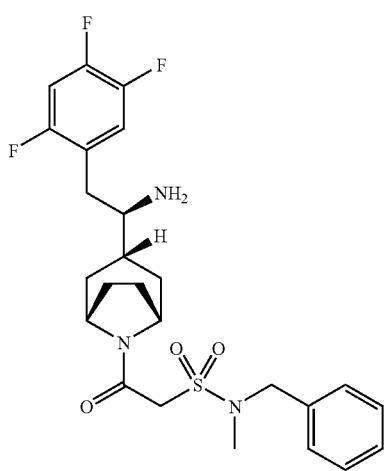
H7
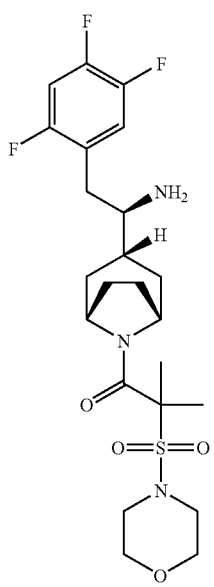
264
-continued
H8
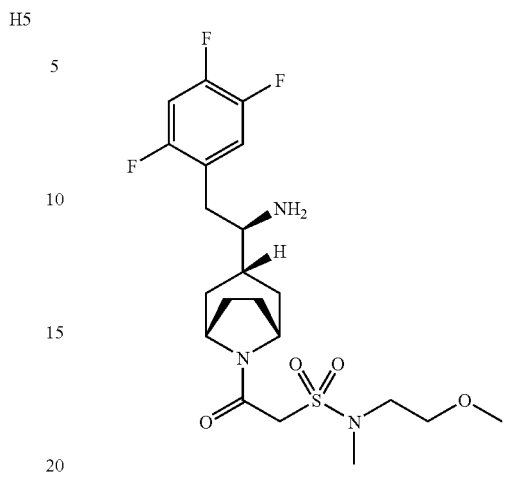
H9
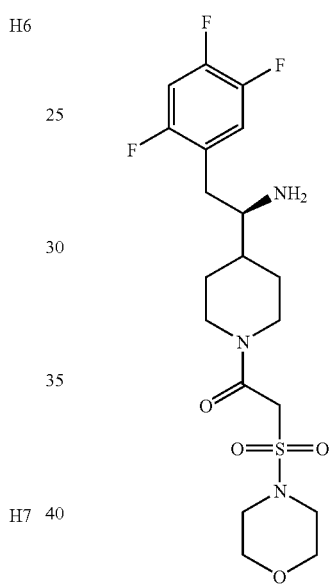
H10
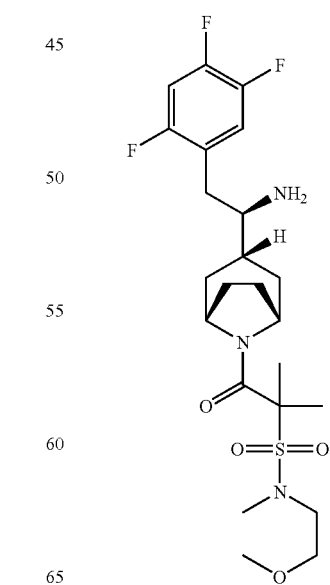

H11
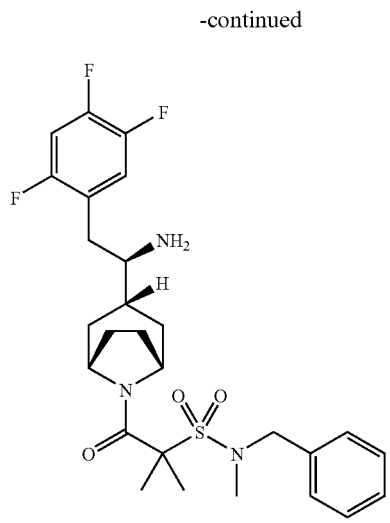
H12
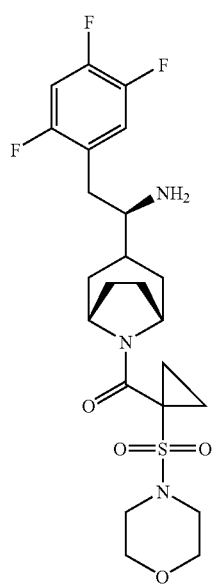
H13
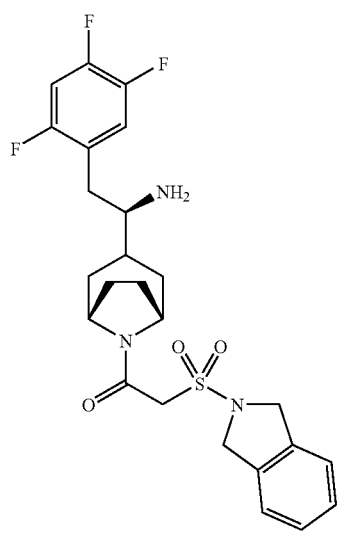
H14
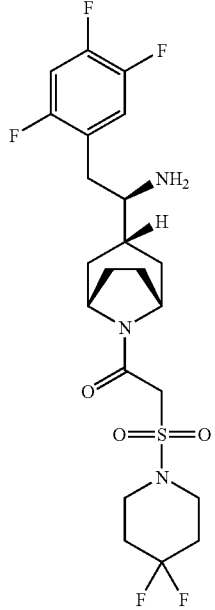
I1
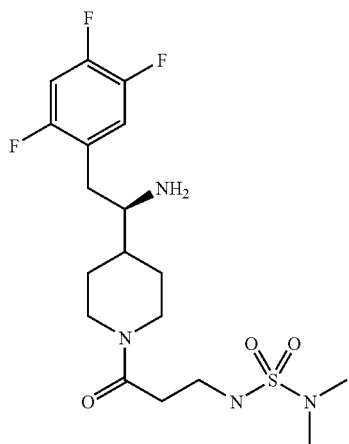
I2
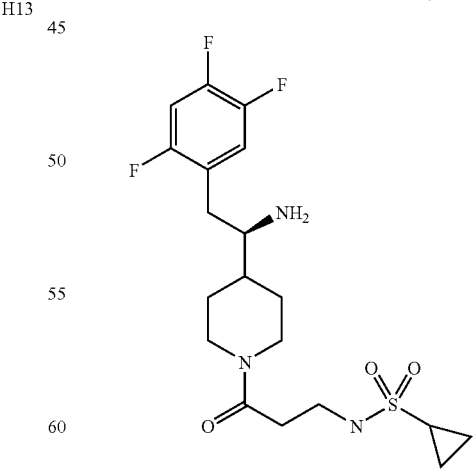

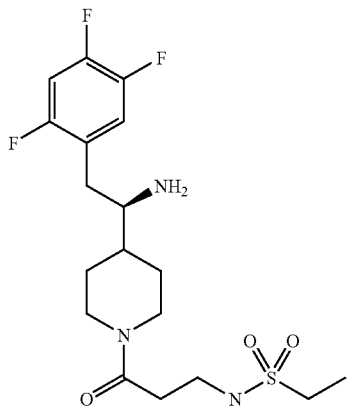
I3
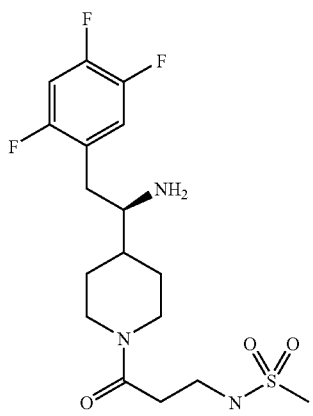
I4
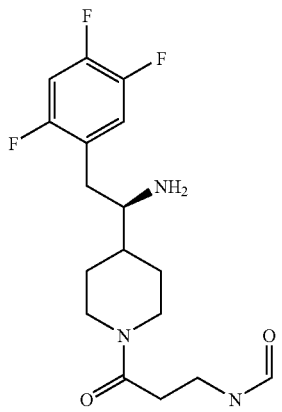
I5
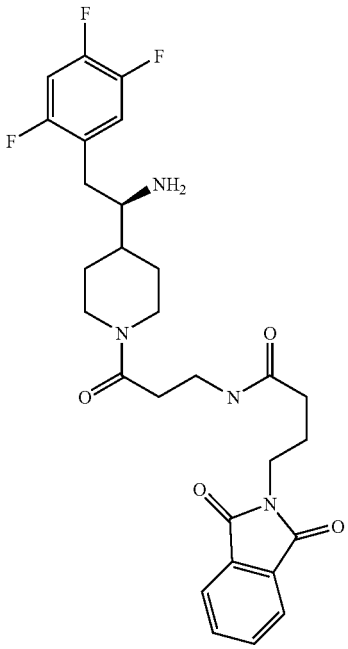
I6
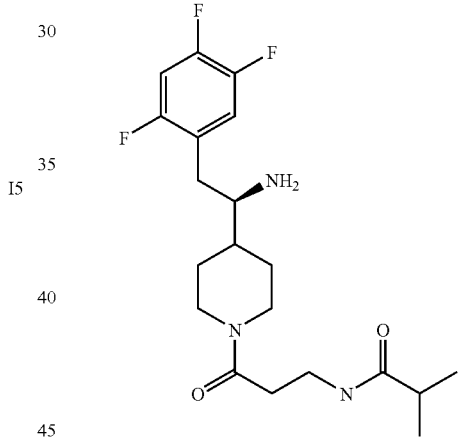
I7
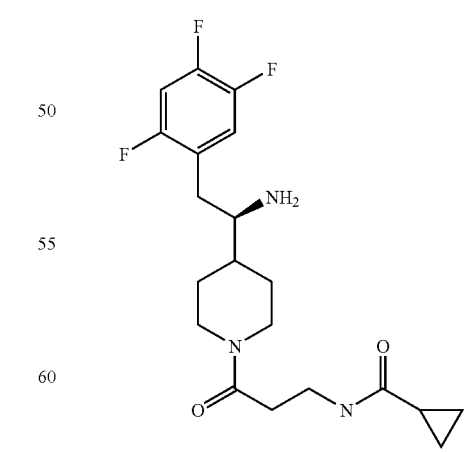
I8

269 270
-continued -continued
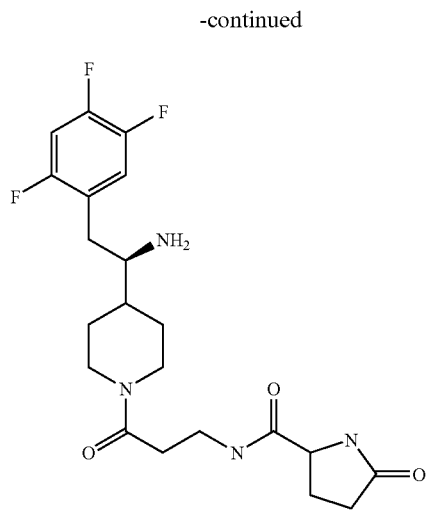
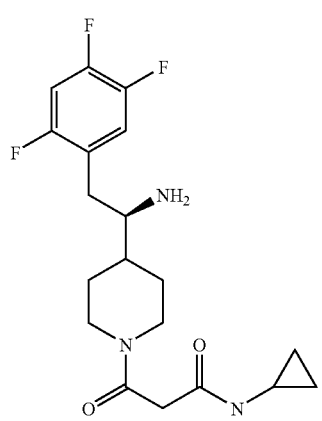
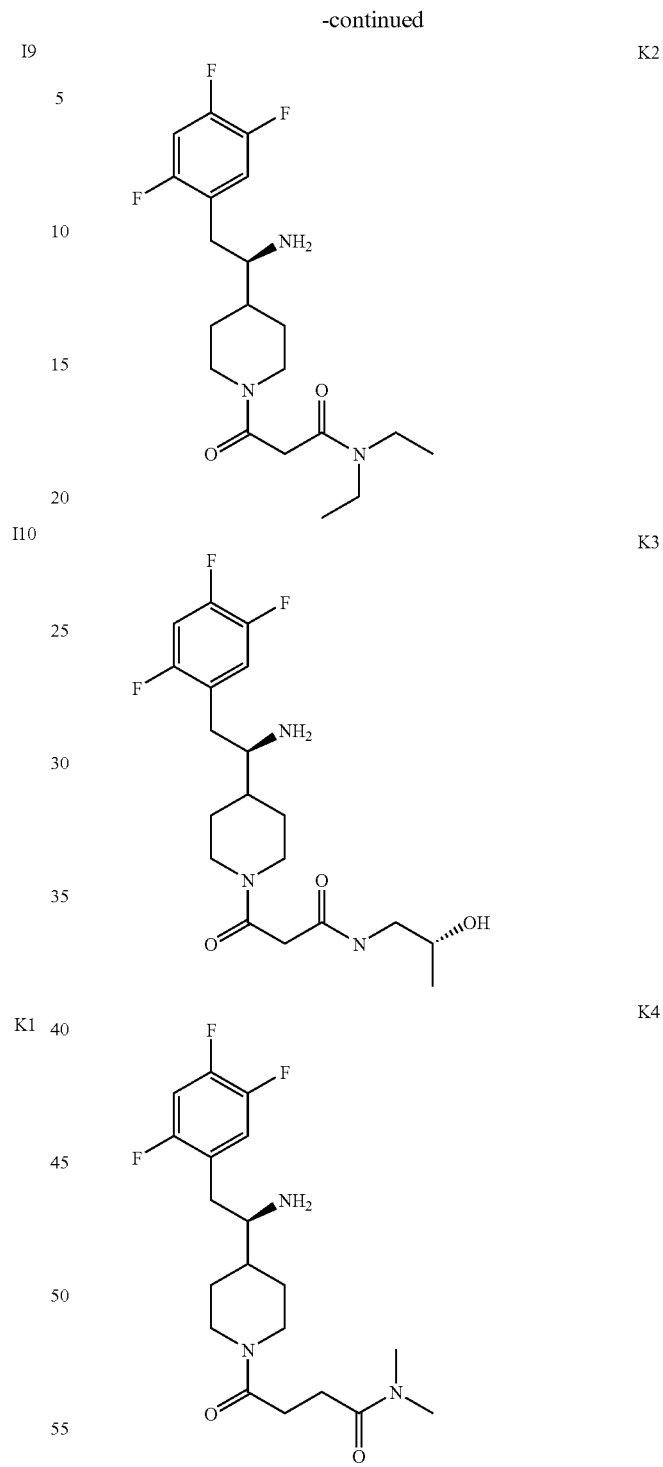

K5 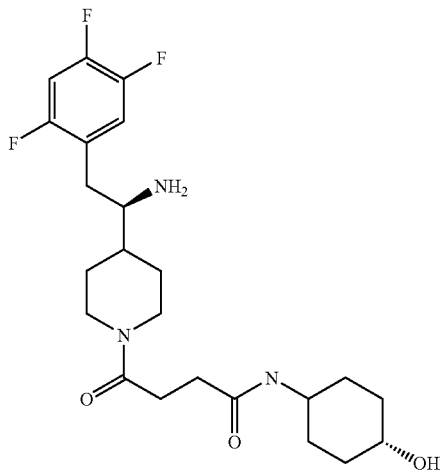
K6 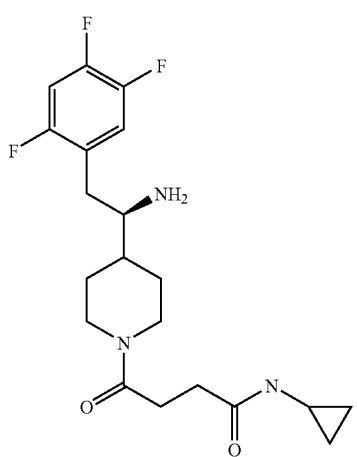
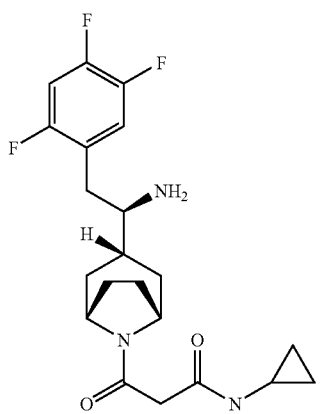
K8 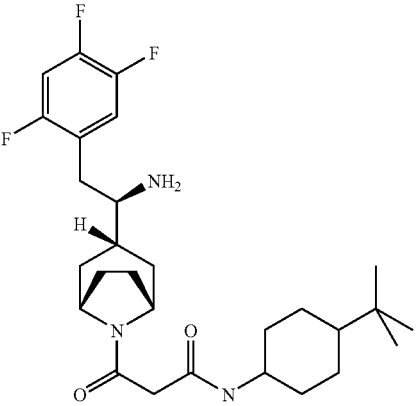
K9 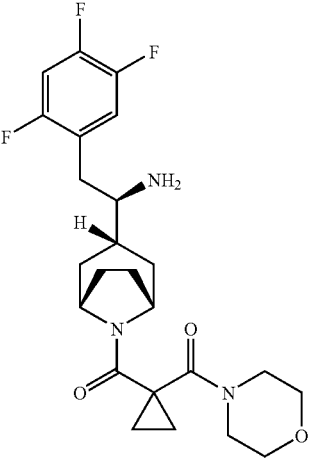
K10 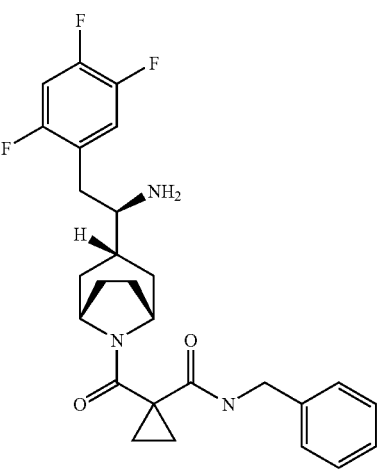

K11 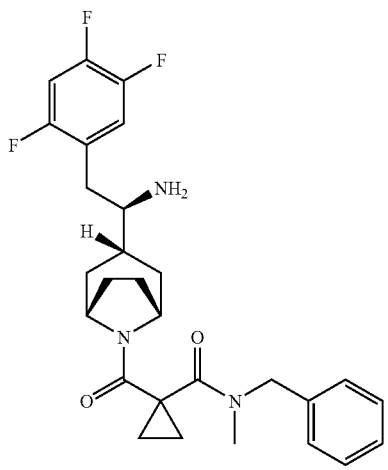
K12 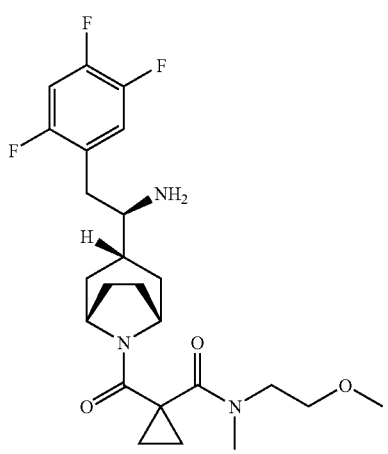
K13 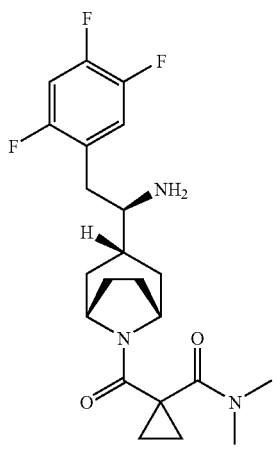
K14 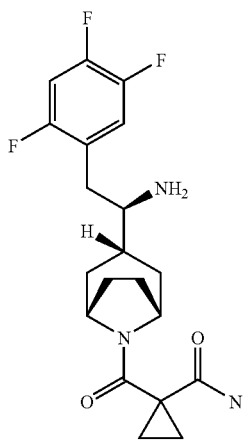
K15 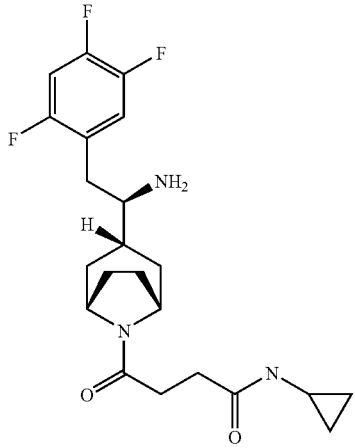
K16 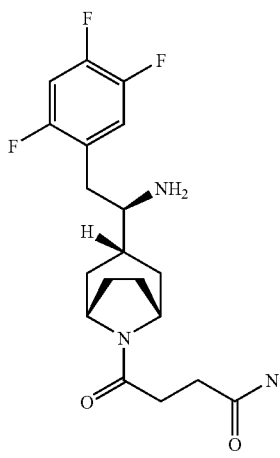

K17
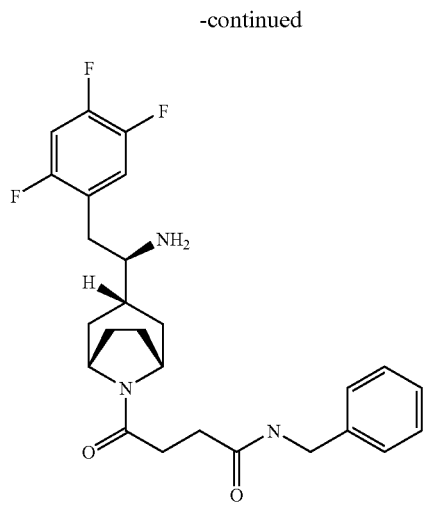
K18
K19
K20
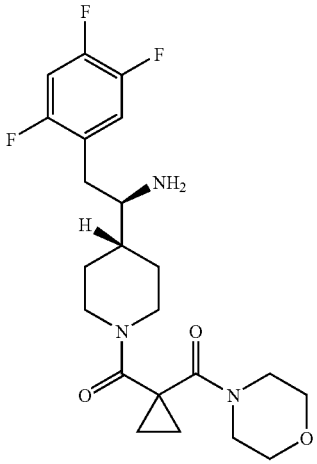
K21
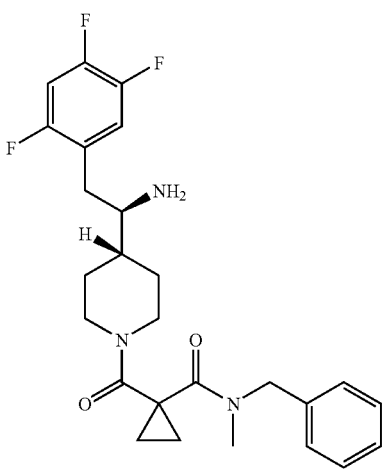
K22
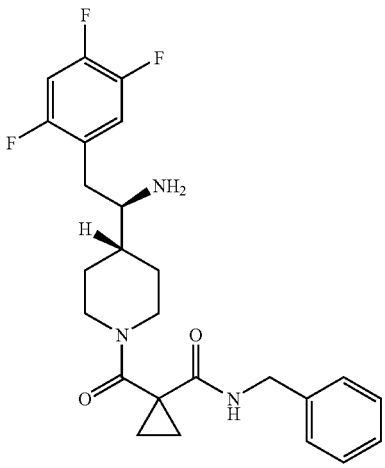

-continued
K23
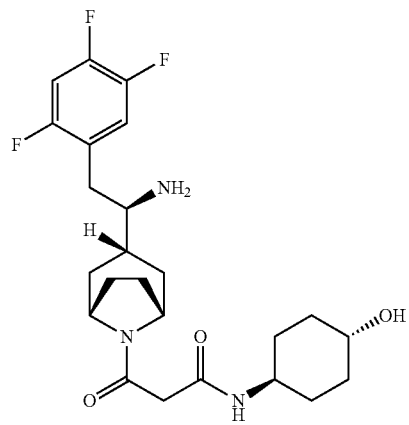
K24
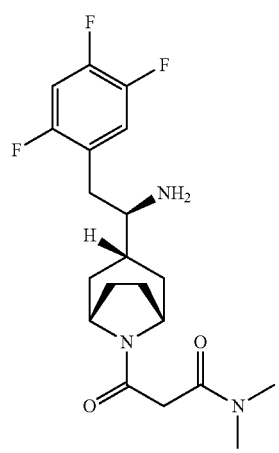
K26
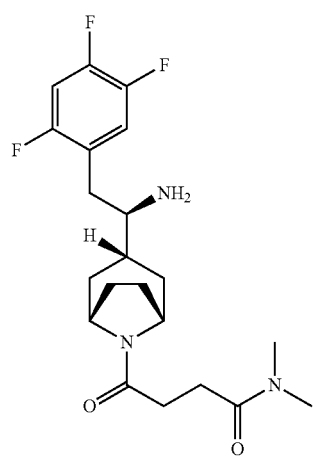
-continued
K27
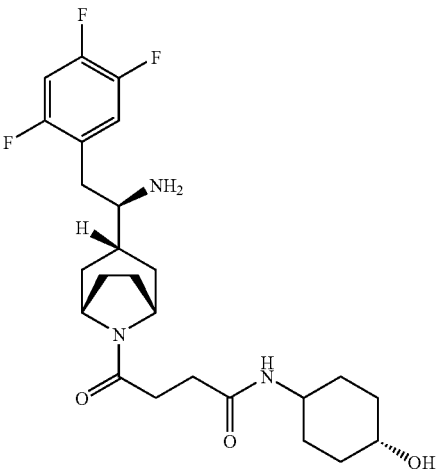
L1
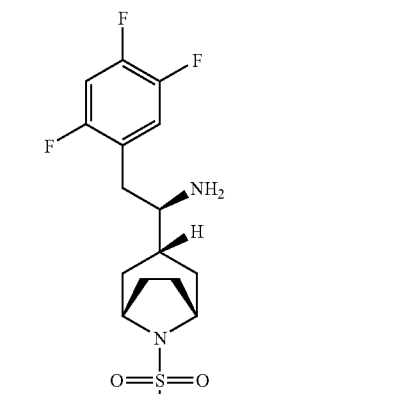
L2
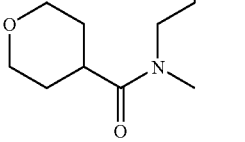
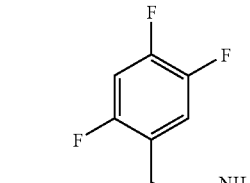
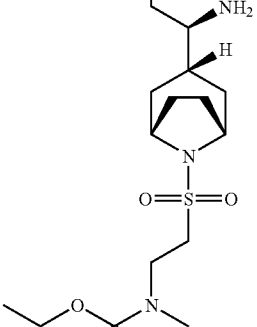

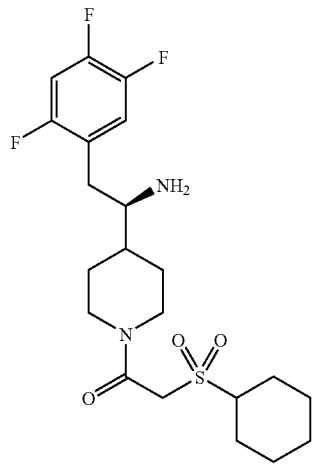
M1
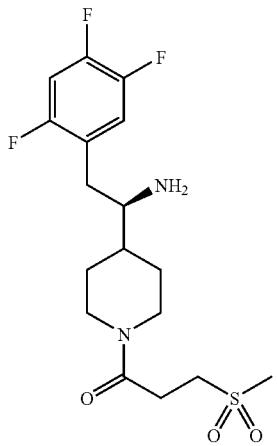
M4
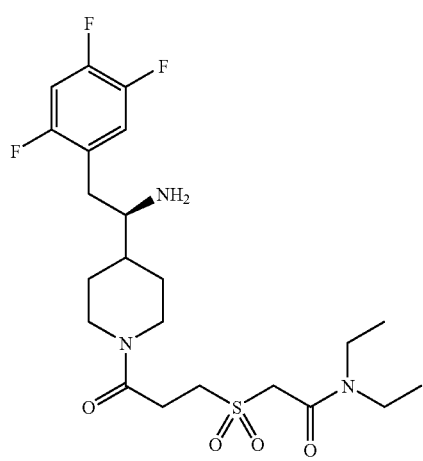
M2
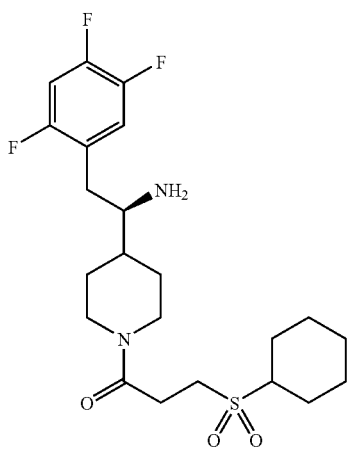
M5
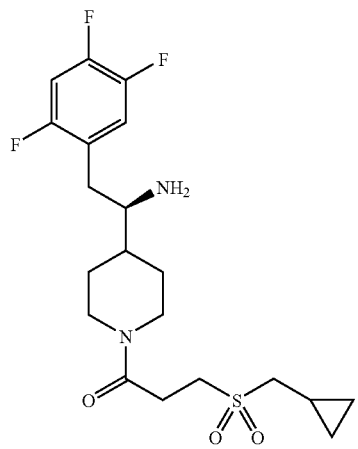
M3
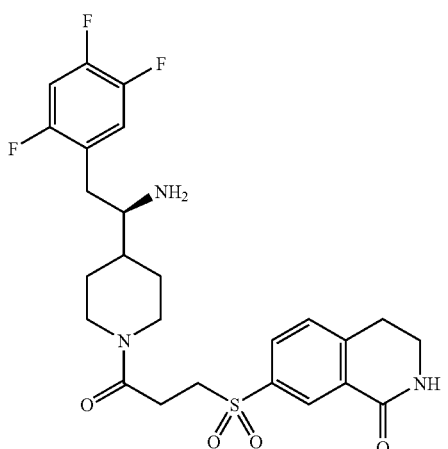
M6

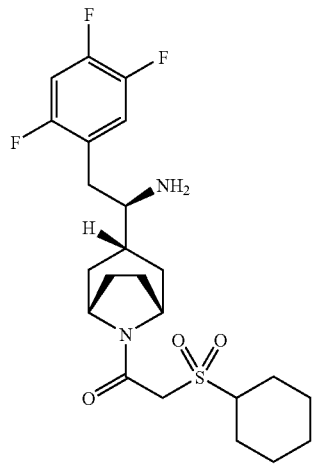
M7
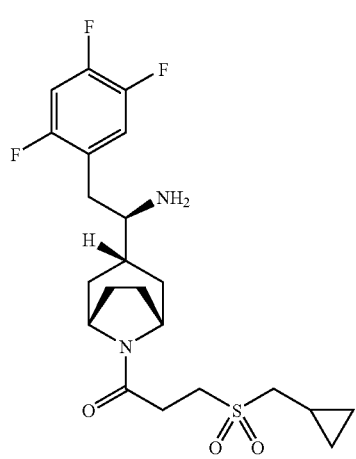
M8
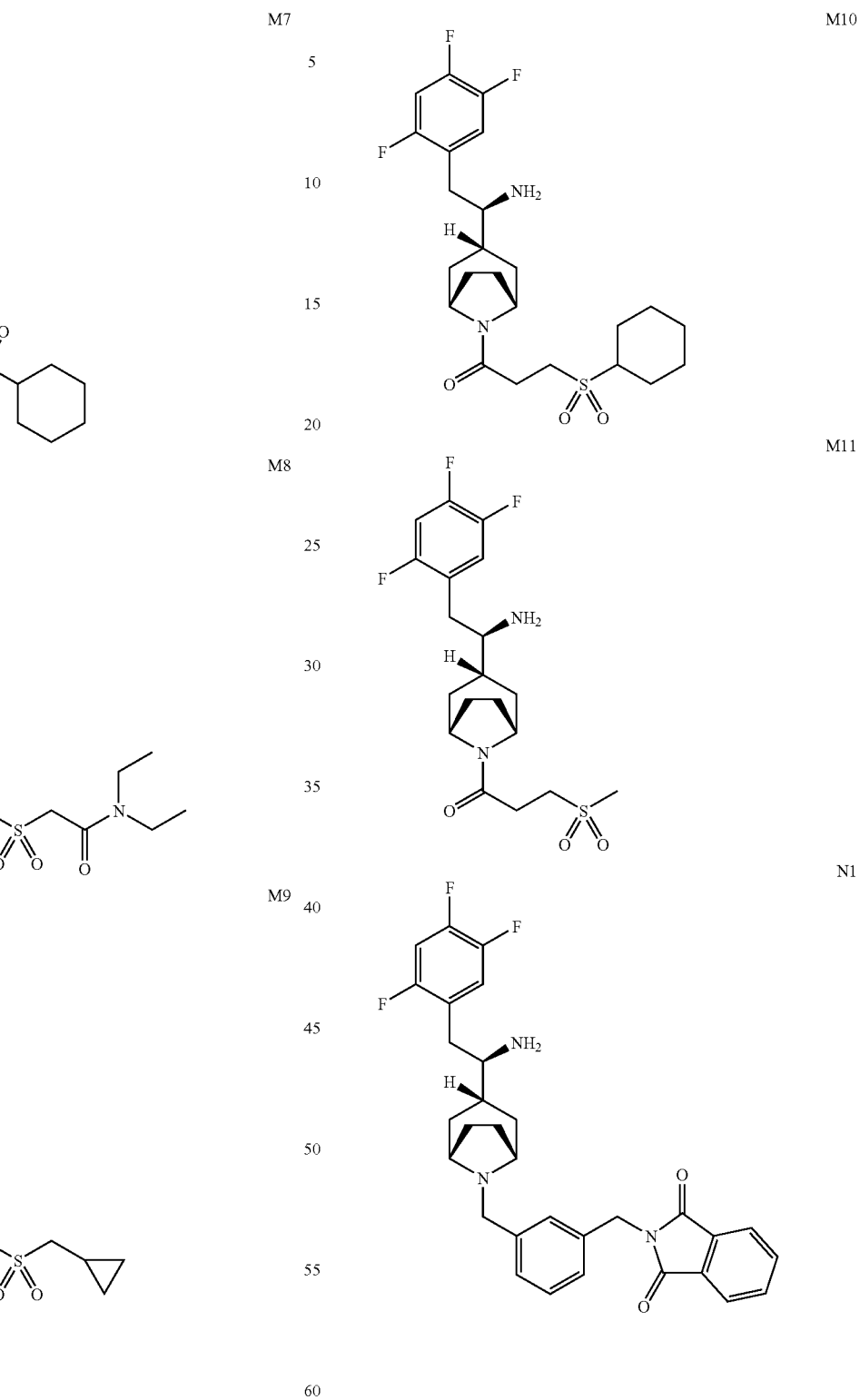
M9
M10
M11
N1

-continued

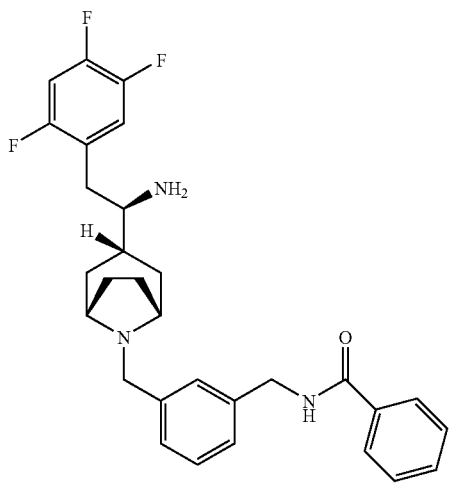

N2 or {(1S,3S,5R)-3-[(R)-1-Amino-2-(2,4,5-trifluoro-phenyl)-ethyl]-8-aza-bicyclo[3.2.1]oct-8-yl}-(1-{(1S,3S,5R)-3-[(R)-1-amino-2-(2,4,5-trifluoro-phenyl)-ethyl]-bicyclo[3.2.1]octane-8-carbonyl}-cyclopropyl)-methanone;

or, in each case, a pharmaceutically acceptable salt or prodrug thereof.

13. A pharmaceutical formulation, comprising:
the compound of claim 1, or a pharmaceutically acceptable salt or prodrug thereof, and
a pharmaceutically acceptable excipient or carrier.

14. The pharmaceutical formulation according to claim 13, which further comprises, a therapeutic agent selected from anti-diabetic agents, hypolipidemic agents, anti-obesity or appetite-regulating agents, anti-hypertensive agents, HDL-increasing agents, cholesterol absorption modulators, Apo-A1 analogues and mimetics, thrombin inhibitors, aldosterone inhibitors, inhibitors of platelet aggregation, estrogen, testosterone, selective estrogen receptor modulators, selective androgen receptor modulators, chemotherapeutic agents, and 5-HT3 or 5-HT4 receptor modulators.

* * * * *